(12) United States Patent
Schneider et al.

(10) Patent No.: US 12,161,359 B2
(45) Date of Patent: Dec. 10, 2024

(54) CATHETER

(71) Applicant: Medtronic Vascular, Inc., Santa Rosa, CA (US)

(72) Inventors: Mark Schneider, Mound, MD (US); Ethan Andrew Guggenheimer, Minnetonka, MN (US); Nickolas Miller, Santa Rosa, CA (US); Sengkham Sirivong, Brooklyn Park, MN (US); Bradley Steele, Plymouth, MN (US); Babak Tabesh, Santa Rosa, CA (US); Akshay Hulasare, Santa Rosa, CA (US); Julie Bu, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 142 days.

(21) Appl. No.: 17/664,173

(22) Filed: May 19, 2022

(65) Prior Publication Data

US 2022/0387069 A1    Dec. 8, 2022

Related U.S. Application Data

(63) Continuation of application No. 16/685,776, filed on Nov. 15, 2019, now Pat. No. 11,357,534.

(Continued)

(51) Int. Cl.
*A61B 17/3207*     (2006.01)
*A61B 17/00*       (2006.01)
(Continued)

(52) U.S. Cl.
CPC ............... *A61B 17/320758* (2013.01); *A61B 2017/00544* (2013.01); *A61B 2017/00867* (2013.01);

(Continued)

(58) Field of Classification Search
CPC ...... A61B 17/320758; A61B 17/32037; A61B 17/3207
(Continued)

(56) References Cited

U.S. PATENT DOCUMENTS

| 4,445,509 A | 5/1984 | Auth |
| 4,549,538 A | 10/1985 | Schadrack, III et al. |

(Continued)

FOREIGN PATENT DOCUMENTS

| CN | 207892951 U | 9/2018 |
| EP | 0268228 A | 5/1988 |

(Continued)

OTHER PUBLICATIONS

US 7,316,661 B2, 01/2008, Zadno Azizi (withdrawn)

(Continued)

*Primary Examiner* — Tuan V Nguyen
(74) *Attorney, Agent, or Firm* — Stinson LLP

(57) ABSTRACT

A catheter can restore the patency of a body lumen, for example, by removing tissue from a body lumen (e.g., a blood vessel). The catheter can be a rotational catheter having a rotatable drive shaft and a tissue-removing element secured to the drive shaft to be driven in rotation by the drive shaft. The catheter can have an abrasive burr configured to abrade tissue in a body lumen. The catheter can have an expandable tissue-removing element. The catheter can include a balloon and an inflation conduit. The catheter can also be configured to move over a guidewire through a body lumen. In one embodiment, the catheter comprises an over-the-wire, balloon-expandable, rotational, and abrasive tissue-removing catheter.

19 Claims, 72 Drawing Sheets

Related U.S. Application Data

(60) Provisional application No. 62/768,659, filed on Nov. 16, 2018.

(51) Int. Cl.
    *A61B 17/32* (2006.01)
    *A61M 25/00* (2006.01)

(52) U.S. Cl.
    CPC ............ *A61B 2017/320004* (2013.01); *A61M 25/0082* (2013.01)

(58) Field of Classification Search
    USPC ................ 606/190, 191, 192, 193, 194, 195
    See application file for complete search history.

(56) References Cited

U.S. PATENT DOCUMENTS

| | | |
|---|---|---|
| 4,650,466 A | 3/1987 | Luther |
| 4,679,557 A | 7/1987 | Opie et al. |
| 4,729,763 A | 3/1988 | Henrie |
| 4,784,636 A | 11/1988 | Rydell |
| 4,795,438 A | 1/1989 | Kensey et al. |
| 4,829,999 A | 5/1989 | Auth |
| 4,850,957 A | 7/1989 | Summers |
| 4,857,046 A | 8/1989 | Stevens et al. |
| 4,883,460 A | 11/1989 | Zanetti |
| 4,886,061 A | 12/1989 | Fischell et al. |
| 4,890,611 A | 1/1990 | Monfort et al. |
| 4,917,085 A | 4/1990 | Smith |
| 4,950,238 A | 8/1990 | Sullivan |
| 4,990,134 A | 2/1991 | Auth |
| 5,030,201 A | 7/1991 | Palestrant |
| 5,041,082 A | 8/1991 | Shiber |
| 5,049,124 A | 9/1991 | Bales, Jr. |
| 5,059,203 A | 10/1991 | Husted |
| 5,100,425 A | 3/1992 | Fischell et al. |
| 5,116,350 A | 5/1992 | Stevens |
| 5,116,352 A | 5/1992 | Schnepp et al. |
| 5,158,564 A | 10/1992 | Schnepp et al. |
| 5,160,342 A | 11/1992 | Reger et al. |
| 5,170,805 A | 12/1992 | Kensey et al. |
| 5,176,693 A | 1/1993 | Pannek, Jr. |
| 5,178,625 A | 1/1993 | Groshong |
| 5,195,954 A | 3/1993 | Schnepp et al. |
| 5,242,460 A | 9/1993 | Klein et al. |
| 5,242,461 A | 9/1993 | Kortenbach et al. |
| 5,250,060 A | 10/1993 | Carbo |
| 5,267,955 A | 12/1993 | Hanson |
| 5,287,858 A | 2/1994 | Hammerslag et al. |
| 5,295,958 A | 3/1994 | Shturman |
| 5,308,354 A | 5/1994 | Zacca et al. |
| 5,312,427 A | 5/1994 | Shturman |
| 5,314,407 A | 5/1994 | Auth et al. |
| 5,314,438 A | 5/1994 | Shturman |
| 5,318,576 A | 6/1994 | Plassche, Jr. et al. |
| 5,344,395 A | 9/1994 | Whalen et al. |
| 5,356,481 A | 10/1994 | Yoshimura et al. |
| 5,360,432 A | 11/1994 | Shturman |
| 5,366,463 A | 11/1994 | Ryan |
| 5,366,464 A | 11/1994 | Belknap |
| 5,376,077 A | 12/1994 | Gomringer |
| 5,376,100 A | 12/1994 | Lefebvre |
| 5,417,703 A | 5/1995 | Brown et al. |
| 5,490,859 A | 2/1996 | Mische et al. |
| 5,501,694 A | 3/1996 | Ressemann et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,540,707 A | 7/1996 | Ressemann et al. |
| 5,554,163 A | 9/1996 | Shturman |
| 5,571,136 A | 11/1996 | Weaver |
| 5,584,843 A | 12/1996 | Wulfman et al. |
| 5,626,562 A | 5/1997 | Castro |
| 5,628,761 A | 5/1997 | Rizik |
| 5,667,490 A | 9/1997 | Keith et al. |
| 5,681,336 A | 10/1997 | Clement et al. |
| 5,728,123 A | 3/1998 | Lemelson et al. |
| 5,728,129 A | 3/1998 | Summers |
| 5,766,190 A | 6/1998 | Wulfman |
| 5,766,192 A | 6/1998 | Zacca |
| 5,779,722 A | 7/1998 | Shturman et al. |
| 5,792,157 A | 8/1998 | Mische et al. |
| 5,836,868 A | 11/1998 | Ressemann et al. |
| 5,836,957 A | 11/1998 | Schulz et al. |
| 5,843,103 A | 12/1998 | Wulfman |
| 5,843,150 A | 12/1998 | Dreessen et al. |
| 5,855,601 A | 1/1999 | Bessler et al. |
| 5,868,767 A | 2/1999 | Farley et al. |
| 5,895,397 A | 4/1999 | Jang et al. |
| 5,895,400 A | 4/1999 | Abela |
| 5,895,402 A | 4/1999 | Hundertmark et al. |
| 5,897,567 A | 4/1999 | Ressemann et al. |
| 5,904,698 A | 5/1999 | Thomas et al. |
| 5,916,227 A | 6/1999 | Keith et al. |
| 5,916,234 A | 6/1999 | Lam |
| 5,919,200 A | 7/1999 | Stambaugh et al. |
| 5,925,055 A | 7/1999 | Adrian et al. |
| 5,938,670 A | 8/1999 | Keith et al. |
| 5,954,747 A | 9/1999 | Lee |
| 5,961,534 A | 10/1999 | Banik et al. |
| 5,976,165 A | 11/1999 | Ball et al. |
| 6,010,449 A | 1/2000 | Selmon et al. |
| 6,027,450 A | 2/2000 | Brown et al. |
| 6,039,747 A | 3/2000 | Shturman et al. |
| 6,080,171 A | 6/2000 | Keith et al. |
| RE36,764 E | 7/2000 | Zacca et al. |
| 6,093,157 A | 7/2000 | Chandrasekaran |
| 6,096,054 A | 8/2000 | Wyzgala et al. |
| 6,099,534 A | 8/2000 | Bates et al. |
| 6,113,613 A | 9/2000 | Spaulding |
| 6,113,614 A | 9/2000 | Mears |
| 6,120,516 A | 9/2000 | Selmon et al. |
| 6,120,517 A | 9/2000 | Daum et al. |
| 6,126,667 A | 10/2000 | Barry et al. |
| 6,129,698 A | 10/2000 | Beck |
| 6,129,734 A | 10/2000 | Shturman et al. |
| 6,156,046 A | 12/2000 | Passafaro et al. |
| 6,165,187 A | 12/2000 | Reger |
| 6,165,209 A | 12/2000 | Patterson et al. |
| 6,193,735 B1 | 2/2001 | Stevens |
| 6,217,595 B1 | 4/2001 | Shturman et al. |
| 6,221,015 B1 | 4/2001 | Yock |
| 6,221,087 B1 | 4/2001 | Anderson et al. |
| 6,235,042 B1 | 5/2001 | Katzman |
| 6,251,121 B1 | 6/2001 | Saadat |
| 6,258,052 B1 | 7/2001 | Milo |
| 6,266,550 B1 | 7/2001 | Selmon et al. |
| 6,295,712 B1 | 10/2001 | Shturman et al. |
| 6,299,623 B1 | 10/2001 | Wulfman |
| 6,300,434 B1 | 10/2001 | Schwager et al. |
| 6,306,151 B1 | 10/2001 | Lary |
| 6,312,444 B1 | 11/2001 | Barbut |
| 6,319,242 B1 | 11/2001 | Patterson et al. |
| D453,833 S | 2/2002 | Hess |
| 6,343,605 B1 | 2/2002 | Lafontaine |
| 6,375,609 B1 | 4/2002 | Hastings et al. |
| 6,391,832 B2 | 5/2002 | Lyons et al. |
| 6,398,798 B2 | 6/2002 | Selmon et al. |
| 6,400,980 B1 | 6/2002 | Lemelson |
| 6,416,523 B1 | 7/2002 | Lafontaine |
| 6,416,526 B1 | 7/2002 | Wyzgala et al. |
| 6,425,904 B1 | 7/2002 | Lemelson |
| 6,428,552 B1 | 8/2002 | Sparks et al. |
| 6,436,111 B1 | 8/2002 | Kadavy et al. |
| 6,440,503 B1 | 8/2002 | Merdan et al. |
| 6,443,967 B1 | 9/2002 | Kadavy et al. |
| 6,443,979 B1 | 9/2002 | Stalker et al. |
| 6,451,037 B1 | 9/2002 | Chandrasekaran et al. |
| 6,461,347 B1 * | 10/2002 | von Hoffmann ... A61M 25/104 604/509 |
| 6,461,383 B1 | 10/2002 | Gesswein et al. |
| 6,468,227 B2 | 10/2002 | Zimmon |

(56) References Cited

U.S. PATENT DOCUMENTS

| | | |
|---|---|---|
| 6,475,225 B1 | 11/2002 | Wulfman et al. |
| 6,482,209 B1 | 11/2002 | Engh et al. |
| 6,482,215 B1 | 11/2002 | Shiber |
| 6,482,216 B1 | 11/2002 | Hiblar et al. |
| 6,488,654 B2 | 12/2002 | Gonzalez et al. |
| 6,491,660 B2 | 12/2002 | Guo et al. |
| 6,497,711 B1 | 12/2002 | Plaia et al. |
| 6,500,186 B2 | 12/2002 | Lafontaine et al. |
| 6,503,227 B1 | 1/2003 | Guo et al. |
| 6,503,261 B1 | 1/2003 | Bruneau et al. |
| 6,537,202 B1 | 3/2003 | Frantzen |
| 6,554,846 B2 | 4/2003 | Hamilton et al. |
| 6,562,049 B1 | 5/2003 | Norlander et al. |
| 6,569,177 B1 | 5/2003 | Dillard et al. |
| 6,579,298 B1 | 6/2003 | Bruneau et al. |
| 6,579,299 B2 | 6/2003 | McGuckin, Jr. et al. |
| 6,602,265 B2 | 8/2003 | Dubrul et al. |
| 6,613,066 B1 | 9/2003 | Fukaya et al. |
| 6,616,676 B2 | 9/2003 | Bashiri |
| 6,620,179 B2 | 9/2003 | Book et al. |
| 6,626,861 B1 | 9/2003 | Hart et al. |
| 6,626,923 B1 | 9/2003 | Wyzgala |
| 6,632,230 B2 | 10/2003 | Barry |
| 6,638,228 B1 | 10/2003 | Chandrasekaran et al. |
| 6,638,288 B1 | 10/2003 | Shturman et al. |
| 6,652,548 B2 | 11/2003 | Evans et al. |
| 6,669,710 B2 | 12/2003 | Moutafis |
| 6,682,543 B2 | 1/2004 | Barbut et al. |
| 6,685,718 B1 | 2/2004 | Wyzgala et al. |
| 6,719,775 B2 | 4/2004 | Slaker et al. |
| 6,719,781 B1 | 4/2004 | Kim |
| 6,723,390 B2 | 4/2004 | Merdan et al. |
| 6,764,498 B2 | 7/2004 | Mische |
| D494,270 S | 8/2004 | Reschke |
| 6,786,876 B2 | 9/2004 | Cox |
| 6,790,215 B2 | 9/2004 | Findlay |
| 6,800,083 B2 | 10/2004 | Hiblar et al. |
| 6,800,085 B2 | 10/2004 | Selmon et al. |
| 6,808,531 B2 | 10/2004 | Lafontaine et al. |
| 6,827,734 B2 | 12/2004 | Fariabi |
| 6,837,890 B1 | 1/2005 | Chludzinski et al. |
| 6,852,097 B1 | 2/2005 | Fulton |
| 6,852,118 B2 | 2/2005 | Shturman et al. |
| 6,872,204 B2 | 3/2005 | Houser et al. |
| 6,899,712 B2 | 5/2005 | Moutafis et al. |
| 6,911,026 B1 | 6/2005 | Hall et al. |
| 6,951,570 B2 | 10/2005 | Linder et al. |
| 6,953,468 B2 | 10/2005 | Jones et al. |
| 6,986,778 B2 | 1/2006 | Zadno et al. |
| 7,004,173 B2 | 6/2006 | Sparks et al. |
| 7,063,714 B2 | 6/2006 | Dorros et al. |
| 7,141,045 B2 | 11/2006 | Johansson et al. |
| 7,169,118 B2 | 1/2007 | Reynolds et al. |
| 7,172,571 B2 | 2/2007 | Moskowitz et al. |
| 7,179,269 B2 | 2/2007 | Welch et al. |
| 7,189,240 B1 | 3/2007 | Dekel |
| 7,211,041 B2 | 5/2007 | Mueller |
| 7,247,269 B2 | 7/2007 | Keidar |
| 7,252,674 B2 | 8/2007 | Wyzgala et al. |
| 7,311,719 B2 | 12/2007 | Bonutti |
| 7,384,407 B2 | 6/2008 | Rodriguez et al. |
| D578,216 S | 10/2008 | Dom et al. |
| 7,494,485 B2 | 2/2009 | Beck et al. |
| 7,507,245 B2 | 3/2009 | Shturman et al. |
| 7,517,352 B2 | 4/2009 | Evans et al. |
| 7,534,249 B2 | 5/2009 | Nash et al. |
| 7,537,588 B2 | 5/2009 | Palasis et al. |
| 7,582,112 B2 | 9/2009 | Scheuermann et al. |
| 7,591,996 B2 | 9/2009 | Hwang et al. |
| 7,594,900 B1 | 9/2009 | Nash et al. |
| 7,618,434 B2 | 11/2009 | Santra et al. |
| 7,632,301 B2 | 12/2009 | Alt |
| 7,645,290 B2 | 1/2010 | Lucas |
| 7,670,327 B2 | 3/2010 | Kucharczyk et al. |
| 7,686,824 B2 | 3/2010 | Konstantino et al. |
| 7,687,144 B2 | 3/2010 | Clark et al. |
| 7,697,996 B2 | 4/2010 | Manning et al. |
| 7,699,865 B2 | 4/2010 | Johnson et al. |
| 7,715,896 B2 | 5/2010 | Ramzipoor et al. |
| 7,731,731 B2 | 6/2010 | Abela |
| 7,734,332 B2 | 6/2010 | Sher |
| 7,744,587 B2 | 6/2010 | Murphy |
| 7,758,604 B2 | 7/2010 | Wu et al. |
| 7,819,863 B2 | 10/2010 | Eggers et al. |
| 7,832,406 B2 | 11/2010 | Ellis et al. |
| 7,854,755 B2 | 12/2010 | Lafontaine et al. |
| 7,887,557 B2 | 2/2011 | Kelley et al. |
| D634,843 S | 3/2011 | Kim et al. |
| 7,951,161 B2 | 5/2011 | Bonnette et al. |
| 7,967,834 B2 | 6/2011 | Tal et al. |
| 7,976,460 B2 | 7/2011 | Richardson |
| 7,985,200 B2 | 7/2011 | Lary et al. |
| 7,993,384 B2 | 8/2011 | Wu et al. |
| 8,002,725 B2 | 8/2011 | Hogendijk |
| 8,012,153 B2 | 9/2011 | Woloszko et al. |
| 8,021,379 B2 | 9/2011 | Thompson et al. |
| 8,043,287 B2 | 10/2011 | Conquergood et al. |
| 8,043,362 B2 | 10/2011 | Gong et al. |
| 8,052,637 B2 | 11/2011 | von Oepen et al. |
| 8,052,716 B2 | 11/2011 | Gilson et al. |
| 8,067,055 B2 | 11/2011 | Savage et al. |
| 8,080,026 B2 | 12/2011 | Konstantino et al. |
| 8,083,713 B2 | 12/2011 | Smith et al. |
| 8,105,351 B2 | 1/2012 | Lehman et al. |
| 8,123,750 B2 | 2/2012 | Norton et al. |
| 8,134,041 B2 | 3/2012 | Etchells |
| 8,142,457 B2 | 3/2012 | Lafontaine |
| 8,158,670 B2 | 4/2012 | Kunz et al. |
| 8,162,964 B2 | 4/2012 | Piippo et al. |
| 8,175,677 B2 | 5/2012 | Sayler et al. |
| 8,177,801 B2 | 5/2012 | Kallok et al. |
| 8,182,499 B2 | 5/2012 | Abraham et al. |
| 8,192,451 B2 | 6/2012 | Cambronne et al. |
| 8,208,990 B2 | 6/2012 | Maschke |
| 8,282,246 B2 | 6/2012 | Kugler et al. |
| 8,221,348 B2 | 7/2012 | Hackett et al. |
| 8,241,335 B2 | 8/2012 | Truckai et al. |
| 8,308,711 B2 | 11/2012 | Lee et al. |
| 8,317,786 B2 | 11/2012 | Dahla et al. |
| 8,323,249 B2 | 12/2012 | Wulfman et al. |
| 8,323,279 B2 | 12/2012 | Dahla et al. |
| 8,337,518 B2 | 12/2012 | Nance et al. |
| 8,348,965 B2 | 1/2013 | Prudnikov et al. |
| 8,348,987 B2 | 1/2013 | Eaton |
| 8,353,923 B2 | 1/2013 | Shturman |
| 8,377,037 B2 | 2/2013 | Sachdeva et al. |
| 8,382,423 B1 | 2/2013 | Frodis et al. |
| 8,382,739 B2 | 2/2013 | Walak |
| 8,388,582 B2 | 3/2013 | Eubanks et al. |
| 8,398,663 B2 | 3/2013 | Paul et al. |
| 8,398,664 B2 | 3/2013 | Lamps et al. |
| 8,435,228 B2 | 5/2013 | Wulfman et al. |
| 8,439,937 B2 | 5/2013 | Montague et al. |
| 8,449,566 B2 | 5/2013 | Finitsis |
| 8,465,510 B2 | 6/2013 | Shturman |
| 8,475,478 B2 | 7/2013 | Robinson |
| 8,475,487 B2 | 7/2013 | Bonnette et al. |
| 8,480,628 B2 | 7/2013 | Hawkins et al. |
| 8,524,132 B2 | 9/2013 | Von Oepen et al. |
| 8,529,614 B2 | 9/2013 | Berez et al. |
| 8,530,783 B2 | 9/2013 | Ow et al. |
| 8,532,746 B2 | 9/2013 | Gelbart et al. |
| 8,551,130 B2 | 10/2013 | Schoenle et al. |
| 8,562,607 B2 | 10/2013 | Truckai et al. |
| 8,568,432 B2 | 10/2013 | Straub |
| 8,579,926 B2 | 11/2013 | Pinto et al. |
| 8,597,239 B2 | 12/2013 | Gerrans et al. |
| 8,597,313 B2 | 12/2013 | Thatcher et al. |
| 8,603,038 B2 | 12/2013 | Nelson |
| 8,612,022 B1 | 12/2013 | Morero et al. |
| 8,613,721 B2 | 12/2013 | Wulfman |
| 8,617,144 B2 | 12/2013 | Ravikumar |
| 8,628,550 B2 | 1/2014 | Narveson |
| 8,628,551 B2 | 1/2014 | Hanson et al. |

(56) References Cited

U.S. PATENT DOCUMENTS

| | | |
|---|---|---|
| 8,632,556 B2 | 1/2014 | Jacobs et al. |
| 8,632,557 B2 | 1/2014 | Thatcher et al. |
| 8,657,821 B2 | 2/2014 | Palermo |
| 8,679,141 B2 | 3/2014 | Goodin et al. |
| 8,696,645 B2 | 4/2014 | Tal et al. |
| 8,702,652 B2 | 4/2014 | Fiorella et al. |
| 8,702,735 B2 | 4/2014 | Rivers |
| 8,709,087 B2 | 4/2014 | Cragg |
| 8,715,227 B2 | 5/2014 | Kontos |
| 8,715,240 B2 | 5/2014 | Cunningham |
| 8,728,106 B2 | 5/2014 | Weber et al. |
| 8,758,325 B2 | 6/2014 | Webster et al. |
| 8,771,302 B2 | 7/2014 | Woolfson et al. |
| 8,779,328 B2 | 7/2014 | Anukhin et al. |
| 8,790,299 B2 | 7/2014 | Gunday et al. |
| 8,792,962 B2 | 7/2014 | Esguerra et al. |
| 8,795,241 B2 | 8/2014 | O'Connell et al. |
| 8,795,303 B2 | 8/2014 | McBroom et al. |
| 8,795,304 B2 | 8/2014 | Piippo Svendsen |
| 8,814,892 B2 | 8/2014 | Galdonik et al. |
| 8,827,951 B2 | 9/2014 | Besser et al. |
| 8,840,566 B2 | 9/2014 | Seibel et al. |
| 8,864,762 B2 | 10/2014 | Gunday et al. |
| 8,882,697 B2 | 11/2014 | Celermajer |
| 8,882,790 B2 | 11/2014 | Kassab et al. |
| 8,888,787 B2 | 11/2014 | Wynberg |
| D719,651 S | 12/2014 | Hoffmann et al. |
| 8,920,402 B2 | 12/2014 | Nash et al. |
| 8,926,560 B2 | 1/2015 | Dinh et al. |
| 8,932,694 B2 | 1/2015 | Rolfes et al. |
| 8,945,089 B2 | 2/2015 | Johnson et al. |
| 8,951,224 B2 | 2/2015 | Wulfman et al. |
| 8,961,533 B2 | 2/2015 | Stahler et al. |
| 8,968,346 B2 | 3/2015 | Lockard et al. |
| 8,974,519 B2 | 3/2015 | Gennrich et al. |
| 8,986,331 B2 | 3/2015 | Chekan et al. |
| 8,992,553 B2 * | 3/2015 | Diamant .......... A61B 17/22032 606/159 |
| 8,992,557 B2 | 3/2015 | Whayne et al. |
| 8,992,717 B2 | 3/2015 | Zeroni et al. |
| 8,998,843 B2 | 4/2015 | Bonnette et al. |
| 9,017,294 B2 | 4/2015 | McGuckin, Jr. et al. |
| 9,050,127 B2 | 6/2015 | Bonnette et al. |
| 9,050,414 B2 | 6/2015 | Schoenle et al. |
| 9,055,951 B2 | 6/2015 | Deshpande |
| 9,055,966 B2 | 6/2015 | Cambronne et al. |
| 9,072,873 B2 | 7/2015 | Lippert et al. |
| 9,078,692 B2 | 7/2015 | Shturman et al. |
| 9,084,620 B2 | 7/2015 | Ludin et al. |
| 9,084,627 B2 | 7/2015 | Weber |
| 9,089,362 B2 | 7/2015 | Shturman |
| 9,101,382 B2 | 8/2015 | Krolik et al. |
| 9,101,387 B2 | 8/2015 | Plowe et al. |
| 9,101,430 B2 | 8/2015 | Müller |
| 9,108,027 B2 | 8/2015 | Eubanks et al. |
| 9,114,235 B2 | 8/2015 | Cambronne |
| 9,119,662 B2 | 9/2015 | Moberg |
| 9,119,944 B2 | 9/2015 | Chambers et al. |
| 9,138,210 B2 | 9/2015 | Schulte et al. |
| 9,162,040 B2 | 10/2015 | Vo et al. |
| 9,162,046 B2 | 10/2015 | Hill et al. |
| 9,174,019 B2 | 11/2015 | Gregersen |
| 9,180,274 B2 | 11/2015 | Cully et al. |
| 9,186,129 B2 | 11/2015 | Blitzer et al. |
| 9,186,170 B2 | 11/2015 | Welty et al. |
| 9,186,210 B2 | 11/2015 | Jenson |
| 9,199,058 B2 | 12/2015 | Lentz |
| 9,205,234 B2 | 12/2015 | Hardin |
| 9,211,138 B2 | 12/2015 | Shturman |
| 9,211,386 B2 | 12/2015 | Aboytes |
| 9,216,033 B2 | 12/2015 | Feld et al. |
| 9,216,034 B2 | 12/2015 | Avneri |
| 9,217,442 B2 | 12/2015 | Wiessler et al. |
| 9,220,529 B2 | 12/2015 | Rivers et al. |
| 9,220,530 B2 | 12/2015 | Moberg |
| 9,226,763 B2 | 1/2016 | To et al. |
| 9,238,126 B2 | 1/2016 | Gerrans et al. |
| 9,254,143 B2 | 2/2016 | Huynh et al. |
| 9,259,215 B2 | 2/2016 | Chou et al. |
| 9,265,563 B2 | 2/2016 | Racz et al. |
| 9,289,230 B2 | 3/2016 | Cambronne |
| 9,295,373 B2 | 3/2016 | Torrance et al. |
| 9,301,769 B2 | 4/2016 | Brady et al. |
| 9,301,774 B2 | 4/2016 | O'Day |
| 9,308,007 B2 | 4/2016 | Cully et al. |
| 9,308,019 B2 | 4/2016 | Kugler et al. |
| 9,314,324 B2 | 4/2016 | Janardhan et al. |
| 9,320,530 B2 | 4/2016 | Grace |
| 9,320,535 B2 | 4/2016 | Zaretzka et al. |
| 9,320,540 B2 | 4/2016 | Badie |
| 9,326,789 B2 | 5/2016 | Fruland et al. |
| 9,333,335 B2 | 5/2016 | Ollivier et al. |
| 9,345,508 B2 | 5/2016 | Hendrick |
| 9,345,511 B2 | 5/2016 | Smith et al. |
| 9,345,858 B2 | 5/2016 | Flaherty et al. |
| 9,351,757 B2 | 5/2016 | Kusleika |
| 9,364,255 B2 | 6/2016 | Weber |
| 9,370,649 B2 | 6/2016 | Chang et al. |
| 9,375,234 B2 | 6/2016 | Vrba |
| 9,375,328 B2 | 6/2016 | Farnan |
| 9,381,062 B2 | 7/2016 | Kapur et al. |
| 9,387,006 B2 | 7/2016 | Shturman |
| 9,387,305 B2 | 7/2016 | Courtney et al. |
| 9,398,837 B2 | 7/2016 | Vazales et al. |
| 9,402,981 B2 | 8/2016 | Anderson |
| 9,413,896 B2 | 8/2016 | Bowe et al. |
| 9,414,852 B2 | 8/2016 | Gifford, III et al. |
| 9,427,553 B2 | 8/2016 | Nelson |
| 9,433,437 B2 | 9/2016 | Kesten et al. |
| 9,439,674 B2 | 9/2016 | Rydberg et al. |
| 9,445,829 B2 | 9/2016 | Brady et al. |
| 9,452,241 B2 | 9/2016 | Gill et al. |
| 9,456,843 B2 | 10/2016 | Kessler et al. |
| 9,463,041 B2 | 10/2016 | Bleich et al. |
| 9,468,457 B2 | 10/2016 | Blackledge et al. |
| 9,474,543 B2 | 10/2016 | McGuckin, Jr. et al. |
| D770,618 S | 11/2016 | Fiksen et al. |
| 9,486,611 B2 | 11/2016 | Petersen et al. |
| 9,498,183 B2 | 11/2016 | Brown et al. |
| 9,498,290 B2 | 11/2016 | Piferi et al. |
| 9,526,519 B2 | 12/2016 | Kessler et al. |
| 9,526,674 B2 | 12/2016 | Heyns et al. |
| 9,532,797 B2 | 1/2017 | Vreeman |
| 9,532,799 B2 | 1/2017 | Simpson et al. |
| 9,539,019 B2 | 1/2017 | Sullivan et al. |
| 9,545,298 B2 | 1/2017 | Ginn et al. |
| 9,597,109 B2 | 3/2017 | Shturman |
| 9,597,110 B2 | 3/2017 | Kessler et al. |
| 9,675,376 B2 | 6/2017 | To et al. |
| 9,687,266 B2 | 6/2017 | Moberg et al. |
| 9,700,346 B2 | 7/2017 | Levine et al. |
| 9,717,520 B2 | 8/2017 | Zeroni et al. |
| 9,901,252 B2 | 2/2018 | Tran |
| D846,738 S | 4/2019 | Kalina, Jr. et al. |
| D903,100 S | 11/2020 | Stats et al. |
| D933,820 S | 10/2021 | Ota |
| D944,395 S | 2/2022 | Harris et al. |
| D944,396 S | 2/2022 | Harris et al. |
| D952,842 S | 5/2022 | Harris et al. |
| 2002/0098278 A1 | 7/2002 | Bates et al. |
| 2002/0165560 A1 | 11/2002 | Danitz et al. |
| 2003/0069522 A1 | 4/2003 | Jacobsen et al. |
| 2003/0109837 A1 | 6/2003 | McBride |
| 2003/0139689 A1 | 7/2003 | Shturman et al. |
| 2003/0187498 A1 | 10/2003 | Bishop |
| 2003/0191435 A1 * | 10/2003 | Shkolnik .......... A61M 25/1034 604/103 |
| 2003/0236533 A1 | 12/2003 | Wilson et al. |
| 2004/0147934 A1 | 7/2004 | Kiester |
| 2004/0158270 A1 | 8/2004 | Wyzgala et al. |
| 2004/0186506 A1 * | 9/2004 | Simpson .......... A61M 25/0009 606/194 |
| 2004/0215222 A1 | 10/2004 | Krivoruchko |
| 2004/0225355 A1 | 11/2004 | Stevens |

(56) References Cited

U.S. PATENT DOCUMENTS

| | | |
|---|---|---|
| 2004/0243162 A1 | 12/2004 | Wulfman et al. |
| 2004/0267191 A1 | 12/2004 | Gifford et al. |
| 2005/0096633 A1 | 5/2005 | Moskowitz |
| 2005/0149083 A1 | 7/2005 | Prudnikov et al. |
| 2005/0187537 A1 | 8/2005 | Loeb et al. |
| 2005/0187556 A1 | 8/2005 | Stack et al. |
| 2005/0203553 A1 | 9/2005 | Maschke |
| 2005/0216044 A1 | 9/2005 | Hong |
| 2005/0228417 A1 | 10/2005 | Teitelbaum et al. |
| 2005/0251187 A1 | 11/2005 | Beane et al. |
| 2006/0030934 A1 | 2/2006 | Hogendijk et al. |
| 2006/0047291 A1 | 3/2006 | Barry |
| 2006/0142630 A1 | 6/2006 | Meretei |
| 2006/0142632 A1 | 6/2006 | Meretei |
| 2006/0264988 A1 | 11/2006 | Boyle |
| 2006/0271155 A1 | 11/2006 | Herr |
| 2007/0088230 A1 | 4/2007 | Terashi et al. |
| 2007/0203516 A1 | 8/2007 | Nayak |
| 2007/0213753 A1 | 9/2007 | Waller |
| 2007/0282367 A1 | 12/2007 | Jeffrey et al. |
| 2008/0033423 A1 | 2/2008 | Peacock |
| 2008/0161840 A1 | 7/2008 | Osiroff et al. |
| 2008/0208230 A1 | 8/2008 | Chin |
| 2008/0221566 A1 | 9/2008 | Krishnan |
| 2009/0112239 A1 | 4/2009 | To |
| 2009/0163940 A1 | 6/2009 | Sliwa |
| 2009/0182359 A1 | 7/2009 | Shturman |
| 2009/0182362 A1 | 7/2009 | Thompson et al. |
| 2009/0216284 A1 | 8/2009 | Chin et al. |
| 2009/0264907 A1 | 10/2009 | Vrba et al. |
| 2009/0306690 A1 | 12/2009 | Rivers et al. |
| 2010/0030251 A1 | 2/2010 | Sandhu et al. |
| 2010/0063534 A1 | 3/2010 | Kugler et al. |
| 2010/0082051 A1 | 4/2010 | Thorpe et al. |
| 2010/0234864 A1 | 9/2010 | Keller |
| 2010/0241148 A1 | 9/2010 | Schon et al. |
| 2011/0046543 A1 | 2/2011 | Brandeis |
| 2011/0077673 A1 | 3/2011 | Grubac et al. |
| 2011/0087254 A1 | 4/2011 | Welty |
| 2011/0172598 A1 | 7/2011 | Sampognaro et al. |
| 2011/0224625 A1 | 9/2011 | Flickinger et al. |
| 2011/0282368 A1 | 11/2011 | Swayze et al. |
| 2012/0035705 A1 | 2/2012 | Giasolli |
| 2012/0046599 A1 | 2/2012 | Schoenle et al. |
| 2012/0046600 A1 | 2/2012 | Kohler et al. |
| 2012/0209176 A1 | 8/2012 | Anderson |
| 2012/0232570 A1 | 9/2012 | Jenson et al. |
| 2012/0259354 A1 | 10/2012 | Kellett |
| 2012/0265229 A1 | 10/2012 | Rottenberg et al. |
| 2013/0005218 A1 | 1/2013 | von Oepen et al. |
| 2013/0060234 A1 | 3/2013 | Besser et al. |
| 2013/0085514 A1 | 4/2013 | Lee et al. |
| 2013/0092298 A1 | 4/2013 | Bregulla et al. |
| 2013/0103067 A1 | 4/2013 | Fabro et al. |
| 2013/0116655 A1 | 5/2013 | Bacino et al. |
| 2013/0123661 A1 | 5/2013 | Dewaele et al. |
| 2013/0158578 A1 | 6/2013 | Ghodke et al. |
| 2013/0253467 A1 | 9/2013 | Gianotti et al. |
| 2013/0267870 A1 | 10/2013 | Lonky |
| 2013/0317529 A1 | 11/2013 | Golden et al. |
| 2013/0331881 A1* | 12/2013 | Rosenman ........ A61M 25/0138 606/191 |
| 2014/0025044 A1 | 1/2014 | Zamarripa et al. |
| 2014/0039494 A1 | 2/2014 | Kick et al. |
| 2014/0094833 A1 | 4/2014 | Malhi |
| 2014/0100521 A1 | 4/2014 | Mizokami |
| 2014/0100585 A1 | 4/2014 | Anderson et al. |
| 2014/0128893 A1 | 5/2014 | Guggenheimer et al. |
| 2014/0163664 A1 | 6/2014 | Goldsmith |
| 2014/0214060 A1 | 7/2014 | Bonnette et al. |
| 2014/0275770 A1 | 9/2014 | Gunday et al. |
| 2014/0276390 A1 | 9/2014 | Eubanks et al. |
| 2014/0276407 A1 | 9/2014 | DeVries et al. |
| 2014/0276684 A1 | 9/2014 | Huennekens et al. |
| 2014/0276696 A1 | 9/2014 | Schneider |
| 2014/0276920 A1 | 9/2014 | Hendrick et al. |
| 2014/0277011 A1 | 9/2014 | Meader |
| 2014/0277061 A1 | 9/2014 | Lam et al. |
| 2014/0296706 A1 | 10/2014 | Chronos et al. |
| 2014/0296742 A1 | 10/2014 | Kalloo et al. |
| 2014/0296897 A1 | 10/2014 | Sotak et al. |
| 2014/0303658 A1 | 10/2014 | Bonnette et al. |
| 2014/0316448 A1 | 10/2014 | Higgins |
| 2014/0316449 A1 | 10/2014 | Grothe et al. |
| 2014/0330286 A1 | 11/2014 | Wallace |
| 2014/0350582 A1 | 11/2014 | Higgins |
| 2014/0358123 A1 | 12/2014 | Ueda et al. |
| 2014/0371770 A1 | 12/2014 | Schoenle et al. |
| 2015/0005791 A1 | 1/2015 | Schoenle et al. |
| 2015/0038902 A1 | 2/2015 | Mark et al. |
| 2015/0051625 A1 | 2/2015 | Petrucci et al. |
| 2015/0068069 A1 | 3/2015 | Tran et al. |
| 2015/0080795 A1 | 3/2015 | Mattison et al. |
| 2015/0088246 A1 | 3/2015 | Astarci et al. |
| 2015/0127035 A1 | 5/2015 | Trapp et al. |
| 2015/0133978 A1 | 5/2015 | Paul, Jr. |
| 2015/0142028 A1 | 5/2015 | Ellering et al. |
| 2015/0150587 A1 | 6/2015 | Smith et al. |
| 2015/0157303 A1 | 6/2015 | Brandeis |
| 2015/0164541 A1 | 6/2015 | Shiber |
| 2015/0164542 A1 | 6/2015 | Wulfman et al. |
| 2015/0201956 A1 | 7/2015 | Higgins et al. |
| 2015/0209066 A1 | 7/2015 | Dahm et al. |
| 2015/0209072 A1 | 7/2015 | Higgins et al. |
| 2015/0224281 A1 | 8/2015 | Kim et al. |
| 2015/0230810 A1 | 8/2015 | Creighton et al. |
| 2015/0230821 A1 | 8/2015 | Batchelor et al. |
| 2015/0238207 A1 | 8/2015 | Cox et al. |
| 2015/0245851 A1 | 9/2015 | McGuckin, Jr. |
| 2015/0258258 A1 | 9/2015 | Bonnette et al. |
| 2015/0273184 A1 | 10/2015 | Scott et al. |
| 2015/0289902 A1 | 10/2015 | Hehrlein |
| 2015/0290438 A1 | 10/2015 | Gerrans et al. |
| 2015/0320971 A1 | 11/2015 | Leeflang et al. |
| 2015/0335348 A1 | 11/2015 | Cohen et al. |
| 2015/0342682 A1 | 12/2015 | Bowe |
| 2015/0342718 A1 | 12/2015 | Weber et al. |
| 2015/0351729 A1 | 12/2015 | Chin et al. |
| 2015/0352330 A1 | 12/2015 | Wasdyke et al. |
| 2015/0359595 A1 | 12/2015 | Ben et al. |
| 2015/0374908 A1 | 12/2015 | Piferi |
| 2016/0001062 A1 | 1/2016 | Weber et al. |
| 2016/0015420 A1 | 1/2016 | Higgins et al. |
| 2016/0015434 A1 | 1/2016 | Stieglitz et al. |
| 2016/0022244 A1 | 1/2016 | Courtney et al. |
| 2016/0022296 A1 | 1/2016 | Brady et al. |
| 2016/0022307 A1 | 1/2016 | Wasdyke et al. |
| 2016/0051323 A1 | 2/2016 | Stigall et al. |
| 2016/0066803 A1 | 3/2016 | Hu et al. |
| 2016/0067465 A1 | 3/2016 | Gerrans et al. |
| 2016/0095733 A1 | 4/2016 | Sharma et al. |
| 2016/0128718 A1 | 5/2016 | Aggerholm et al. |
| 2016/0136393 A1 | 5/2016 | Tsai et al. |
| 2016/0157872 A1 | 6/2016 | Cage et al. |
| 2016/0157886 A1 | 6/2016 | WasDyke et al. |
| 2016/0158490 A1 | 6/2016 | Leeflang et al. |
| 2016/0166265 A1 | 6/2016 | Nita |
| 2016/0183963 A1 | 6/2016 | Richter et al. |
| 2016/0183966 A1 | 6/2016 | McGuckin, Jr. |
| 2016/0183967 A1 | 6/2016 | McGuckin, Jr. et al. |
| 2016/0199091 A1 | 7/2016 | Pigott |
| 2016/0199617 A1 | 7/2016 | Pigott |
| 2016/0206340 A1 | 7/2016 | Vetter et al. |
| 2016/0228681 A1 | 8/2016 | di Palma et al. |
| 2016/0242790 A1 | 8/2016 | Brandeis |
| 2016/0242805 A1 | 8/2016 | Kohler et al. |
| 2016/0249942 A1 | 9/2016 | Olson |
| 2016/0256620 A1 | 9/2016 | Scheckel et al. |
| 2016/0263361 A1 | 9/2016 | Vadivelu et al. |
| 2016/0263391 A1 | 9/2016 | Tasci et al. |
| 2016/0270814 A1 | 9/2016 | Palme et al. |
| 2016/0278805 A1 | 9/2016 | Hatta et al. |
| 2016/0287283 A1 | 10/2016 | Vetter et al. |
| 2016/0287438 A1 | 10/2016 | Badawi et al. |

(56) References Cited

U.S. PATENT DOCUMENTS

| | | |
|---|---|---|
| 2016/0296683 A1 | 10/2016 | Jin et al. |
| 2016/0324535 A1 | 11/2016 | Chang et al. |
| 2016/0331394 A1 | 11/2016 | Rottenberg et al. |
| 2016/0346003 A1 | 12/2016 | Grothe et al. |
| 2016/0354107 A1 | 12/2016 | Nakano et al. |
| 2016/0354108 A1 | 12/2016 | Nakano et al. |
| 2016/0361528 A1 | 12/2016 | Kanz et al. |
| 2016/0374714 A1 | 12/2016 | Majercak et al. |
| 2016/0374715 A1* | 12/2016 | McPeak ......... A61B 17/320758 606/159 |
| 2016/0375235 A1 | 12/2016 | Schoenle et al. |
| 2017/0000518 A1 | 1/2017 | Smith et al. |
| 2017/0000977 A1 | 1/2017 | Dtorbeck et al. |
| 2017/0020556 A1 | 1/2017 | Sutton et al. |
| 2017/0071624 A1 | 3/2017 | McGuckin, Jr. |
| 2017/0156749 A1 | 6/2017 | Pigott |
| 2017/0173262 A1 | 6/2017 | Veltz |
| 2019/0216496 A1 | 7/2019 | Grothe et al. |

FOREIGN PATENT DOCUMENTS

| | | |
|---|---|---|
| EP | 1864618 B1 | 10/2009 |
| EP | 2819586 A2 | 1/2015 |
| EP | 3302308 A1 | 12/2016 |
| EP | 2967635 B1 | 6/2017 |
| EP | 3384860 A1 | 10/2018 |
| WO | WO1994028803 A1 | 12/1994 |
| WO | WO1997043949 A1 | 11/1997 |
| WO | WO1998008554 A1 | 3/1998 |
| WO | 9850101 A1 | 11/1998 |
| WO | WO1999018862 A1 | 4/1999 |
| WO | WO1999018864 A1 | 4/1999 |
| WO | 9929240 A1 | 6/1999 |
| WO | WO1999035980 A1 | 7/1999 |
| WO | WO1999044516 A1 | 9/1999 |
| WO | WO2000056230 A2 | 9/2000 |
| WO | 0232329 A2 | 4/2002 |
| WO | WO2002049518 A2 | 6/2002 |
| WO | WO2004073524 A1 | 9/2004 |
| WO | WO2005112834 A2 | 12/2005 |
| WO | WO2008099424 A2 | 8/2008 |
| WO | WO2011057060 A2 | 5/2011 |
| WO | WO2014022866 A1 | 2/2014 |
| WO | WO2014080424 A2 | 5/2014 |
| WO | WO2015148284 A1 | 10/2015 |
| WO | WO2016019991 A1 | 2/2016 |
| WO | WO2016044406 A1 | 3/2016 |
| WO | WO2016108860 A1 | 7/2016 |
| WO | WO2016133931 A1 | 8/2016 |
| WO | WO2016133932 A1 | 8/2016 |
| WO | 2019/118522 A1 | 6/2019 |
| WO | 2019/135976 A1 | 7/2019 |
| WO | 2019/136009 A1 | 7/2019 |
| WO | 2019/140121 A1 | 7/2019 |
| WO | 2019/161140 | 8/2019 |
| WO | 2019/168784 | 9/2019 |
| WO | 2019/168862 | 9/2019 |
| WO | 2019/199672 | 10/2019 |
| WO | 2019/199981 | 10/2019 |

OTHER PUBLICATIONS

European Communication Pursuant to Article 94(3) EPC for corresponding Application No. 19 821 342.3, dated Oct. 31, 2023, 6 pages, München, Germany.

Invitation to Pay Additional Fees with Communication Relating to the Results of the Partial International Search and Provisional Opinion Accompanying the Partial Search Result, Feb. 4, 2020, 20 pages, Europe.

International Search Report and Written Opinion of PCT/US2018/022843 filed Mar. 16, 2018, dated Jun. 11, 2018, 13 pages.

European Communication Pursuant to Article 94(3) EPC for corresponding Application No. 19 821 342.3, dated Jul. 18, 2022, 7 pages, München, Germany.

Non-Final Office action from corresponding U.S. Appl. No. 29/713,502, filed Oct. 17, 2022, 9 pages.

Chinese Office action for Application No. 201980074480.7, Mar. 1, 2024 20 pages with English translation.

* cited by examiner

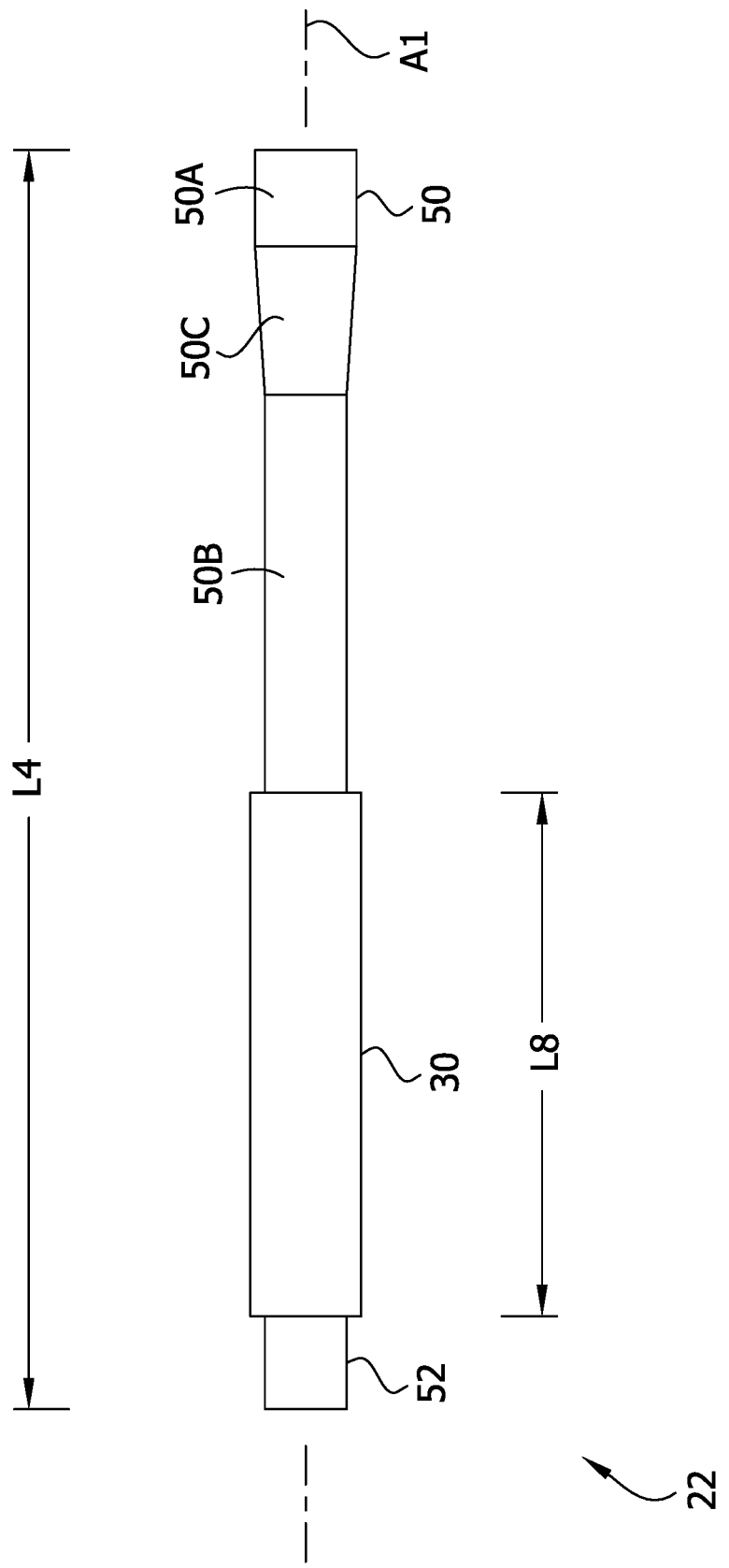

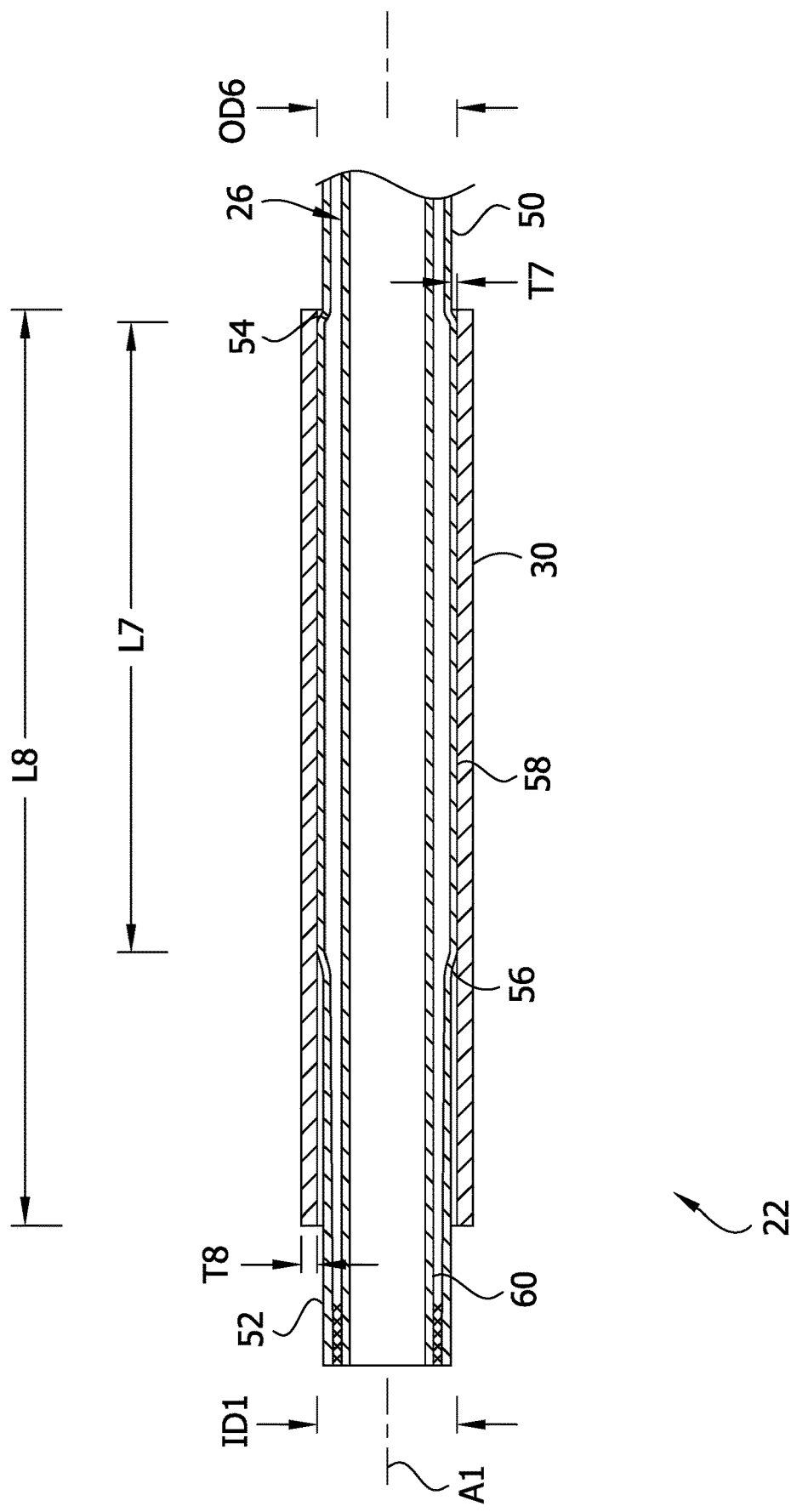

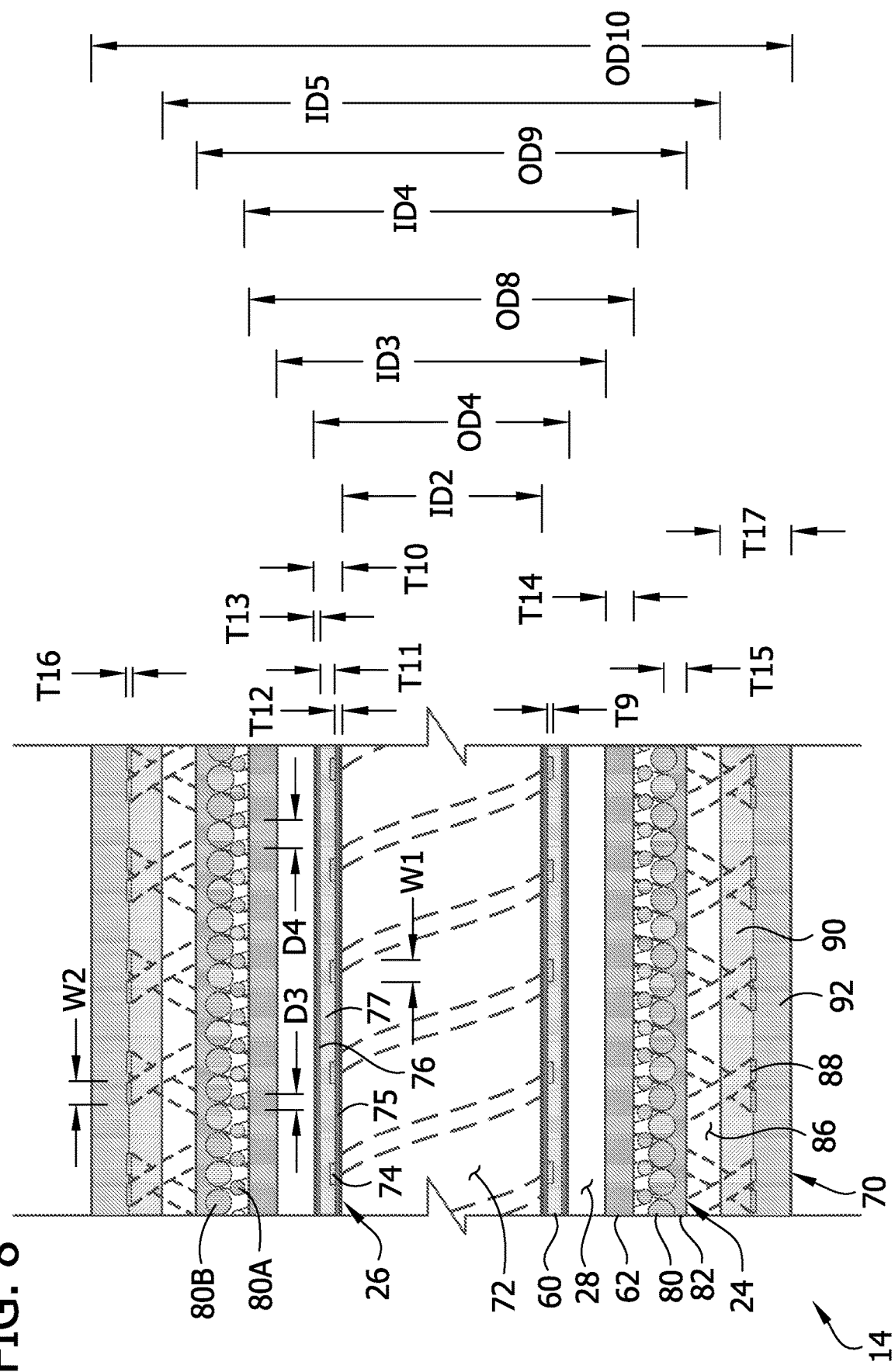

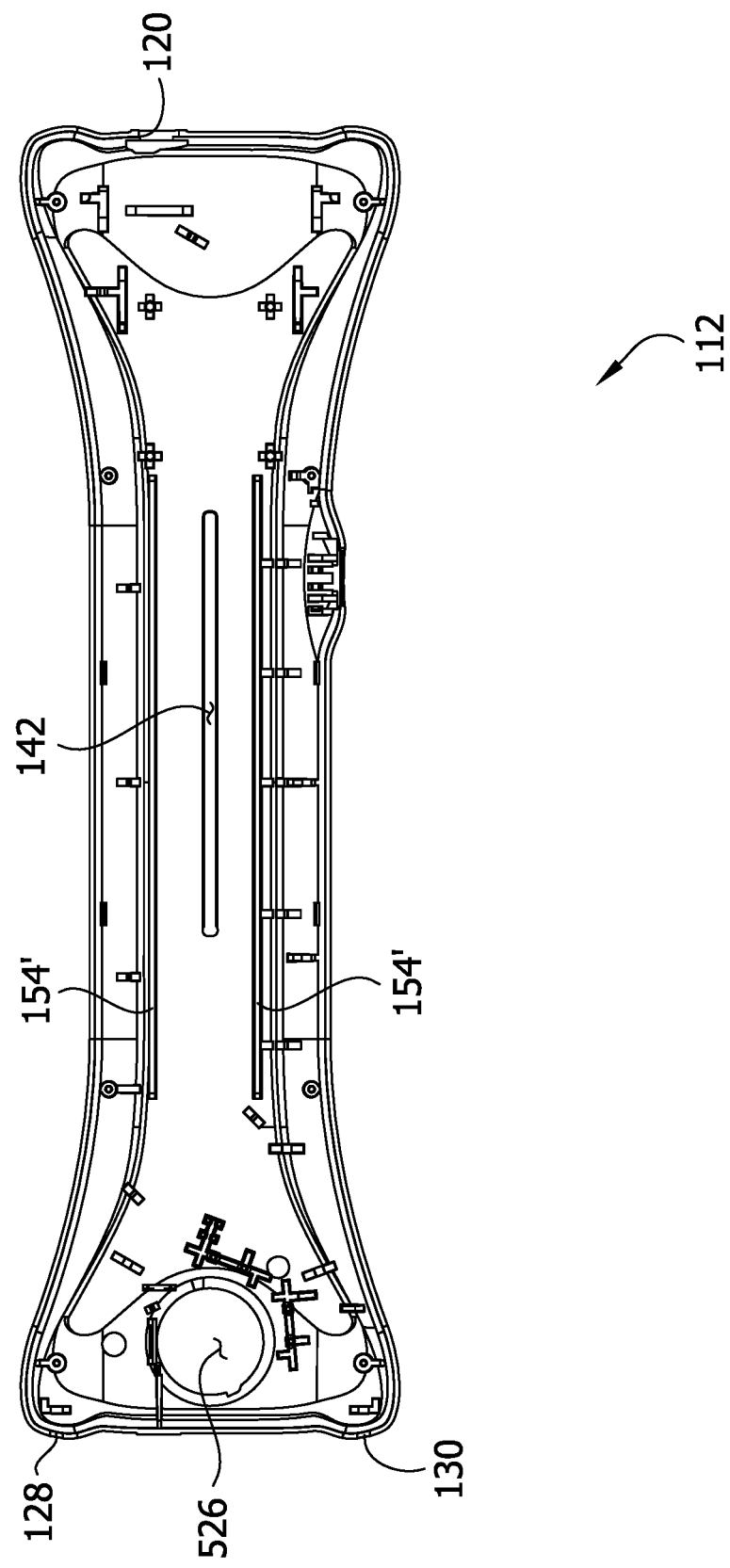

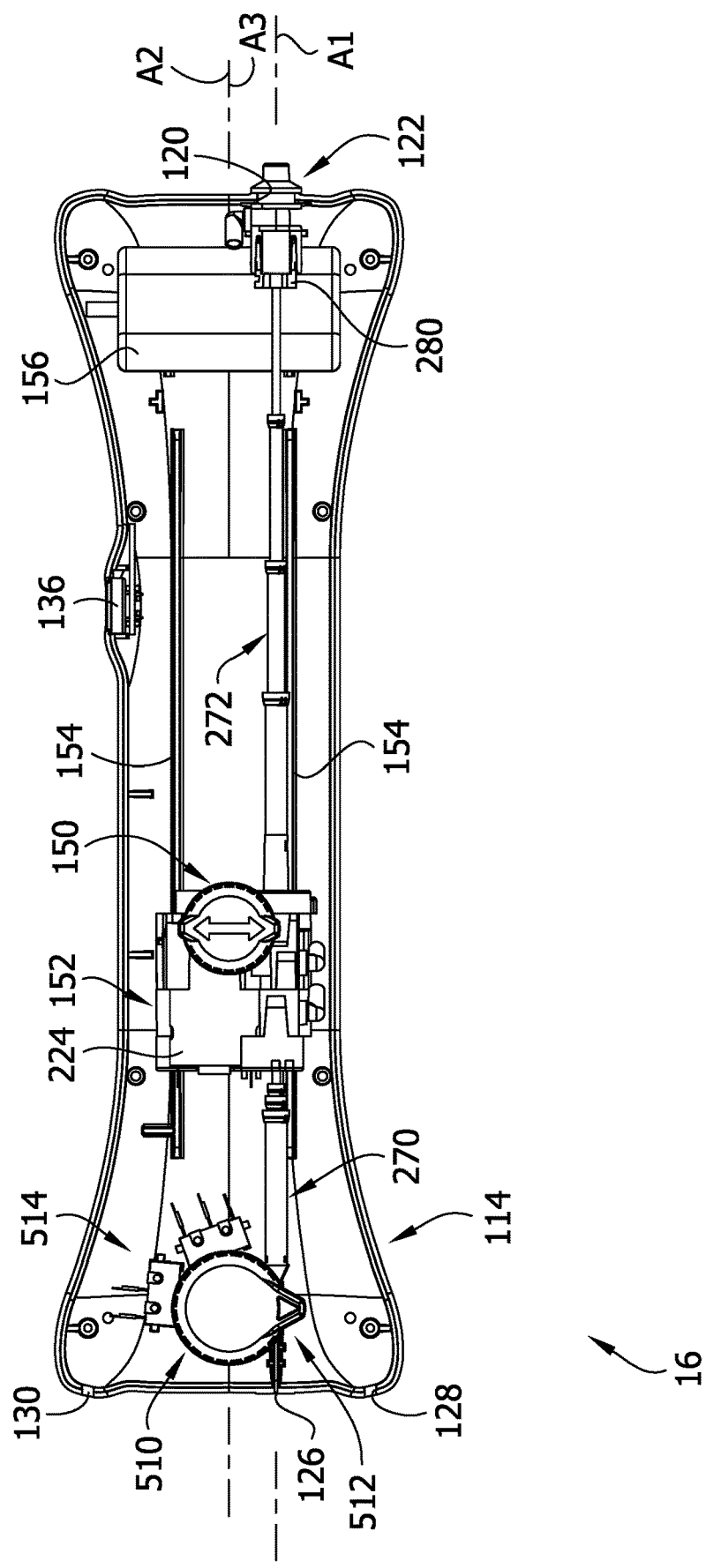

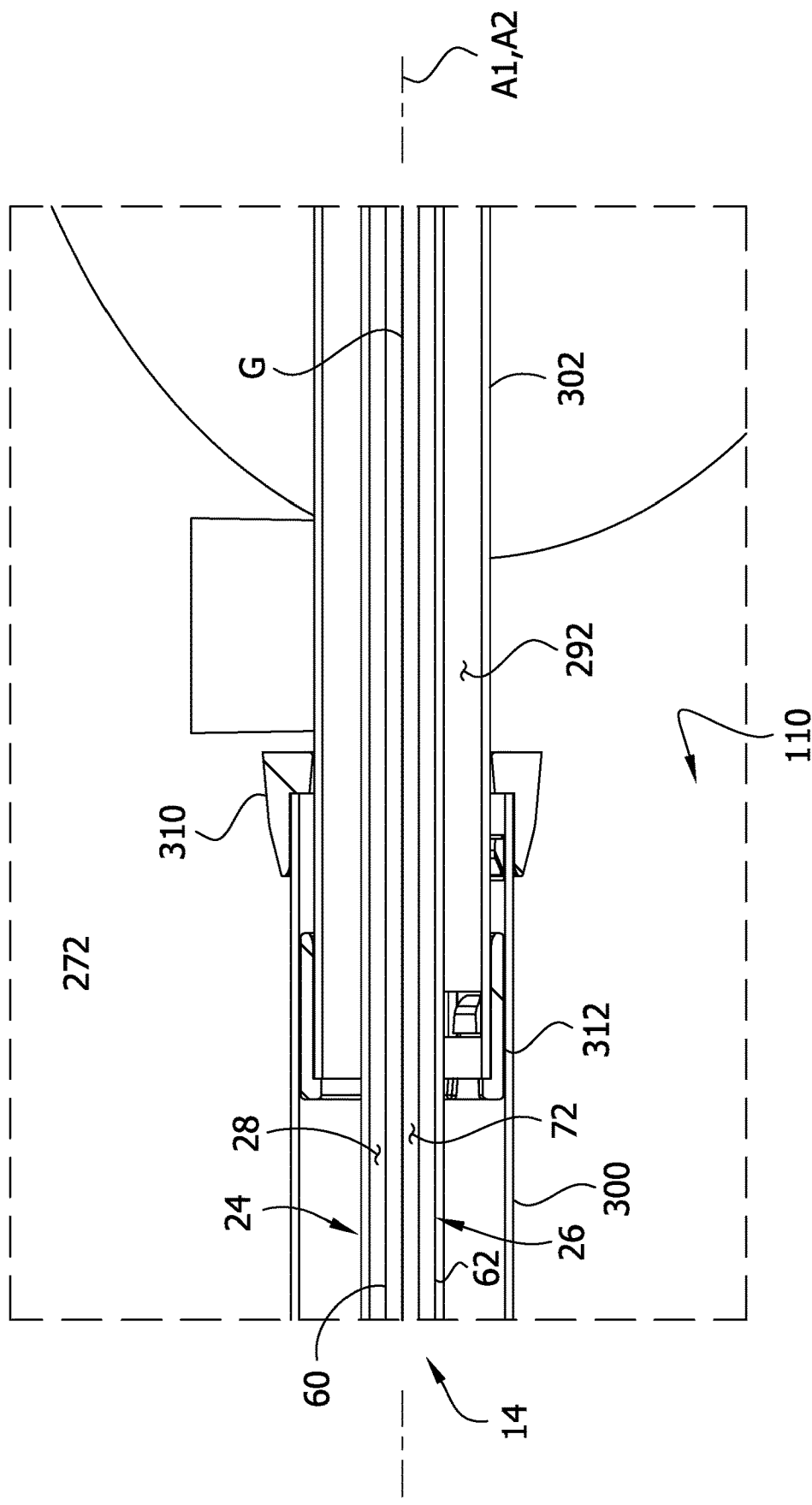

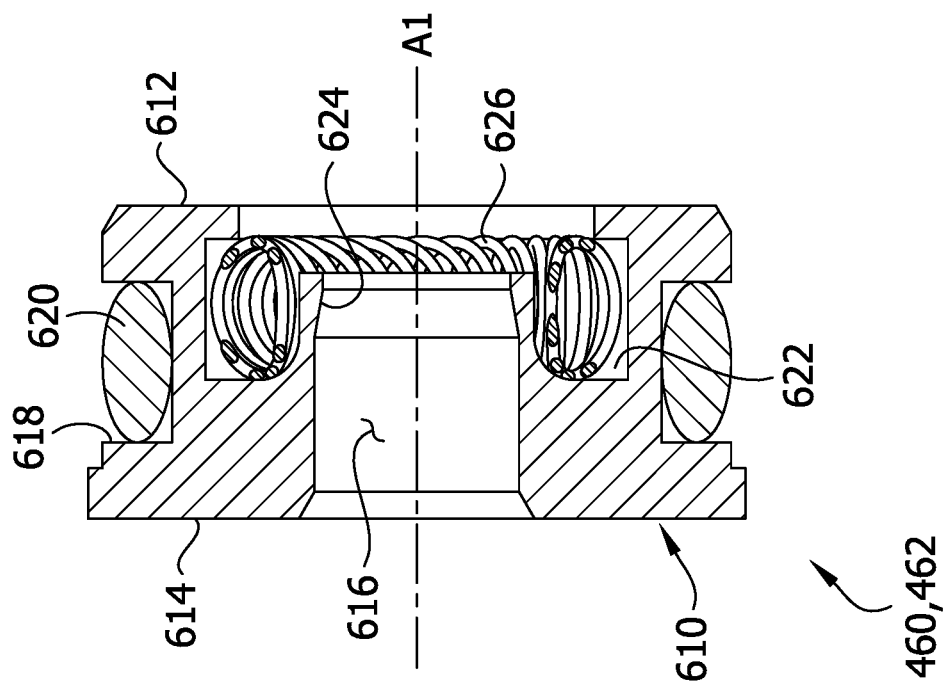
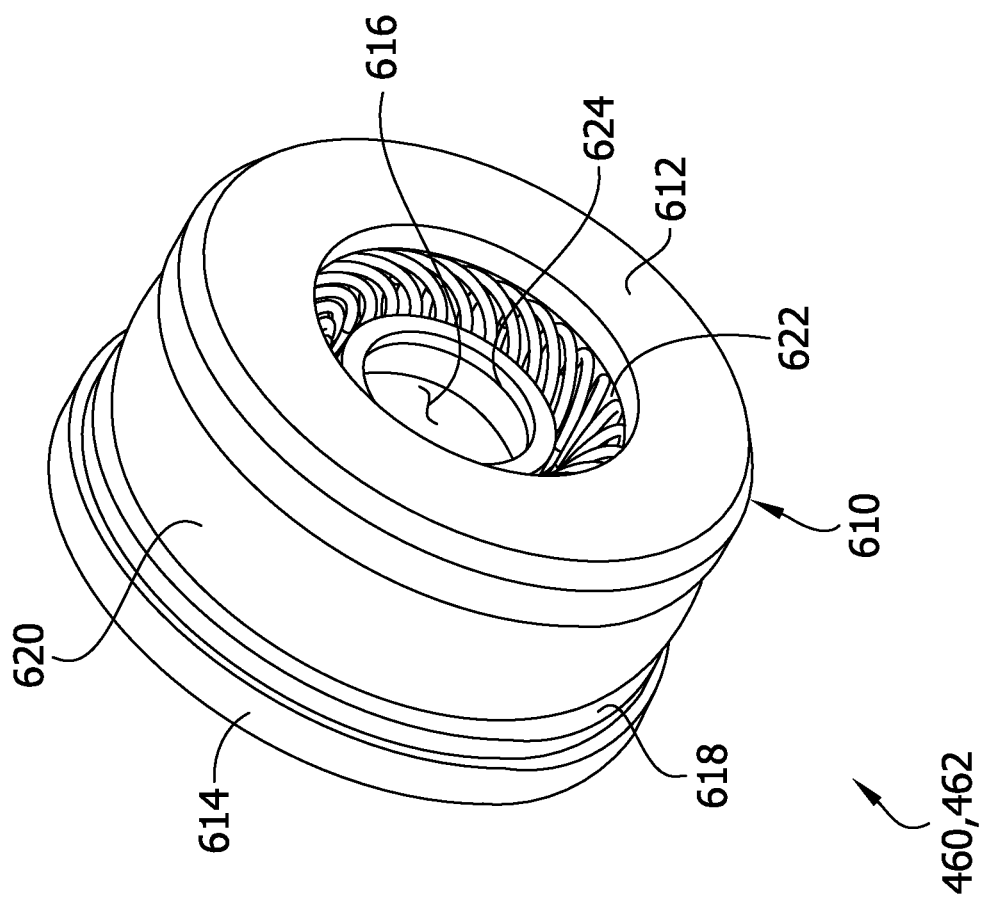

CATHETER

FIELD OF THE DISCLOSURE

This disclosure generally relates to a catheter, including, but not limited to, an over-the-wire, balloon-expandable, rotational, and/or abrasive tissue-removing catheter.

BACKGROUND

The patency of a body lumen can be affected by the build-up of tissue or other material in the body lumen. A variety of methods for removing occlusive material from a body lumen, such as a blood vessel, have been proposed. For example, tissue-removing catheters can be used to restore the patency of a body lumen. These catheters are intended to abrade, cut, or otherwise remove material from the body lumen and can employ a rotatable tissue-removing element that can be advanced into or past the occlusive material in order to remove such material from the wall of the body lumen. Expandable catheters such as balloon catheters have also been used in various ways to restore the patency of body lumen. For example an expandable element such as a balloon can be used to enlarge a passage through an occlusion in a body lumen.

SUMMARY

Embodiments of a catheter are disclosed. For example, the disclosed catheters can be configured to restore the patency of a body lumen. In one or more embodiments, the catheter is configured to remove tissue, such as hard or soft tissue (e.g., plaque, atheroma) from a body lumen (e.g., a blood vessel). In one or more embodiments, the catheter is a rotational catheter having a rotatable drive shaft and a tissue-removing element secured to the drive shaft to be driven in rotation by the drive shaft. In one or more embodiments, the catheter comprises an abrasive burr configured to abrade tissue in a body lumen. In one or more embodiments, the catheter comprises an expandable tissue-removing element. The catheter can comprise balloon and an inflation conduit configured to selectively inflate the balloon. The catheter can also be configured to move over a guidewire through a body lumen. In one embodiment, the catheter comprises an over-the-wire, balloon-expandable, rotational, and abrasive tissue-removing catheter.

In one aspect, a catheter comprises a balloon that has a convex shape configured to expand an abrasive burr.

In another aspect, a catheter comprises a balloon comprising a proximal neck including a portion that is configured to be nested between an inflation conduit and a drive shaft.

In still another aspect, the catheter comprises an expandable burr and a balloon. The balloon comprises a proximal cone having a first conical portion that is radially overlapped by a proximal annular hub of the balloon and a second conical portion spaced apart from the first conical portion that is radially overlapped by an expandable middle portion of the burr.

In another aspect, a catheter comprises an elongate catheter body that is configured for simultaneously inflating and rotating an expandable burr.

In still another aspect, a catheter comprises a balloon-containment sleeve situated to inhibit a balloon from being pinched between the struts of an expandable burr.

In yet another aspect, a catheter comprises an adaptor that is configured to secure a burr to a distal end portion of a catheter body.

In another aspect, a catheter comprises an inflation conduit and a rotatable drive shaft that are joined together at a joint adjacent the distal end portion of the catheter for conjoint rotation about a rotational axis.

In another aspect, a catheter comprises a handle, an elongate catheter body, and a carriage slidably received in the handle, wherein the catheter body is secured to the carriage for movement with the carriage with respect to the handle. The carriage comprises a block assembly comprising a plurality of blocks that are secured together.

In still another aspect, a catheter comprises a handle, a carriage that is movable with respect to the handle, and an alignment guide that is configured to align a flexible elongate body extending inside the housing with the movement of the carriage.

In yet another aspect, the catheter comprises a telescoping alignment guide comprising stops configured to prevent at least one of over-extension and over-retraction of the alignment guide.

In another aspect, the catheter comprises a telescoping alignment guide comprising a plurality of telescoping members, and at least one of the telescoping members comprises an end cap that has a bearing surface for slidably engaging another telescoping member.

In still another aspect, the catheter comprises a handle, a carriage movable with respect to the handle, and a slider knob that is configured to facilitate moving the carriage with respect to the handle. The slider knob is configured to be selectively oriented in a slide orientation in which it can slide along the handle to move the carriage and a locked orientation in which it is compressed by the handle to limit movement.

In yet another aspect, the catheter comprises a handle, a carriage movable with respect to the handle, and a slider knob that is configured to facilitate moving the carriage with respect to the handle. The slider knob has a homed position with respect to the handle in which the slider knob is inhibited from moving with respect to the handle without deforming the slider knob.

In another aspect, the catheter comprises a prime mover and a driven gear configured to be rotated by the prime mover. The driven gear comprises a hub opening configured to receive a hub therein that connects a drive shaft of a catheter body to the driven gear for conjoint rotation with the driven gear.

In still another aspect, the catheter comprises a connector tube that is configured to rotationally connect a prime mover to a drive shaft of a catheter body such that the prime mover can rotate the drive shaft about a rotational axis. The connector tube is further configured to provide fluid communication between the catheter body and a source of fluid.

In yet another aspect, the catheter comprises a connector tube having a main lumen and one or more radial ports in fluid communication with the main lumen. The connector tube is configured to receive a plurality of tubes of an elongate catheter body therein and be separately joined to the tubes at respective spaced apart locations along the main lumen. At least one of the joints is configured to provide a fluid seal between the connector tube and the respective tube of the catheter body such that the main lumen of the connector tube provides fluid communication between the respective tube of the catheter body and the radial port.

In another aspect, the catheter comprises a catheter body defining an inflation lumen and a guidewire lumen and a manifold tube defining a main lumen. The manifold tube also defines an inflation port and a flushing port that are each in fluid communication with the main lumen. The catheter body is received in the main lumen such that the inflation lumen is in fluid communication with the inflation port, the guidewire lumen is in fluid communication with the flushing port, and the guidewire lumen and the inflation lumen are fluidly separate from one another.

In still another aspect, the catheter comprises a fluid manifold tube configured to provide fluid communication between a source of fluid and a lumen of an elongate catheter body. The fluid manifold tube comprises a key portion that is configured to be received in a keyway of a transmission assembly such that the transmission assembly is configured to rotate the manifold tube about an axis thereof.

In yet another aspect, the catheter comprises a fluid block assembly having a main passage including an inflation chamber and a flushing chamber therein and a catheter body defining an inflation lumen in fluid communication with the inflation chamber and a guidewire lumen in fluid communication with the flushing chamber.

In another aspect the catheter comprises a handle having a single external flushing port and passaging configured to convey flushing fluid from the external flushing port to first and second flushing lumens of a catheter body.

In still another aspect, the catheter comprises a handle, a carriage configured for movement along the handle, and a catheter body configured for movement with the carriage with respect to the handle. The handle has an external inflation port and an external flushing port. The carriage has an inflation port and a flushing port. The inflation port of the carriage is configured to provide fluid communication between the external inflation port and an inflation lumen of the catheter body. The flushing port of the carriage is configured to provide fluid communication between the external flushing port and a flushing lumen of the catheter body.

In yet another aspect, the catheter body comprises a handle, a carriage configured for movement along the handle, and a catheter body configured for movement with the carriage with respect to the handle. The catheter is configured such that a guidewire is passable longitudinally through a guidewire lumen of the catheter body, the carriage, and the handle. The carriage includes a flushing chamber in fluid communication with the guidewire lumen and an imperforate web that seals an end of the flushing chamber. The web is configured to be pierced by the guidewire being passed through the catheter or by the tip of a guidewire introducer tool. The web is configured to form a seal about the guidewire after the guidewire is passed through the web.

In another aspect, the catheter body comprises a handle, a carriage configured for movement along the handle, and a catheter body configured for movement with the carriage with respect to the handle. The catheter is configured such that a guidewire is passable longitudinally through a guidewire lumen of the catheter body, the carriage, and the handle. The carriage includes a flushing chamber in fluid communication with the guidewire lumen and duckbill seal that is configured to slidably accept the guidewire and seal an end of the flushing about the guidewire.

In another aspect, the catheter body comprises a handle, a carriage configured for movement along the handle, and a catheter body. The catheter body includes an isolation sheath that is attached to the handle and a rotatable drive shaft that extends longitudinally through the isolation sheath and is attached to the carriage for movement with the carriage with respect to the handle and the isolation sheath. The catheter further comprises a hub that defines a flushing lumen in fluid communication with the isolation sheath and duckbill seal that is configured to slidably and rotatably accept the drive shaft and seal an end of the flushing about the drive shaft.

In still another aspect, the catheter comprises a driver regulator that is configured to selectively operate a driver for rotating a drive shaft of a catheter in first and second operating modes. In the first operating mode, the driver regulator operates the driver to drive continuous rotation of the drive shaft; and in the second operating mode, the driver operates the driver to drive a discrete burst of rotation of the drive shaft.

In yet another aspect, the catheter comprises a control knob or lever that is pivotable with respect to a handle through a range of motion. The control knob is configured to both actuate a guidewire brake and adjust the mode of a driver regulator as the control knob pivots through the range of motion.

In another aspect, the catheter comprises an elongate catheter body and a handle that are configured to slidably receive a guidewire therein. The catheter further comprises a guidewire brake comprising a spring having first and second legs defining a guidewire channel through which the guidewire is passed when it is received in the handle. The spring is resiliently deflectable such that the first leg moves toward the second leg to impart a braking force on the guidewire received in the guidewire channel.

Other aspects and features will be apparent or described hereinafter.

BRIEF DESCRIPTION OF THE DRAWINGS

FIG. 7 is an elevation of the balloon and a balloon-containment sleeve illustrating the balloon in a deflated configuration and the balloon-containment sleeve in a collapsed configuration on the balloon;

FIG. 7A is an enlarged longitudinal cross section of a portion of the assembly of FIG. 7 connected to an inflation conduit;

FIG. 8 is an enlarged longitudinal cross section of a segment of an elongate body of the catheter that includes an isolation sheath, a laminated drive coil, and an inflation conduit;

FIG. 13A is a bottom plan view of a top housing member of the handle;

FIG. 14 is a top plan view of the handle with the top housing member removed;

FIG. 15B is an enlarged view of another portion of FIG. 15;

FIG. 62 is a perspective of a spring-energized rotary inflation seal; and

FIG. 63 is a cross section of the spring-energized rotary inflation seal.

Corresponding reference characters indicate corresponding parts throughout the drawings.

DETAILED DESCRIPTION OF THE DISCLOSURE

The present disclosure describes features for a catheter. One or more of these features can be incorporated, in whole in or in part or otherwise adapted to be incorporated, into various types of catheters, including but not limited to balloon catheters, abrasive catheters, expandable catheters, flushing catheters, fluid-delivery catheters, rotational catheters, crossing catheters, or combinations thereof.

In one or more embodiments, the catheter including one or more of the described features herein can comprise a rotational, balloon-expandable, over-the-wire, abrasive tissue-removing catheter. In one or more embodiments, the catheter including one or more of the described features herein can comprise a balloon catheter without tissue-removing features. It is understood that balloon catheters can be rotational or non-rotational in various embodiments. In one or more embodiments, the catheter including one or more of the described features herein can comprise a tissue-removing catheter that includes a tissue-removing element having fixed dimensions. For example, catheters comprising solid abrasive burrs mounted for concentric or eccentric rotation are expressly contemplated. Likewise, rotational catheters comprising one or more cutting blades in lieu or in addition to an abrasive surface can also include one or more of the described features herein in one or more embodiments. Furthermore, in one or more embodiments the catheter including one or more of the described features herein can comprise a tissue-removing catheter that is non-rotational. For example, in one embodiment the tissue-removing catheter comprises a scoring catheter, an electro-ablation catheter, or a thermo-ablation catheter. In one or more embodiments, the catheter including one or more of the described features herein can comprise an expandable catheter that facilitates expansion of an end effector without using a balloon. It is understood that catheters within the scope of this disclosure can be introduced into the subject anatomy (e.g., a body lumen) by being advanced along a guidewire or any other method of introduction. Thus, in one or more embodiments, the catheter can include a guidewire lumen for receiving a guidewire, and in one or more one or more embodiments, the catheter can lack a lumen for slidably receiving a guidewire therein.

Figure 1:
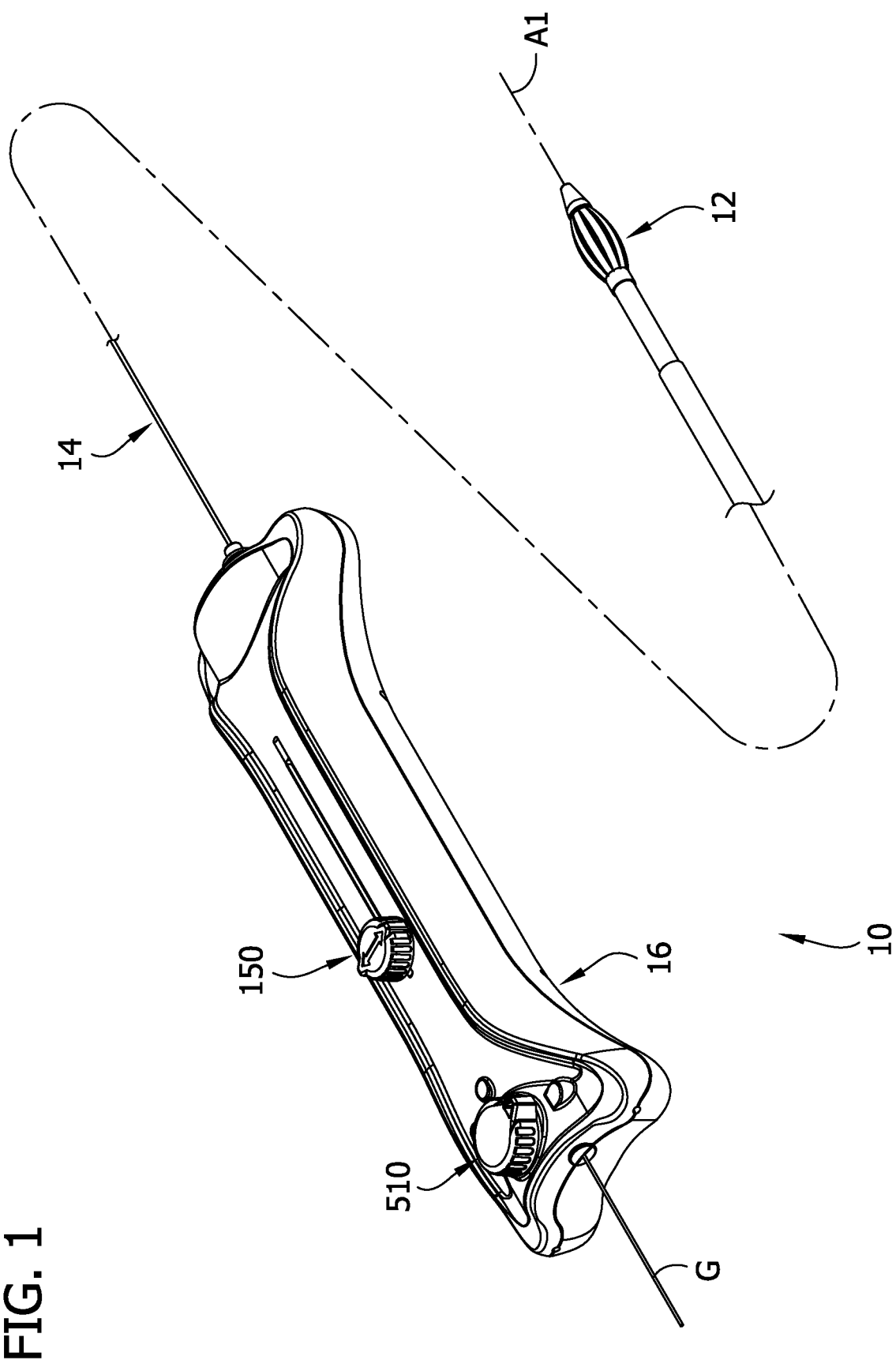
FIG. 1 is a fragmentary perspective of a tissue-removing catheter including an expandable burr assembly shown in an expanded configuration.

Referring to FIG. 1, one embodiment of a catheter constructed according to one or more teachings of the present disclosure, is generally indicated at reference numeral 10. In general, the catheter 10 is configured to remove tissue from a body lumen. In particular, the catheter 10 is configured to remove tissue, such as plaque and/or soft tissue (e.g., atheroma), from the wall of a blood vessel. Features of the catheter 10 are also suitable for treating chronic total occlusion (CTO) of blood vessels, such as peripheral arteries, and stenoses of other body lumens and other hyperplastic and neoplastic conditions in other body lumens, such as the ureter, the biliary duct, respiratory passages, the pancreatic duct, the lymphatic duct, and the like. For example, neoplastic cell growth will often occur as a result of a tumor surrounding and intruding into a body lumen. Removal of such material can thus be beneficial to maintain patency of the body lumen. While the following discussion is directed toward a catheter 10 for removing tissue from and penetrating occlusions in blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Referring still to FIG. 1, the illustrated catheter 10 generally comprises an expandable burr assembly (broadly, an end effector), generally indicated at 12; an elongate catheter body, generally indicated at 14; and a control handle, generally indicated at 16. The expandable burr assembly 12, the elongate catheter body 14, and the handle 16 are described in detail under respective section headings I-III below. As will be explained below, the expandable burr assembly 12 and the elongate catheter body 14 are configured to be advanced over a guidewire G and through a body lumen to the site of an occlusion. While the catheter 10 is tracking to the site of the occlusion, the expandable burr assembly 12 can be maintained in a non-expanded configuration. At the site of the obstruction, the burr assembly 12 can be expanded increase a cross-sectional dimension of the burr. The non-expanded burr assembly 12 has a low profile for navigating past or through narrow features or constrictions and/or tortuous paths in the anatomy. The expanded burr assembly 12 can engage tissue in the body lumen at locations that are radially outward of what the burr assembly can reach when it is not expanded. Using controls on the handle 16, a user can control rotation of the expanded burr assembly 12 in the body lumen. The user can also use the handle 16 to move the burr assembly 12 axially along the guidewire G as it rotates. An abrasive surface of the expanded burr assembly 12 abrades tissue that is occluding the body lumen as it rotates, thereby removing tissue from the wall of the body lumen.

I. Expandable Burr Assembly

Figure 2:
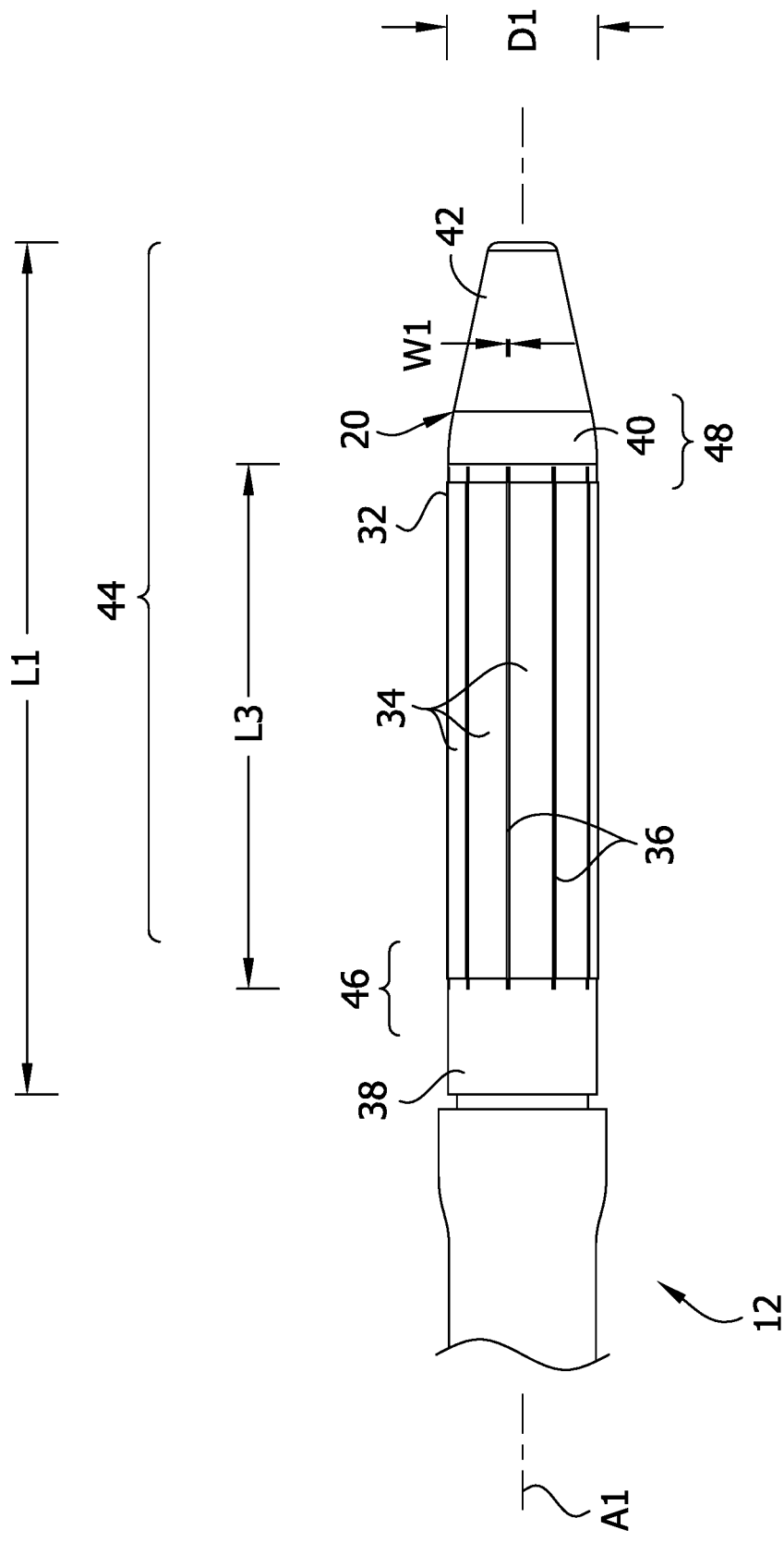
FIG. 2 is an enlarged front elevation of the expandable burr assembly in a non-expanded configuration.
Figure 3:
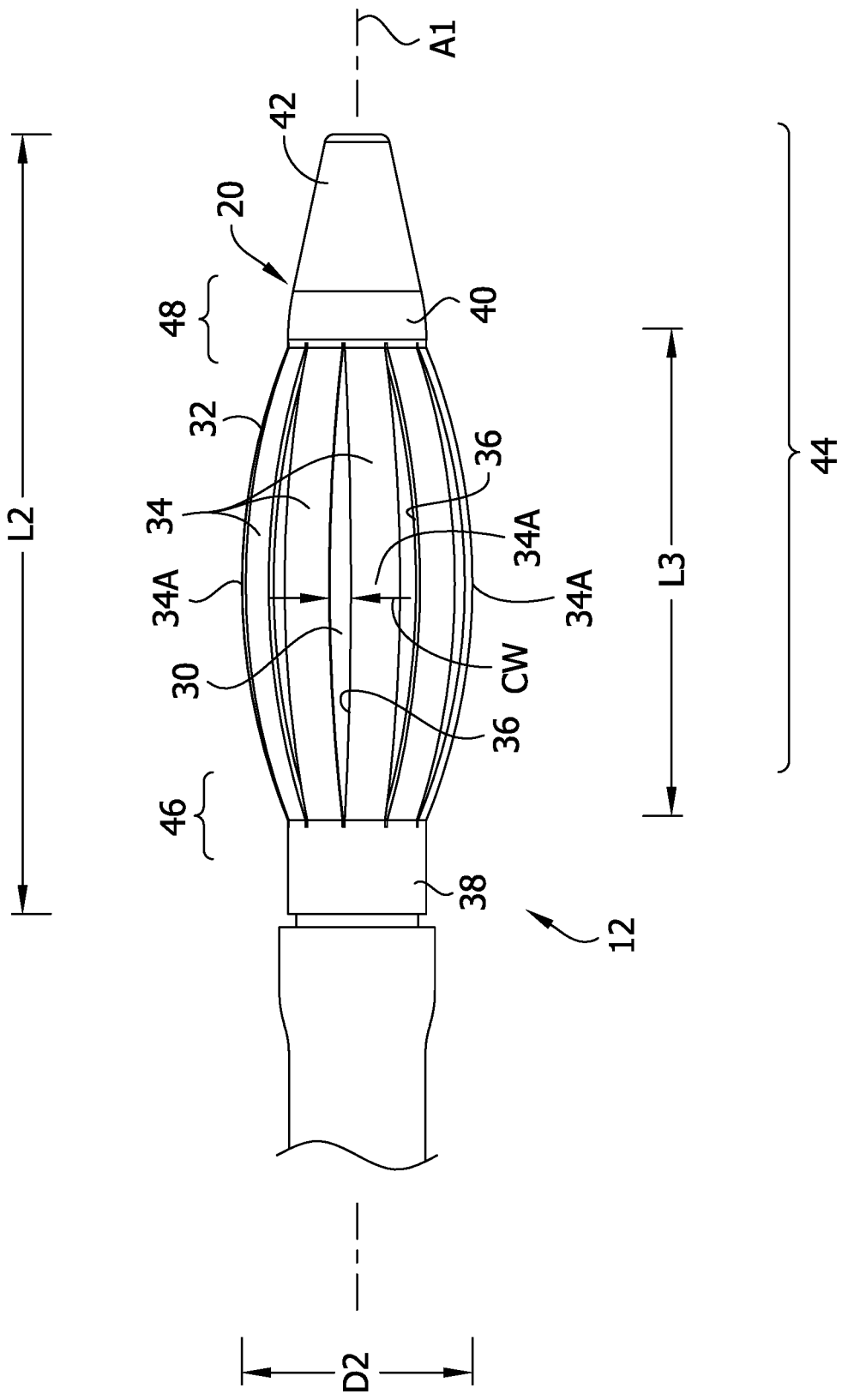
FIG. 3 is an enlarged front elevation similar to FIG. 2, with the expandable burr assembly in the expanded configuration.
Figure 4:
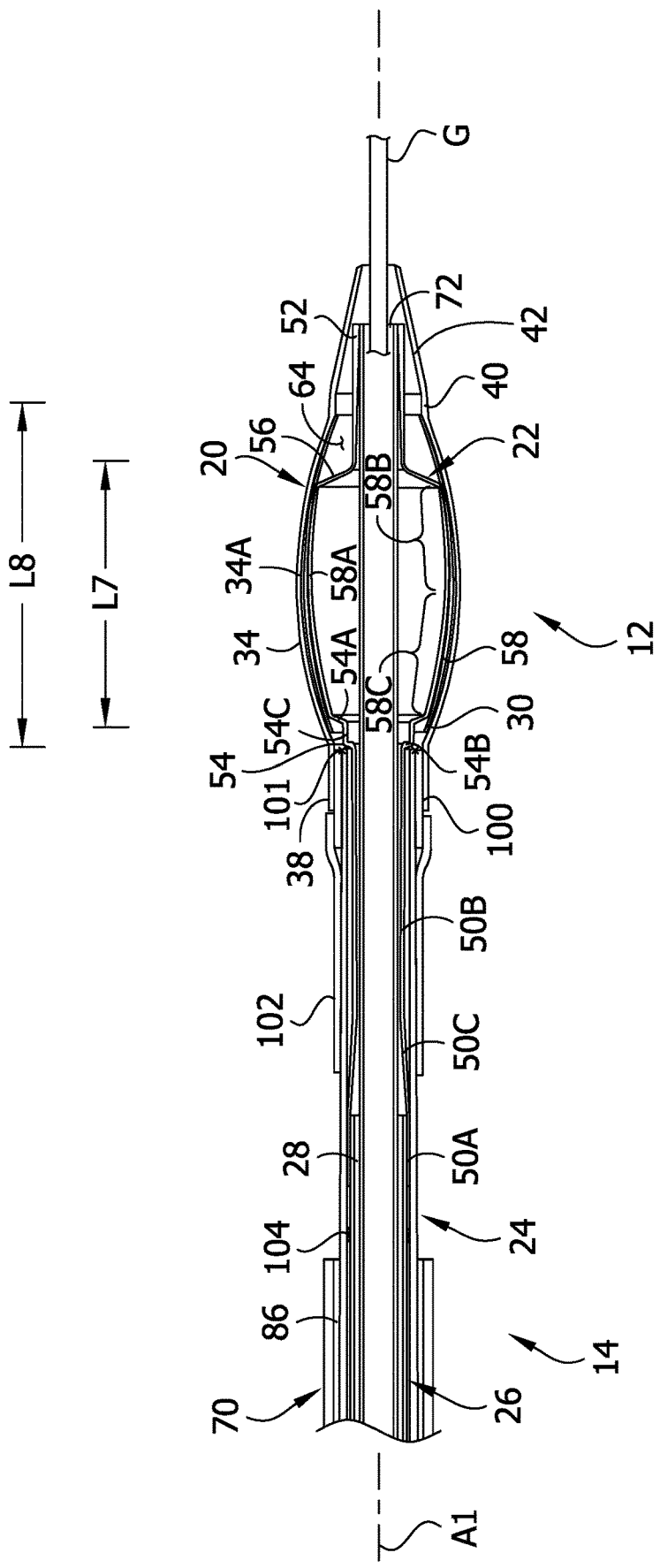
FIG. 4 is an enlarged fragmentary longitudinal cross section of a distal end portion of the catheter including the expandable burr assembly in the expanded configuration.

Referring to FIGS. 2-4, the illustrated expandable burr assembly 12 generally comprises an expandable abrasive burr (broadly, an ablation burr or a tissue-removing element), generally indicated at 20, and a balloon 22 (broadly, an expandable member) inside the burr that is configured to be inflated to expand the burr. As will be explained in greater detail below, the catheter body 14 includes a rotational drive shaft, generally indicated at 24, which is configured to rotate the burr 20 about a rotational axis A1, and an inflation conduit, generally indicated at 26, which is configured to direct inflation fluid through an inflation lumen 28 to the interior of the balloon 22 to inflate the balloon. The illustrated expandable burr assembly 12 further comprises a balloon-containment sleeve 30 that is configured to collapse the balloon 22 when the balloon is deflated. Although the illustrated burr assembly 12 is balloon-expandable and configured to remove tissue by abrasion, it will be understood that other types of tissue-removing elements and other types of end effectors generally can be used in one or more embodiments. For example, in one or more embodiments, a non-expandable abrasive burr may be included.

A. Abrasive Burr

Referring to FIGS. 2 and 3, the abrasive burr 20 includes a generally tubular body 32 including circumferentially spaced longitudinal struts 34 (broadly, a middle portion of the burr) defining longitudinal slots 36 between adjacent struts, and proximal and distal hubs (e.g., annular hubs) 38, 40, respectively, secured to the respective proximal and distal ends of the struts. The longitudinal slots 36 permit the struts 34 to expand circumferentially relative to the proximal and distal hubs 38, 40, respectively, as described below. The abrasive burr 20 further includes a distal head 42 having a generally conical or dome-shape that tapers distally. The distal head 42 can be suitable for boring through tissue (e.g., plaque) occluding a body lumen. It is contemplated that the distal head can comprise a cutting edge (e.g., a distally facing cutting edge configured to, for example, core tissue) in one or more embodiments. The tubular body 32 and the distal head 42 can be a single, one-piece component that is integrally, monolithically formed from a single piece of material. For example, the tubular body 32 and the distal head 42 can be formed from a single piece of hypotube or deep drawn from sheet stock. In other examples, the tubular body 32 and the distal head 42 can be formed separately and secured to one another in any suitable way. The tubular body 32 and the distal head 42 can be made of Nitinol, spring steel, stainless steel, or any other suitable material.

The abrasive burr 20 has an initial, non-expanded or minimum cross-sectional dimension D1 (see FIG. 2) and a first longitudinal length L1. In one or more embodiments, the non-expanded cross-sectional dimension D1 is such that the burr 20 is compatible with a 5 French introducer sheath (not shown). In one or more embodiments, the minimum cross-sectional dimension D1 is in an inclusive range of from about 0.050 inches to about 0.070 inches. The abrasive burr 20 is expandable circumferentially to increase the cross-sectional dimension to an expanded or maximum cross-sectional dimension D2 (FIG. 3), which is larger than the initial cross-sectional dimension D1. For example, the expanded cross-sectional dimension D2 can be at least about 10% greater than the non-expanded cross-sectional dimension, such as about at least about 15% greater, at least about 25% greater, at least about 40% greater, at least about 50% greater, or about 67% greater. In one or more embodiments, the minimum cross-sectional dimension D1 is in an inclusive range of from about 0.090 inches to about 0.110 inches. The burr 20 can be configured to abrasively bore a channel through an occlusion in a body lumen that has a cross-sectional dimension that is at least as great as the maximum expanded cross-sectional dimension D2. For example, in one or more embodiments, the burr is configured to form a channel through an occlusion having an inner diameter of at least about 0.060 inches, such as about at least about 0.075 inches, or about 0.090 inches.

As illustrated, the initial cross-sectional dimension D1 is about the same as a cross-sectional dimension of the catheter body 14, and the expanded cross-sectional dimension D2 is larger than the cross-sectional dimension of the catheter body, although other configurations are within the scope of the present disclosure. In the expanded configuration, the struts 34 of the abrasive burr 20 flex or bend (broadly, deflect) outward to increase the cross-sectional dimension of the burr, which, in turn, shortens the length L1 of the burr to a second longitudinal length L2 (FIG. 4). Thus, as the cross-sectional dimension of the abrasive burr 20 increases, the longitudinal length of the abrasive burr decreases. In one or more embodiments, the abrasive burr 20 can be expanded and contracted to have any cross-sectional dimension in the range between the initial cross-sectional dimension D1 and a maximum expanded cross-sectional dimension D2.

The balloon 22 is positioned in the interior of the abrasive burr 20. The balloon 22 is selectively inflated and selectively deflated to control the cross-sectional dimension of the burr 20. Moreover, as will be explained in further detail below, the illustrated balloon 22 is specially shaped to bend the struts 34 so that they bow outwardly between the hubs 38, 40 when the balloon is inflated. Referring to FIG. 4, and as will be described in greater detail below, the balloon 22 is inflated by delivering fluid (e.g., liquid or gas) through the inflation lumen 28 to the interior of the balloon. As the balloon 22 is inflated, it pushes the struts 34 of the abrasive burr 20 radially outward to expand the circumference of the burr. The burr 20 can be adjustable to different cross-sectional dimensions based on the extent the balloon 22 is inflated. When the balloon 22 is deflated, the burr 20 contracts toward its initial cross-sectional dimension. As will be explained below, the balloon-containment sleeve 23 aids in collapsing the balloon 22 when the pressure inside the balloon decreases to prevent portions of the balloon from being pinched or captured in the slots 36 between the struts 34 as the tubular body 32 rebounds toward the initial cross-sectional dimension D1.

The burr expansion mechanism can be of other types and configurations for expanding the circumference of the abrasive burr 20. For example, in one or more embodiments the burr expansion mechanism may not include a balloon. Instead, the expansion mechanism can include a compressible elastomer, or other mechanism for expanding the circumference of the abrasive burr. Other suitable mechanisms are disclosed in co-pending U.S. application Ser. No. 15/189,785, filed Jun. 22, 2016, the entirety of which is hereby incorporated by reference.

Referring again to FIGS. 2 and 3, each of the struts 34 has a length L3 extending from a respective proximal end portion to a respective distal end portion. When the burr 20 is in a non-expanded configuration, the length L3 of each strut 34 extends generally parallel to the rotational axis A1. When the burr 20 is expanded as shown in FIG. 3, the struts 34 each have a generally convex (e.g., outwardly curved) shape along their length L3 with respect to the rotational axis A1. In the illustrated embodiment, each strut 34 has a generally symmetrical parabolic shape in the expanded configuration. In the expanded configuration of the burr 20, each strut 34 has a vertex 34A at about a midpoint along the length L3 of the strut. Each expanded strut 34 has a proximal portion that slopes proximally from the vertex 34A and a distal portion that slopes distally from the vertex. The proximally and distally sloping portions of each strut 34 have about the same arc length in the illustrated embodiment. Although the illustrated embodiment of the expandable burr 20 includes an expandable middle portion comprising circumferentially spaced struts 34 that bow outwardly along a generally parabolic arc in the expanded configuration, one or more embodiments of burrs or expandable tissue-removing elements can have expandable portions (e.g., middle portions) having other configurations.

The abrasive burr 20 includes an abrasive exterior surface configured to abrade tissue (e.g., plaque and/or atheroma). The abrasive exterior surface can be formed by texturing the tubular body 32 and/or the distal head 42. For example, the tubular body 32 and the distal head 42 can be textured using a laser or can be textured in other ways to form an abrasive exterior surface. In another embodiment, the abrasive exterior surface can be formed by applying abrasive particles, such as diamond-coated or silicon carbide particles (e.g., diamond-coated grit and/or silicon carbide grit), to the tubular body 32 and/or the distal head 42. In these embodiments and one or more embodiments, the abrasive exterior surface has a suitable roughness to abrade tissue (e.g., plaque, calcium, and/or atheroma) as the abrasive burr 20 is rotated about the rotational axis A1. In one example, the exterior abrasive surface has a roughness of from about 1 Ra (μm) to about 2 Ra (μm), or from about 4 Ra (μm) to about 10 Ra (μm). Where the exterior abrasive surface is defined by abrasive particulate applied to the burr, the exterior abrasive surface can have a grit in an inclusive range of from about 10 μm to about 50 μm, e.g., an inclusive range of from about 20 μm to about 30 μm.

In the illustrated embodiment, a contiguous abrasive segment 44 of the burr 20 includes the abrasive exterior surface. The abrasive exterior surface extends circumferentially about the entire perimeter of the burr 20 in one embodiment. The abrasive segment 44 extends along the entire distal head 42, the distal annular hub 40, and all but a short proximal end portion of the struts 34. In one embodiment, at least about 75% of the length of the struts 34 is coextensive with the abrasive segment 44. In another embodiment, at least about 96% of the length of the struts 34 is included in the abrasive segment 44. In one or more embodiments, the entire abrasive segment 44 has about the same surface roughness and/or grit. In one or more embodiments the surface roughness can vary along the length of the abrasive segment 44 or burr 20. It will be understood that in one or more embodiments the abrasive segment can have other configurations. For example, in one or more embodiments, the burr has a contiguous abrasive segment along the entire length of the burr. In one or more embodiments, the abrasive segment is discontinuous along the length of the burr and/or varies in surface roughness or grit along the length of the burr, for example, as disclosed in co-pending U.S. Provisional Patent Application Ser. No. 62/473,546, which is hereby incorporated by reference in its entirety. In still one or more embodiments, the abrasive segment can be discontinuous circumferentially of the burr.

In the illustrated embodiment, the entire exterior surface of the burr 20 extending from the distal tip of the burr to the proximal ends of the struts 34 at least one of (i) is textured to form an abrasive surface and (ii) has abrasive particulate applied. The proximal hub 38 is not textured to form an abrasive surface. Likewise, the proximal hub 38 does not include abrasive particulate applied to its exterior. It is contemplated that other portions of a balloon can be abrasive and/or non-abrasive in one or more embodiments.

B. Balloon

Figure 5:
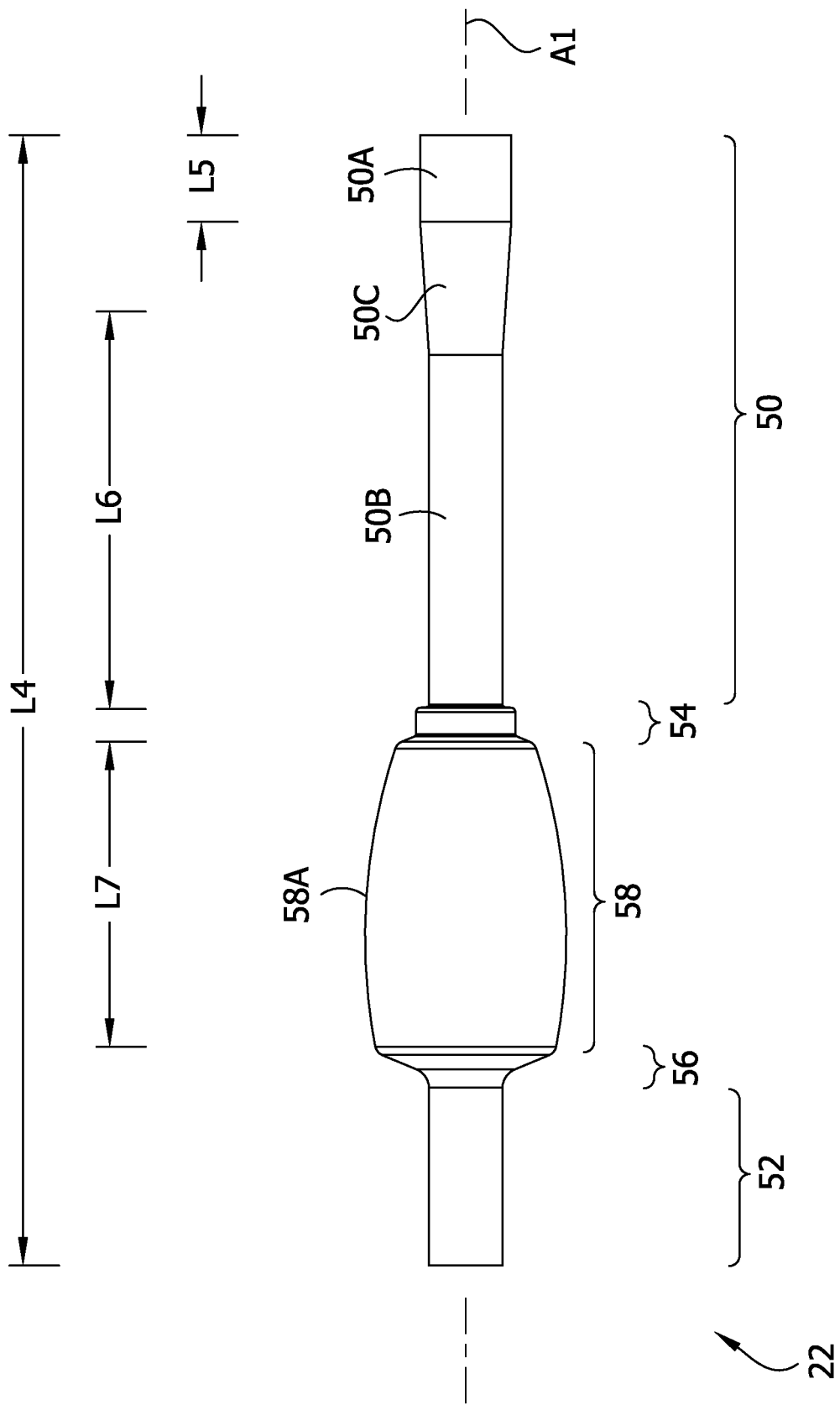
FIG. 5 is an enlarged rear elevation of a balloon of the expandable burr assembly illustrating the balloon in an inflated configuration.
Figure 6:
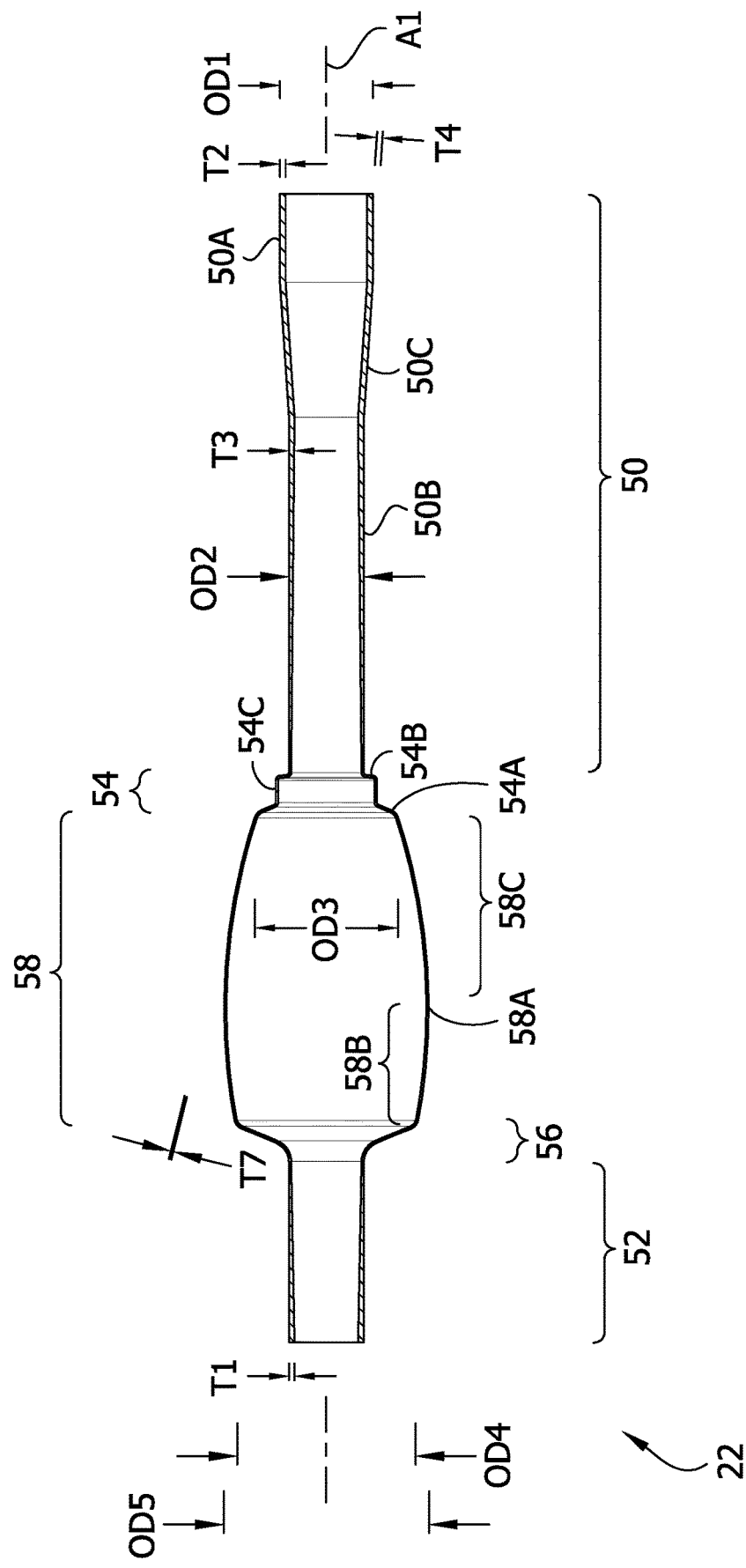
FIG. 6 is a longitudinal cross section of the balloon in the inflated configuration.

Referring to FIGS. 5-7, the illustrated expandable burr assembly 12 includes a balloon 22 that is configured to expand the abrasive burr 20. In general, the balloon 22 is configured to be inflated by fluid delivered through the inflation conduit 26. Moreover, the illustrated balloon 22 is configured to deflect the struts 34 (broadly, middle portion) of the burr 20 radially outward as the balloon is inflated. As is further explained below, the balloon 22 is also configured to be rotationally connected to the drive shaft 24 so that the burr 20 and the balloon rotate substantially in unison about the rotational axis A1 during use. Although the balloon 22 is used in the illustrated embodiment to expand an abrasive burr 20, it will be understood that the balloon can also be used for other purposes. For example, in one or more embodiments, the balloon 22 is positioned inside another type of expandable shell (e.g., a scoring cage, or a stent) for expanding an expandable portion (e.g., a middle portion) of the shell. The balloon 22 can also be used without an expandable shell in one or more embodiments. Accordingly, the teachings set forth herein relating to the balloon 22 are not limited to the catheter 10.

The balloon 22 comprises a proximal neck 50 defining a proximal end of the balloon, and a distal neck 52 defining a distal end of the balloon. As will be explained below, the proximal and distal necks 50, 52 are configured to be joined to the catheter body 14 to both fluidly couple the balloon 22 to the inflation conduit 26 and rotationally couple the balloon to the drive shaft 24. The balloon 22 has a length L4 extending from the proximal end to the distal end thereof. In the illustrated embodiment, the length L4 of the balloon 22 extends generally parallel to the rotational axis A1 (FIG. 4), and the rotational axis is coaxial with a center axis of the balloon. Since the axis of the balloon 22 is coaxial with the rotational axis A1 in the illustrated embodiment, this disclosure will use the same characters (i.e., "A1") when referring to both axes. It will be understood that the axis of the balloon can be other than coaxial with the rotational axis in one or more embodiments. A proximal cone 54 extends distally along the axis A1 of the balloon 22 from the proximal neck 50. A distal cone 56 extends proximally along the axis A1 from the distal neck 52. As will be explained below, the proximal cone 54 has a stepped shape that limits contact between the balloon 22 and the proximal annular hub 38 of the burr 20 when the balloon is inflated and also limits relative movement between the balloon and the drive shaft 24. A body 58 of the balloon 22 extends along the length L4 of the balloon between the proximal and distal cones 54, 56. As will be explained in further detail below, the body 58 is configured to be inflated to have a generally convex shape that deflects the struts 34 (broadly, middle portion) of the burr 20 radially outward.

The balloon 22 is generally configured to be inflated by an inflation fluid delivered through the inflation lumen 28 into the interior of the balloon. The balloon 22 is configured to be inflated from a non-inflated configuration (FIG. 7) to an inflated configuration (FIGS. 5 and 6). In addition, the balloon 22 is configured to resiliently rebound from the inflated configuration toward the non-inflated configuration (e.g., be deflated) when the inflation fluid is released from the balloon (e.g., when pressure inside the balloon is decreased). The radial dimensions of an expandable portion of the balloon 22, which includes the proximal cone 54, the distal cone 56, and the body 58, increase as the balloon is inflated and decrease as the balloon is deflated. As will be explained below, the illustrated balloon-containment sleeve 30 is also configured to forcibly collapse the balloon 22 when the balloon is deflated. However, it will be understood that, in one or more embodiments, the expandable burr assembly does not include a balloon-containment sleeve. Non-expandable portions of the balloon 22 including the proximal and distal necks 50, 52 do not substantially increase or decrease in size as the balloon is inflated. In one embodiment, the balloon 22 comprises a folded balloon. For example, the body 58 can comprise pleats or wings that wrap circumferentially around the balloon 22 when the balloon is in the non-inflated configuration. In another embodiment the balloon is not folded when the balloon is in the non-inflated configuration.

The balloon 22 can be formed in various ways and from various materials. For example, the balloon can comprise a one-piece component that is integrally, monolithically formed from a single piece of material. In one or more embodiments, the balloon can be formed from nylon, such as nylon 12. However, it will be understood that other materials can be used in one or more embodiments. In one embodiment, the balloon 22 comprises a semi-compliant balloon. The balloon 22 can also comprise a non-compliant or compliant balloon in one or more embodiments.

Figure 4A:
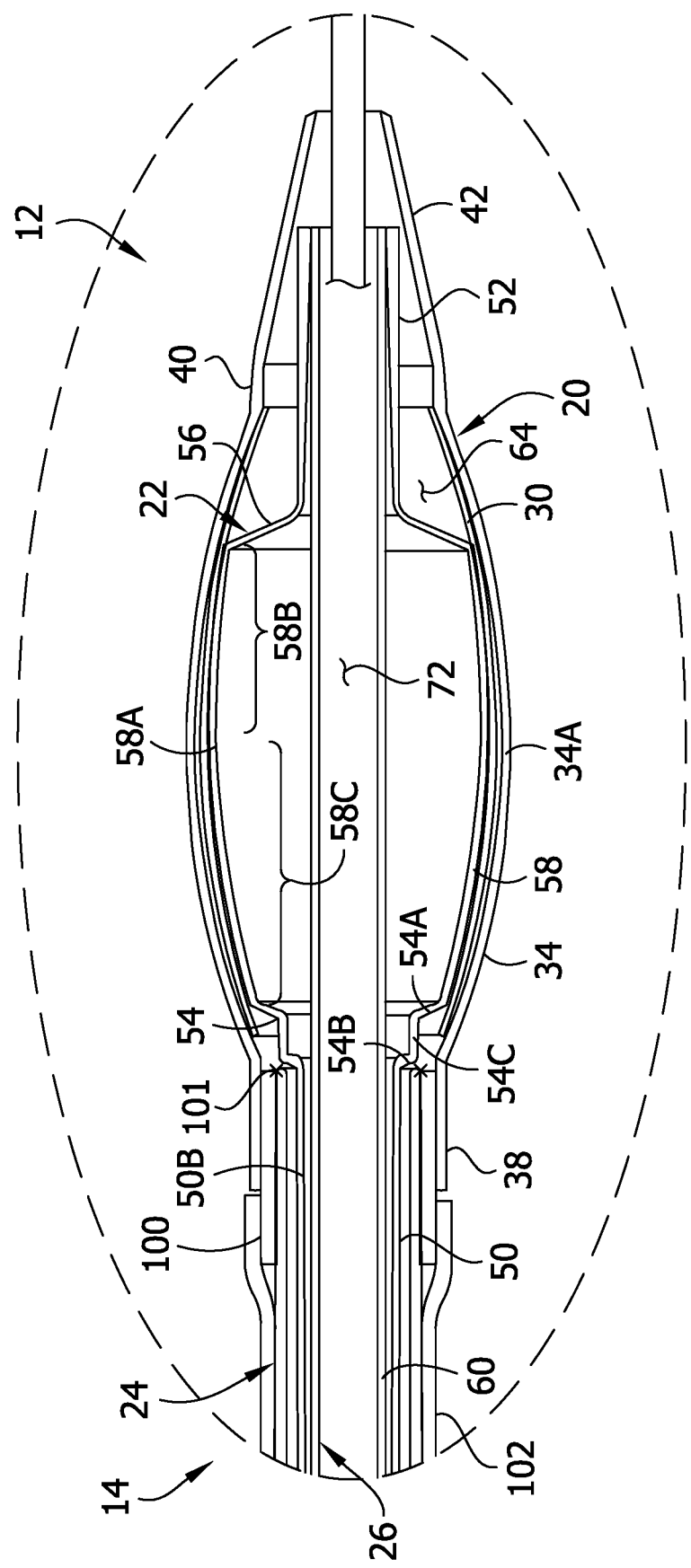
FIG. 4A is an enlarged view as indicated in FIG. 4.
Figure 4B:
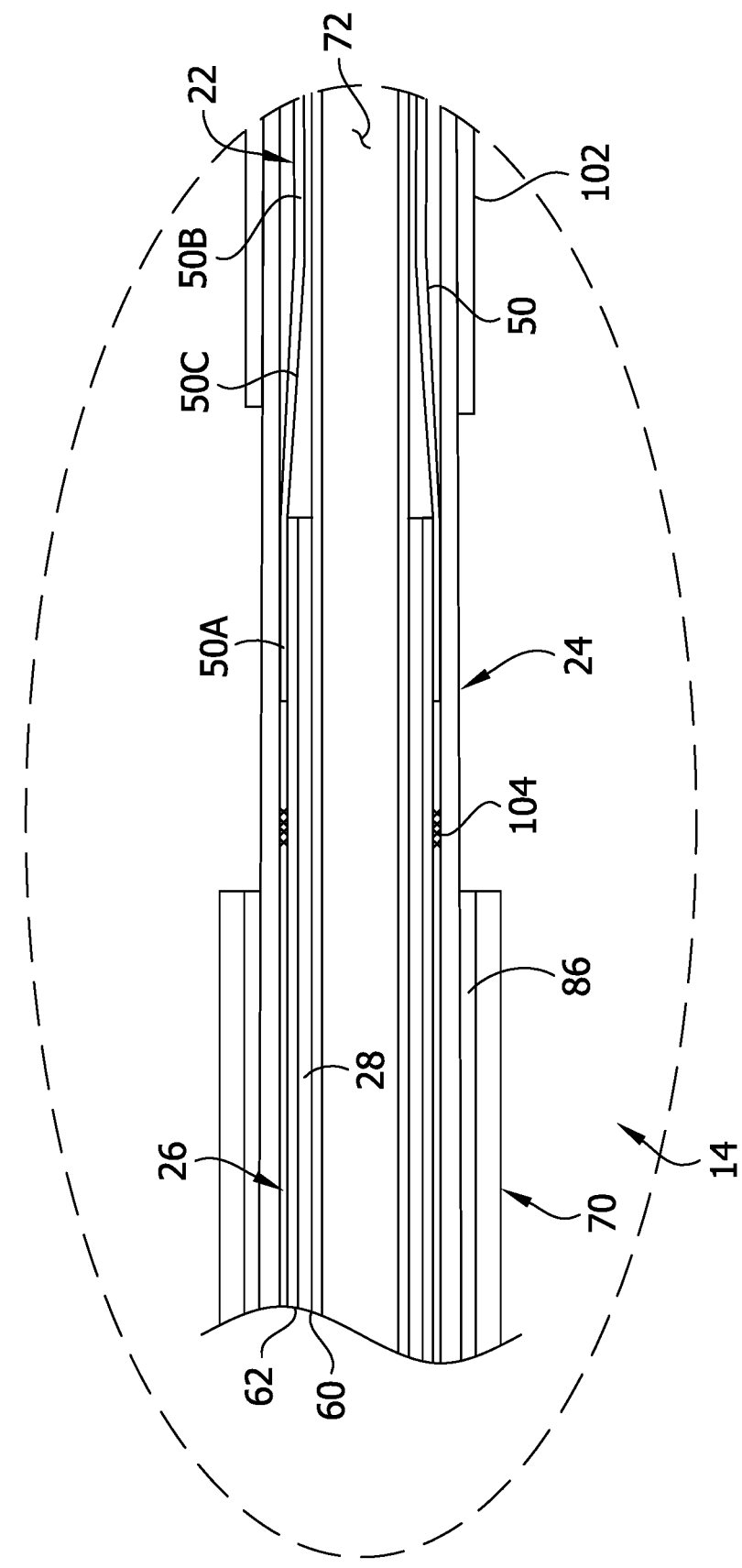
FIG. 4B is an enlarged view as indicated in FIG. 4.

Referring to FIGS. 4, 4A, and 4B, the proximal neck 50 and the distal neck 52 are each bonded to the inflation conduit 26 to fluidly couple the interior of the balloon 22 to the inflation lumen 28. As will be explained in further detail below, the illustrated inflation conduit 26 comprises an inner inflation tube 60 and an outer inflation tube 62. The inflation lumen 28 is located radially between the inner inflation tube 60 and the outer inflation tube 62, and extends circumferentially around the entire perimeter of the inner inflation tube. The inner inflation tube 60 protrudes distally from the distal end portion of the outer inflation tube 62 along the axis A1 through the interior of the balloon 22 and the burr 20.

The inflation conduit 26 is received in a longitudinal lumen of the drive shaft 24, and a small annular gap extends radially between the outer inflation tube 62 and the interior surface of the drive shaft along most of the length of the catheter body 12. As will be explained below, the geometry of the balloon 22 is designed and constructed to fluidly and rotationally couple the balloon to the inflation conduit at joints located radially inside of the drive shaft 24 and the burr 20.

A distal end portion of the distal neck 52 is attached (e.g., bonded) to a distal end portion of the inner inflation tube 60, and a proximal end portion of the proximal neck 50 is attached (e.g., bonded) to a distal end portion of the outer inflation tube 62. Although both the proximal and distal necks 50, 52 are attached to respective tubes 60, 62 of the inflation conduit 26 in the illustrated embodiment, it will be understood that the balloon can be fluidly coupled to an inflation conduit in other ways. For example, in one or more embodiments, the distal end of the balloon is closed and only the proximal end portion of the balloon is bonded to the inflation conduit. Still other designs are also possible in one or more embodiments.

The balloon 22 can be attached (e.g., bonded) to the inflation conduit 26 in a suitable manner. For example, in one or more embodiments, at least one of the proximal neck 50 and the distal neck 52 is bonded to the inflation conduit 26 by a welding (e.g., laser welding). In another embodiment, an adhesive bond, a chemical bond, and/or a heat bond operably attaches (e.g., fluidly and rotationally couples) the balloon 22 to the inflation conduit 26. Suitably, the attachment between the proximal neck 50 and/or distal neck 52 and the inflation conduit 26 is configured to transmit a rotational force from the inflation conduit to the balloon 22 such that the balloon rotates conjointly with the inflation conduit about the rotational axis A1. As will be explained below, the inflation conduit 26 is generally configured to rotate conjointly with the drive shaft 24 about the rotational axis A1, and therefore, the bonds between the proximal and distal necks 50, 52 and the inflation conduit rotationally couple the balloon 22 to the drive shaft 24. In addition, each bond between the balloon 22 and the inflation conduit 26 forms a fluid-tight seal that is configured to hold inflation fluid inside the balloon at an inflation pressure during use (e.g., a pressure of from about 5 atm to about 30 atm, such as a pressure of about 20 atm).

In the illustrated embodiment, the distal neck 52 has a single wall thickness T1 in an inclusive range of from about 0.00125 inches to about 0.005 inches. The distal necks of other balloons can have other configurations in one or more embodiments. As shown in FIG. 4, the bonded distal end portions of the inner inflation tube 60 and the balloon 22 are freely positioned in the interior of the head 42 of the burr 20. In other words, neither the distal end portion of the balloon 22 nor the distal end portion of the inner inflation tube 60 is directly attached to the burr 20.

The proximal neck 50 is sized and arranged to radially overlap the outer inflation tube 62 of the inflation conduit 26 along an overlap section 50A. Moreover, the overlap section 50A is sized and arranged for being received radially inside of the longitudinal lumen of the drive shaft 24. The overlap section 50A defines the proximal end of the proximal neck 50. The proximal neck 50 is coupled (e.g., welded) to the inflation conduit 26 at the overlap section 50A for fluid communication and/or conjoint rotation with the inflation conduit. The overlap section 50A has a length L5 (FIG. 5). The overlap section 50A can radially overlap the outer inflation tube 62 along substantially the entire length L5 or along less than the entire length of the overlap section. For example, a distal end segment of the overlap section 50A can protrude distally of the outer inflation tube 62. The overlap section 50A of the proximal neck 50 has a relatively thin single wall thickness T2 (FIG. 6) such that the overlap section is sized for being received in the thin annular gap between the drive shaft 24 and the outer inflation tube 62 as shown in FIG. 4. In the illustrated embodiment, the overlap section 50A has a substantially uniform single-wall thickness T2 along its length L5. In one embodiment, the single wall thickness T1 of the distal neck 52 is at least about 10% greater (e.g., at least about 20% greater) than the single wall thickness T2 of the overlap section 50A. In one or more embodiments, the single wall thickness T2 of the overlap section 50A is in an inclusive range of from about 0.001 inches to about 0.004 inches. The proximal neck of a balloon can also have other configurations in one or more embodiments.

The illustrated proximal neck 50 also comprises a distal section 50B spaced apart distally from the overlap section 50A along the axis A1. The overlap section 50A has an outer diameter OD1 (FIG. 6) and the distal section 50B has an outer diameter OD2 that is less than the outer diameter of the overlap section. The outer diameter OD2 of the distal section 50B can be at least about 10% less than the outer diameter OD1 of the overlap section 50A in one or more embodiments (e.g., at least about 15% less, or at least about 20% less). In one or more embodiments, the distal section 50B has a substantially constant outer diameter OD2 along a length L6 (FIG. 5) thereof. In one or more embodiments the length L6 of the distal section 50B along the axis A1 is at least about 90% of a length L7 of the body 58 of the balloon 22 along the axis.

The distal section 50B has a single wall thickness T3 (FIG. 6) that tapers as it extends distally along the axis A1 from the proximal end of the distal section. An annular inner surface of the distal section 50B extends radially outwardly as it extends distally from the proximal end of the distal section along the axis A1. The single wall thickness T3 of the distal section 50B is thinnest at the distal end portion thereof, where it is connected to the proximal cone 54. The proximal cone 54 has a comparably thin single wall thickness, which is believed to be suitable for inflating the balloon 22 and expanding the burr 20 under moderate fluid pressure. The wall of the distal section 50B is thickest at the proximal end portion thereof. In one or more embodiments, the single wall thickness T3 at the proximal end of the distal section 50B is at least about 10% greater than the single wall thickness at the distal end of the distal section, e.g., at least about 25% greater, or at least about 40% greater. The proximal neck of a balloon can have other configurations in one or more embodiments, however.

The proximal neck 50 further comprises a conical transition section 50C extending distally from the overlap section 50A to the distal section 50B. The transition section 50C has a frusto-conical shape having an outer diameter that tapers as the transition section extends distally. In the illustrated embodiment, the proximal end of the transition section 50C has about the same outer diameter OD1 as the overlap section 50A, and the distal end of the transition section has about the same outer diameter OD2 as the distal section 40B. The transition section 50C has a single wall thickness T4 that tapers proximally along the transition section. The single wall thickness T4 at the proximal end of transition section 50C is about the same as the single wall thickness T2 of the overlap section 50A. The single wall thickness T4 at the distal end of the transition section 50C is about the same as the single wall thickness T3 of the proximal end of the distal section 50B. In one or more embodiments, the single wall thickness T4 at the distal end of the transition section 50C is at least about 10% greater than the single wall thickness at the proximal end of the transition section, e.g., at least about 25% greater, or at least about 40% greater. The proximal neck of a balloon can have other configurations in one or more embodiments, however.

Figure 6A:
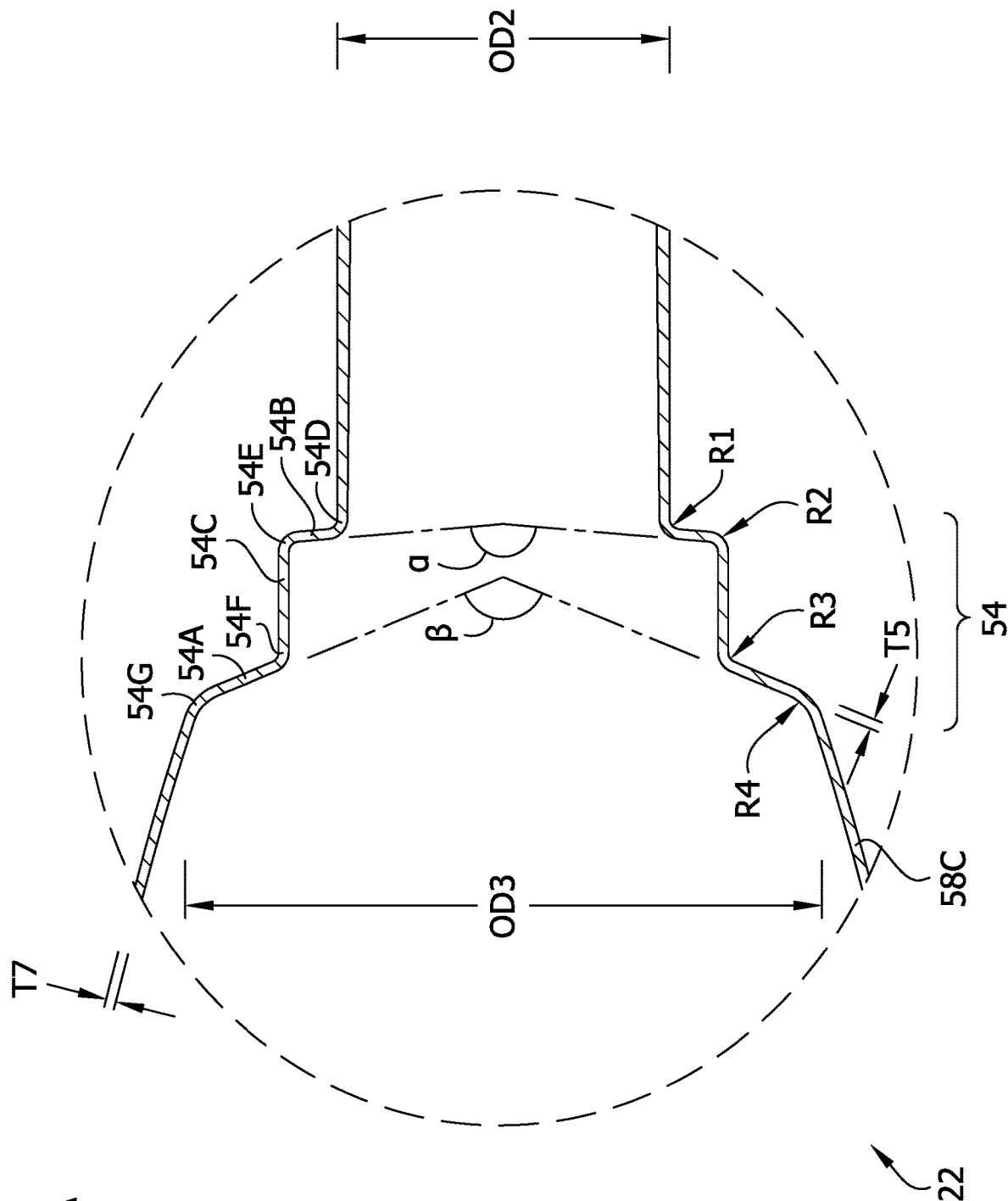
FIG. 6A is an enlarged view of a portion of FIG. 6.

Referring to FIG. 6A, the illustrated proximal cone 54 has a stepped longitudinal cross-sectional shape. It will be understood, however, that balloons can have proximal cones having other shapes in one or more embodiments. The proximal cone 54 comprises a distal conical section 54A located adjacent to the body 58 of the balloon 22, a proximal conical section 54B spaced apart proximally of the distal conical section, and a generally cylindrical section 54C extending between the conical sections. In addition, the proximal cone 54 comprises a first transition region 54D extending between the proximal neck 50 and the proximal conical section 54B, a second transition region 54E extending between the proximal conical section and the cylindrical section 54C, a third transition region 54F extending between the cylindrical section and the distal conical section 54A, and a fourth transition region 54G extending between the distal conical section 54A and the body 58 of the balloon 22. In the illustrated embodiment, each of the transition sections 54D-54G has an arcuate longitudinal cross-sectional shape that has a respective radius of curvature R1-R4 when the balloon 22 is in the expanded configuration. In one or more embodiments, each radius of curvature R1-R3 is about the same (e.g., each radius of curvature R1-R3 is in an inclusive range of from about 0.0005 inches to about 0.0035 inches) and the transition region 54G has a greater radius of curvature R4 (e.g., the radius of curvature R4 is in an inclusive range of from about 0.0035 inches to about 0.0065 inches). Other proximal cones can have other shapes in one or more embodiments.

In one or more embodiments, the proximal cone 54 has a substantially uniform single wall thickness T5 along its length. For example, the proximal cone 54 can have a single wall thickness that is about the same as the single wall thickness T3 at the distal end of the proximal neck 50. The proximal cone 54 can also have a single wall thickness T3 that is about the same as a single wall thickness T7 of the body 58 of the balloon 22. The proximal cone 54 can also have a single wall thickness T5 that differs from the single wall thicknesses T3, T7 of the proximal neck 50 and the body 58. In one or more embodiments, the single wall thickness T5 of the proximal cone 54 can vary (e.g., taper) along the length of the proximal cone.

The proximal conical section 54B has a proximal end that is connected to the proximal neck 50 and a distal end that is connected to the cylindrical section 54C. When the balloon 22 is in the expanded configuration, the proximal conical section 54B extends radially outward as it extends from the proximal end to the distal end thereof. In one or more embodiments, the proximal cone 54 has a cone apex angle α that is greater than about 150° (e.g., greater than about 160°, such as about 190°). As shown in FIG. 4, the proximal end of the proximal conical section 54B forms a stop that is configured to oppose the distal end of the drive shaft 24. If the drive shaft 24 moves distally relative to the balloon 22 during use, the proximal conical section 54B engages the distal end of the drive shaft to limit distal movement of the drive shaft. Moreover, the proximal end of the proximal conical section 54B can engage the distal end of the drive shaft 24 during manufacturing to align the balloon 22 with the drive shaft along the axis A1. For example, in one embodiment, the inflation conduit 26 is bonded to the drive shaft 24 after the balloon is bonded to the inflation conduit, and the inflation conduit is positioned in the longitudinal passage of the drive shaft such that the distal end of the drive shaft engages the proximal conical section 54B.

Referring to FIGS. 4 and 6A, the cylindrical section 54C extends distally along the axis A1 from the distal end of the proximal conical section 54B to the proximal end of the distal conical section 54A. In the expandable burr assembly 12, the cylindrical section 54C protrudes distally of the proximal annular hub 38 of the burr 20. In the expanded configuration of the balloon 22, an outer diameter of the cylindrical section 54A can be less than an inner diameter of the proximal annular hub 38. Moreover, because cylindrical section 54C is sized to protrude distally of the proximal annular hub 38, the distal conical section 54A (which extends from the distal end of the cylindrical section) is spaced apart distally from the distal end of the proximal annular hub. The distal conical section 54C, therefore, protrudes distally so that the expandable portions of the balloon 22 are spaced apart from the non-expandable proximal annular hub 38 of the burr 20.

Referring to FIG. 6A, the distal conical section 54A has a proximal end that is connected to the cylindrical section 54C and a distal end that is connected to the body 58 of the balloon 22. When the balloon is in the expanded configuration, the distal conical section 54A extends radially outward from the proximal end to the distal end thereof. In one or more embodiments, the distal conical section 54A has a cone apex angle β that is greater than about 120° (e.g., greater than about 130°, such as about 135°). In one or more embodiments, the cone apex angle β of the distal conical section 54A is less than the cone apex angle α of the proximal conical section 54B. Referring to FIG. 4, in one or more embodiments, the distal end of the distal conical section 54A is spaced apart distally from the proximal end of the struts 34A when the balloon is inflated. As shown in FIG. 6, the distal end of the distal conical section 54A has an outer diameter OD3 when the balloon 22 is inflated. The outer diameter OD3 can be greater than the cross-sectional dimension D1 of the struts 34 (broadly, the middle portion) of the burr 20 when the burr is in the non-expanded configuration.

Figure 6B:
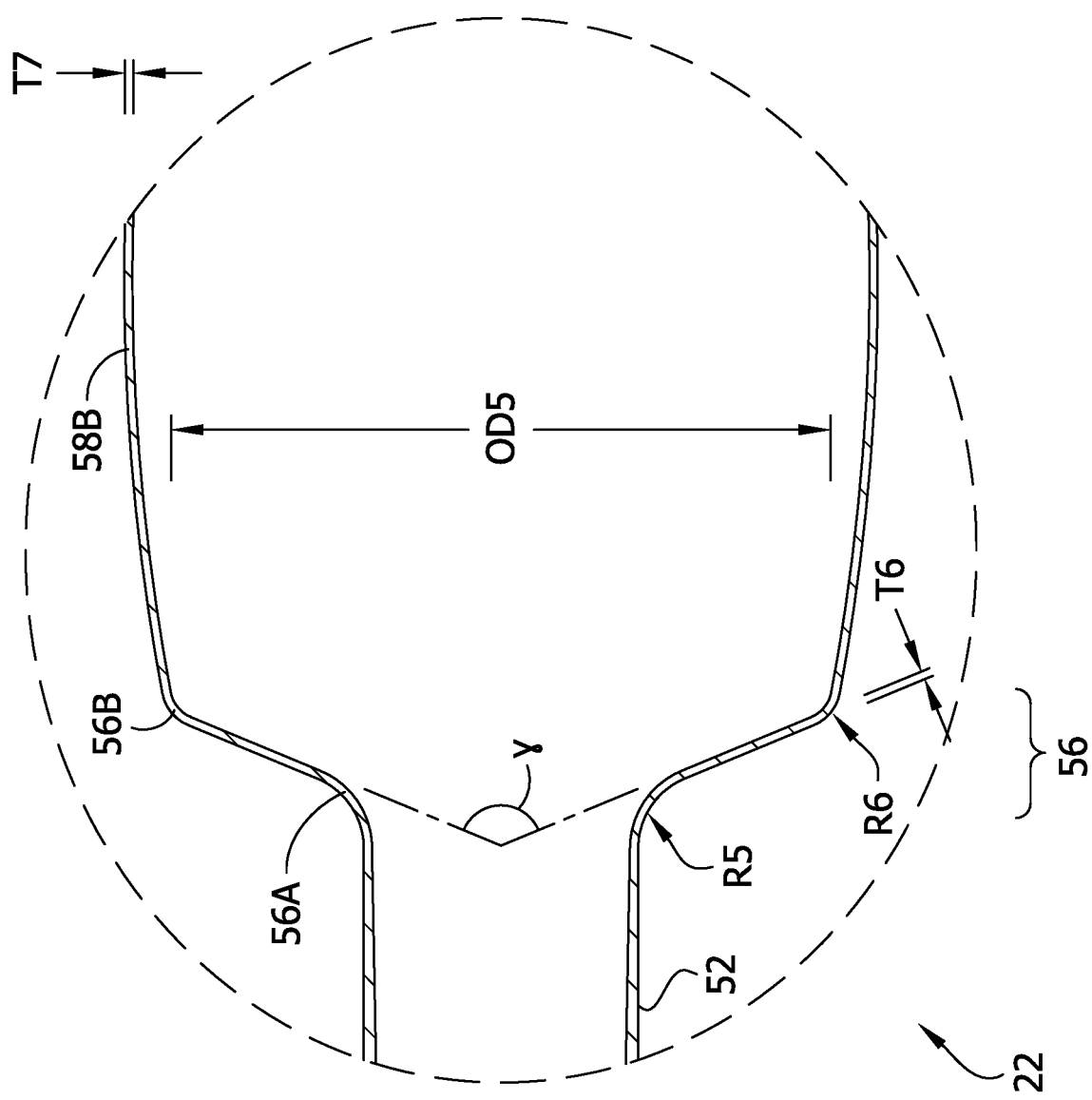
FIG. 6B is an enlarged view of another portion of FIG. 6.

Referring to FIG. 6B, the distal cone 56 has a proximal end that is connected to the body 58 of the balloon 22 and a distal end that is connected to the distal neck 52. When the balloon 22 is in the expanded configuration, the distal cone 56 extends radially outward as it extends along the axis A1 from the distal end to the proximal end thereof. In one or more embodiments, the distal cone has a cone apex angle γ that is greater than about 120° (e.g., greater than about 130°, such as about 135°). In one or more embodiments, the cone apex angle γ is about the same as the cone apex angle β of the distal conical segment 54A of the proximal cone 54. When the balloon 22 is inflated, the proximal (large) end of the distal cone 54 has an outer diameter OD4 that is greater than the outer diameter OD3 (FIG. 6A) of the distal (large) end of the proximal cone. (Correspondingly, when the balloon 22 is inflated, a diameter of a proximal end of the body 58 of the balloon 22 is less than a diameter of a distal end of the body of the balloon.) In one or more embodiments, the cones of a balloon can have axially inboard ends of about the same cross-sectional size or the cones can be configured such that the axially inboard end of the proximal cone has a greater cross-sectional dimension than the axially inboard end of the distal cone. As shown in FIG. 4, when the balloon 22 is inflated, the distal cone 56 is spaced apart from the distal end portion of the burr 20 to define a longitudinal gap 64 extending along the axis A1 between the distal end portion of the burr and the distal cone. For example, in the illustrated embodiment, the distal end portions of the struts 34 protrude distally of the distal cone 56 along the axis A1 (e.g., in one embodiment, the struts protrude distally beyond the proximal end of the distal cone; in another embodiment, the struts protrude distally beyond the distal end of the distal cone) when the balloon 22 is inflated.

In one or more embodiments, the distal cone 56 has a substantially uniform single wall thickness T6 along its length. For example, the distal cone 56 can have a single wall thickness T6 that is about the same as the single wall thickness T1 at the proximal end of the distal neck 52. The distal cone 56 can also have a single wall thickness T6 that is about the same as the single wall thickness T7 of the body 58 of the balloon 22. The distal 56 cone can also have another single wall thickness T6 in one or more embodiments. In one or more embodiments, the single wall thickness of the distal cone 56 can vary (e.g., taper) along the length of the distal cone.

Referring again to FIG. 6B, the distal cone 56 comprises a first transition region 56A between the distal end of the distal cone and the distal neck 52 and a second transition region 56B between the proximal end of the distal cone and the body 58. In the illustrated embodiment, each of the transition sections 56A, 65B has a longitudinal cross-sectional shape that has a respective radius of curvature R5, R6 when the balloon 22 is in the expanded configuration. In one or more embodiments, the radius of curvature R5 is greater than the radius of curvature R6. In one or more embodiments the radius of curvature R5, R6 of the transition region 54G, 56B between each of the proximal and distal cones 54, 56 and the body 58 is about the same. In one or more embodiments, the radius of curvature R4 of the transition region 56A is in an inclusive range of from about 0.0075 inches to about 0.0105 inches. In one or more embodiments, the radius of curvature R6 of the transition region 54B is in an inclusive range of from about 0.0035 inches to about 0.0065 inches.

Referring again to FIG. 4, the body 58 of the balloon 22 has a generally convex shape when the balloon is inflated. The body 58 has a length L7 extending from the proximal cone 54 to the distal cone 54. When the balloon 22 is expanded, the body 58 is configured to impart a radially outward force on the struts 34 substantially continuously along the length L7. In the illustrated embodiment, the balloon-containment sleeve 30 prevents the body 58 from directly contacting the struts 34. The body 58 of the balloon 22 contacts the balloon-containment sleeve 30 substantially continuously along its length L7 when the balloon is inflated. It is understood that the balloon-containment sleeve can be omitted such that the body 58 of the balloon would directly contact the struts 34 substantially continuously along its length L7 when the balloon is inflated. When inflated, the body 58 is generally in the shape of a parabolic segment having proximal and distal segment ends adjacent the proximal and distal cones 54, 56, respectively, and rotated 360 degrees about the axis A1 of the balloon 22. The parabolic segment has a radial vertex 58A that is closer along the axis A1 of the balloon 22 to the distal cone 56 than the proximal cone 54. However, the vertex 58A is about equidistant between the proximal and distal ends of the struts 34 and is generally aligned along the axis A1 with the vertexes 34A of the struts 34 when the burr 20 is expanded. A distally sloping portion 58B of the parabolic segment extends distally from the vertex 58A and has an arc length that is less than an arc length of a proximally sloping portion 58C of the parabolic segment. The distally truncated parabolic shape of the balloon body 58 shifts the position of the distal cone 56 proximally in comparison to where the distal cone would be located if the distally sloping portion 58B was extended to have an equal arc length to the proximally sloping portion 58C. As a result, the distal cone 56 spaced proximally from the distal ends of the struts 34 when the balloon 22 is expanded. Moreover, the gap 64 is provided between the distal cone 56 and the distal end portion of the burr 20, which allows the distal end portion of the burr 20 (e.g., the head 42 and the distal annular hub 40) to move proximally with respect to the balloon 22 so that length of the burr can decrease from the initial length L1 to the second length L2 without interfering with the balloon when the burr is expanded. The inflated balloon 22 has a maximum outer diameter OD5 at the vertex 58A. The maximum outer diameter OD5 is greater than the outer diameters OD3, OD4 of the large ends of the proximal and distal cones 54, 56.

In one or more embodiments, the body 58 has a substantially uniform single wall thickness T7 (FIG. 6) along its length L7. For example, the body 58 can have a single wall thickness T7 that is about the same as the single wall thickness T5, T6 of either or both of the proximal and distal cones 54, 56. In one or more embodiments, the single wall thickness T7 of the body 58 when the balloon 22 is inflated is in an inclusive range of from about 0.0006 inches to about 0.0015 inches (e.g., from about 0.0006 inches to about 0.0008 inches). The body of the balloon can have another single wall thickness in one or more embodiments. In still one or more embodiments, the single wall thickness of the body of the balloon can vary (e.g., taper) along the length L7 of the body.

C. Balloon-Containment Sleeve

Referring to FIGS. 3-4 and 7-7A, the illustrated expandable burr assembly further includes a balloon-containment sleeve 30 that is configured to facilitate the collapse of the balloon 22 as the balloon is deflated. For example, the balloon-containment sleeve 30 is configured to radially collapse the balloon 22 as the balloon is deflated. As explained below, the balloon-containment sleeve 30 is also configured to inhibit the balloon 22 from being pinched between the struts 34 of the burr 20 as the struts resiliently rebound toward the non-expanded configuration.

The balloon-containment sleeve 30 is located radially inside of the burr 20 and extends circumferentially around the balloon 22 with respect to the axis A1. In general, the balloon-containment sleeve 30 is configured to be expanded by inflation of the balloon 22 from a non-expanded configuration (FIGS. 7-7A) to an expanded configuration (FIGS. 3-4). As explained below, the balloon-containment sleeve 30 is radially resilient. As the balloon is deflated, the balloon-containment sleeve 30 is configured to rebound toward the non-expanded configuration. Moreover, as the balloon-containment sleeve 30 rebounds, it is configured to impart radially inward forces on the balloon 22 to radially collapse the balloon.

Referring to FIG. 7A, the balloon-containment sleeve 30 can have a non-expanded inner cross-sectional shape that is configured to closely conform to the external cross-sectional shape of the deflated balloon 22. For example, the balloon-containment sleeve 30 defines a cylindrical passage having a resting inner diameter ID1. Here, 'resting' is understood to mean the condition of the balloon-containment sleeve 30 when the sleeve is not stretched by inflation of the balloon. The balloon 22 has a maximum outer diameter OD6 when the balloon is fully deflated. In one or more embodiments, the resting inner diameter ID1 is about the same as the fully deflated, maximum outer diameter OD6 (e.g., the resting inner diameter ID1 is no more than about 15% different than the maximum outer diameter OD6, such as no more than about 10% different, or no more than about 5% different). It is believed that a radially resilient balloon-containment sleeve 30 having a resting internal cross-sectional shape that can closely conform to the external cross-sectional shape of the deflated balloon 22 can facilitate collapse of the balloon as the balloon is deflated during use. It will be appreciated, however, that other configurations of balloon-containment sleeves and balloons can also be used in one or more embodiments. For example, in one embodiment, the resting internal cross-sectional shape of the balloon-containment sleeve can be smaller than the resting external cross-sectional shape of the balloon such that the balloon-containment sleeve is radially stretched by the balloon even when the balloon is fully deflated.

In one or more embodiments, the balloon-containment sleeve 30 is more radially resilient than the balloon 22. For example, in one embodiment, the balloon-containment sleeve 30 is more radially resilient than at least the body 58 of the balloon 22. In another embodiment, the balloon-containment sleeve 30 is more radially resilient than at least the expandable portion of the balloon 22 including the body 58 and the proximal and distal cones 54, 56. In yet another embodiment, the balloon-containment sleeve 30 is more radially resilient than the entire balloon 22. Still other configurations are also possible in one or more embodiments. Suitably, the balloon-containment sleeve 30 can be a single, one-piece component that is integrally, monolithically formed from a single piece of radially resilient material. For example, in one embodiment, the balloon-containment sleeve 30 comprises a single tubular piece of monolithically formed silicone (e.g., Dow Corning C6-150), which is believed to be a suitably radially resilient material. The balloon-containment sleeve can be formed from other materials and/or have other configurations in one or more embodiments.

In one or more embodiments, the balloon-containment sleeve 30 has a single wall thickness T8 that is greater than the single wall thickness T7 of the body 58 of the balloon 22. The balloon-containment sleeve 30 can have a single wall thickness T8 that is greater than the single wall thicknesses T5, T6, T7 of the proximal cone 54, the distal cone 56, and the body 58 of the expandable portion of the balloon 22. In one or more embodiments, the single wall thickness T8 is greater than the single wall thickness of the balloon 22 along the entire length L4 of the balloon. In the one or more embodiments, the single wall thickness T8 of the balloon-containment sleeve 30 is at least about 50% greater than the single wall thickness of the body 58 of the balloon 22. For example, the single wall thickness T8 is at least two-times greater than the single wall thickness T7, e.g., three-times greater, four-times greater, or five-times greater. In one embodiment, the single wall thickness T8 of the balloon is at least about 10% of the radial thickness of each of the struts 34 of the burr 20 (e.g., at least about 25%, at least about 50%, at least about 75%, or at least about 100%).

The balloon-containment sleeve 30 has a proximal end and a distal end and a length L8 extending along the axis A1 from the proximal end to the distal end. The length L8 of the balloon-containment sleeve 30 can extend along at least an entirety of the length L7 of the body 58 of the balloon 22. In one or more embodiments, the length of the balloon-containment sleeve can extend along only a portion of the length of the length of the body of the balloon. In one or more embodiments, the length L8 of the balloon-containment sleeve 30 is longer than the length L8 of the body 58 of the balloon. The length of the balloon-containment sleeve can also be less than the length of the body of the balloon in one or more embodiments. In the illustrated embodiment, the length L8 of the balloon-containment sleeve 30 is less than the overall length L4 of the balloon 22 and less than the length L1, L3 of the burr 20. A distal end portion of the balloon-containment sleeve 30 radially overlaps the distal cone 56. Moreover, the distal end portion of the illustrated balloon-containment sleeve 30 protrudes distally of the distal cone 56 (e.g., a distal end portion of the balloon-containment sleeve radially overlaps a portion of the distal neck 52). The illustrated balloon-containment sleeve 30 also includes a proximal segment that radially overlaps at least a portion of the proximal cone 54. In the illustrated embodiment, the proximal end portion of the balloon-containment sleeve 30 does not radially overlap the proximal neck 50. Referring to FIG. 4, the distal end of the balloon-containment sleeve 30 is spaced apart along the axis A1 proximally of the distal end portion of the ablation burr 20. Likewise, the proximal end of the balloon-containment sleeve 30 spaced apart along the axis A1 distally of the proximal end portion of the ablation burr 20. The balloon-containment sleeve can also have other configurations with respect to the burr in one or more embodiments.

Referring to FIGS. 7 and 7A, the balloon-containment sleeve 30 comprises a contiguous tube of resilient material. Along the entire length L8, the balloon-containment sleeve 30 is free of radial openings that penetrate the wall of the tube from the interior through the exterior surface of the tube. For example, the balloon-containment sleeve 30 is radially fluid-impermeable along its entire length L8 in one or more embodiments. It will be understood that the balloon-containment sleeve can have other configurations in one or more embodiments. For example, the balloon-containment sleeve can be formed from a mesh material, a braided material, a woven material, or another material that is radially porous in one or more embodiments. Still other configurations are also possible. For example, in one embodiment, the balloon-containment sleeve can comprise one or more radially resilient coils that are wound around a portion of the exterior of the balloon.

The balloon-containment sleeve 30 can be unattached to the balloon 22 and the burr 20. In other words, the expandable burr assembly 12 can be free of attachment structure that attaches the balloon-containment sleeve to either the balloon 22 or the burr 20. In the illustrated embodiment, the balloon-containment sleeve 30 is held on the balloon 22 by friction. In one or more embodiments, the balloon-containment sleeve can be attached to one or both of the burr and the balloon by an attachment structure such as a weld, an adhesive bond, a heat bond, and/or a mechanical fastener.

When the balloon 22 is deflated and the burr 20 transitions from the expanded configuration to the non-expanded configuration, the balloon-containment sleeve 30 is configured to prevent portions of the balloon body 58 from being captured in the slots 36 or being pinched by the struts 34. Referring to FIG. 3, the struts 34 have opposite longitudinal edges that define the slots 36. The slots 36 have circumferential widths CW (e.g., strut-spacing distances) that define the distance between the adjacent longitudinal edges of adjacent ones of the struts 34. When the struts 34 rebound from the expanded configuration to the non-expanded configuration, the widths CW of the slots 36 decrease (e.g., the strut-spacing distances decrease). And when the burr 20 reaches the fully non-expanded configuration, the adjacent edges of adjacent ones of the struts 34 are immediately adjacent to one another such that the width CW of each slot 36 is nearly zero (e.g., the width CW of each slots in the fully non-expanded configuration of the burr 20 can be less than about 0.0020 inches, such as about 0.0010 inches). While radially collapsing the balloon 22 as the balloon is deflated, the balloon-containment sleeve 30 is configured to prevent portions of the balloon from being pinched between opposed edges of the struts 34 as the widths CW between the lateral edges decrease. It is believed that, because the balloon-containment sleeve 30 has a relatively thick single wall thickness T8 and is formed from relatively resilient material, the balloon-containment sleeve 30 substantially maintains its shape as the struts 34 rebound to the non-expanded configuration. The struts 34 are believed to be substantially incapable of deforming the balloon-containment sleeve 30 in such a way as to grip or pinch portions of the balloon-containment sleeve between the longitudinal edges thereof. Moreover, the balloon-containment sleeve 30 is believed to thereby form a protective sheath around the balloon 22 that prevents portions of the balloon from being pinched between the struts 34 during deflation.

II. Catheter Body

Referring to FIG. 1, the elongate catheter body 14 has a length and a proximal end portion and a distal end portion spaced apart along the length. In the illustrated embodiment, the length of the catheter body 14 extends along the rotational axis A1, and the catheter body has a center axis that is generally coaxial with the rotational axis. Since the axis of the catheter body is generally coaxial with the rotational axis A1, this disclosure will use the same characters (i.e., 'A1') when referring to both axes. It will be understood that the rotational axis can be other than coaxial with the center axis of the catheter body in one or more embodiments. In one or more embodiments, the catheter body 14 can have a length extending from the handle 16 to the burr assembly 12 in an inclusive range of form about 50 inches to about 60 inches.

Referring to FIGS. 4 and 8, the illustrated catheter body 14 generally includes the drive shaft 24, the inflation conduit 26, and an outer isolation sheath, generally indicated at reference number 70. It will be understood that, in one or more embodiments, the catheter body can comprise any combination of one or more of the drive shaft 24, the inflation conduit 26, and the isolation sheath 70. Still other catheter body configurations are also possible. The drive shaft 24 extends longitudinally through a lumen 86 of the isolation sheath 70, and the inflation conduit 26 extends longitudinally through a lumen of the drive shaft. In one or more embodiments, the parts of the catheter body can have other configurations. As will be explained in further detail below, the drive shaft 24, the inflation conduit 26, and/or the isolation sheath 70 facilitate one or more of inserting the catheter body through the body lumen of a subject along a guidewire G, inflating the balloon 22, and rotating the burr assembly 12. In an exemplary embodiment, the catheter body 14 is configured to perform all of these functions. The catheter body 14 suitably comprises various reinforcements and wear layers that are believed to protect patient anatomy and withstand the myriad forces associated with guidewire navigation, balloon inflation, and/or high speed rotation during a procedure.

A. Inflation Conduit

In the illustrated embodiment, the inflation conduit 60 extends longitudinally through the drive shaft 24 from a proximal end portion received in the handle 16 to a distal end portion that is connected to the balloon 22. As explained above, the illustrated inflation conduit 26 comprises an inner inflation tube 60 and an outer inflation tube 62, and the inner and outer inflation tubes define radially between them an annular inflation lumen 28. Each of the inflation tubes 60, 62 has a proximal end portion that extends into the handle 16 of the catheter 10 and a distal end portion that is coupled to the balloon 22 as explained above. As will be explained below, the proximal end portions of the inflation tubes 60, 62 are configured to be fluidly coupled to passaging in the handle 16, which provides fluid communication between a source of inflation fluid and the inflation lumen 28. As will also be explained below, the proximal end portions of the inflation tubes 60, 62 are configured to be rotatably connected to a rotational prime mover or driver at joints located in the handle 16. The same rotational prime mover is also rotatably connected to the drive shaft such that the inflation conduit 26 is coupled to the drive shaft for conjoint rotation with the drive shaft. As is further explained below, the distal end portion of the inflation conduit 26 can also be directly attached to the distal end portion of the drive shaft 24 to ensure conjoint rotation at the distal end portion of the catheter body 14.

The catheter body 14 can be configured for insertion into a body lumen of a subject over a guidewire G that extends along the body lumen. In the illustrated embodiment, the inner inflation tube 60 defines a guidewire lumen 72 configured to slidably receive a guidewire G therein. In one or more embodiments, the guidewire lumen 72 extends along the entire length of the inner inflation tube 60. For example, as shown in FIG. 1, in the illustrated embodiment, the catheter 10 is configured so that the guidewire G can extend from a proximal end portion proximal of the handle 16, longitudinally through the handle, the guidewire lumen 72, and the burr assembly 12, to a distal end portion distal to the distal end of the burr assembly. In one or more embodiments, it is understood that the catheter body can have other guidewire lumen configurations. In the illustrated embodiment, the inflation conduit 26 (and the catheter body 14) is configured to rotate about a guidewire G received in the guidewire lumen 72. The inner inflation tube 60 is located radially between the guidewire lumen 72 and the inflation lumen 28. As will be explained in further detail below, the illustrated inner inflation tube 60 is radially reinforced to limit inward radial compression in response to a pressurized inflation fluid in the inflation lumen 28 so that the inflation conduit 26 can rotate about the guidewire G while simultaneously inflating the balloon 22. As is also explained below, in one or more embodiments, the guidewire lumen 72 is configured to be fluidly coupled to a source flushing fluid. Directing flushing fluid from the source of flushing fluid through the guidewire lumen 72 can reduce or minimize friction between the guidewire and the catheter body 14 as the catheter body rotates and/or slides longitudinally with respect to the guidewire G.

In one or more embodiments, the inner inflation tube 60, is configured to slidably and rotatably receive various types of guidewires in the guidewire lumen 72. For example, the inflation conduit 26 can be configured, while the inflation lumen 28 is pressurized, to slide along and rotate about any commercially available guidewire G of suitable size for the guidewire lumen 72. In one or more embodiments, the catheter body 14 is configured to slide along and rotate about any of at least the following types of guidewires: bare stainless steel guidewires, bare nitinol guidewires, silicone coated guidewires, and PTFE coated guidewires. The catheter body 14 can also be configured to slide along and rotate about other types of guidewires in certain embodiments. Accordingly, the catheter 10 may be guided through a body lumen of a subject along a general purpose guidewire in one or more embodiments. A dedicated or special purpose guidewire may not be required for use of one or more embodiments of the catheter 10; although it is understood that the catheter can be used with a dedicated or special purpose guidewire in one or more embodiments.

As shown in FIG. 8, the illustrated inner inflation tube 60 comprises a reinforcing coil 74 that extends along the length (e.g., entire length) of the inner inflation tube 60. The coil 74 is configured to radially reinforce the inner inflation tube 60 to limit inward radial deflection or compression of the inner inflation tube in response to a pressurized inflation fluid in the inflation lumen 28 that is inflating the balloon 22. By limiting radial compression of the inner inflation tube 60, the inflation conduit 26 is capable of being rotated about the guidewire G while the balloon 22 is inflated. In general, the coil 74 comprises a helically wound or coiled wire of metal or other reinforcing material. The coil 74 is wound circumferentially about the axis A1. In one or more embodiments, the coil 74 comprises one of stainless steel and nitinol. Other metals and non-metal coils can also be used in one or more embodiments. In the illustrated embodiment, the coil 74 has a pitch of from about 50 wraps-per-inch to about 250 wraps-per-inch, for example, from about 100 wraps-per-inch to about 200 wraps-per-inch, such as about 150 wraps-per-inch. Other coils can have other configurations in one or more embodiments. Other types of reinforcement (e.g., a braid) can also be used to strengthen the inner inflation tube in certain embodiments.

The wire forming the coil 74 has a generally rectangular cross sectional shape having a cross-sectional width W1 and a cross-sectional thickness T9. In the illustrated embodiment, the wire is oriented so that the cross-sectional width W1 extends generally parallel to the axis A1 and the thickness T9 extends generally radially of the axis. In one or more embodiments, the coils can have other orientations. One or more embodiments also have coils formed from wires having other (e.g., non-rectangular) cross-sectional shapes in one or more embodiments. The cross-sectional width W1 is greater than the thickness T9 of the illustrated coil 79. For example, in one embodiment, the cross-sectional width W1 is more than two-times the thickness T9. In one or more embodiments, the coil 74 can have a cross-sectional width W1 in an inclusive range of from about 0.0010 inches to about 0.0030 inches and a thickness T9 in an inclusive range of from about 0.0001 inches to about 0.001 inches. The coil can have other cross-sectional sizes in one or more embodiments. Although the illustrated embodiment, uses a coil to radially reinforce the inner inflation tube 60, inner inflation tubes can be radially reinforced in other ways in one or more embodiments.

The reinforcing coil 74 is embedded in a fluid-impermeable polymer tube having open proximal and distal ends in communication with the guidewire lumen 72. The proximal end portion of the inner tube 60 extends into the handle 16, where it is fluidly coupled to a source of flushing fluid as explained below. The distal end portion of the inner inflation tube 60 is fluidly coupled to the distal neck 52 of the balloon 22 as explained above. The distal end portion of the inner inflation tube 60 protrudes distally from the distal end portion of the outer inflation tube 62 in the illustrated embodiment.

In the illustrated embodiment, the polymer tube has three tubular layers 75, 76, 77, each extending along the length (e.g., entire length) of the inner inflation tube 60. In one or more embodiments, the polymer tube can comprises one layer, two layers, more than three layers, or another configuration. The inner layer 75 (e.g., innermost layer) is lubricious and/or is formed from material having a low coefficient of friction. In an exemplary embodiment, the inner layer 75 comprises a PTFE, including blends thereof, but other materials can be used in one or more embodiments. The inner surface of the inner layer 75 can also be coated with a lubricious coating in one or more embodiments. The polymer tube further comprises an outer layer 76. The outer layer 76 can comprise the same material as the inner layer 75 or a different material. In the illustrated embodiment, the outer layer comprises a PEBA, such as PEBAX 55D commercially available from Arkema. Forming the outer layer 76 from a PEBA is believed to enhance the radial crush resistance of the inner inflation tube 60. Other materials can be used for the outer layer in one or more embodiments. A middle layer 77 is disposed radially between the inner layer 75 and the outer layer 76. In one or more embodiments, the middle layer 76 can comprise a different material from either inner layer 75 or the outer layer 76. For example, in one embodiment, the middle layer 76 can comprise a polyimide, including blends thereof.

In one or more embodiments, the coil 74 can be embedded in the middle layer 76. For example, in the illustrated embodiment, in cross section, the coil 74 is surrounded on three sides by the middle layer 77 and the inner layer 75 covers a radially inner side of the coil. Thus, in the illustrated embodiment, the coil 74 is embedded in the middle layer 77 at the interface between the middle layer and the inner layer 75. In one or more embodiments, the middle layer 77 extends around the entire cross-sectional perimeter of the coil 74 such that the coil is only in contact with the middle layer. The coil can be embedded in the polymer tube 76 in still other ways in one or more embodiments.

In the illustrated embodiment, the polymer tube 76 defines the inner and outer radial surfaces of the inner inflation tube 60. In one or more embodiments, the inner inflation tube 60 has an inner diameter ID2 in an inclusive range of from about 0.010 inches to about 0.030 inches and an outer diameter OD7 in an inclusive range of from about 0.015 inches to about 0.035 inches. In one or more embodiments, the inner diameter ID2 is greater than about 0.014 inches such that the catheter body 14 is compatible with guidewires G having diameters of 0.014 inches. In one or more embodiments, the inner diameter ID2 is greater than about 0.018 inches such that the catheter body 14 is compatible with guidewires G having diameters of 0.018 inches. The inner inflation tube 60 can have a single wall thickness T10 in an inclusive range of from about 0.001 inches to about 0.010 inches. The middle layer 77 has a single wall thickness T11, the inner layer 75 has a single wall thickness T12, and the outer layer 76 has a single wall thickness T13. The single wall thickness T11 of the middle layer is greater than the single wall thickness T9 of the coil 74 in one or more embodiments. In the illustrated embodiment, the single wall thickness T11 of the middle layer 77 is greater than the single wall thicknesses T12, T13 of the inner and outer layers 75, 76. For example, the single wall thickness T11 can be at least about two times the single wall thickness T12 and/or the single wall thickness T13. In one or more embodiments, the single wall thickness T11 can be at least two times each of the single wall thicknesses T12, T13. In one or more embodiments, the single wall thickness T11 is in an inclusive range of from about 0.0005 inches to about 0.0015 inches; the single wall thickness T12 is in an inclusive range of from about 0.0001 inches to about 0.0008 inches; and the single wall thickness T13 is in an inclusive range of from about 0.0001 inches to about 0.0008 inches. The inner inflation tube can also have other configurations in one or more embodiments.

In the illustrated embodiment, the outer inflation tube 62 comprises a fluid-impermeable polymer tube having open proximal and distal ends in communication with the inflation lumen 28. The proximal end portion of the outer tube 62 extends into the handle 16, where it is fluidly coupled to a source of inflation fluid as explained below. The distal end portion of the outer tube 62 is fluidly coupled to the proximal neck of the balloon 22 as explained above. The distal end portion of the outer inflation tube 62 is spaced apart proximally from the distal end portion of the inner inflation tube 60 in the illustrated embodiment. The outer inflation tube 64 can be a single, one-piece component that is integrally, monolithically formed from a single piece of material. The outer inflation tube 62 can also be a multilayer and/or reinforced tube in one or more embodiments. In the illustrated embodiment, the outer inflation tube 62 comprises a monolithic nylon tube. The outer inflation tube 62 can also comprise other materials in one or more embodiments.

The outer inflation tube 62 has an inner diameter ID3 that is between about 0.001 inches and about 0.008 inches greater than the outer diameter OD7 of the inner inflation tube 60. In other words, the annular inflation conduit 28 can have a single wall thickness of from about 0.001 inches and about 0.008 inches in one or more embodiments. For example, the inner diameter ID3 of the outer inflation tube 62 can be in an inclusive range of from about 0.023 inches to about 0.034 inches. The outer inflation tube 62 can also have an outer diameter OD8 in an inclusive range of from about 0.028 inches to about 0.038 inches. In one or more embodiments, the outer inflation tube 62 has a single wall thickness T14 in an inclusive range of from about 0.0017 inches to about 0.0027 inches. It will be understood that the outer inflation tube can have other configurations in one or more embodiments.

B. Drive Shaft

In the illustrated embodiment, the drive shaft 24 extends longitudinally through the isolation sheath 70 from a proximal end portion received in the handle 16 to a distal end portion that is connected to the burr 20. The proximal end portion of the drive shaft 24 is rotatably coupled to a prime mover (e.g., a driver) in the handle 16 such that the prime mover is configured to impart a rotational drive force on the drive shaft that rotates the drive shaft about the rotational axis A1. As explained in further detail below, the drive shaft 24 is operably coupled to the burr assembly 12 to conjointly rotate the burr assembly about the rotational axis A1. The drive shaft 24 is configured to rotate about the rotational axis A1 relative to the isolation sheath 70.

The illustrated drive shaft 24 comprises a laminated drive coil. The drive shaft can have other configurations in one or more embodiments. The drive shaft 24 comprises a drive coil 80 extending circumferentially about the rotational axis A1 along the length of the drive shaft and a laminate 82 extending circumferentially about the rotational axis A1 along the length of the drive shaft. In the illustrated embodiment, the laminate 82 is applied only to the exterior of the drive coil 80. In one or more embodiments, a laminate can also or exclusively be applied to the interior of the drive coil 80. In still one or more embodiments, multiple laminates can be applied to one or both of the interior and the exterior of the drive coil 80. The laminate 82 can be integrally, monolithically formed from a single piece of material. For example, the laminate 82 can comprise a polymer, for example, an elastomer such as a polyurethane. Suitably, the laminate 82 can comprise a radially outer surface having a low coefficient of friction and/or other properties that enable the laminated drive shaft 24 to withstand rotation inside the isolation sheath 70. The laminate 82 can suitably be sufficiently flexible to allow the drive shaft 24 to bend as required to track through small-radius curves in a body lumen. In an exemplary embodiment, the laminate comprises a thermoplastic polyurethane elastomer such as Pellethane® material, e.g., a 55D Pellethane® material, a 65D Pellethane® material, or a 75D Pellethane® material. Other materials can also be used in one or more embodiments. The laminate 82 can have a single wall thickness T15 in an inclusive range of from about 0.0015 inches to about 0.0025 inches. The laminate 82 defines the exterior surface of the drive shaft 24. In one or more embodiments, the exterior surface of the drive shaft 24 has an outer diameter OD9 in an inclusive range of from about 0.040 inches to about 0.070 inches.

In the illustrated embodiment, the drive coil 80 comprises a bi-layer drive coil. Drive coils having other configurations can also be used in one or more embodiments. The illustrated drive coil 80 comprises an inner coil 80A forming an inner layer and an outer coil 80B forming an outer coil layer. Each of the inner coils 80A, 80B comprises helical windings that extend circumferentially about the rotational axis A1 along the entire length of the drive shaft 24. Suitably, the inner coil 80A can comprise one of left-hand windings and right-hand windings. The outer coil 80B can comprise the other of left-hand windings and right-hand windings. In other words, the inner and outer coils 80A, 80B can be counter-wound.

The inner coil 80A extends longitudinally through the outer coil 80B and defines an inner diameter ID4 of the drive shaft 24. In one or more embodiments, the inner diameter ID4 of the drive shaft 24 is from about 0.0001 inches and 0.005 inches greater than the outer diameter OD8 of the outer inflation tube 62 (e.g., the outer diameter of the inflation conduit 26). In other words, the single wall thickness of the annular gap between the drive shaft 24 and the inflation conduit 26 can be in an inclusive range of from about 0.001 inches to about 0.005 inches. In one or more embodiments, the inner diameter ID4 is in an inclusive range of from about 0.031 inches to about 0.041 inches.

In the illustrated embodiment, each of the inner coil 80A and the outer coil 80B comprises a metal wire having a generally circular cross-sectional shape. The wire forming each of the inner and outer coils 80A, 80B can comprise nitinol and/or stainless steel in one or more embodiments. The coils 80A, 80B can also be formed from non-metal materials or other metal materials. The wire forming the inner coil 80A has a diameter D3 and the wire forming the outer coil 80B has a diameter D4. The diameter D4 of the wire forming the outer coil 80B is greater than the diameter D3 of the wire forming the inner coil 80A. In one or more embodiments, the diameter D4 is at least about 0.0005 inches greater than the diameter D3. In one or more embodiments, the diameter D3 is in an inclusive range of from about 0.0012 inches to about 0.0022 inches. The diameter D4 can be in an inclusive range of from about 0.0022 inches to about 0.0032 inches. The inner coil 80A can have a pitch in an inclusive range of from 0.027 inches nominal to 0.037 inches nominal (e.g., 0.032 inches nominal). The outer coil can have a pitch in an inclusive range of from 0.048 inches nominal to 0.058 inches nominal (e.g., 0.053 inches nominal). The inner and outer coils can have other configurations in one or more embodiments.

C. Isolation Sheath

The isolation sheath 70 comprises a tube having a length extending along the axis A1 from a proximal end portion mounted on in the handle 16 (as explained below) to a distal end portion that is spaced apart proximally of the distal end of the burr assembly 12 along the axis. The isolation sheath 70 extends circumferentially around the drive shaft 24 and the inflation conduit 26 along its entire length but does not rotate with either the drive shaft or inflation conduit. Instead, when the catheter body 14 is being used in a body lumen, the isolation sheath 70 is configured to provide a non-rotating barrier between the rotating exterior of the drive shaft 24 and the wall of the body lumen. As will be explained below, the drive shaft 24 and the inflation conduit 26 are conjointly slidable along the axis A1 with respect to the isolation sheath 70 to adjust a distance along the axis A1 between the burr assembly 12 and the distal end of the isolation sheath.

The isolation sheath 70 has an inner surface that is spaced apart radially outward from the outer surface of the drive shaft 24 with respect to the axis A1. The inner surface of the isolation sheath 70 and the outer surface of the drive shaft 24 define an annular flushing lumen 86 that extends along the length of the isolation sheath. As explained below, the proximal end portion of the isolation sheath 70 can be fluidly coupled at the handle 16 to a source of flushing fluid whereby flushing fluid can be delivered through the flushing lumen 86. Flushing fluid in the flushing lumen 86 can limit or mitigate friction between the drive shaft 24 and the isolation sheath 70 as the drive shaft rotates about the rotational axis A1 inside the stationary isolation sheath. In the illustrated embodiment, the distal end portion of the isolation sheath defines 70 an outlet of the flushing lumen 86.

In the illustrated embodiment, the isolation sheath 70 comprises a reinforced tube. More specifically the illustrated isolation sheath 70 is reinforced by a braid 88. The braid can be formed from metal wires, such as stainless steel and/or nitinol wires. In one or more embodiments, the braid 88 is annealed. Other metals or non-metal reinforcing materials can also be used in one or more embodiments. In still one or more embodiments, the isolation sheath 70 can be reinforced by structure other than a braid. For example, in one or more embodiments, the isolation sheath can comprise a reinforcing coil. In still one or more embodiments, the isolation sheath can comprise a non-reinforced material. In the illustrated embodiment, the braid 88 is formed from a plurality of braided coils, each having from about 40 wraps-per-inch to about 120 wraps-per-inch, for example, from about 60 wraps-per-inch to about 100 wraps-per-inch, such as about 80 wraps-per-inch. The braid can have other configurations in one or more embodiments.

Each wire forming the braid 88 has a generally rectangular cross sectional shape having a cross-sectional width W2 and a cross-sectional thickness T16. Other coils can have other cross-sectional shapes in one or more embodiments. The cross-sectional width W2 is greater than the cross-sectional thickness T16. For example, in one embodiment, the cross-sectional width W2 is more than two-times the cross-sectional thickness T16. In one or more embodiments, the wire of the braid 88 can have a cross-sectional width W2 in an inclusive range of from about 0.0030 inches to about 0.0050 inches and a cross-sectional thickness T16 in an inclusive range of from about 0.0005 inches to about 0.0015 inches. Thus, in one or more embodiments the cross-sectional width W2 and/or cross-sectional thickness T16 of a wire forming a portion of the braid 88 can be greater than the cross-sectional width W1, cross-sectional thickness T9 of the wire forming the inner inflation tube coil 74. The coil can have other cross-sectional sizes in one or more embodiments.

In the illustrated embodiment, the isolation sheath 70 comprises a bi-layer polymer tube that encases the braid 88. In one or more embodiments, the isolation sheath can comprise more than two layers of polymer, a single layer of polymer, or another configuration. The illustrated isolation sheath 70 comprises an inner layer 90 and an outer layer 92. The inner layer 90 can be formed from a different material than the outer layer 92. In one embodiment the inner layer comprises an HDPE and the outer layer comprises a PEBA (e.g., PEBAX 63D). The HDPE inner layer 90 can have a low coefficient of friction at the inner surface of the isolation sheath 70. In one or more embodiments one or both of the inner surface of the isolation sheath and the outer surface of the drive shaft can have a lubricious coating. It will be appreciated that the inner layer and/or the outer layer can be formed from other materials in one or more embodiments.

The isolation sheath 70 has an inner diameter ID5 and an outer diameter OD10. In one or more embodiments, the outer diameter OD10 is such that the isolation sheath 70 can be inserted through an introducer sheath (not shown) of less than or equal to 5 French (e.g., in one or more embodiments, the isolation sheath is compatible with a 4 French introducer sheath). In certain embodiments, the catheter could be configured for use with introducer sheaths of a size greater than 5 French. Suitably, the isolation sheath 70 can pass through the introducer sheath and allow contrast media to be flushed through a space radially between the isolation sheath and the introducer sheath. In one or more embodiments, the outer diameter OD10 is substantially isodiametric with the cross-sectional dimension D1 (broadly, cross-sectional dimension) of the burr 20 in the non-expanded configuration (FIG. 2). For example, in one embodiment, one or both of the non-expanded burr 20 and the isolation sheath 70 can have a respective cross-sectional dimension D1, OD10 in an inclusive range of from about 0.050 inches to about 0.070 inches. The outer diameter OD10 of the isolation sheath 70 can also be greater than or less than the minimum cross-sectional dimension D1 of the non-expanded burr 20 in one or more embodiments. In one or more embodiments, the inner diameter ID5 of the isolation sheath 70 is between about 0.004 inches and 0.006 inches greater than the outer diameter OD9 of the drive shaft. In other words, the single wall thickness of the flushing lumen 86 can be in an inclusive range of from about 0.004 inches to about 0.006 inches. In one or more embodiments, the inner diameter ID4 is in an inclusive range of from about 0.045 inches to about 0.055 inches. The isolation sheath 70 can have a single wall thickness T17 in an inclusive range of from about 0.0035 inches to about 0.0045 inches in one or more embodiments.

E. Burr Adaptor

Referring to FIG. 4, the distal end portion of the catheter body 14 is configured to be operably connected to the expandable burr assembly 12 for expanding and rotating the burr assembly. As explained above, the distal end portion of the inflation conduit 26 is configured to be connected to the balloon 22 (e.g., by a distal bond between the inner inflation tube 60 and the distal neck 52 of the balloon and a proximal bond between the outer inflation tube 62 and the proximal neck 50 of the balloon) such that the balloon is configured to rotate conjointly with the inflation conduit and the drive shaft 24 about the rotational axis A1 and such that the balloon is fluidly coupled to the inflation lumen 28. As explained below, a burr adaptor 100 is configured to connect the distal end portion of the drive shaft 24 to the burr 20 to transmit a rotational force from the drive shaft to the burr.

The burr adaptor 100 comprises a tube having a proximal end portion and a distal end portion. The burr adaptor 100 has a length extending along the axis A1 from the proximal end portion to the distal end portion. The burr adaptor 100 defines a passage extending along the entire length of the burr adaptor from the proximal end portion through the distal end portion. In one or more embodiments, the burr adaptor 100 can be formed from a relatively rigid material. In one or more embodiments, the burr adaptor 100 is formed from metal, such as stainless steel, or nitinol. Other materials can also be used in one or more embodiments. In the illustrated embodiment, the burr adaptor 100 is substantially free of openings that extend radially through the tubular wall of the burr adaptor. For example, excluding the open proximal and distal ends, the burr adaptor 100 is substantially free of openings in the tubular wall that fluidly couple the internal passage of the burr adaptor to the exterior of the burr adaptor. In other words the tubular wall of the burr adaptor is substantially non-porous. In one or more embodiments, the burr adaptor 100 can have one or more holes, slots, or other openings in the tubular wall of the burr adaptor. For example, the burr adaptor can have one or more elongate slots (e.g., a single helical slot extending along a portion of the length of the burr adaptor) that impart flexibility to the burr adaptor.

In the illustrated embodiment, the burr adaptor 100 comprises a reinforcing sleeve in which the distal end portion of the drive shaft 24 is received. In other words, the distal end portion of the drive shaft 24 is received in the internal passage of the burr adaptor 100. The burr adaptor 100 radially overlaps the distal end portion of the drive shaft 24 with respect to the axis A1. In the illustrated embodiment, the burr adaptor 100 radially overlaps the distal end portion of the drive shaft 24 along substantially the entire length of the burr adaptor and the distal ends of the burr adaptor and the drive shaft are aligned in substantially the same radial plane with respect to the axis A1. In one or more embodiments, the burr adaptor can have other positions with respect to the drive shaft.

The proximal annular hub 38 of the burr 20 radially overlaps the burr adaptor 100. For example, in the illustrated embodiment, a distal segment of the burr adaptor 100 is received in the proximal hub 38 and the hub radially overlaps the burr adaptor along substantially its entire length. In one or more embodiments, the proximal annular hub of the burr can overlap the burr adaptor along less than the entire length of the proximal annular hub; for example, only a proximal segment of the proximal hub can overlap the burr adaptor while a distal segment protrudes distally of the burr adaptor. A proximal end portion of the burr adaptor 100 protrudes proximally of the proximal annular hub 38 in the illustrated embodiment.

As explained above, the burr adaptor 100 can be substantially rigid. The proximal annular hub 38 can also be substantially rigid in one or more embodiments. In contrast, the drive shaft 24 is flexible. However, the burr adaptor 100 (e.g., a rigid reinforcing sleeve) substantially inhibits the drive shaft 24 from bending, flexing, or deflecting along the segment of the drive shaft that is radially overlapped by the burr adaptor. By inhibiting the drive shaft 24 from bending, flexing, or deflecting along a distal end segment, the burr adaptor 100 limits forces on the connection between the burr 20 and the drive shaft that can otherwise be caused by the flexible drive shaft moving (e.g., bending, flexing, or deflecting) relative to the more rigid proximal annular hub 38 of the burr 20. Moreover, the burr adaptor 100 limits relative movement between the drive shaft 24 and the burr 20 at the location of the connection between the drive shaft and the burr.

The burr adaptor 100 connects the burr 20 to the drive shaft 24. It will be understood that, in one or more embodiments, the burr can be directly attached to the drive shaft (e.g., the burr adaptor can be omitted) or connected to the drive shaft in another way. But in the illustrated embodiment, the burr adaptor 100 is coupled to the drive shaft 24 for conjoint rotation with the drive shaft about the rotational axis A1. The proximal annular hub 38 of the burr 20 is also coupled to the burr adaptor 100 such that the burr rotates substantially conjointly with the burr adaptor about the rotational axis A1. Thus, the burr adaptor 100 couples the burr 20 to the drive shaft 24 for conjoint rotation with the drive shaft. The burr adaptor 100 can be coupled to the drive shaft 24 and the burr 20 in any suitable way. For example, in one embodiment, the burr adaptor is bonded to each of the drive shaft 24 and the proximal annular hub 38 of the burr 20 by one or more of a weld, an adhesive bond, and/or a heat bond. Mechanical fasteners can also be used in one or more embodiments. In certain embodiments, the burr adaptor 100 is bonded to each of the drive shaft 24 at a weld joint located generally at the distal end of the burr adaptor.

In the illustrated embodiment, the burr adaptor 100 is welded to the drive shaft 24 at a weld joint 101. The weld joint 101 can extend around the entire circumference of the drive shaft 24. It is understood that the weld joint 101 bonds the burr adaptor with the drive coil 80 of the drive shaft 24. Suitably, the burr adaptor 100 can be welded to the drive shaft 24 at a weld joint 101 that is spaced apart along the axis A1 distally from the proximal end of the burr adaptor. Thus, the weld joint 101 is located along a segment of the drive shaft 24 that is reinforced and made substantially non-bendable or inflexible (e.g., substantially rigid) by the burr adaptor 100. This is believed to limit forces on the weld joint 101 associated with bending, flexing, or deflection of the drive shaft 24. In the illustrated embodiment, the weld joint 101 is located at the distal end of the burr adaptor 100. The burr adaptor and/or burr can be welded to the drive shaft 24 at other locations in one or more embodiments.

The burr adaptor 100 can also be welded to the proximal annular hub 38 of the burr 20 at a weld joint (not shown). Though the weld joint between the burr adaptor 100 and the burr 20 is not shown, in one or more embodiments the weld joint between the burr adaptor and the burr radially overlaps the drive shaft 24. In one or more embodiments, the weld joint between the burr adaptor 100 and the burr 20 is spaced apart proximally of the distal end of the drive shaft 24 along the axis A1. Likewise, the weld joint between the burr adaptor 100 and the burr 20 can be spaced apart proximally from the distal end of the burr adaptor.

In the illustrated embodiment, the proximal end portion of the burr adaptor 100, which protrudes proximally from the proximal end of the proximal annular hub 38 of the burr 20, is received in a flexible sleeve 102. The sleeve 102 has a length extending from a distal end that radially overlaps the burr adaptor 100 to proximal end that is spaced apart proximally of the proximal end of the burr adaptor along the axis A1. In the illustrated embodiment, the distal end of the sleeve 102 substantially abuts the proximal end of the burr 20. A proximal end segment of the sleeve 102 radially overlaps the drive shaft 24. The sleeve 102 thus extends contiguously along and circumferentially around a proximally protruding segment of the burr adaptor 100 and a segment of the drive shaft 24 immediately proximal of the burr adaptor. In the illustrated embodiment, the proximal end of the sleeve 102 is spaced apart distally from the distal end of the isolation sheath 70. The sleeve can also have other arrangements or be omitted in one or more embodiments. In one or more embodiments, the sleeve 102 comprises a polymer heat-shrink tube that is heat-shrunk onto the drive shaft 24 and the burr adaptor 100 after the burr adaptor is welded or otherwise attached to the drive shaft. In one or more embodiments, the sleeve 102 can provide strain relief to the distal end portion of the drive shaft 24 and/or the burr adaptor 100.

In one method of making the catheter 10, the burr adaptor 100 can be positioned over the distal end portion of the drive shaft 24 and welded (broadly, attached) to the drive shaft at the weld 101 (broadly, a joint location). For example, the step of welding the burr adaptor 100 to the drive shaft 24 can comprise welding the burr adaptor to a drive coil 80 of the drive shaft. Before or after welding the burr adaptor 100 to the drive shaft 24, the proximal annular hub 38 of the burr 20 can be positioned over the burr adaptor and attached (e.g., welded) to the burr adaptor at a joint location that will radially overlap the drive shaft relative to the axis A1. In one embodiment, the burr 20 is welded to the burr adaptor 100 while the proximal end portion of the burr adaptor 100 protrudes proximally of the proximal end of the burr. Before attaching the burr 20 to the burr adaptor 100, the balloon 22 can be loaded into the burr. For example, in one embodiment, the balloon 22 is fluidly and rotationally coupled to the inflation conduit 26 (as described above) before or after the inflation conduit is loaded longitudinally through drive shaft 24. The balloon 22 can be loaded into the burr 20 before or after the balloon is coupled to the inflation conduit 26. The drive shaft 24 can be loaded into the isolation sheath 70 before or after the drive shaft is welded to the burr adaptor, connected to the burr 20, and/or has the inflation conduit 26 loaded therein.

F. Distal Joint Between Inflation Conduit and Drive Shaft

Referring still to FIG. 4, in the illustrated embodiment, the inflation conduit 26 is joined to the drive shaft 24 at a joint 104 located adjacent the distal end portion of the catheter body 14. As will be explained below, both the drive shaft 24 and the inflation conduit 26 are connected to a rotational prime mover in the handle 16. The prime mover is configured to rotate the drive shaft 24 and the inflation conduit 26 about the rotational axis A1. Because the drive shaft 24 and the inflation conduit 26 may have different constructions, they may not have identical rotational responses at their distal ends to the same rotational drive force imparted on them adjacent their proximal ends. To counteract potential differences in the dynamic responses of the distinct structures, the joint 104 couples the inflation conduit 26 to the drive shaft 24 for conjoint rotation with the drive shaft at a location adjacent the distal end of the catheter body 14. Thus, the joint 104 ensures that the balloon 22, which is conjointly attached to the inflation conduit 26, rotates substantially conjointly with the burr 20, which is conjointly attached to the drive shaft 24.

In one or more embodiments, the distal joint 104 comprises a heat bond between the inflation conduit 26 and the drive shaft 24. In other words, the inflation conduit 26 is heat bonded to the drive shaft 24 at the distal joint 104. For example, the outer inflation tube 62 can be heat bonded to an inner surface portion of the drive shaft 24. The distal joint 104 between the drive shaft 24 and the inflation conduit 26 can be formed in other ways in one or more embodiments. For example, the joint 104 can be formed by welding, and/or an adhesive bond in one or more embodiments.

In the illustrated embodiment, the distal joint 104 is spaced apart proximally from the proximal end of the burr 20. The distal joint 104 is also spaced apart proximally of the proximal end of the burr adaptor 100, as well as from the bonds between the burr adaptor and the burr 20 and the drive shaft 24 (e.g., the weld 101). The distal joint 104 is also spaced apart proximally from the distal end of the balloon 22. For example, as shown in FIG. 4, the distal joint 104 can comprise an annular joint located at about the same radial distance from the axis A1 as the annular overlap segment 50A of the proximal neck 50 of the balloon 22. In the illustrated embodiment, the distal joint is located immediately adjacent to the distal end of the overlap segment 50A. The distal joint can have other locations or configurations in one or more embodiments. For example, it is expressly contemplated that the distal joint could have a length that differs from what is shown. It is further contemplated that the distal joint could include a plurality of discrete bonds at spaced apart locations.

In one method of making the catheter 10, at least the outer inflation tube 62 of the inflation conduit 26 is loaded into the drive shaft 24. For example, the outer inflation tube 62 can be positioned in the drive shaft 24 so that the distal end of the outer inflation tube is spaced apart proximally from the distal end of the drive shaft. In this position, at least a distal portion of the inflation lumen 28 is pressurized until the outer inflation tube 62 radially expands to contact inner surface of the drive shaft 24 adjacent the distal end thereof. In one embodiment, this step of expanding the outer inflation tube 62 under pressure can be performed after the inner inflation tube 60 is loaded into the outer inflation tube, and in one or more embodiments, also after the balloon 22 is operably coupled to the inflation conduit 26. In one or more embodiments, the coil 74 (FIG. 8) of the inner inflation tube 60 radially reinforces the inner inflation tube to inhibit radial compression of the inner inflation tube while the outer inflation tube 62 is radially expanded. In another embodiment, the outer inflation tube 62 is pressurized and expanded before the inner inflation tube 60 is loaded into the outer inflation tube. While the outer inflation tube 62 is radially expanded under pressure to contact the inner surface of the drive shaft 24, heat is applied to at least one of the drive shaft 24 and the outer inflation tube at the location of the joint 104. The applied heat creates a heat bond 104 between the drive shaft 24 and the outer inflation tube 62. For example, the applied heat causes the polymer of the drive shaft laminate 82 and/or the polymer of the outer inflation tube 62 to flow to form the heat bond 104. It will be appreciated that the distal joint 104 between the inflation conduit 26 and the drive shaft 24 can be formed in other ways in one or more embodiments.

III. Handle

Referring to FIGS. 1 and 9-15, a handle 16 can be operably connected to the proximal end portion of the catheter body 14 to facilitate using various aspects of the catheter 10. For example, as will be explained in further detail below, the handle 16 can include a rotational prime mover that is configured to be connected to the drive shaft 24 and the inflation conduit 26 such that the prime mover can selectively rotate the drive shaft and inflation conduit about the rotational axis A1. Furthermore, the illustrated handle 16 includes controls for controlling the prime mover to selectively rotate the drive shaft 24 and the inflation conduit 26 as the catheter 10 navigates through a body lumen and/or removes tissue from a body lumen. In addition, the handle 16 can include passaging (described below) that is configured to fluidly couple a source of inflation fluid (not shown) to the inflation lumen 28 and/or a source of flushing fluid (not shown) to one or both of the flushing lumen 86 and the guidewire lumen 72 of the catheter body 14. As is still further explained below, the handle 16 can also include a mechanism for moving the drive shaft 24, the inflation conduit 26, and/or the burr assembly 12 along the axis A1 relative to the isolation sheath 70. The handle 16 can also be configured such that the guidewire G is passable from the catheter body 14 proximally through the handle such that the handle is then slidable along the guidewire. It will be understood that embodiments of the handle can include any one or more of the features described herein and/or other features.

A. Housing

The handle 16 comprises a housing 110. The illustrated housing 110 includes a bottom housing member 114, and a top housing member 112 that is configured to be secured (e.g., using mechanical fasteners such as screws, integral locking features such as tabs and recesses) to the bottom housing member as shown, for example in FIG. 9. Each of the housing members 112, 114 can comprise an individually injection-molded plastic component. Handles can have housings of other configurations in one or more embodiments. The assembled housing 110 defines an interior. Various components of the handle 16 described below are received in the interior of the housing 110. The housing 110 has length and a distal end portion and a proximal end portion spaced apart along the length. The distal and proximal end portions of the housing 110 can be defined by distal and proximal end walls, respectively. In addition, the housing 110 can have a top wall, a bottom wall, and opposite first and second side walls. The walls of the housing 110 define the interior. In the illustrated embodiment, the bottom wall of the housing has a contoured surface that generally conforms to the top of a human thigh, such that the handle 16 can be positioned on the thigh of a practitioner as the practitioner uses the handle. The contoured bottom surface of the housing also defines a plurality of elongate stabilizing ribs 111 (FIGS. 11 and 12) for stabilizing the handle 16 on the thigh or other curved surface. The practitioner can also control the catheter 10 using the handle 16 while the handle is positioned on a flat surface or any other suitable support. In the illustrated embodiment, the bottom wall of the handle is configured to sit level on a flat surface such as a tabletop.

Figure 13:
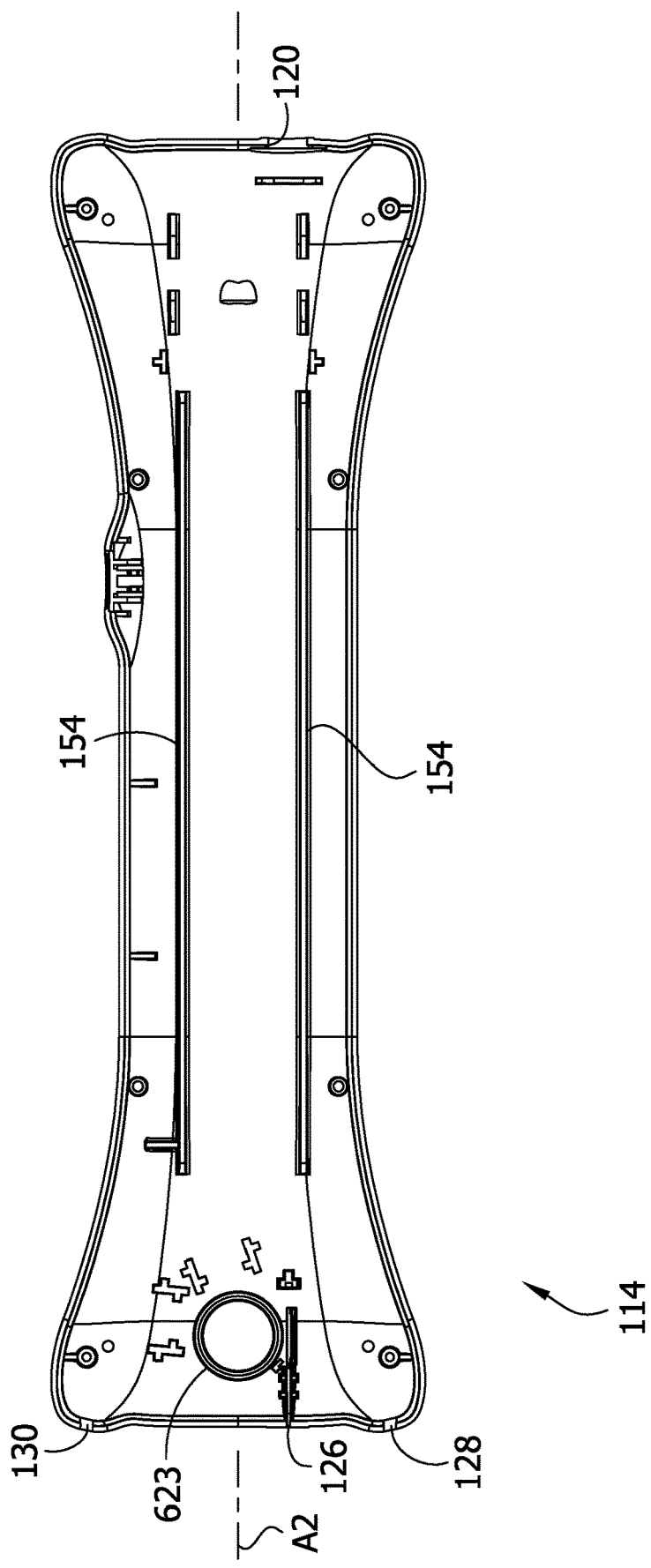
FIG. 13 is a top plan view of a bottom housing member of the handle.
Figure 15:
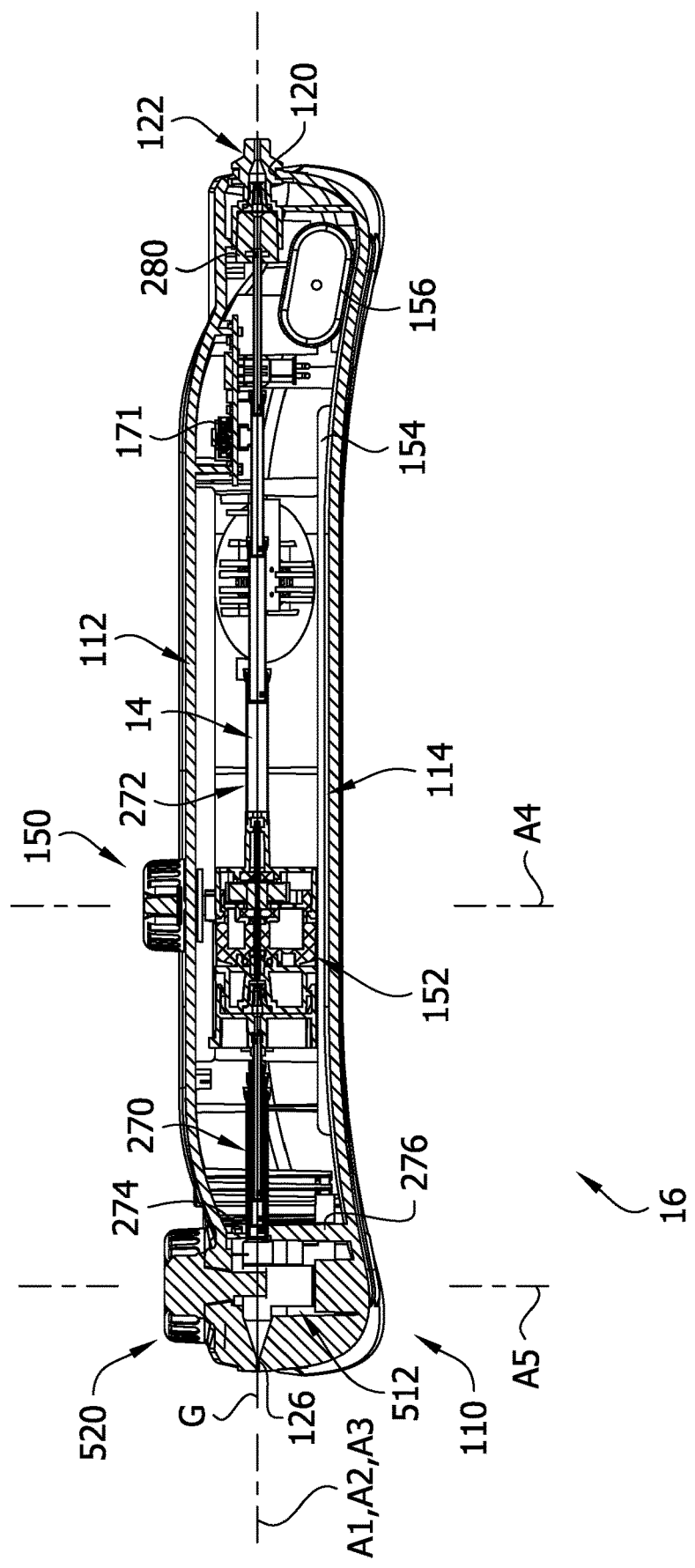
FIG. 15 is a cross section taken in the plane of line 15-15 of FIG. 11.

Referring to FIGS. 13-15, in the illustrated embodiment, the distal wall of the housing 110 defines a catheter body opening 120 that is configured to receive the proximal end of the catheter body 14 into the interior of the housing 110. In use, the guidewire G passes through the catheter body opening 120 in the distal wall of the housing 110 through the guidewire lumen 72 of the catheter body 14. In the illustrated embodiment, only the drive shaft 24 and the inflation conduit 26 pass proximally through the catheter body opening 120 into the middle portion of the housing 110. A distal hub, generally indicated at 122, which is received in the catheter body opening 120, attaches the proximal end portion of the isolation sheath 70 to the housing 110 such that substantially the entire length of the isolation sheath is external to the housing. As explained below, the drive shaft 24 and the inflation conduit 26 extend into the interior of the housing 110 through the distal hub 122 and are movable along the length of the housing and the length of the isolation sheath 70. In contrast, the isolation sheath 70 is anchored in the distal hub 122 such that the isolation sheath cannot move with respect to the housing along the length of the housing. In the illustrated embodiment, the catheter body opening 120 is formed in the distal wall of the housing 110 at the parting line between the housing members 112, 114. The catheter body opening can have other configurations in one or more embodiments.

Figure 10:
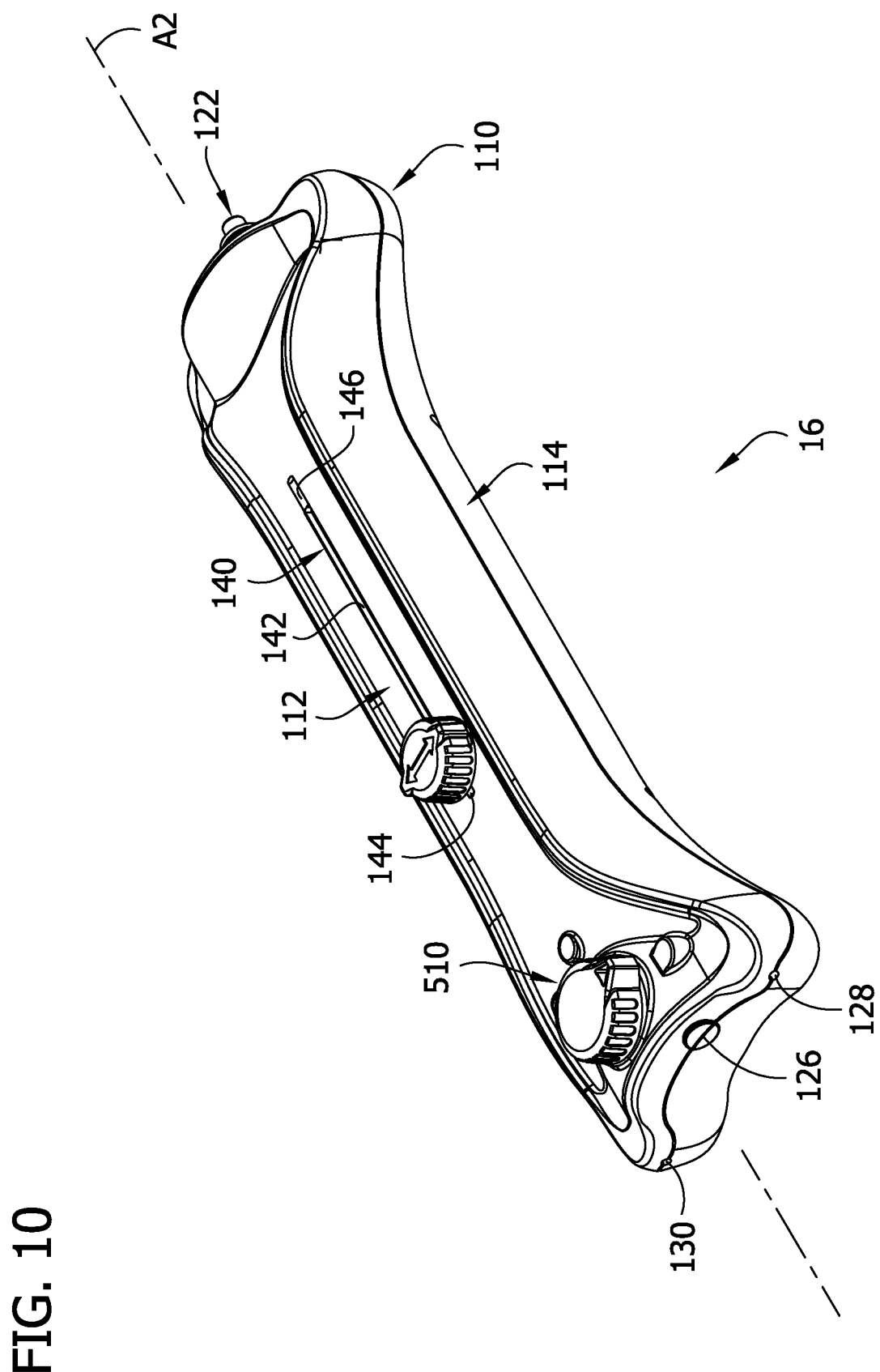
FIG. 10 is a front perspective of the handle.
Figure 11:
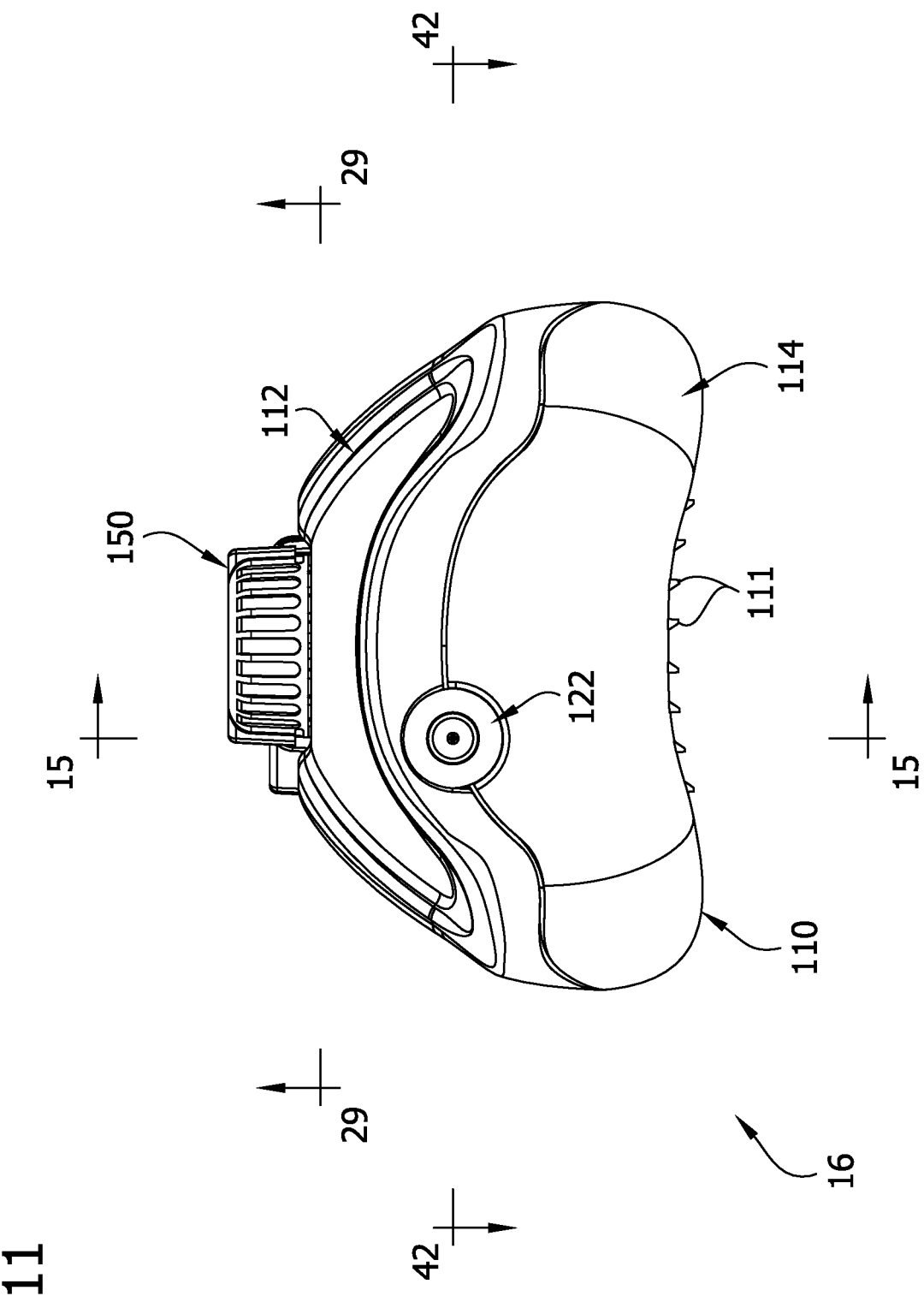
FIG. 11 is a distal end elevation of the handle.
Figure 12:
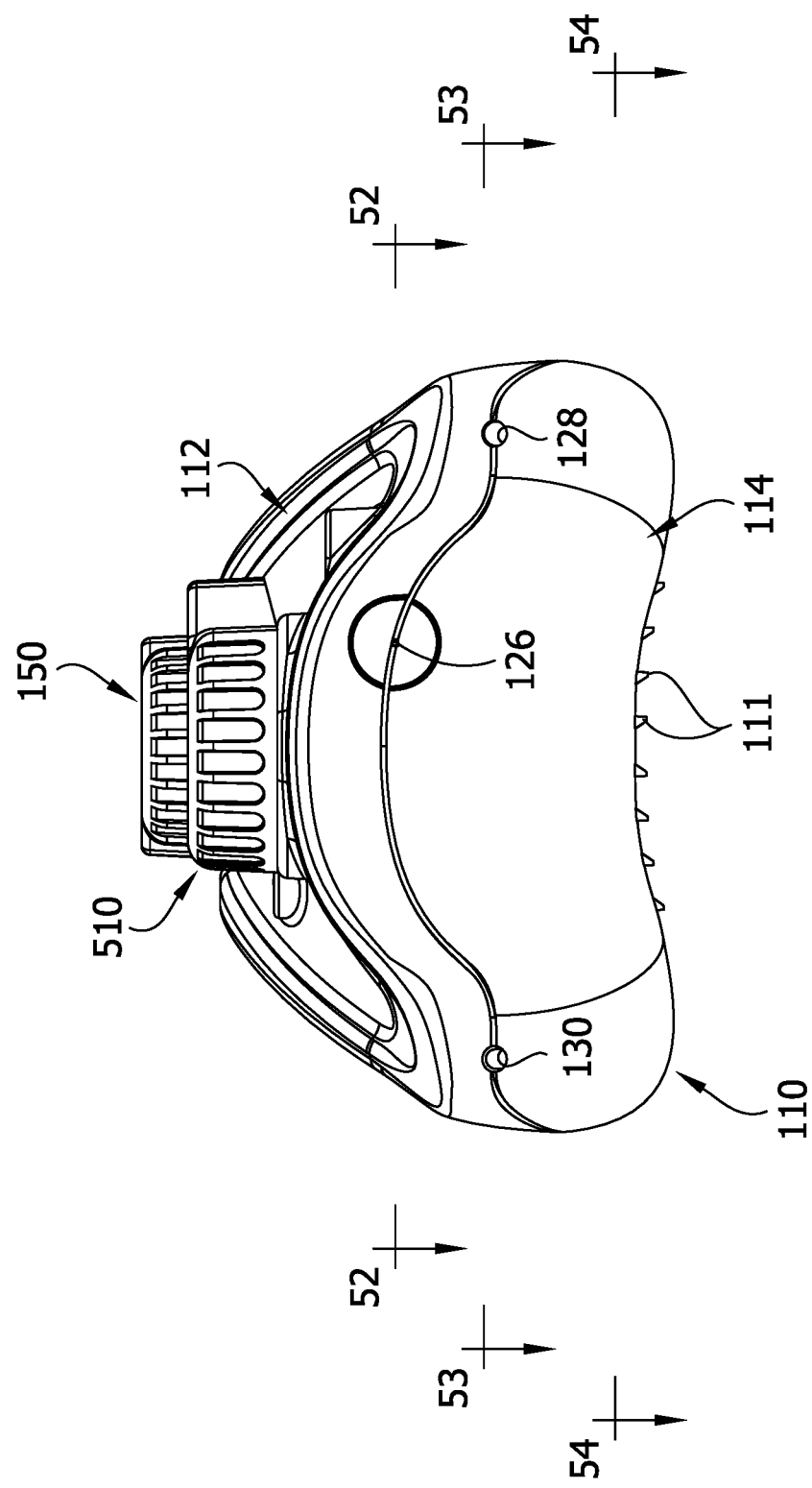
FIG. 12 is a proximal end elevation of the handle.

Referring to FIG. 10, in the illustrated embodiment, the proximal wall of the housing 110 defines a guidewire opening 126. The guidewire opening 126 is configured so that the guidewire G is passable through the guidewire opening from the interior 116 of the housing 110. In one or more embodiments, the guidewire opening 126 is generally aligned with the catheter body opening 120 such that the guidewire G is passable through the catheter body 14 along the length of the handle 110 and further through the guidewire opening. Suitably, the guidewire opening 126 and the catheter body opening 120 are configured such that the housing 110 is slidable along the guidewire G and/or the guidewire is slidable through the handle 16. As will be explained below, the handle 16 can also be configured to selectively impart a braking force on the guidewire G that inhibits relative movement between the housing 110 and the guidewire (e.g., one or both of rotation and longitudinal translation of the guidewire with respect to the housing). In the illustrated embodiment, the guidewire opening 126 is formed in the proximal wall of the housing 110 at the parting line between the housing members 112, 114. The guidewire opening can have other configurations in one or more embodiments.

The proximal wall of the illustrated handle housing 110 also defines an inflation port 128 and a flushing port 130. In one or more embodiments, one or both of the inflation port and the flushing port can have another location and/or be omitted. As explained below, passaging inside the handle 110 is configured to provide fluid communication between the inflation port 128 and the inflation lumen 28 of the catheter body. Passaging inside the handle 110 is also configured to provide fluid communication between the flushing port 130 and each of the flushing lumen 86 and the guidewire lumen 72. The inflation port 128 can suitably be configured to be fluidly coupled to a source of inflation fluid (not shown) external to the handle 110. Likewise, the flushing port 130 can be configured to be fluidly coupled to a source of flushing fluid (not shown) external to the handle 110. For example, in one or more embodiments, fluid couplers or fittings (e.g., a luer fitting) are installed in one or both of the inflation port 128 and the flushing port 130. In one or more embodiments, the source of flushing fluid and/or inflation fluid can instead be located inside the handle. For example, the handle can comprise a compressed gas cylinder or an air compressor that is configured to be fluidly coupled to the inflation lumen of the catheter body. Likewise, an internal source of flushing fluid can be connected to one or both of the flushing lumen and the guidewire lumen in one or more embodiments. In the illustrated embodiment, the inflation port 128 and the flushing port 130 are formed in the proximal wall of the housing 110 at the parting line between the housing members 112, 114. The ports can have other configurations in one or more embodiments.

Figure 9:
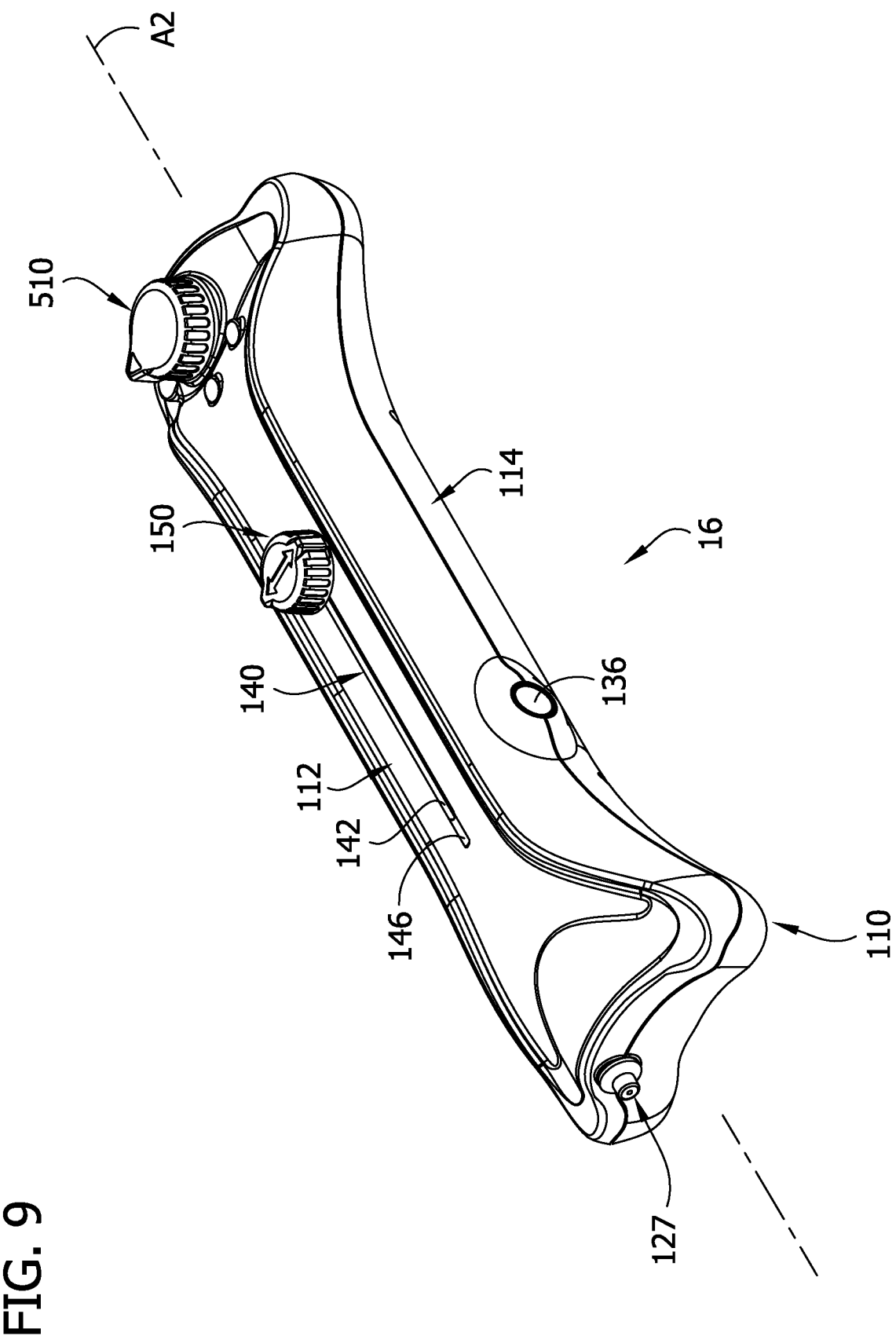
FIG. 9 is a rear perspective of a handle of the catheter.

Referring to FIG. 9, the illustrated handle 16 includes a push button 136 (broadly, a rotation actuator or user control; e.g., a rotation actuator) that is accessible outside the housing 110 (e.g., through a sidewall of housing). For example, the push button 136 can extend through an appropriately sized hole in the side wall of the housing 110. As explained below, in certain operating modes of the catheter 10, the button 136 is configured to be depressed to selectively actuate the prime mover to rotate the drive shaft 24, the inflation conduit 26, and the burr assembly 12. In other modes of the catheter 10, depressing the button does not actuate rotation. The button can have other functions in one or more embodiments. Although the push button 136 is located on the side of the handle housing 110 in the illustrated embodiment, it will be understood that a rotation actuator can be located elsewhere in one or more embodiments. Furthermore, it will be understood that the push button can be replaced with a different type of actuator for selectively actuating rotation in one or more embodiments.

The housing 110 can, in one or more embodiments, include structure that guides movement along a predefined path with respect to the housing. Referring to FIGS. 9 and 10, in the illustrated embodiment, the top wall (e.g., the top housing member 112) of the housing 110 defines an elongate race, generally indicated at 140, which extends along an axis A2. As will be explained in further detail below, the race 140 includes an elongate slot 142 and proximal and distal grooves 144, 146 that each extend generally along the axis A1. The slot 142 extends through the entire thickness of the top wall of the housing 110. As will be explained below, a portion of a slider knob, generally indicated at 150, is received in the slot 142 and is passable through the slot along the axis A2. Referring to FIGS. 14 and 15, the slider knob 150 is attached to a carriage inside the housing 110, which is generally indicated at 152. As will be explained below, the carriage is configured for movement with the slider knob through a range of motion extending along the axis A2. Referring to FIGS. 13 and 13A, in the illustrated embodiment, the bottom wall (e.g., the bottom housing member 114) of the housing 110 defines rails or tongues 154 and the top wall of the housing 110 defines corresponding rails or tongues 154'. In the illustrated embodiment, the bottom housing member 114 includes two rails 154 that protrude up from the bottom wall of the housing 110 and extend generally along the axis A2. The top housing member 112 likewise includes two rails 154' that protrude down from the top wall of the housing 110 and extend generally along the axis A2. As explained below, the carriage 152 is configured to slidably engage the rails 154', whereby the carriage is constrained to move with respect to the housing 110 along the axis A2. It will be understood that other housings can have other features for guiding movement of a carriage and/or have other configurations (e.g., a configuration that does not facilitate movement of a carriage) in one or more embodiments.

As shown in FIGS. 13-15, the housing members 112, 114 can include various additional features that support the internal components of the handle 16. For example, in the illustrated embodiment, the bottom housing member 114 is configured to mount a battery 156 (broadly, a power supply; e.g., a removable 9-volt battery) inside the housing 110. The battery 156 is suitably configured to provide power to various features of the catheter 10. In one or more embodiments the housing 110 is configured to mount a control circuit 171 (e.g., a printed circuit board; FIG. 15) inside the housing. The control circuit 171 can comprise control electronics such as a memory storing control software and a processor in communication with the memory and configured to execute the control software. The control software can be configured, when executed, to control various aspects of the catheter 10. For example, as described below, in one or more embodiments, the control software can be configured to execute a drive regulation procedure that dictates how the catheter 10 responds to the push button 136 being depressed. Still other aspects of the housing 110 that are configured to support internal components of the handle 16 are described in further detail below.

The handle housing can have configurations other than the illustrated configuration in one or more embodiments. Certain features of the housing 110 are included to support or interoperate with particular components or functional features of the illustrated handle 16. As has been explained and will also be explained further below, it is understood that the components and features of a handle can vary from those of the illustrated embodiment. Thus, different configurations of the handle housing that are suitable for handles having other components and/or functional features.

B. Sliding Carriage

Referring to FIGS. 14-19, the carriage 152 comprises a block assembly 210. The block assembly 210 comprises a proximal block member 212 that defines a proximal end of the carriage 152 and a distal block member 214 that defines a distal end of the carriage. In addition, the block assembly 210 includes a flushing block member 216 that, as explained below, is configured to provide fluid communication between a source of flushing fluid (e.g., a source of flushing fluid coupled to the flushing port 130) and the guidewire lumen 72 of the catheter body 14. The block assembly 210 further includes an inflation block member 218 that, as is also explained below, is configured to provide fluid communication between a source of inflation fluid (e.g., a source of inflation fluid coupled to the inflation port 128) and the inflation lumen 28 of the inflation conduit 126. The inflation block member 218 is located generally between the distal block member 214 and the flushing block member 216 in the illustrated embodiment. The flushing block member 216 is located generally between the proximal block member 212 and the inflation block member 218. Each of the blocks 212, 214, 216, 218 can comprise an individually injection-molded plastic component. The blocks can also be formed in other ways in one or more embodiments. Although the illustrated carriage 152 comprises the block assembly 210, it will be understood that carriages can have other configurations in one or more embodiments.

Figure 19:
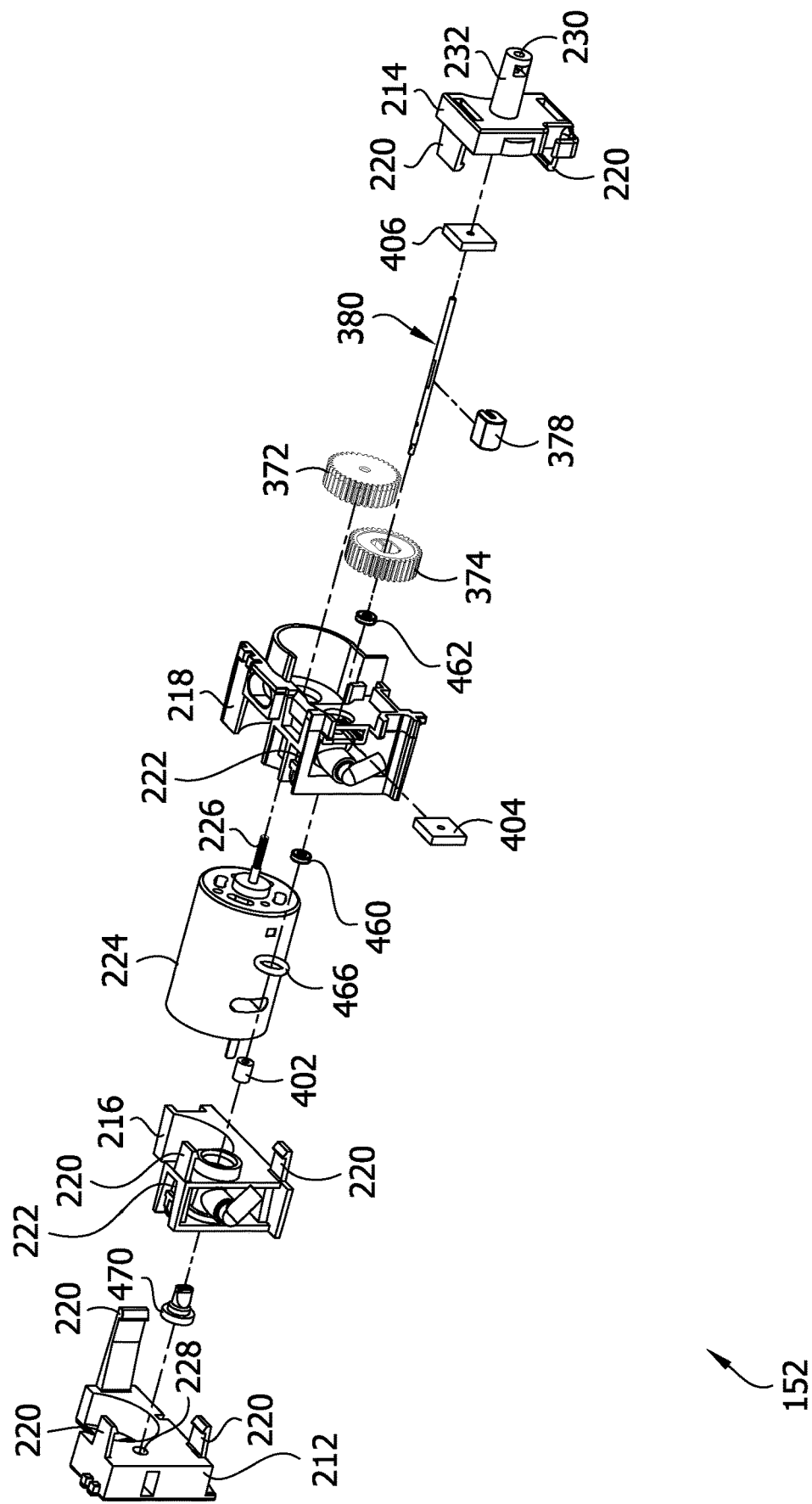
FIG. 19 is an exploded perspective of the carriage.

In the illustrated embodiment, the blocks 212, 214, 216, 218 of the block assembly 210 are configured to be secured to one another without the use of separate fasteners, adhesives, or the like. For example, the illustrated block assembly 210 comprises an assembly of interlocking blocks 212, 214, 216, 218. The block assembly can also be assembled in other ways in one or more embodiments. As shown in FIG. 19, the illustrated blocks 212, 216, 218 include locking tabs 220 (broadly, locking formations) that define catches that are configured to snap into recesses 222 (broadly, complementary locking formations) formed in one of the blocks 216, 218. When the tabs 220 are received in the recesses 222, the block members 212, 214, 216, 218 become interlocked and hold themselves together such that a distal end of the proximal block member engages a proximal end of the flushing block member, a distal end of the flushing block member engages a proximal end of the inflation block member, and a distal end of the inflation block member engages the proximal end of the distal block member. Various components can be mounted on the carriage 152 by being captured between the interlocked block members 212, 214, 216, 218 as described in further detail below. In one embodiment, each of the blocks 212, 214, 216, 218 is formed from a single piece of integrally, monolithically formed material. For example, in one or more embodiments, each of the blocks 212, 214, 216, 218 is a unitary injection-molded plastic component.

For example, the block assembly 110 is configured to mount an electric motor 224 (broadly, a driver or prime mover) in this fashion. As explained in further detail below, the electric motor 224 comprises the prime mover that is configured to drive rotation of the drive shaft 24 and the inflation conduit 26 about the rotational axis A1. In one or more embodiments, the motor 224 is configured to rotate the drive shaft 24 and the inflation conduit 26 about the axis A1 at a speed in an inclusive range of from about 500 rpm to about 100,000 rpm (e.g., an inclusive range of from about 5,000 rpm to about 25,000 rpm, an inclusive range of from about 8,000 rpm to about 15,000 rpm, an inclusive range of from about 10,000 rpm to about 12,000 rpm). One or more embodiments can use other types of rotational prime movers such as turbines, or pneumatic motors. The electric motor 224 can be powered by any suitable electrical power source such as the internal battery 156, or an external power source. In the assembled block assembly 210, the motor 224 is captured between the proximal block member 212 and the inflation block member 218. More specifically, the motor 224 extends from a proximal end portion received in a recess of the proximal block member 212, through a recess formed in the flushing block member 216, to a distal end portion that is received in a recess of the inflation block member 218. The recesses that are configured to receive the motor 224 are laterally spaced apart from inflation and flushing lumens defined in the block assembly 110, which are described in greater detail below. An output shaft 226 extends along a drive axis A3 of the motor 224 through a hole in a distal end wall of the inflation block member 218. As will be explained in further detail below, the drive axis A3 and the motor output shaft 226 are laterally spaced apart from the rotation axis A1 and the drive shaft 224 of the catheter body 214 (see FIG. 14).

The block assembly 210 (broadly, the carriage 152) is configured to slidably receive the guidewire G therein. The block assembly 210 defines a proximal opening 228, a distal opening 230, and a main passage, generally indicated at 231, which extends from the proximal opening through the distal opening, which is described in greater detail below. In the illustrated embodiment, the proximal opening 228 is formed in a proximal end wall of the block assembly, which is defined by the proximal block member 212. The illustrated distal opening 230 is formed at the distal end of an elongate tube 232 of the distal block member 214, and which defines a portion of the main passage 231 (FIG. 39A) through the block assembly 210. The main passage 231 can extend generally parallel to the axis A2 along which the carriage 152 is configured to move. For example, an axis of the main passage 231 can be coaxial with the axis A1 of the catheter body 14 in the handle 16 in one or more embodiments. The main passage 231 is configured so that the guidewire G is passable through the main passage from the distal opening 230 through the proximal opening 228. When the guidewire G is received in the main passage 231, the carriage 152 can slide with respect to the guidewire as it moves along the axis A2. In one embodiment, the axis A2 along which the carriage 152 is configured to move with respect to the housing 110 is generally parallel to the axis A1 of the portion of the catheter body 14 that is received in the handle 16. Suitably, the proximal and distal openings 230 can be located at spaced apart locations along the axis A1 such that the guidewire passes through the main passage 231 along the axis A1. Thus, the guidewire G can extend generally along the axis A1 of the catheter body through the block assembly 210 such that guidewire can be configured to be passed through the carriage 152 into the guidewire lumen 72 of the catheter body 14.

The carriage 152 is configured for sliding along the axis A2 with respect to the handle housing 110. The bottom portion of the block assembly 210 comprises feet 234 (broadly, bearings) that are configured to slide along the carriage rails 154. In the illustrated embodiment, the feet 234 project downward at the bottom end portions of the proximal block member 212 and the inflation block member 218, but the feet can have other configurations in one or more embodiments. The feet 234 are configured to slidably engage the outboard longitudinal edges of the carriage rails 154 to inhibit the carriage 152 from moving transverse to the carriage rails. It is understood that the feet can also slidably engage the inboard longitudinal edges of the carriage rails to achieve the same effect. In addition, the top portion of the illustrated carriage 152 defines grooves 236 for slidably receiving the rails 154' of the top wall of the housing 110. In the illustrated embodiment, the grooves 236 are formed in tabs 238 projecting upward at the top end portions of the proximal block member 212 and the inflation block member 218, but the grooves can have other configurations in one or more embodiments. The engagement of the bottom and top portions of the block assembly 210 with rails 154, 154' of the housing 110 substantially constrains the carriage 152 to move only along the axis A2 with respect to the handle housing 110. In one or more embodiments, the block assembly 210 can have a smaller clearance connection with the bottom rails 154 such that bottom rails provide the main constraint against transverse movement of the carriage during use. In such an embodiment, the top rails 154' can provide an alignment feature that is useful during manufacturing. The carriage 152 is substantially prevented from moving in vertical and lateral directions transverse to the axis A2. It is understood that that a carriage can be movably coupled to handle housing in other ways in one or more embodiments. For example, the block assembly can comprise other types of bearings in addition to or in lieu of the feet 234.

C. Alignment Guides for Catheter and Guidewire

Referring to FIGS. 14-15B, in one or more embodiments, the handle 16 can comprise a guidewire alignment guide, generally indicated at 270, and/or a catheter body alignment guide, generally indicated at 272. In general, the alignment guides 270, 272 are respectively configured to align the guidewire G and the catheter body 14 (each, broadly, a flexible elongate body) with the carriage 152 as the carriage moves along the axis A2 relative to the housing 110. For example, the guidewire alignment guide 270 is configured to engage and support a portion of the guidewire G received in the handle 16 proximal to the carriage 152 such that the alignment guide orients the portion of the guidewire to extend parallel to the axis A2. More specifically, the illustrated guidewire alignment guide 270 aligns the portion of the guidewire G so that it extends generally along the axis A1 of the catheter body 14, which is oriented parallel to the axis A2 inside the handle 16. In addition, the guidewire alignment guide 270 is configured to orient a portion of the guidewire G such that it extends in a substantially straight line between the guidewire opening 126 and the proximal opening 228 of the carriage 152.

The catheter body alignment guide 272 is configured to engage and support a proximal end portion of the catheter body 14 in the handle 16 such that the alignment guide orients the portion of the catheter body to extend parallel to the axis A2. In addition, the catheter body alignment guide 272 is configured to orient the portion of the catheter body 14 so that it extends in a substantially straight line from the end of the carriage 152 to the distal hub 122. In the illustrated embodiment, only the drive shaft 24 and the inflation conduit 26 of the catheter body 14 are received in the handle housing 110. The proximal end of the isolation sheath 70 terminates at the distal wall of the housing 110. Thus, in the illustrated embodiment, the catheter body alignment guide 272 does not engage any portion of the isolation sheath 70. Moreover, the isolation sheath 70 does not provide a barrier between the rotating drive shaft 24 and the catheter body alignment guide 272. Suitably, the catheter body alignment guide 272 is configured to allow the drive shaft 24 to rotate with respect to the alignment guide about the rotational axis A1. For example, in one or more embodiments the catheter body alignment guide 272 can extend generally along the rotational axis A1. Although the illustrated embodiment includes both a guidewire alignment guide 270 and a catheter body alignment guide 272, in one or more embodiments, one or both of the alignment guides can be omitted. In addition, alignment guides having other configurations and/or that are configured to support other types of flexible elongate bodies associated with a catheter can also be used in one or more embodiments.

Each of the alignment guides 270, 272 is extendable and retractable such that the alignment guide can maintain the alignment of the respective one of the guidewire G and the catheter body 14 as the carriage 152 moves along the axis A2 through its range of motion with respect to the housing 110. Each alignment guide 270, 272 has a fixed end portion that is fixed in place with respect to the handle housing 110 and a movable end portion that is configured to move conjointly with the carriage 152. The guidewire alignment guide 270 has a fixed proximal end portion and a moveable distal end portion, and the catheter body alignment guide 272 has a fixed distal end portion and a moveable proximal end portion. The alignment guides can have other arrangements or orientations in one or more embodiments. In the illustrated embodiment, the fixed end portion of the guidewire alignment guide 270 is staked between top and bottom pins 274, 276 (FIG. 15A) located adjacent the proximal end portion of the housing 110. The movable end portion of the guidewire alignment guide 270 is secured to the proximal end portion of the carriage 152. For example, in the illustrated embodiment, the movable end portion of the guidewire alignment guide 270 is secured to the block assembly 210 inside the proximal opening 228. The fixed end portion of the catheter body alignment guide 272 is secured in an anchor member 280 (described below) that is mounted on the housing 110 adjacent the distal end portion thereof. The movable end portion of the catheter body alignment guide 272 is secured to the distal end of portion of the carriage 152. For example, in the illustrated embodiment, the movable end portion of the catheter body alignment guide 272 is secured about the distal tube 232 of the block assembly 210. The fixed and movable end portions of an alignment guide can be secured to the handle housing and carriage in other ways in one or more embodiments.

Referring to FIGS. 20-24, each of the illustrated alignment guides 270, 272 comprises a substantially identical telescoping assembly, which is generally indicated at reference number 290. Although the illustrated embodiment uses two identical telescoping assemblies 270 to form the guidewire alignment guide 270 and the catheter alignment guide 272, in one or more embodiments the two alignment guides can have different configurations and/or one or both of the alignment guides can be other than a telescoping assembly. In the illustrated embodiment, the telescoping assembly 290 is a tubular telescoping assembly. The tubular telescoping assembly 290 defines an open-ended longitudinal passage 292. In the guidewire alignment guide 270, a portion of the guidewire G is configured to extend longitudinally through the passage 292 (see FIG. 15A). In the catheter body alignment guide 272, a portion of the catheter body 14 is configured to extend longitudinally through the passage 292 (see FIG. 15B). The guidewire G can also extend longitudinally through the guidewire lumen 72 in the portion of the catheter body 14 that extends through the passage 292 of the catheter body alignment guide 272. In each alignment guide 270, 272, the telescoping assembly 290 extends circumferentially around the respective one of the guidewire G and the catheter body 14, and thereby aligns the respective one of the guidewire and the catheter body along the length of the telescoping assembly. In the illustrated embodiment, each telescoping assembly 290 is generally coaxial with the axis A1 when installed in the handle 16. Thus, each alignment guide 270, 272 is configured to receive the respective one of the guidewire G and the catheter body 14 in the longitudinal passage 292 and thereby align the respective one of the guidewire and the catheter body for extending generally along the axis A1 through the handle 16. The telescoping assembly 290 of the catheter body alignment guide 272 is suitably configured so that the catheter body 14 can rotate about the axis A1 (and about the guidewire G) inside the passage 292. In one or more embodiments, the telescoping assembly can have other configurations for maintaining longitudinal alignment of a flexible elongate body.

Figure 20:
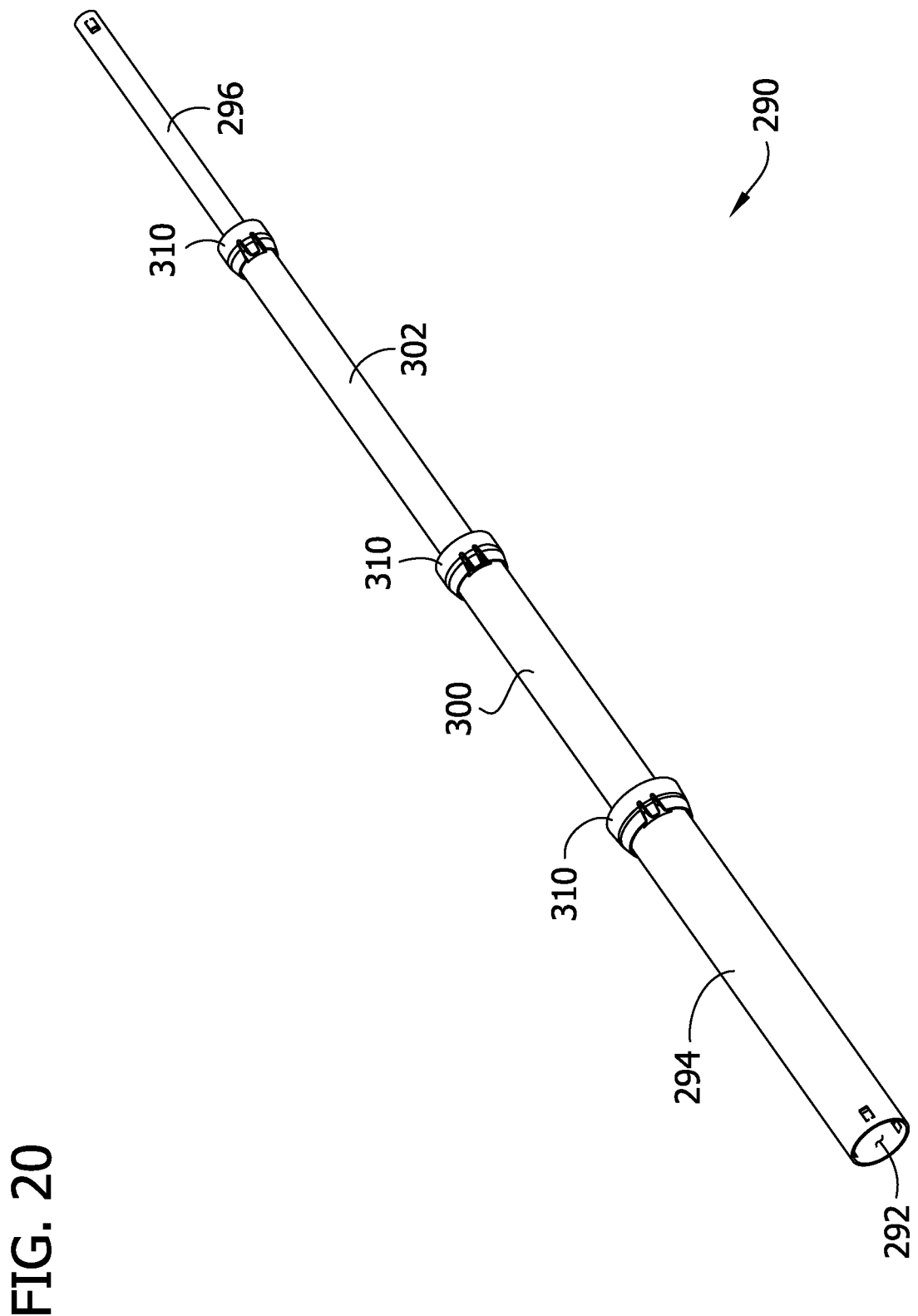
FIG. 20 is a perspective of a telescoping alignment guide of the handle in an extended configuration.
Figure 21:
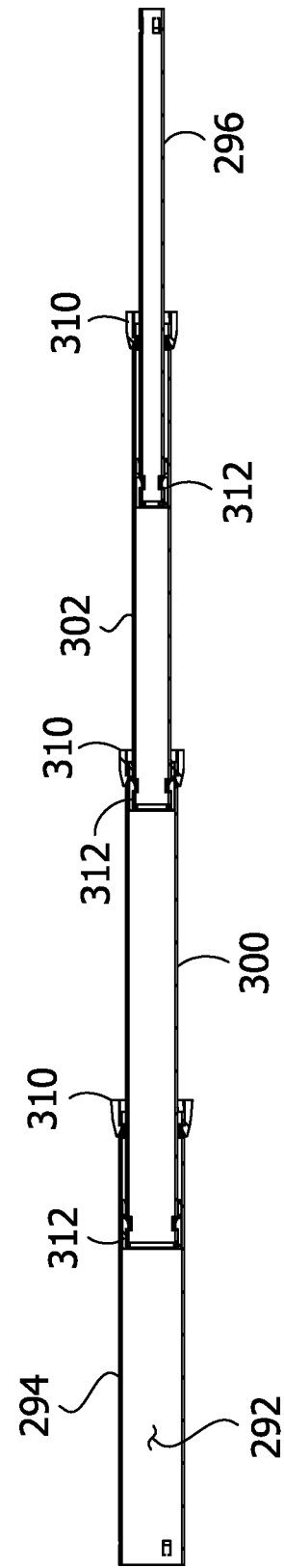
FIG. 21 is a longitudinal cross section of the telescoping alignment guide in the extended configuration.
Figure 22:
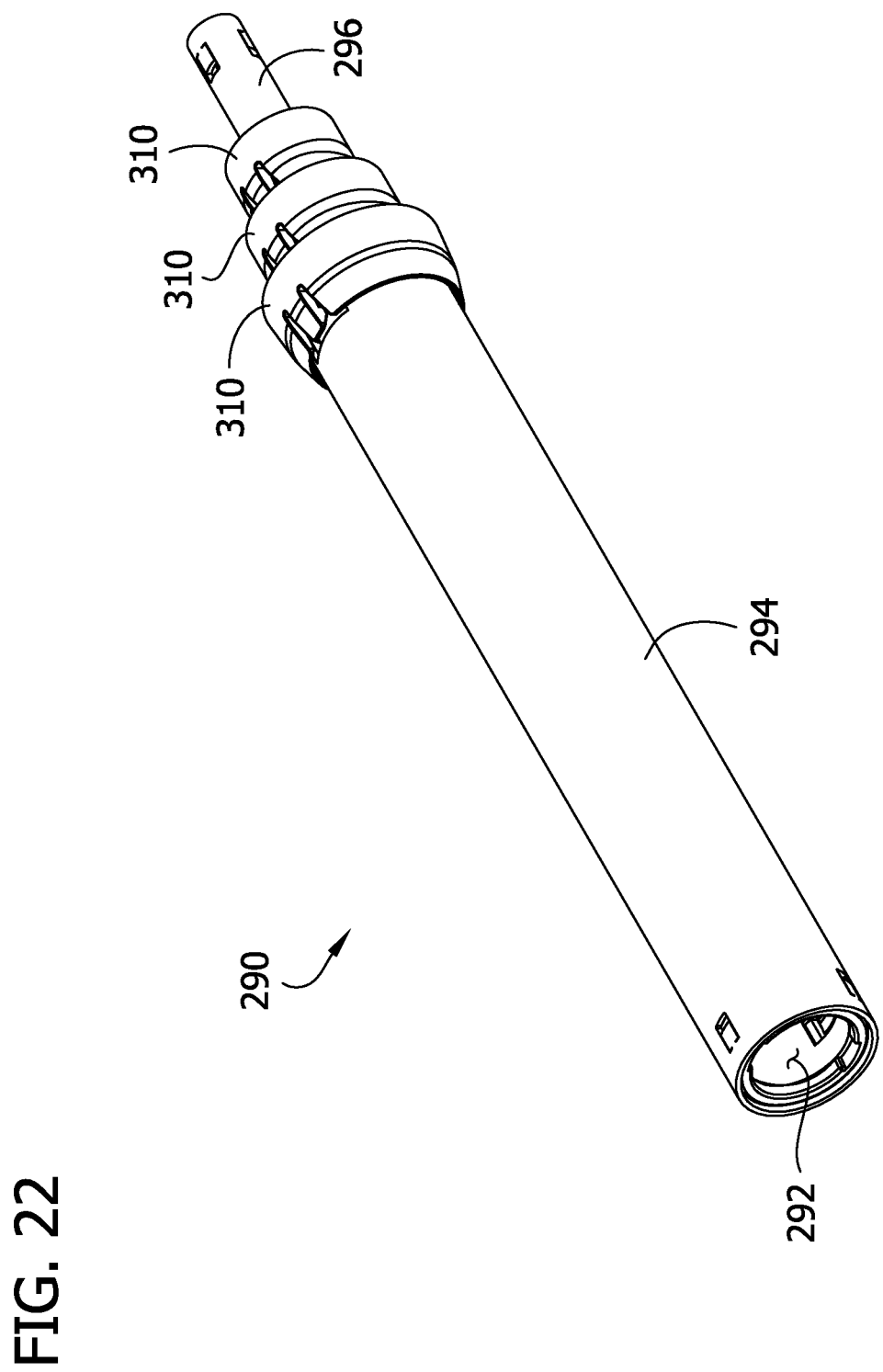
FIG. 22 is a perspective of the telescoping alignment guide in a retracted configuration.
Figure 23:
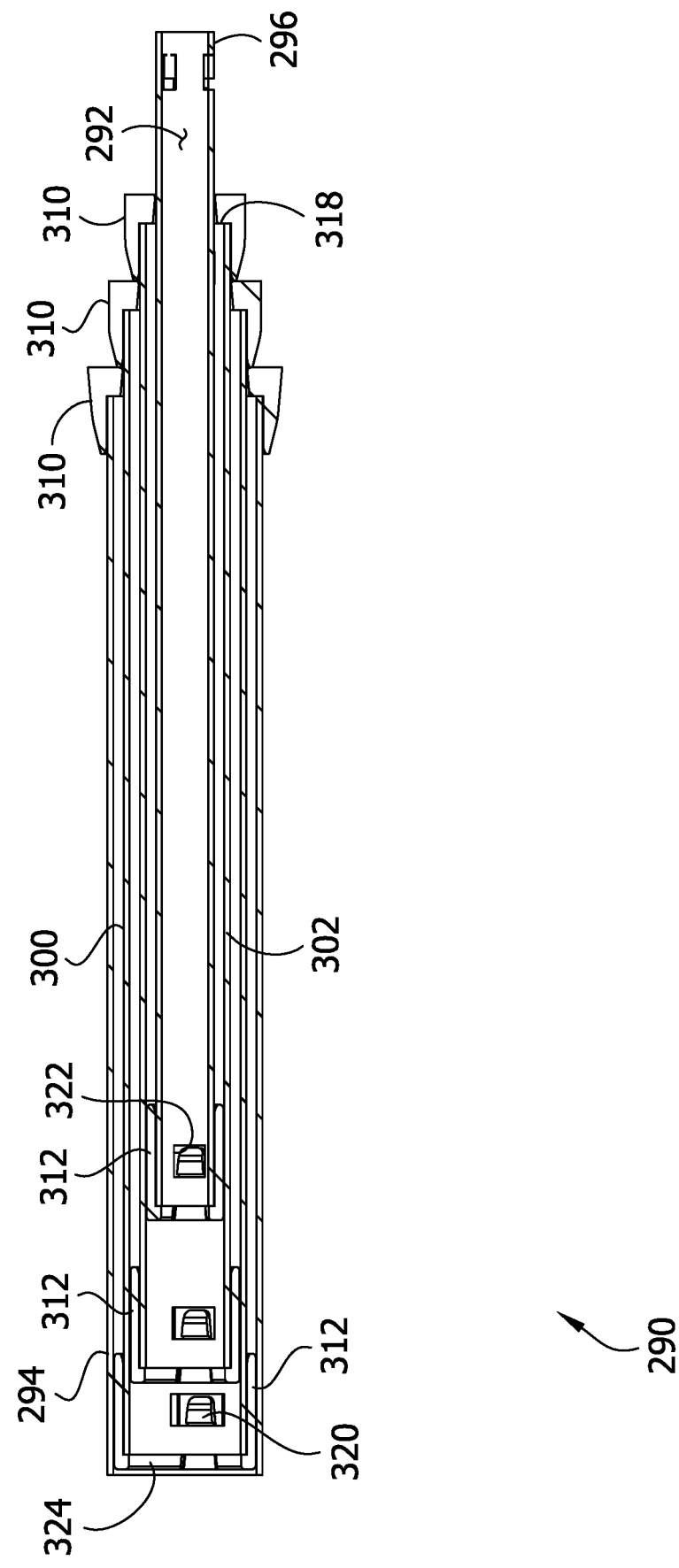
FIG. 23 is a longitudinal cross section of the telescoping alignment guide in the retracted configuration.

The illustrated telescoping assembly 290 comprises a plurality of generally concentric telescoping tubes 294, 296, 302, 304 (each, broadly, a telescoping member) that are configured to telescopically extend to a fully extended position shown in FIGS. 20 and 21 and telescopically retract to a fully retracted position shown in FIGS. 22 and 23. More specifically, the telescoping assembly 290 comprises a large end tube 294 that defines a large end portion of the telescoping assembly and a small end tube 296 that defines a small end portion of the telescoping assembly. In the illustrated handle 16, the large end tube 294 forms the proximal end portion in each of the guidewire alignment guide 270 and the catheter body alignment guide 272. The small end tube 296 forms the distal end portion of each in the guidewire alignment guide 270 and the catheter body alignment guide 272. Thus, the large end tube 294 can also be referred to as a proximal end tube and the small end tube 296 can also be referred to as a distal end tube in the illustrated embodiment. It is understood that the telescoping assemblies can have other orientations in one or more embodiments. For ease and clarity of reference, however, in this disclosure the terms 'distal' and 'proximal' will be used to describe relative positions along the length of the telescoping assembly 290 as installed in the illustrated handle 16 (e.g., the small end tube defines the 'distal' end of the telescoping assembly and the large end tube defines the 'proximal' end of the telescoping assembly). It is understood that the same components can have other relative positions in one or more embodiments.

In the illustrated embodiment the large end tube 294 of the guidewire alignment guide 270 comprises a fixed end tube (e.g., defines the fixed end portion of the alignment guide) and the small end tube 296 of the guidewire alignment guide comprises a movable end tube (e.g., defines the movable end portion of the alignment guide). Conversely, the large end tube 294 of the catheter body alignment guide 272 comprises a movable end tube (e.g., defines the movable end portion of the alignment guide) and the small end tube 296 of the catheter body alignment guide comprises a fixed end tube (e.g., defines the fixed end portion of the alignment guide).

In addition to the large end tube 294 and the small end tube 296, the illustrated telescoping assembly 290 includes a middle telescoping subassembly comprising a large middle tube 300 and a small middle tube 302 (broadly, first and second tubes of the middle telescoping assembly). The small middle tube 302 is slidably received in the large middle tube 300. In the illustrated embodiment, the large middle tube 300 is concentrically and slidably received in the large end tube 296, the small middle tube 302 is concentrically and slidably received in the large middle tube, and the small end tube 296 is concentrically and slidably received in the small middle tube. The middle telescoping subassembly is extendable and retractable between the large end tube 294 and the small end tube 296. In the fully extended configuration of the telescoping assembly 290 the middle telescoping assembly is fully extended such that only a distal end portion of the large end tube 294 radially overlaps a proximal end portion of the large middle tube 300, only a distal end portion of the large middle tube radially overlaps a proximal end portion of the small middle tube 302, and only a distal end portion of the small middle tube radially overlaps the small end tube 296. The middle telescoping subassembly is nested concentrically between the large end tube 294 and the small end tube 296 in the fully retracted configuration of the telescoping assembly 290 (FIGS. 22 and 23). For example, the large end tube 294 radially overlaps a portion of each of the other tubes 296, 300, 302 in the fully retracted configuration. In the illustrated embodiment, the middle telescoping subassembly comprises two slidably engaged tubes 300, 302. In one or more embodiments, a middle telescoping subassembly can comprise more than two tubes. In addition, in one or more embodiments, no middle tubes or only a single middle tube can be slidably and concentrically arranged between the large end tube and the small end tube.

In the illustrated embodiment, each of the tubes 294, 296, 300, 302 comprises a single-piece tube (e.g., a single piece of hypotube) that has at least one annular end cap 310, 312 secured thereto. As will be explained below, the caps 310, 312 provide the slide bearings that facilitate the sliding extension and retraction of the telescoping assembly 290 and stops that prevent over-extension or over-retraction of the telescoping assembly. The telescoping assembly can have other configurations in one or more embodiments.

Figure 21A:
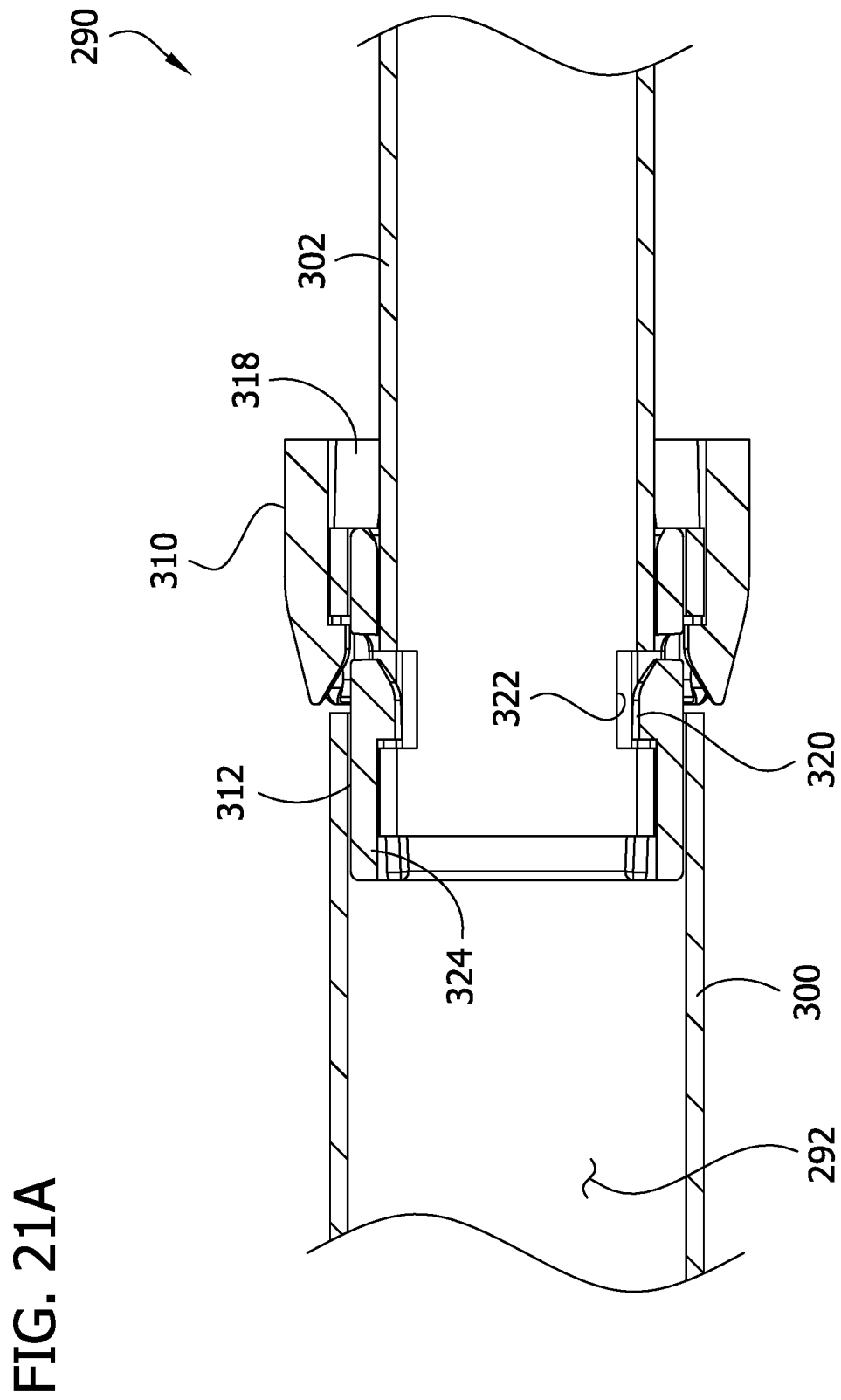
FIG. 21A is an enlarged view of a portion of FIG. 21.
Figure 24:
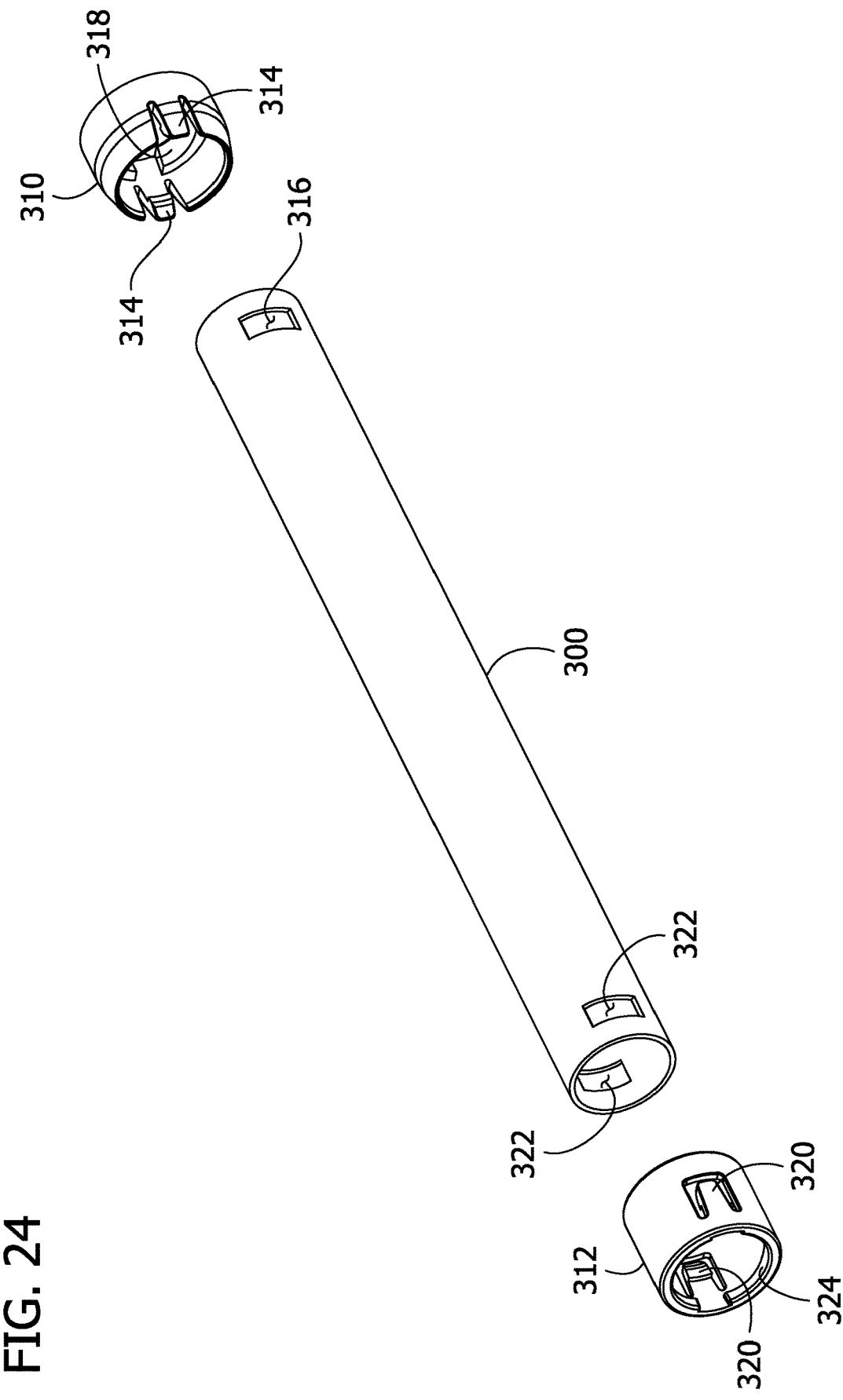
FIG. 24 is an exploded perspective of a middle telescoping member of the telescoping alignment guide.

In the illustrated embodiment, a distal annular end cap 310 (e.g., an outer annular end cap) is secured to the distal end portion of each of the large end tube 294, the large middle tube 300, and the small middle tube 302. No distal annular end cap is secured to the small end tube 296 because the distal end portion of the small end tube is secured in the anchor member 280 as explained above. As shown in FIGS. 21, 21A, and 24, each distal end cap 310 can comprise a proximal annular end portion that has an inner diameter that is approximately the same as the outer diameter of the distal end portion of the tube 294, 300, 302 to which it is secured. Thus, the distal annular end cap 310 can be pressed onto the distal end portion of the respective tube 294, 300, 302. In addition, as shown in FIG. 24, the distal end cap 310 can comprise one or more resilient locking tabs 314 (broadly, locking formations). Each tab 314 can include a catch or barb configured to be lockingly received in a respective distal locking slot 316 adjacent the distal end portion of the respective tube 294, 300, 302. For example, in one embodiment, the distal end cap 310 is configured such that the catches of the tabs 314 snap into respective slots 316 to lockingly secure the distal end cap to the respective tube 294, 300, 302 as the proximal annular end portion of the distal end cap is pressed onto the distal end portion of the respective tube with the tabs angularly aligned with the respective slots.

The illustrated distal end cap 310 also defines a generally annular, inwardly extending distal lip portion or shoulder 318. The shoulder 318 that has a proximal end that engages the distal-facing end of the tube 294, 300, 302 to which the end cap 310 is secured. As shown in FIG. 21A, the lip portion 318 defines a generally annular, radially inner surface that has an inner diameter that is smaller than the inner diameter of the tube 294, 300, 302 to which the distal end cap 310 is secured. The inner surface of the lip portion 318 is configured to provide a bearing surface that slidably engages the outer surface of a radially inwardly adjacent one of the concentric tubes 300, 302, 296. Because the lip portions 318 protrude radially inwardly, the inner surface of each of the tubes 294, 300, 302 to which a distal end cap 310 is secured is spaced apart radially outwardly from the outer surface of the respective radially inwardly adjacent one of the tubes 300, 302, 296. As will be explained in further detail below, the proximal end of the lip portion 318 is configured to engage a proximal end cap 312 of the radially inwardly adjacent one of the concentric tubes to provide a stop preventing over-extension beyond the fully extended configuration of the telescoping assembly 290.

Figure 15A:
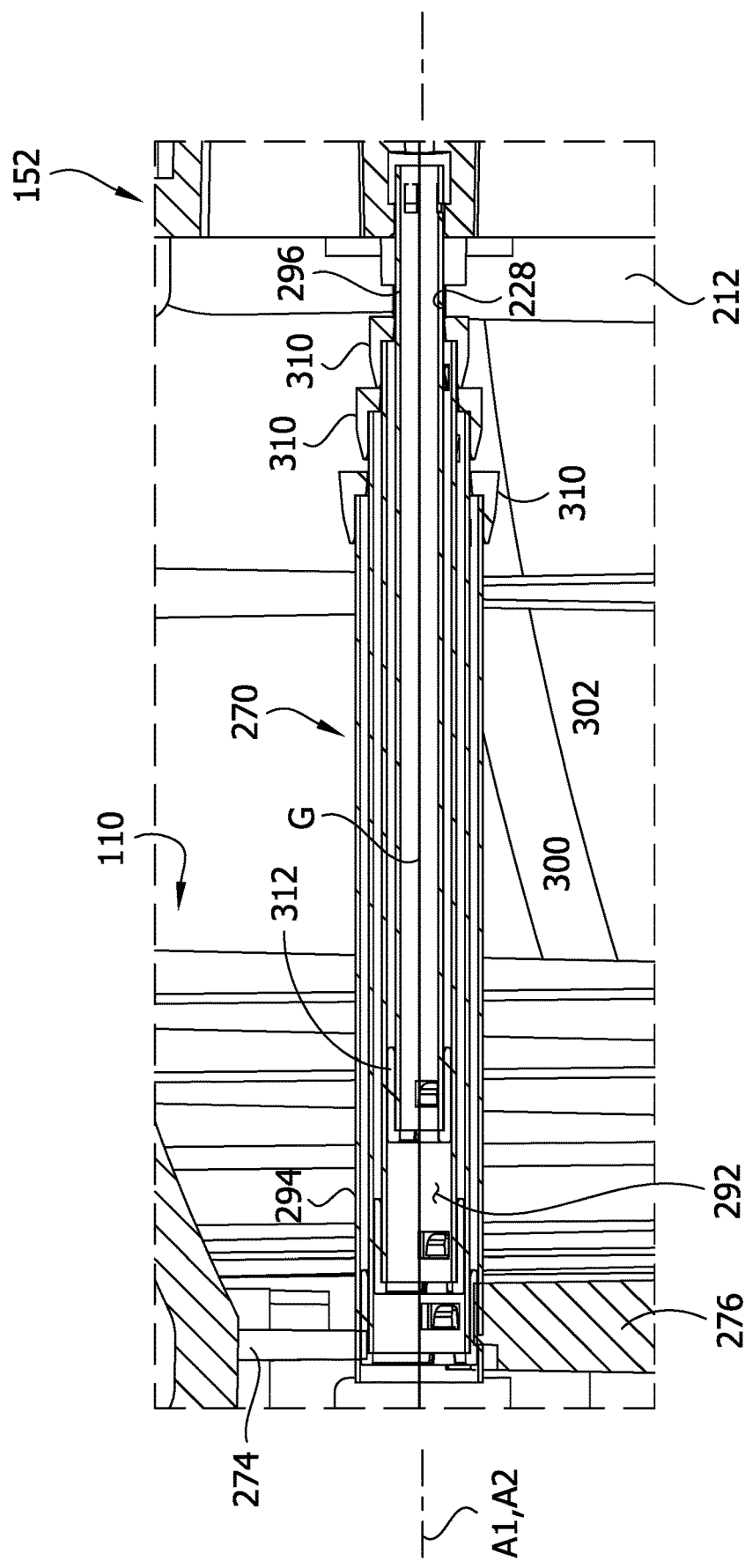
FIG. 15A is an enlarged view of a portion of FIG. 15.
Figure 16:
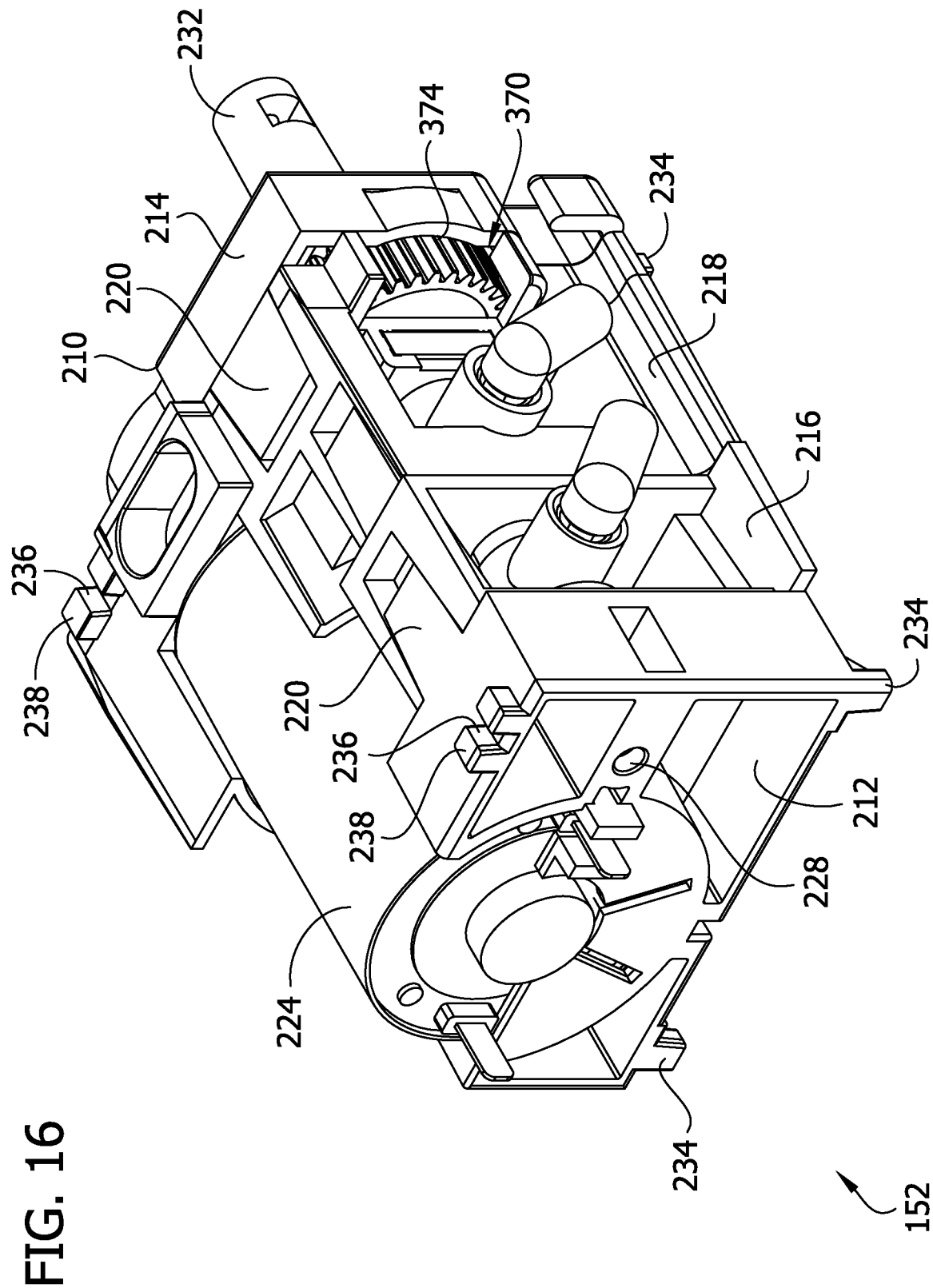
FIG. 16 is a perspective of a carriage of the handle.
Figure 17:
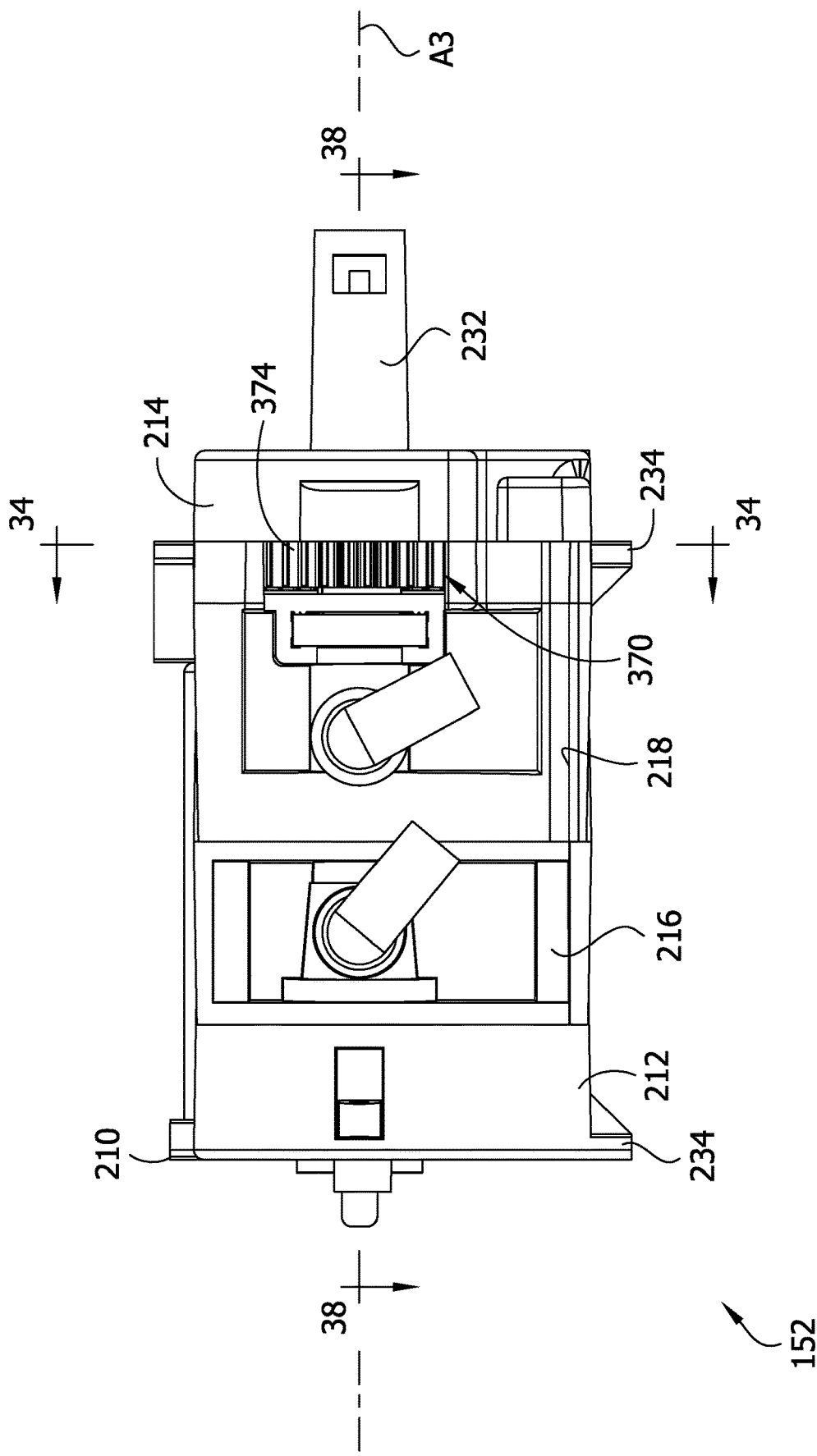
FIG. 17 is a front elevation of the carriage.
Figure 18:
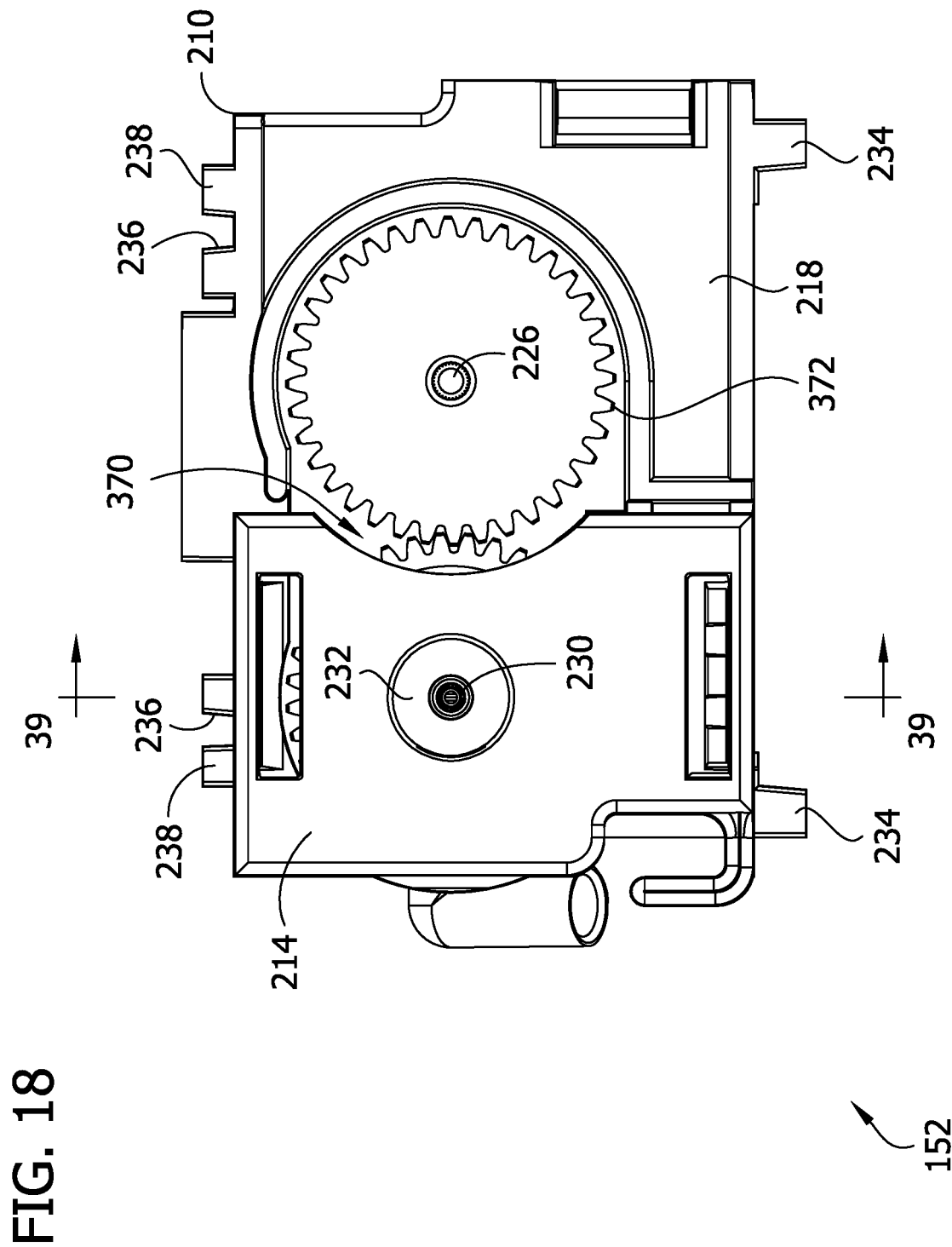
FIG. 18 is a distal end elevation of the carriage.

As shown in FIGS. 15A and 22, the ends of the distal end caps 310 are configured to provide stops that engage one another as the telescoping assembly 290 is retracted to prevent over-retraction of any of the middle tubes 300, 302. More specifically, the distal end of a larger distal end cap 310 is configured to engage the proximal end of an adjacent smaller distal end cap as the telescoping assembly 290 is retracted. For example, the stops of the distal end caps 310 that are secured to the middle tubes 300, 302 are configured prevent either of the middle tubes from radially overlapping the other of the middle tubes along the entirety of the length of either of the tubes. The distal end of the distal end cap 310 that is secured to the large middle tube 300 is configured to engage the proximal end of the distal end cap that is secured to the small middle tube 302 as the telescoping assembly 290 is retracted to prevent the distal end portion of the small middle tube from radially overlapping the distal end portion of the large middle tube. In other words, the stops formed by distal end of the distal end cap 310 that is secured to the large middle tube 300 and the proximal end of the distal end cap that is secured to the small middle tube 302 are configured to engage one another as the telescoping assembly 290 is retracted such that the distal end portion of the small middle tube always protrudes distally from the distal end portion of the large middle tube. Similarly, in one or more embodiments, the distal end of the distal end cap 310 that is secured to the large end tube 294 is configured to engage the proximal end of the distal end cap that is secured to the large middle tube 300 to prevent the distal end portion of the large middle tube from radially overlapping the distal end portion of the large end tube. That is, the stops formed by distal end of the distal end cap 310 that is secured to the large end tube 294 and the proximal end of the distal end cap that is secured to the large middle tube 300 are configured to engage one another as the telescoping assembly 290 is retracted such that the distal end portion of the large middle tube must always protrude distally from the distal end portion of the large end tube. Over-retraction prevention stops can be formed in other ways in one or more embodiments.

A proximal end cap 312 (e.g., an inner annular end cap) is secured to the proximal end portion of each of the large middle tube 300, the small middle tube 302, and the small end tube 296. As shown in FIGS. 21, 21A, and 24, each proximal end cap 312 can comprise a distal annular end portion that has an inner diameter that is approximately the same as the outer diameter of the proximal end portion of the tube 296, 300, 302 to which it is secured. Thus, in one or more embodiments, the distal annular end portion of the proximal end cap 312 can be pressed onto the proximal end portion of the respective tube 296, 300, 302. As shown in FIG. 24, each proximal end cap 312 can comprise one or more resilient locking tabs 320 (broadly, locking formations) that includes a catch or barb configured to be lockingly received in a respective proximal locking slot 322 adjacent the proximal end portion of the respective tube 296, 300, 302. For example, in one embodiment, the proximal end cap 312 is configured such that the catches of the tabs 320 snap into to respective slots 322 to lockingly secure the proximal end cap to the respective tube 296, 300, 302 as the distal annular end portion of the proximal end cap is pressed onto the respective tube with the tabs angularly aligned with the respective slots. Suitably, the tabs 320 do not protrude past the inner surface of the respective tube 296, 300, 302. As such, the tabs 320 do not define a substantial obstruction or catch point that would interfere with passage of the guidewire G proximally through the guidewire alignment guide 270.

The illustrated proximal end cap 312 also defines a generally annular proximal lip portion or shoulder 324. The shoulder 324 has a distal end that engages the proximal-facing end of the respective tube 296, 300, 302. Suitably, the shoulder 324 has an inner diameter that is about equal to or slightly greater than the inner diameter of the respective tube 296, 300, 302. As such, the shoulder 324 does not define a substantial obstruction or catch point that would interfere with passage of the guidewire G proximally through the guidewire alignment guide 270. Furthermore, the outer annular surface of each of the proximal end caps 312 has an outer diameter that is greater than the outer diameter of the tube 296, 300, 302 to which it is secured. For example, the outer annular surface of each proximal end cap 312 can be about the same as the inner diameter of the respective radially outwardly adjacent tube 294, 300, 302 such that the outer surface of the proximal end cap provides a bearing surface that slidably engages the internal surface of the respective radially outwardly adjacent tube. The outer surface of each tube 296, 300, 302 is spaced apart radially inwardly from the internal surface of the respective radially outwardly adjacent tube 294, 300, 302. It can be seen, therefore, that in the illustrated embodiment, the proximal and distal end caps 310, 312 provide the sole points of contact between the tubes 294, 296, 300, 302 in the telescoping assembly 290. The end caps 310, 312 thus form bearings that provide the sliding engagement between the tubes 294, 296, 300, 302.

As shown in FIGS. 15B and 21A, the proximal end cap 312 has a distal end that provides a stop that is configured to engage the proximal end of the lip 318 of an adjacent distal end cap 310 as the telescoping assembly is extended. For example, the distal end of the proximal end cap 312 that is secured to the large middle tube 300 is configured to engage the proximal end of the lip 318 of the distal end cap 310 of the large end tube 294 as the telescoping assembly is extended. This engagement prevents the proximal end portion of the large middle tube 300 from being over-extended by sliding distally past the distal end portion of the large end tube 297. Likewise, the distal end of the proximal end cap 312 that is secured to the small middle tube 302 is configured to engage the proximal end of the lip 318 of the distal end cap 310 secured to the large middle tube 300 as the telescoping assembly is extended and the distal end of the proximal end cap that is secured to the small end tube 296 is configured to engage the proximal end of the lip of the distal end cap of the small middle tube as the telescoping assembly is extended. In combination the various potential points of engagement between the distal ends of the proximal end caps 312 and the proximal ends of the distal end cap lips 318 prevent over-extending any links of the telescoping assembly 290. It will be appreciated that over-extension prevention stops can be formed in other ways in one or more embodiments.

Referring to FIG. 15A, it can be seen that the interior surface of the guidewire alignment guide 270 is substantially free of openings or structure that defines catch points that would interfere with the guidewire G as it is inserted proximally through the interior 292 of the guidewire alignment guide. Because the small end of the telescoping alignment guide 270 defines the distal end and the large end defines the proximal end within the handle 16, the guidewire G does not oppose any exposed shoulders or lips defined by the ends of the telescoping links as it is inserted proximally through the guidewire alignment guide. Furthermore, besides the opening 316 in the small end tube 296, the only openings that are exposed at the interior surface of the guidewire alignment guide 270 are the slots 220 in which the tabs 222 of the proximal end caps 312 are received. The tabs 222 are thought to substantially fill the slots 220 such that the guidewire G is inhibited from passing out of the guidewire alignment guide through the slots. Moreover, the only structure other than the smooth interior surfaces of the hypotubes 294, 296, 300, 302 that is exposed on the interior of the guidewire alignment guide is the lips 324 and tabs 320 of the proximal end caps 312. As explained above, this structure is sized so as not to protrude inward into the interior 292 of the guidewire alignment guide and thus is believed to not form a meaningful obstruction to passage of the guidewire proximally through the guidewire alignment guide 270. The guidewire alignment guide 270 is free of screw heads and rivets along the interior surface thereof.

Referring to FIGS. 14-15B and 20-24, in use, the guidewire alignment guide 270 is configured to be extended and the catheter body alignment guide 272 is configured to be retracted as the carriage 152 moves distally relative to the housing 110. The guidewire alignment guide 270 aligns the guidewire G to extend from the guidewire opening 126 into and through the carriage 152 as it is extended. Likewise, the catheter body alignment guide 272 aligns the catheter body 14 to extend from the carriage 152 to the catheter body opening 120. Moreover, the catheter body 14 moves conjointly with the carriage 152 and is thereby extended distally through the opening 120 as the carriage moves distally. The small tube 296 of the guidewire alignment guide 270 and the large tube 294 of the catheter body alignment guide 272 each move conjointly with the carriage 152. The large tube 294 of the guidewire alignment guide 270 remains fixed in place with respect to the housing 110, and the small tube of the catheter body alignment guide 272 likewise remains fixed in place with respect to the housing.

When the carriage 152 moves proximally relative to the housing, the guidewire alignment guide 270 is configured to be retracted and the catheter body alignment guide 272 is configured to be extended. The guidewire alignment guide 270 aligns the guidewire G to extend from the guidewire opening 126 into and through the carriage 152 as it is retracted. Likewise, the catheter body alignment guide 272 aligns the catheter body 14 to extend from the carriage 152 through the catheter body opening 120 as it is extended. Moreover, the catheter body 14 moves conjointly with the carriage 152 with respect to the housing 110 and is thereby withdrawn proximally through the catheter body opening 120. As above, the small tube 296 of the guidewire alignment guide 270 and the large tube 294 of the catheter body alignment guide 272 each move conjointly with the carriage 152, and the large tube of the guidewire alignment guide and the small tube of the catheter body alignment guide each remain fixed in place with respect to the housing.

As the guidewire alignment guide 270 or the catheter body alignment guide 272 is extended, the middle tubes 300, 302 and the small end tube 296 move distally with respect to the respective radially outwardly adjacent tube; or in other words, the large end tube 294 and the middle tubes 300, 302 move proximally with respect to the respective radially inwardly adjacent tube. The outer surfaces of the proximal end caps 312 slidingly bear against the internal surfaces of the respective radially outwardly adjacent tubes, and the inner surfaces of the lip portions 318 slidingly bear against the external surfaces of the respective radially inwardly adjacent tubes. If the distal end of a proximal end cap 312 engages the proximal end of the lip 318 of a distal end cap 310, further relative movement between the tube 296, 300, 302 to which the proximal end cap is secured and the respective radially outwardly adjacent tube 294, 300, 302 to which the distal end cap is secured is prevented, thereby preventing over-extension of the telescoping assembly 290.

As either the guidewire alignment guide 270 or the catheter body alignment guide 272 is retracted, the large end tube 294 and the middle tubes 300, 302 slide distally with respect to the respective radially inwardly adjacent tube 300, 302, 296; or in other words, the middle tubes 300, 302 and the small end tube 296 slide proximally with respect to the respective radially outwardly adjacent tube 294, 296, 300. The outer surfaces of the proximal end caps 312 slidingly bear against the internal surfaces of the respective radially outwardly adjacent tubes, and the inner surfaces of the lip portions 318 slidingly bear against the external surfaces of the respective radially inwardly adjacent tubes. If the distal end of a distal end cap 310 that is secured to the large end tube 294 or the large middle tube 300 engages the proximal end of a distal end cap that is secured to the respective radially inwardly adjacent tube 300, 302, further relative movement between the adjacent tubes is respectively prevented, thereby preventing over-retraction of the telescoping assembly 290. In the guidewire alignment guide 270, if the distal end of the distal end cap 310 that is secured to the small middle tube 302 engages the proximal end of the carriage block assembly 210, further relative movement between the small middle tube and the small end tube 296 is likewise prevented. In the catheter body alignment guide 272, if the distal end of the distal end cap 310 that is secured to the small middle tube 302 engages the proximal end of the anchor member 280, further relative movement between the small middle tube and the small end tube 296 is also prevented.

D. Slider Lock

Figure 25:
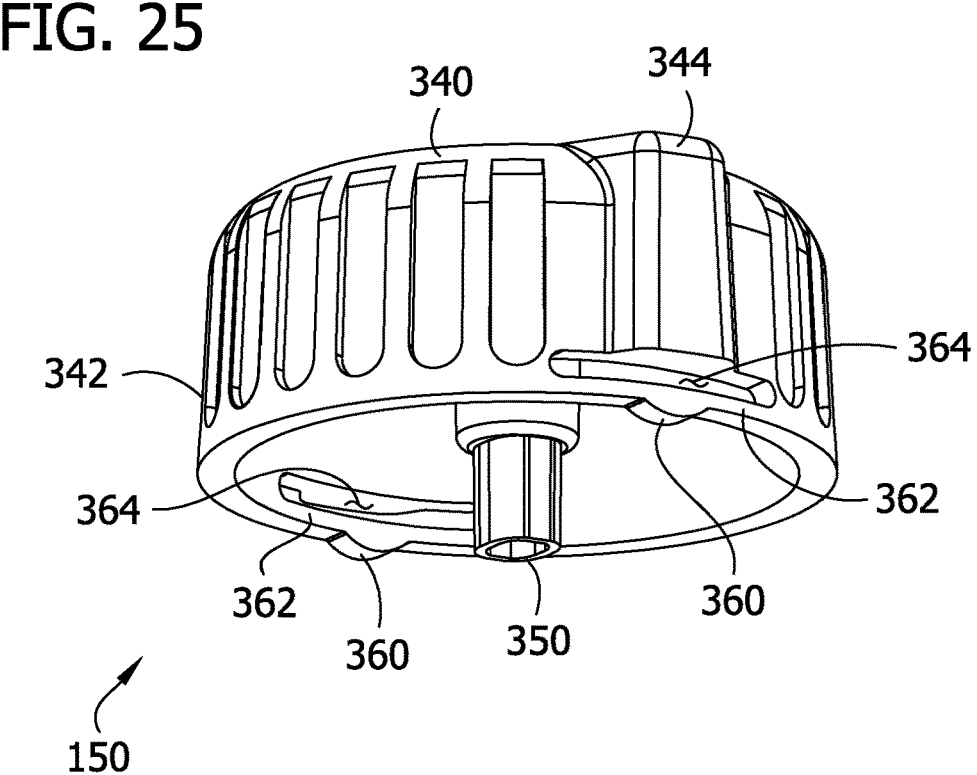
FIG. 25 is a perspective of a slider knob of the handle.
Figure 26:
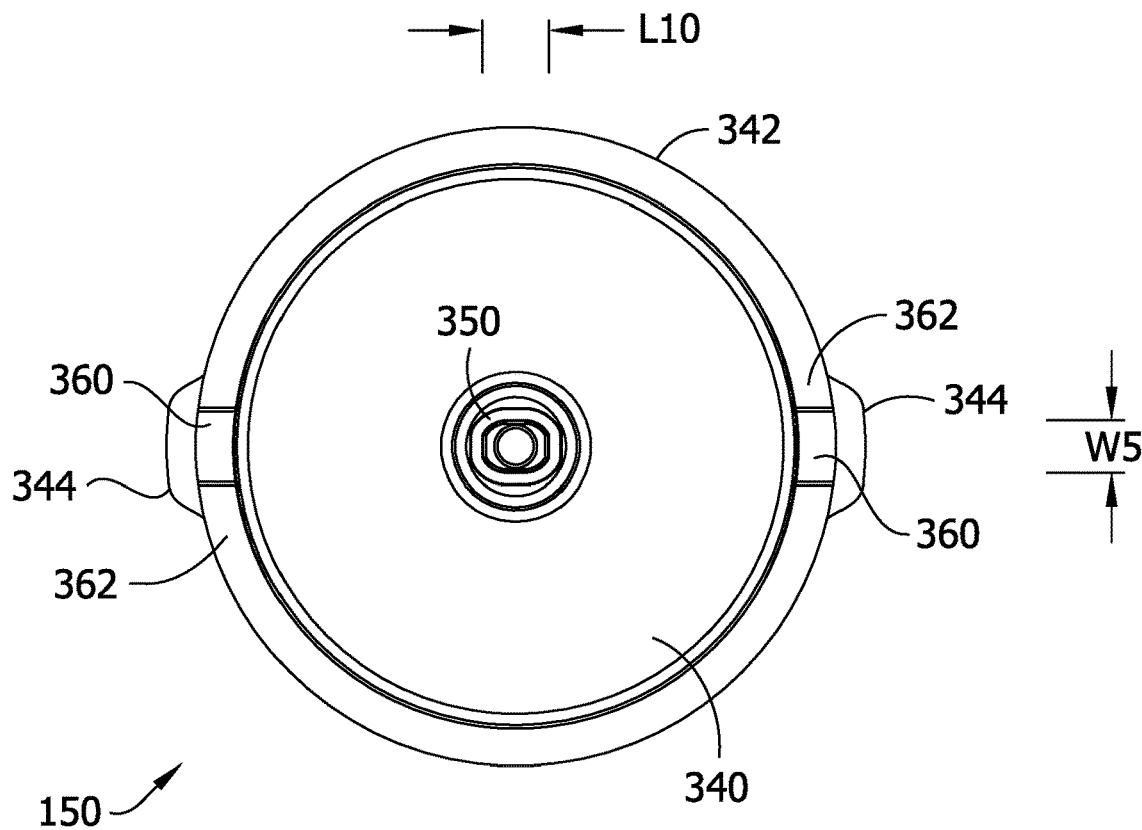
FIG. 26 is a bottom plan view of the slider knob.
Figure 27:
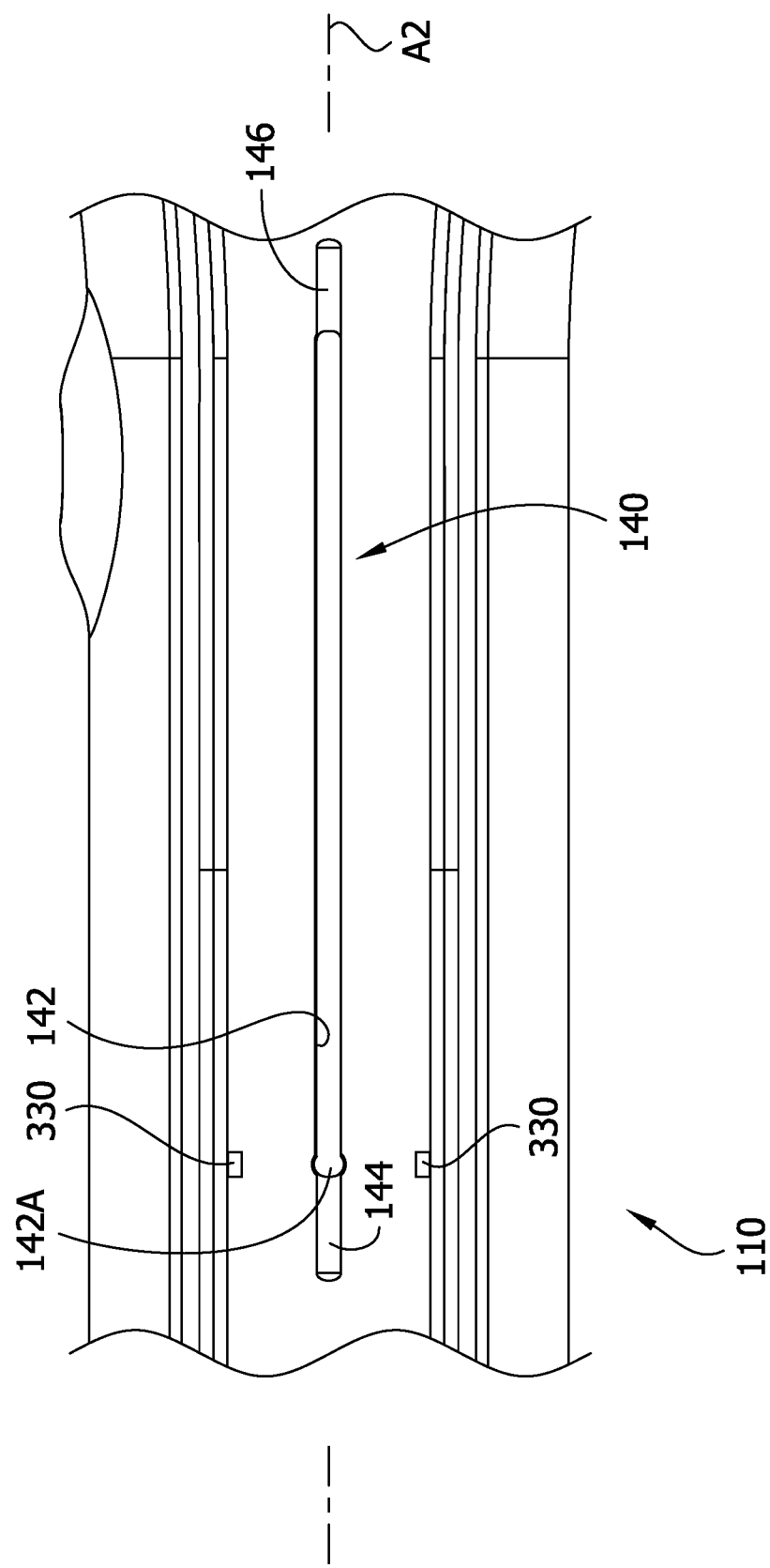
FIG. 27 is a partial top plan view of a portion of the top housing member that includes a slider race.

Referring to FIGS. 25-27, as set forth above, the top wall of the housing 110 of the illustrated handle 16 defines a race 140 that is configured to constrain a slider knob 150 to move along an axis A2 with respect to the housing. The slider knob 150 is operably coupled to the carriage 152 such that the carriage moves conjointly with the slider knob along the axis A2. And as explained above, the carriage 152 thereby extends and retracts the alignment guides 270, 272 and extends and withdraws the drive shaft 24 and the inflation conduit 26 (i.e., portions of the catheter body 14) through the distal end of the housing 110 and the isolation sheath 70. As will be explained below, the top wall of the housing 110 and the slider knob 150 include features that allow the slider knob to be selectively locked at a selected position along the length of the race 140 (e.g., along the axis A2). The handle 16 also includes features for maintaining the slider knob 150 in a homed position without imparting forces on the slider knob that cause deformation of the slider knob. Handles of catheters can also have differently configured slider knobs or lack a slider knob entirely in one or more embodiments.

As explained above, the race 140 comprises the slot 142 that extends through the entire thickness of the top wall of the housing 110 and longitudinally along the axis A2. Portions of or the entire race can also be formed in other walls of the housing in one or more embodiments. The slot 142 has a prevailing width W3 (FIGS. 29, 29A, 32) along a majority of the length of the slot. The proximal end segment of the slot 142 comprises a widened segment 142A having an enlarged width W4 (FIGS. 29, 29A, 32) that is wider than the prevailing width W3. The widened segment 142A of the slot 142 has a relatively short length L9 in comparison to the overall length of the slot.

As shown in FIG. 27, each of the proximal and distal grooves 144, 146 is formed in the top surface of the top wall of the housing 110 end extends through only a portion of the thickness of the top wall. The proximal groove 144 extends longitudinally along the axis A2 from the proximal end of the slot 142 (e.g., from the widened segment 142A) in a proximal direction. The distal groove 146 extends longitudinally along the axis A2 from the distal end of the slot 142 in a distal direction. In the illustrated embodiment, each of the proximal and distal grooves 144, 146 has about the same width as the prevailing width W3 of the slot 142. In one or more embodiments, the slider knob race can have other configurations.

In addition to the race 140, the top wall of the housing 110 also defines first and second detent depressions 330 (broadly, recesses). The detent depressions 330 are spaced apart from the widened segment 142A of the slot 142 in opposite perpendicular directions with respect to the axis A2. The depressions 330 are about equidistant from the widened segment 142A of the slot in the illustrated embodiment. As explained in further detail below, the detent depressions 330 are configured to provide a detent feature in combination with the slider knob 150. The depressions 330 also provide a homing feature that is configured to retain the knob 150 in a homed position without deforming any portion of the knob when the handle 16 is not being used. It is contemplated that other detent or homing structures (e.g., projections on the top wall of the housing) can be used in one or more embodiments.

Figure 28:
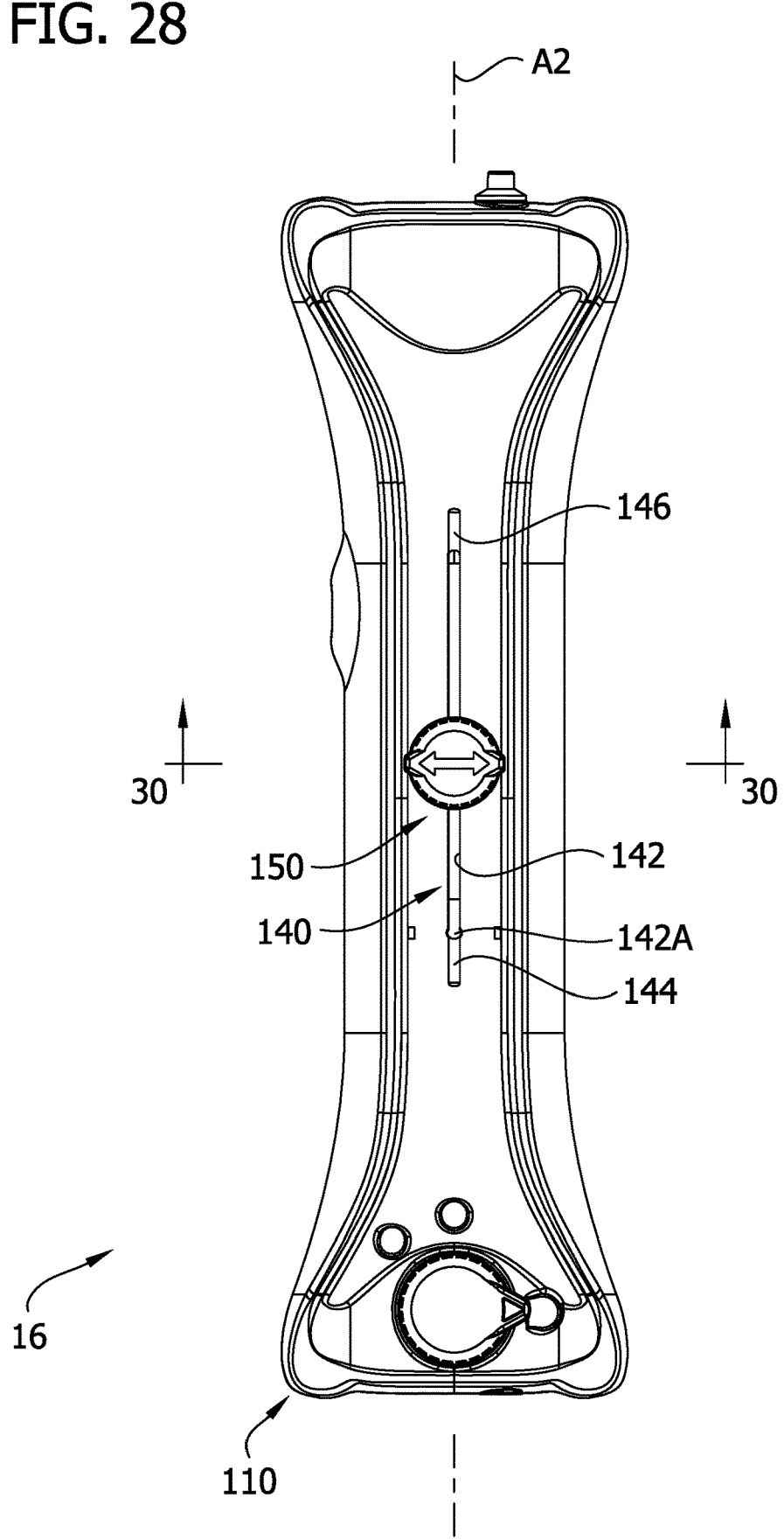
FIG. 28 is a top plan view of the handle illustrating the slider knob in a locked orientation.
Figure 28A:
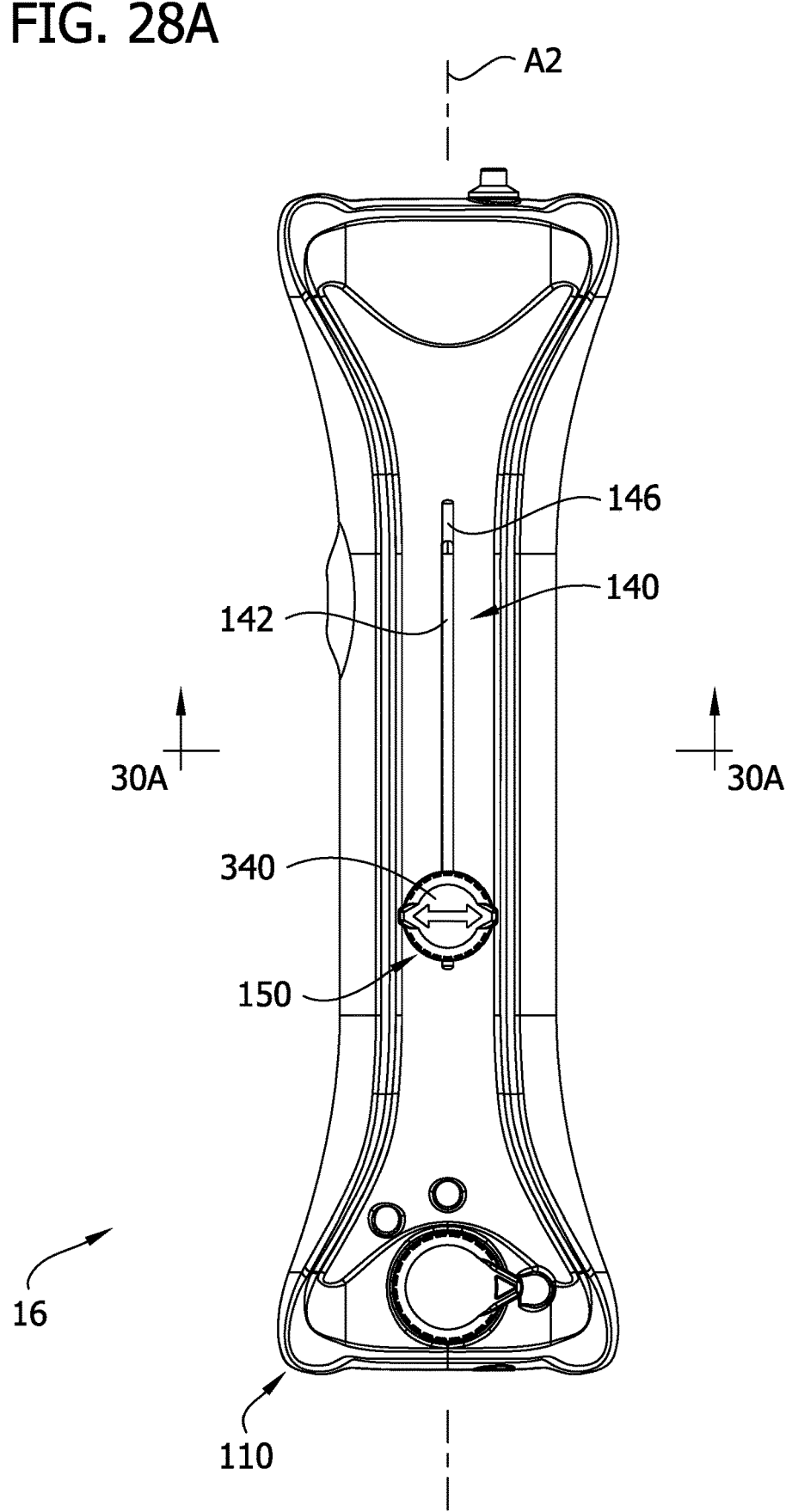
FIG. 28A is a top plan view of the handle illustrating the slider knob in a homed position.
Figure 30:
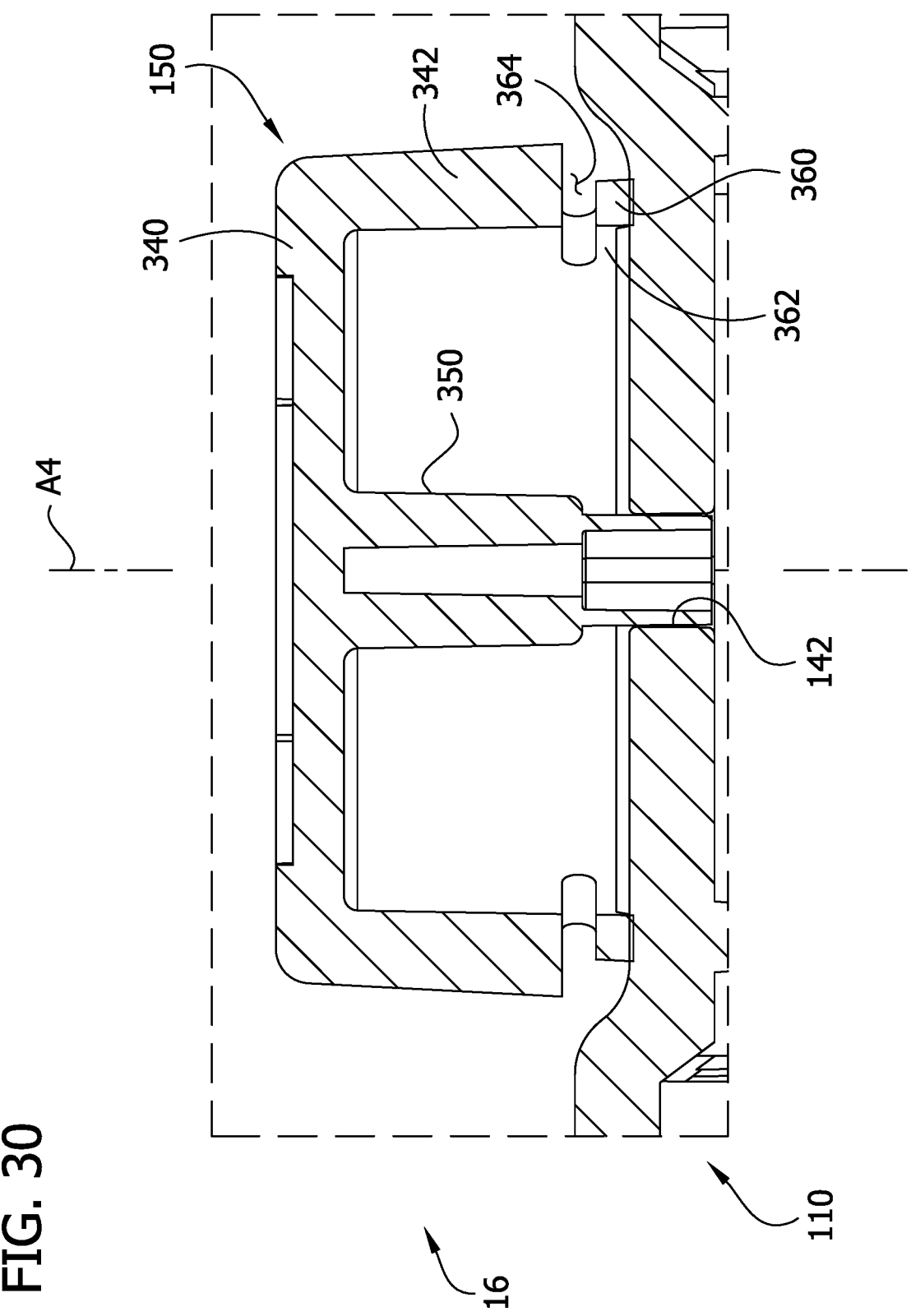
FIG. 30 is an enlarged partial cross section of a portion of the handle including the slider knob taken in the plane of line 30-30 of FIG. 28.
Figure 30A:
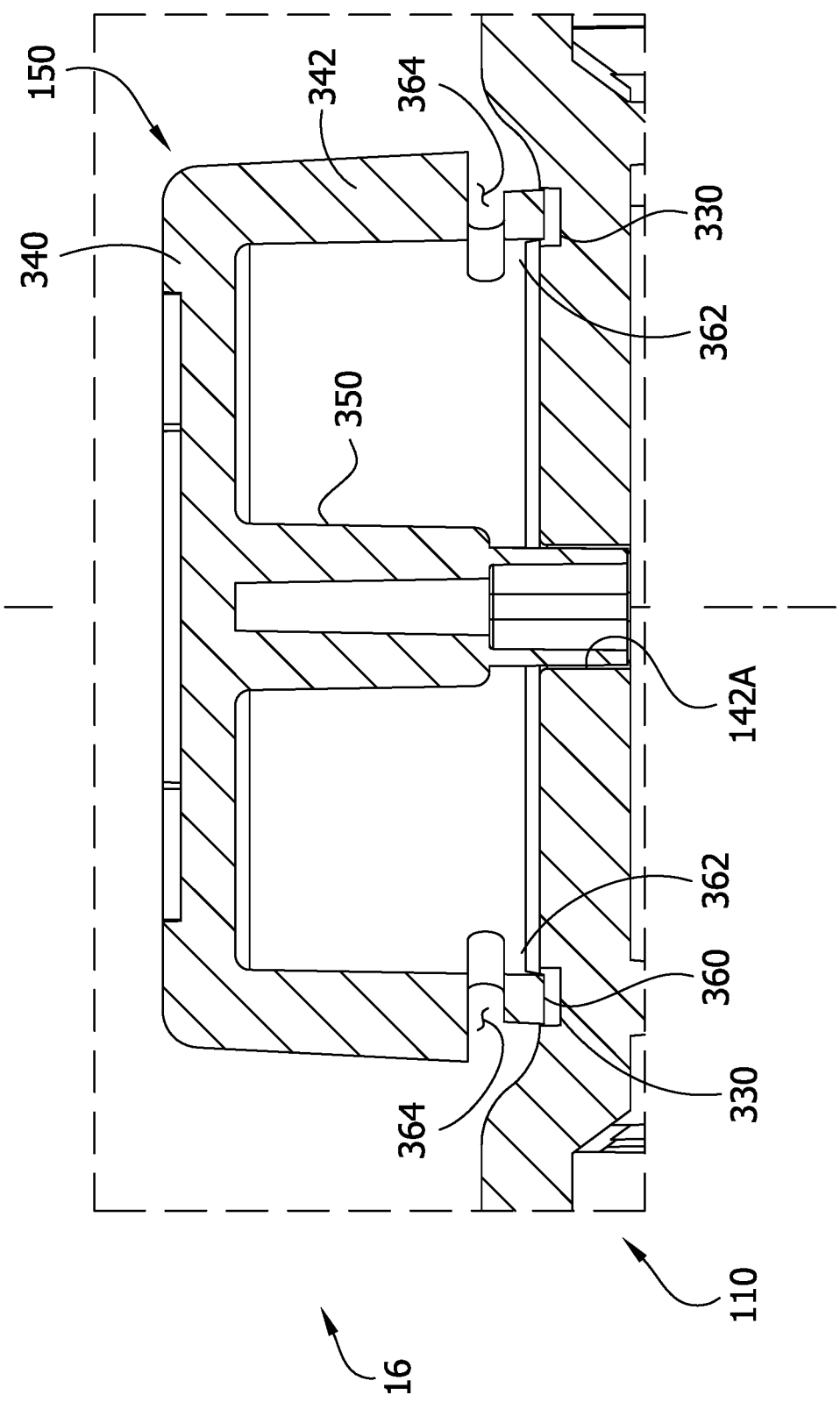
FIG. 30A is an enlarged partial cross section of a portion of the handle including the slider knob taken in the plane of line 30A-30A of FIG. 28A.
Figure 31:
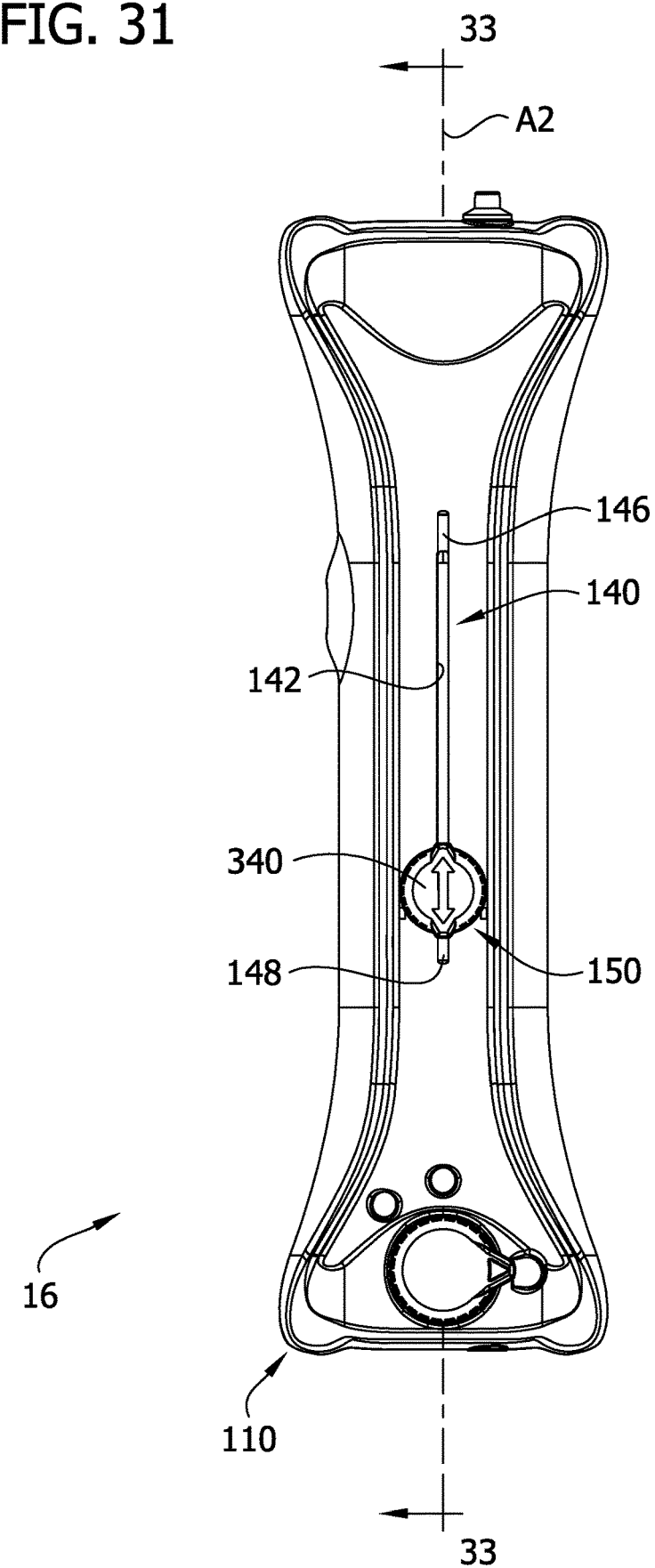
FIG. 31 is a top plan view of the handle illustrating the slider knob in a slide orientation.
Figure 33:
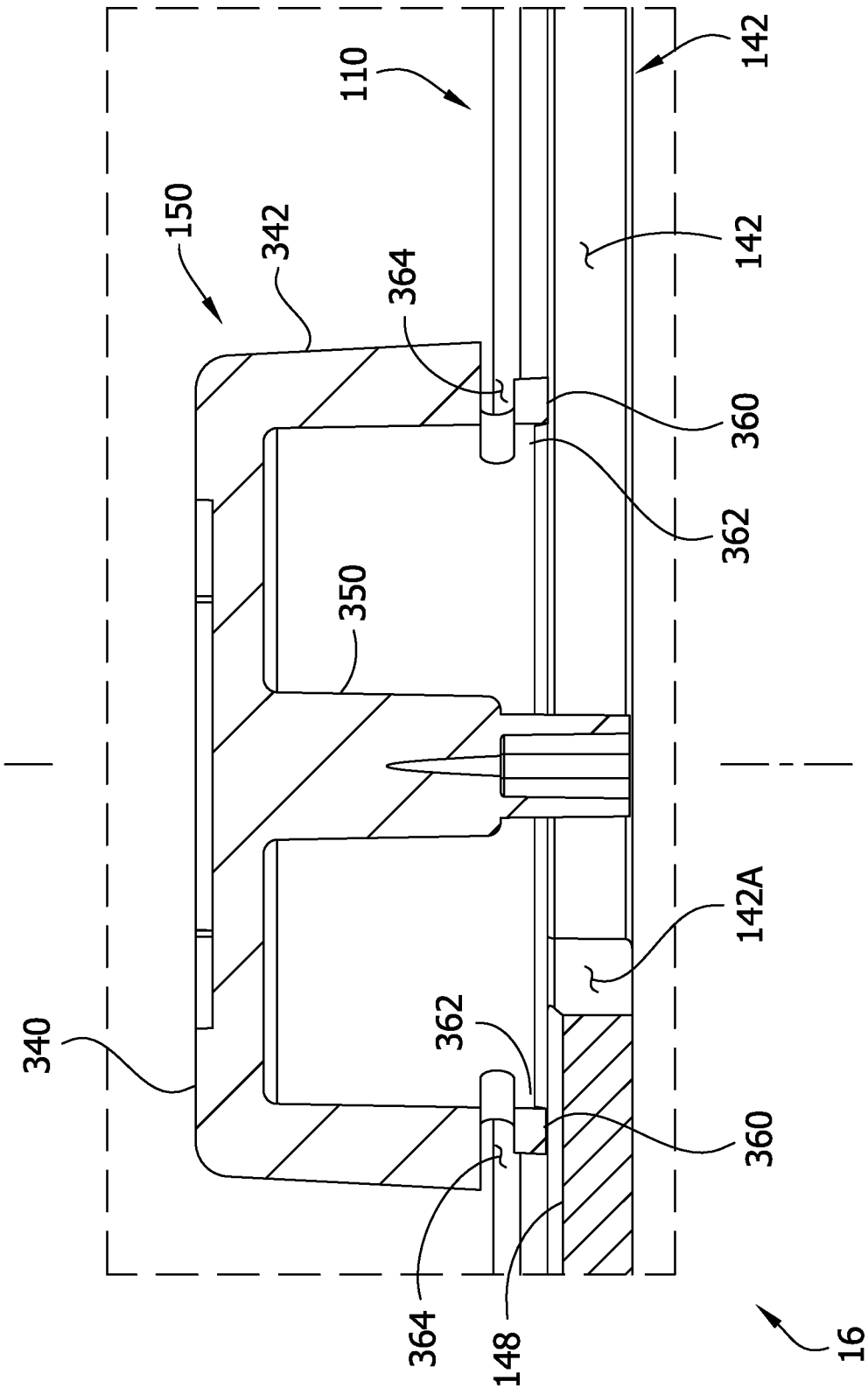
FIG. 33 is an enlarged partial cross section of a portion of the handle including the slider knob taken in the plane of line 33-33 of FIG. 31.

Referring to FIGS. 25 and 26, the illustrated slider knob 150 comprises a top wall 340 and a skirt 342. The skirt 342 includes two diametrically opposed, radially extending wing portions 344 that are configured to facilitate gripping the knob 150 and/or indicate the angular position of the knob about a pivot axis A4 thereof (FIGS. 30, 30A, 33). As shown in FIGS. 28, 28A, and 31, the top wall 340 includes a two-headed arrow indicator that points in the directions of the wing portions. The arrow indicator also provides an indication of the angular position of the knob 150 about the pivot axis A4. In one embodiment, when the arrow indicator and/or wing portions 344 are pointed in directions generally along the axis A2 as shown in FIG. 31, the knob 150 is oriented in a slide orientation in which the knob is configured to slide along the axis A2 through the race 140. The knob 150 can be oriented in a locked orientation in which the knob is inhibited from sliding along the race 142 when the arrow indicator and/or wing portions 344 point in directions generally perpendicular to the axis A2 as shown in FIGS. 28 and 28A. In one or more embodiments, the wing portions and/or arrow indicator can be omitted or other indicators of the angular orientation of the knob can be used.

Referring to FIGS. 25 and 26, the illustrated slider knob 150 has a shaft 350 that extends downward from the top wall 340, generally along the pivot axis A4. The shaft 350 is configured to extend through the slot 142 and be connected to the carriage 152 inside the housing 110 such that carriage moves conjointly with the knob 150 as the knob slides along the race 140 and the axis A2. The pivot axis A4 is coaxial with the axis of the shaft 350 (see FIGS. 30, 30A, 33). In the slide orientation of the knob 150 shown in FIGS. 31, 32, and 33, the shaft 350 is configured to pass through the slot 142 along the length of the slot. The range of motion of the knob 150 along the axis A2 is limited by engagement of the shaft 350 with the portions of the top wall of the housing 110 that define the ends of the slot 142. As explained in further detail below, in the locked orientation of the knob 150 shown in FIGS. 28, 29, and 30, the shaft 350 is configured to be compressed by the inner edges of the top wall of the housing 110 that define the longitudinal sides of the slot 142. The knob 150 is thereby inhibited from moving along the length of the slot 142 in the locked orientation. The illustrated knob also has a homed position shown in FIGS. 28A, 29A, and 30A, which is another locked configuration of knob. As explained below, however, in the homed position no forces are imparted on the knob 150 that cause deformation of the knob.

As shown in FIG. 26, the illustrated shaft 350 has a rounded rectangular cross-sectional shape. In cross-section, the shaft 350 has a major cross-sectional dimension L10 along a major cross-sectional axis, and a minor cross-sectional dimension W5 along a minor cross-sectional axis transverse (e.g., perpendicular) to the major cross-sectional axis. The major cross-sectional dimension L10 is greater than the minor cross-sectional dimension W5. The prevailing width W3 of the slot 142 is less than the major cross-sectional dimension L10 and greater than the minor cross-sectional dimension W5 of the slot. In contrast, the widened width W4 of the widened portion 142A of the slot is greater than the major cross-sectional dimension L10 of the slot. The length L9 of the widened segment 142A is greater than the minor cross-sectional dimension W10 of the shaft 350. The shaft 350 has opposite first and second cross-sectional ends extending along the minor cross-sectional dimension W5. The cross-sectional ends are spaced apart from one another along the major cross-sectional dimension L10. The shaft 350 also has opposite first and second cross-sectional sides extending along the major cross-sectional dimension L1. The cross-sectional sides are spaced apart from one another along the minor cross-sectional dimension W5. The cross-sectional ends and cross-sectional sides of the shaft 350 are substantially planar in the illustrated embodiment. Moreover, each of the cross-sectional ends and cross-sectional sides extends in a respective plane oriented substantially parallel to the shaft axis A4. In the illustrated embodiment, the cross-sectional ends are oriented substantially parallel to one another and the cross-sectional sides are oriented substantially parallel to one another. In addition, the illustrated cross-sectional ends are oriented substantially perpendicular to the cross-sectional sides of the shaft 350. In the illustrated embodiment, a curved cross-sectional corner surface having an arcuate cross-sectional shape extends from each end of each cross-sectional side to the adjacent cross-sectional end of the shaft. Although the illustrated shaft 350 has a rounded rectangle cross-sectional shape, the shaft of a knob can have other shapes in one or more embodiments.

Figure 29:
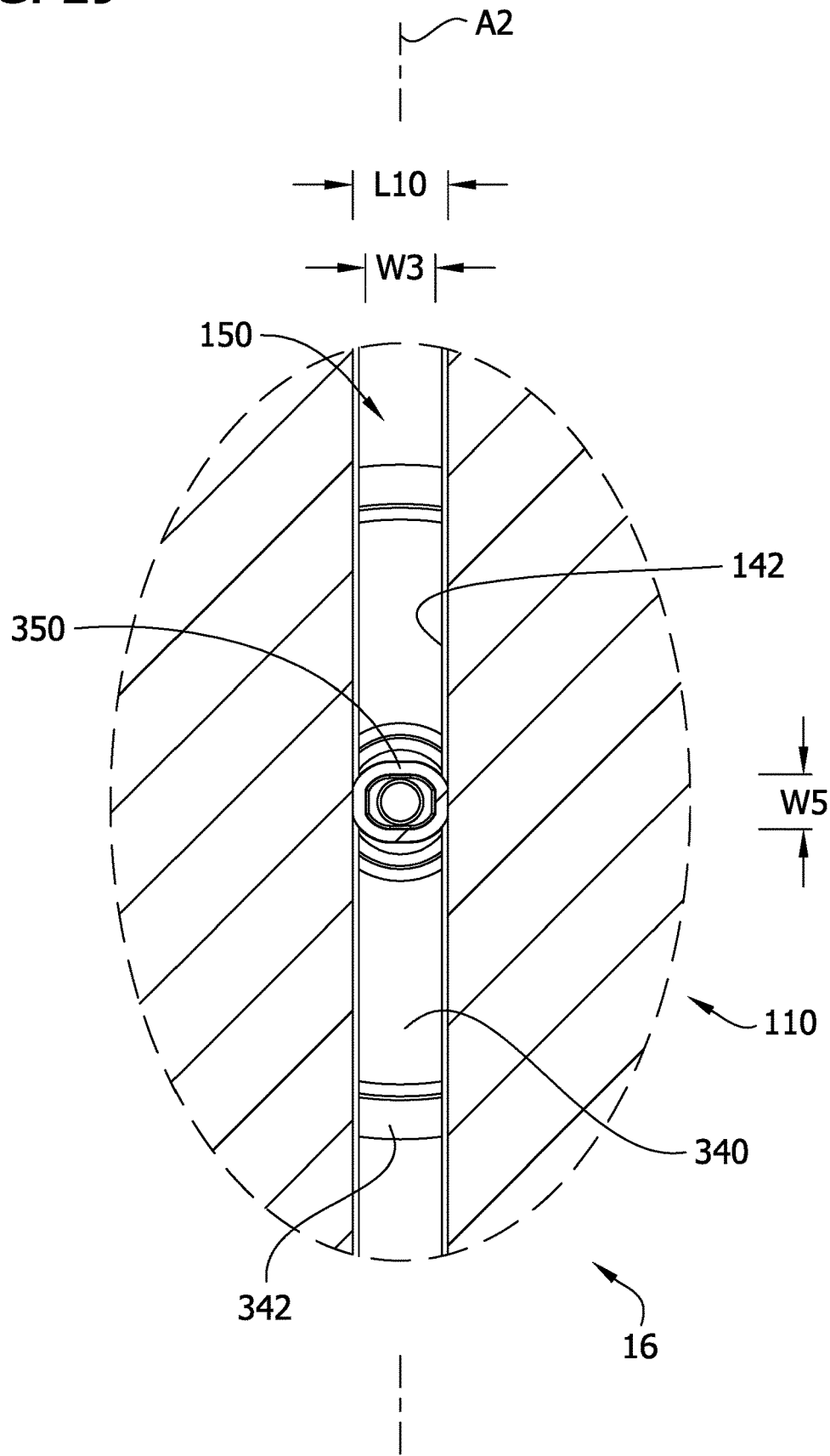
FIG. 29 is an enlarged partial cross section taken in the plane of line 29-29 of FIG. 11 showing a portion of the handle in the configuration of FIG. 28.

As shown in FIG. 29, in the locked orientation of the knob 150, the shaft 350 is oriented about the pivot axis A4 such that the major cross-sectional dimension L10 is oriented parallel to the prevailing width W3 of the slot and the minor cross-sectional dimension W5 is oriented parallel to the slide axis A2 and length of the slot 142. Thus, in the locked orientation of the illustrated knob 150, the cross-sectional sides of the shaft 350 are oriented parallel to the prevailing width W3 and the cross-sectional ends engage surfaces or edges of the top wall of the housing 110 that define the longitudinal sides of the slot 142. Moreover, in the locked orientation, when the major cross-sectional dimension L10 is oriented parallel to the prevailing width W3, the portions of the top wall of the housing 110 defining the longitudinal sides of the slot interfere with sliding movement of the shaft 350 through the slot. When, as shown in FIG. 29, the knob 150 is in the locked orientation about the pivot axis A4 and is located along the length of the race 140 such that the shaft 350 is received in a portion of the slot having the prevailing width W3, portions of the top wall defining the longitudinal sides of the slot 142 compress the shaft along its major cross-sectional dimension L10 to inhibit movement of the shaft along the race 140. In other words, when the knob 150 is pivoted about the pivot axis A4 to the locked orientation along the prevailing width segment of the slot 142, the shaft 350 is configured to be compressed by the inboard surface of the top wall of the housing 110 such that the compression inhibits the shaft, the knob, and the carriage 152 from moving along the length of the slot.

Figure 29A:
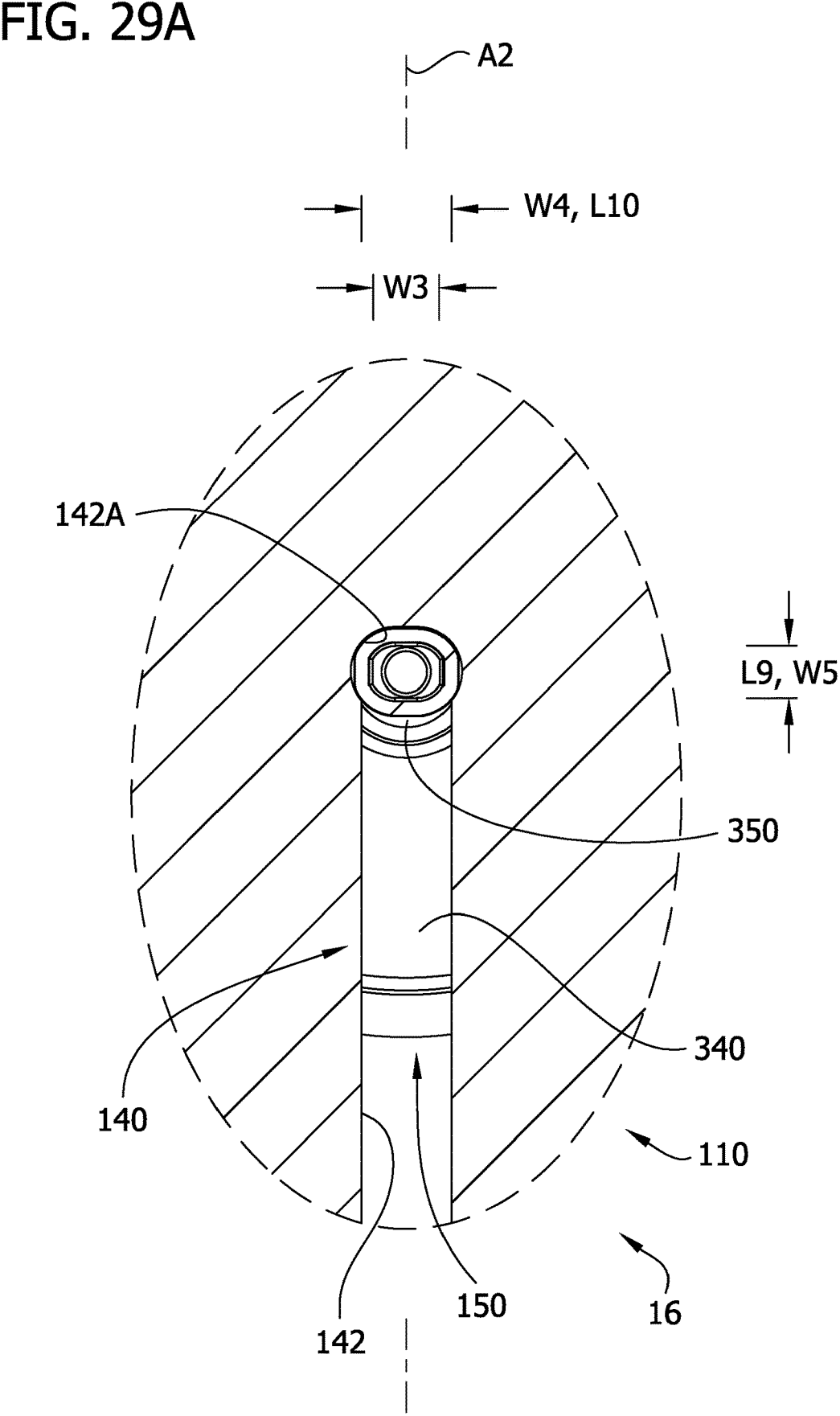
FIG. 29A is an enlarged partial cross section similar to FIG. 29 but illustrating the slider knob in the homed position.

FIG. 29A shows the knob 150 in the same angular orientation as shown in FIG. 29, but the knob is received in the widened segment 142A instead of a prevailing width segment of the slot 142. This configuration of the knob 150 is referred to herein as the "homed position" or "homed configuration" of the knob. When the knob 150 is positioned in the homed position, the top wall of the housing 110 does not compress but the shaft 350 (e.g., because the length L9 of the widened segment 142A is greater than the minor cross-sectional dimension W5 of the shaft and the width W4 of the widened segment is greater than the major cross-sectional dimension L10), but nevertheless the top wall of the housing interferes with movement of the shaft in both directions along the axis A2. The portion of the housing 110 defining the proximal end of the slot 142 prevents the shaft 350 from moving proximally along the race 140, and the portion of the housing defining the proximal end of the prevailing width segment of the slot inhibits movement in the distal direction. Thus, in the homed position, the knob 150 is substantially inhibited from sliding along the race 140. Additional features of the handle 16 when the knob 150 is in the homed position are described below.

Figure 32:
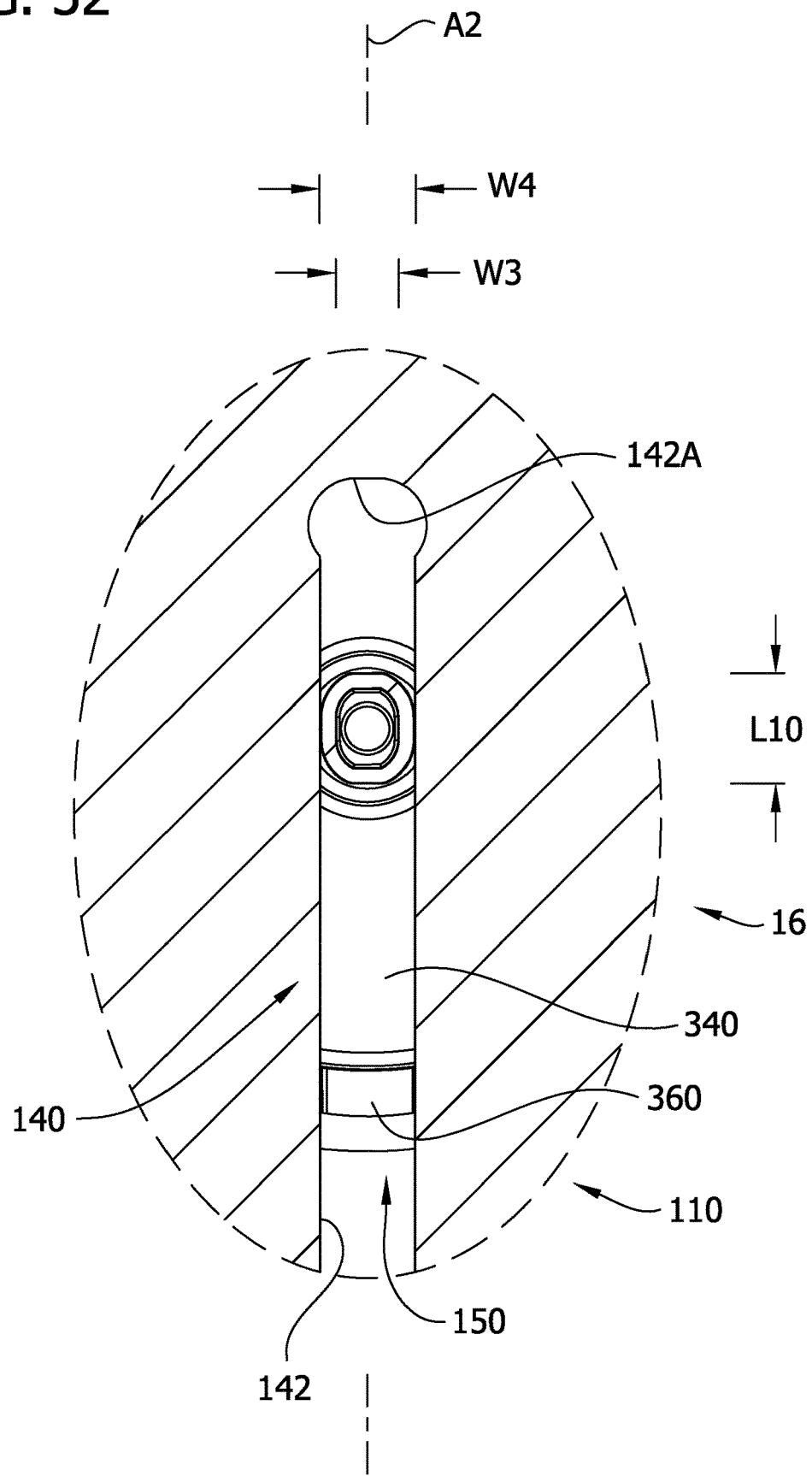
FIG. 32 is an enlarged partial cross section similar to FIG. 29 but illustrating the slider knob in the slide orientation of FIG. 31.

As shown in FIG. 32, in the slide orientation or configuration of the knob 150, the shaft 350 is oriented about the pivot axis A4 such that the minor cross-sectional dimension W5 is oriented parallel to the prevailing width W3 of the slot and the major cross-sectional dimension L10 is oriented parallel to the axis A2 and length of the slot 142. Thus, in the slide orientation of the illustrated knob 150, the cross-sectional ends of the shaft 350 are oriented parallel to the prevailing width W3 and the cross-sectional sides oppose the edges of the housing 110 that define the longitudinal sides of the slot 142. Moreover, in the slide orientation, when the minor cross-sectional dimension W5 of the shaft 350 is oriented parallel to the prevailing width W3 of the slot 142, the shaft can slide along the length of the slot substantially without interference from the top wall of the housing 110.

The curved cross-sectional corner surfaces of the shaft 350 can facilitate pivoting the knob 150 about the axis A4 through angular orientation (e.g., the locked orientation) in which the top wall of the housing interferes with the shaft. For example, when the knob 150 is pivoted about the axis A4 from the slide position (FIG. 32) to the locked position (FIG. 29), the curved cross-sectional corner surfaces of the shaft 350 allow the shaft to smoothly engage the edges of the top wall that define the longitudinal sides the slot 142. The smooth transitions provided by the curved cross-sectional corner surfaces allow the user to progressively overcome the increasing compressive forces on the shaft as the knob 150 is pivoted from the slide position to the locked position.

Referring to FIGS. 25 and 26, the skirt 342 of the illustrated knob has a bottom edge portion that is configured to oppose the top surface of the top wall of the housing 110. In the illustrated embodiment, the bottom edge portion of the skirt 342 defines a pair of detent projections 360 that are formed along respective spring sections 362 having top ends that are bounded by respective spring slots 364. Units of each pair of detent projections 360, spring sections 362, and spring slots 364 are formed at diametrically opposite locations along the bottom edge portion of the skirt 342 in the illustrated embodiment. One or more embodiments can include other numbers and arrangements of detent formations, spring sections, and/or spring slots. For example, in one or more embodiments, the detents can be formed by depressions along the bottom edge margin of the skirt. Each detent projection 360 protrudes downward from the bottom edge portion of a respective spring section 362 and protrudes downward beyond the prevailing vertical position along the axis A4 of the bottom edge portion of the skirt 342. The spring slots 364 extend radially through the skirt 342 at the top of each spring section 362. Each spring slot 364 extends angularly along a spring section 362 of the bottom edge portion of the skirt that defines the detent projection 360. The spring sections 362 of the bottom edge portion of the skirt 342 are resiliently deflectable. For example, the spring sections 362 can deflect upward into the slots 364 when an upwardly oriented force is imparted on the detent projections 360 and rebound when the force is released.

Referring to FIG. 30, the detent projections 360 are configured to engage the top of the top wall of the housing 310 when the knob 150 is in a locked orientation about the pivot axis A4. When the knob 150 is in the locked orientation about the pivot axis A4 and the shaft 350 is received in a portion of the slot 142 having the prevailing width W3, the detent projections 360 are configured to engage the top of the housing 110. The engagement between the projections 360 and the housing 110 causes the spring sections 362 to deflect upward into the spring slots 364. The resilient spring sections 362 urge the detent projections 360 downward against the top of the housing 110, creating additional engagement between the knob 150 and the housing in the locked orientation of the knob.

As shown in FIGS. 28A, 29A, and 30A, when the knob 150 is in the homed position, the detent projections 360 are configured to be received in the detent depressions 330. The detent projections 360 being received in the depressions 330 provides a restraint against movement of the knob 150, e.g., a restraint against pivoting movement and/or sliding movement of the knob. The restraint can, however, be overcome with a moderate amount of force. When the detent projections 360 are received in the detent depressions 330 (e.g., homing depressions), the spring sections 362 are not deflected. In general, no forces are being imparted on the spring sections 362 in the homed position. In other words, the detent depressions 330 provide clearance for the detent projections 360 in the homed position of the knob 150. Similarly, though in the same angular orientation as the locked configuration shown in FIG. 30, in the homed position, the shaft 350 is not compressed by the top wall of the housing. The widened segment 142A provides clearance for the shaft 350 so that substantially no forces are being imparted on the shaft 350. Accordingly, when the knob 150 is in the homed position, neither the skirt 342 nor the shaft 350 is deformed by the housing 110 yet a restraint against relative movement between the knob and the housing is still provided. Accordingly, the handle 16 can be placed in the homed position when the catheter 10 is not being used, such as when the handle 16 is packaged for sale.

Referring to FIGS. 32 and 33, when the knob 150 is pivoted to the slide orientation the detent projections 360 are received in the race 140. As the knob 150 is pivoted from the locked orientation to the slide orientation, the detent projections 360 enter the race 140 to disengage the detent projections from the housing 110 and allow the spring sections 362 to resiliently rebound toward their non-deformed configuration. The disengagement of the detent projections 360 from the housing 110 as the knob 150 is pivoted to the slide orientation provides a tactile indication to the user that the knob is properly oriented in the slide orientation. Furthermore, in the slide orientation, the detent projections 360 are configured to be slidably received in the race 140. The detent projections 360 thus provide a slight restraint against pivoting the knob 150 about the pivot axis A4 away from the slide orientation. Again, the detent projections 360 can be withdrawn from the race 140 with a moderate pivot force when pivoting the knob 150 to the locked orientation is desired. As shown in FIG. 33, a detent projection 360 is configured to be slidably received in the proximal groove 144 as the knob 150 slides along the race 140 toward the proximal end of its range of motion. Likewise, a detent projection 360 is configured to be received in the distal groove 146 as the knob 150 slides along the race 140 toward the distal end of its range of motion. Thus, in the illustrated embodiment, the grooves 144, 146 comprise clearance grooves. The detent projections 360 are passable longitudinally through the clearance grooves 144, 146 to provide for a full range of motion of the knob 150 along the length of the slot 142.

In use the slider knob 150 can be used to move the carriage 152 along the axis A2 when in the slide orientation about the axis A4. For example, the user can slide the slider knob 150 distally along the race 140 to move the carriage 152, the drive shaft 24, the inflation conduit 26, and the burr assembly 12 relative to the handle housing 110, the isolation sheath 70, and/or the guidewire G. The slider knob 150 thus can be used in the slide orientation to provide fine grain adjustments of the position of the burr assembly 112. For example, the slider knob 150 can be moved distally and proximally in a repetitive sequence to cause the burr to repeatedly engage (e.g., peck or tap at) an occlusion in a body lumen in a hammer action. The slider knob 150 can be pivoted to the locked orientation about the axis A4 when no movement of the carriage 152 is desired. For example, when navigating the catheter body 14 over a guidewire G through a body lumen to the site of an occlusion, it can be desirable to lock the slider knob 150 with respect to the housing 110 and move the entire catheter 10 as a unit along the guidewire G. Other uses of the slider knop 150 are also possible.

E. Rotational Drive Mechanism

Referring to FIGS. 16-19 and 34-36, in the illustrated embodiment, the handle 16 comprises a drive linkage or transmission assembly, generally indicated at 370, which is configured to convey a rotational drive force from the motor 224 (broadly, prime mover) to the catheter body 14. In the illustrated embodiment, the drive linkage 370 includes a gear train comprising a drive gear 372 (e.g., an input gear) and a driven gear 374 (e.g., an output gear). The drive gear 372 is pressed onto (broadly, connected to) the output shaft 226 and rotates with the shaft about the motor axis A3. As explained below, the driven gear 374 is conjointly rotatable with the drive shaft 24 and inflation conduit 26 of the catheter body 14 about the rotational axis A1. In the illustrated embodiment, the axes A1, A3 are spaced apart and generally parallel to one another (see FIG. 14). Thus the illustrated drive linkage 370 comprises an offset drive linkage. The offset drive linkage 370 allows for rotation of the drive shaft 24 and the inflation conduit 26 about the guidewire G without requiring the guidewire to pass through the motor 224. In one or more embodiments, the drive linkage can have other configurations. For example, it is contemplated that the motor and drive linkage can be cannulated (to allow passage of a guidewire) and located in line with the drive coil of the catheter in one or more embodiments. The drive gear 372 is operatively connected to the driven gear 374 (e.g., the teeth of the drive gear are meshed with the teeth of the driven gear) to drive rotation of the driven gear about the axis A1 in response to rotation of the drive gear about the axis A3. The drive gear 372 thus operatively connects the driven gear 372 to the motor 224 such that the motor can drive rotation of the driven gear about the axis A1. One or more embodiments can have transmission assemblies of other configurations.

Figure 34:
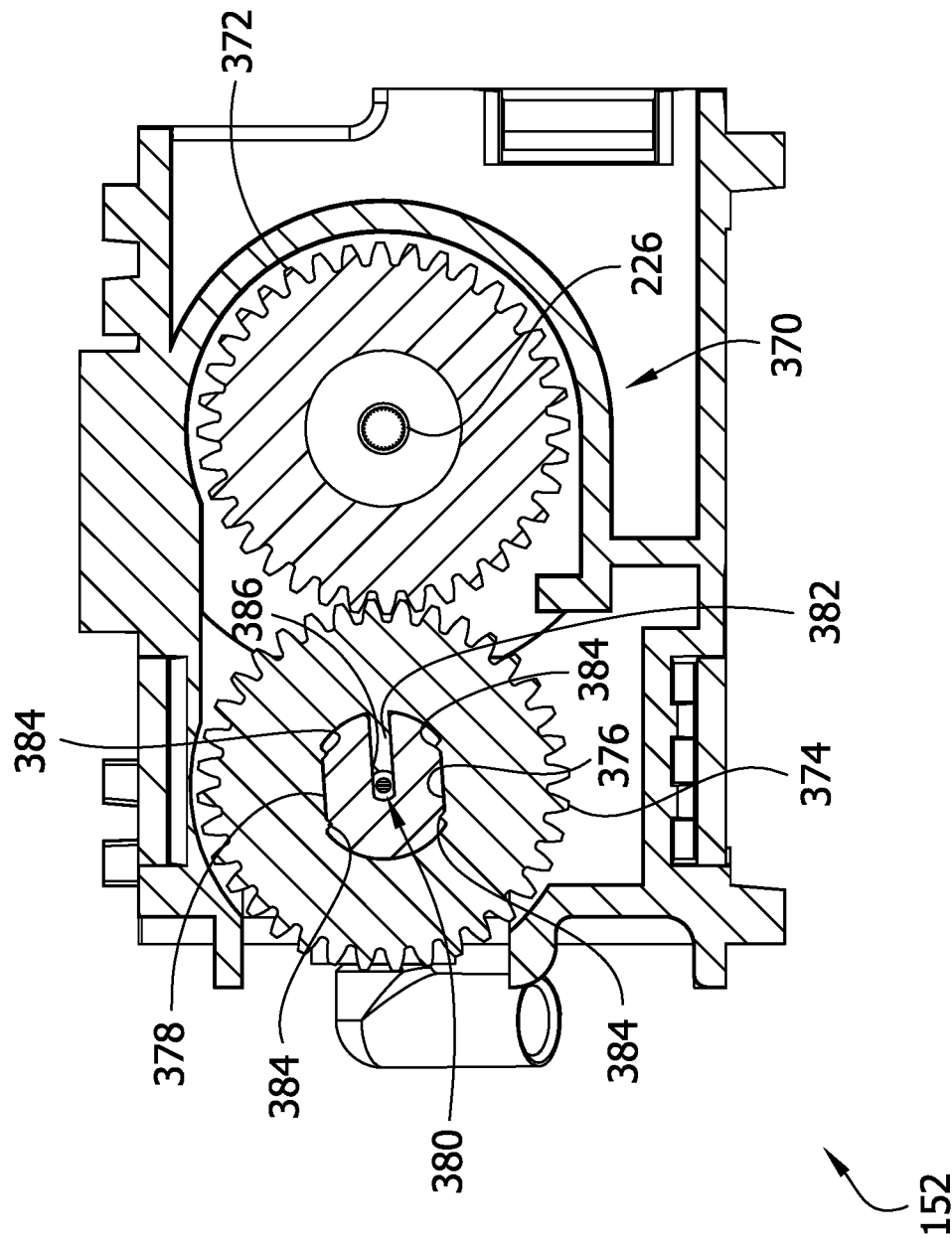
FIG. 34 is a cross section taken in the plane of line 34-34 of FIG. 17.
Figure 35:
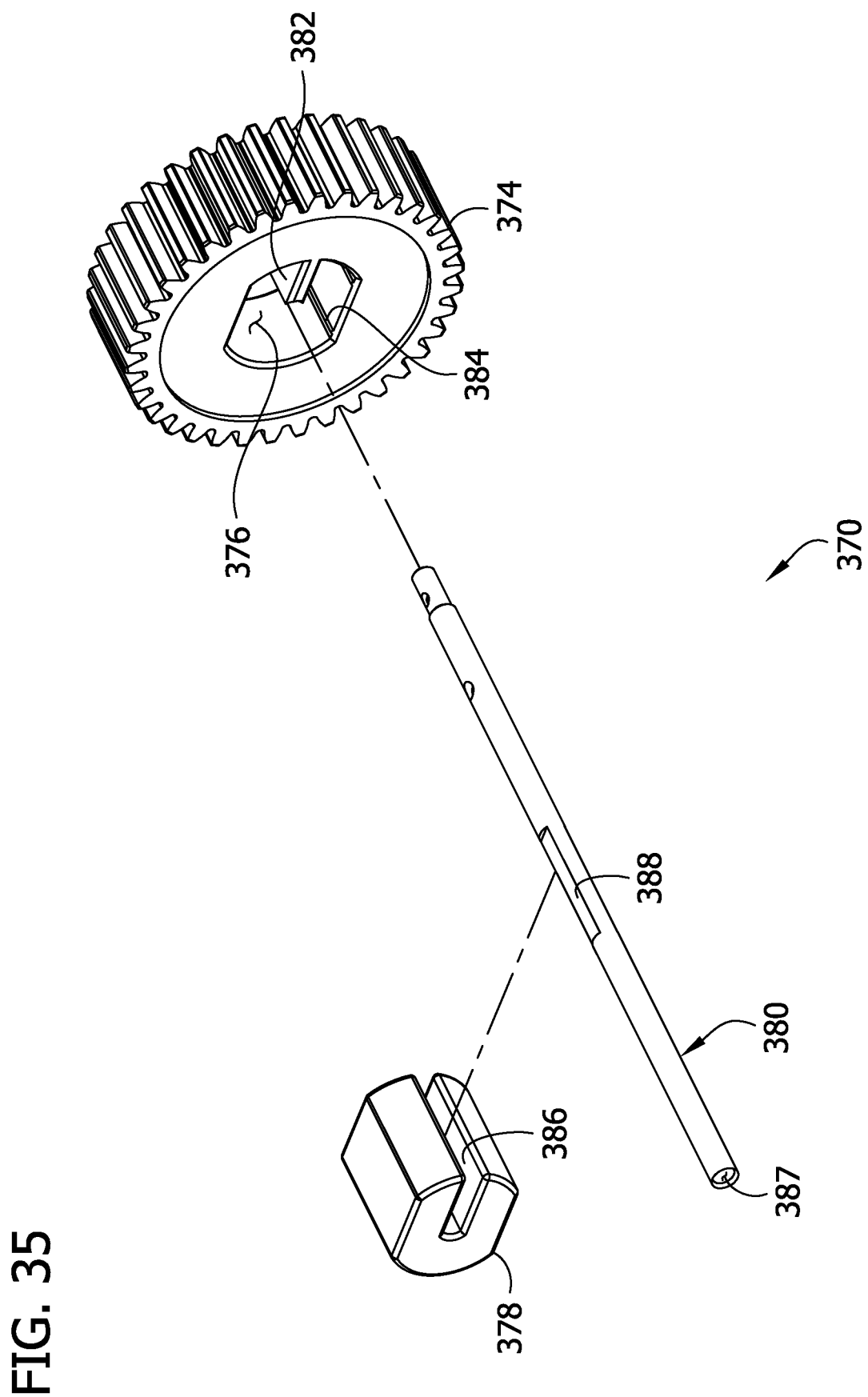
FIG. 35 is an exploded perspective of a subassembly of a rotational drive linkage of the catheter.

Referring to FIGS. 34 and 35, the driven gear 374 defines a hub opening 376 that is shaped and arranged for receiving a hub 378 (e.g., a hub insert) and a connector tube 380 (e.g., a connector shaft) therein. As explained in further detail below, the hub 378 and the connector tube 380 being received in the hub opening 376 attaches the hub and the connector tube to the driven gear 374 for conjoint rotation with the driven gear about the axis A1. The hub opening 376 extends through the thickness of the driven gear 374 and has a generally U-shaped cross-sectional shape in a plane extending radially of the axis A1. In one or more embodiments, the driven gear can define a hub opening having another cross-sectional shape. The driven gear 374 has two opposed internal cross-sectional flats that face radially inward of the axis A1 and define portions of the cross-sectional perimeter of the hub opening 376. In addition, the driven gear 374 includes a tang 382 (e.g., a key) that extends radially into the hub opening 376. The tang 382 can suitably have flat side portions and a concavely curved free end portion. In the illustrated embodiment, the driven gear 374 further includes crush ribs 384 (i.e., one or more crush ribs; e.g., four crush ribs) protruding from the cross-sectional flats that define the perimeter of the hub opening 376. One or more embodiments can have other numbers (e.g., zero or more) and arrangements of crush ribs.

The hub 378 is attached to the driven gear 374 such that the hub is rotatable with the driven gear about the axis A1 of the driven gear. As explained below, the hub 378 also operatively connects the driven gear 374 to the proximal end portion of the drive shaft 24 (not shown in FIGS. 34 and 35) such that the drive shaft rotates about the rotational axis A1 with the driven gear. The hub 378 is U-shaped in a cross section defined by a plane extending radially of the driven gear axis A1. For example, the hub 378 has a cross-sectional shape that generally corresponds to the cross-sectional shape of the hub opening 376. The hub 378 defines a groove 386 (e.g., a keyway) that is sized and arranged for receiving the tang 382 of the driven gear 372 therein. In the assembled drive linkage 370, the tang 382 extends into the groove 386 as shown in FIG. 34. The hub 376 includes two opposed internal cross-sectional flats that define opposite sides of the groove 386 and are configured to engage the flat sides of the tang 382. The tang 382, functioning as a key, slots into the groove 386, functioning as a keyway, to connect the hub 376 to the driven gear 374 for conjoint rotation.

As shown in FIG. 34, the groove 386 has an inner end that is configured to be diametrically spaced apart from the inboard end of the tang 382 about the axis A1 when the hub is received in the groove. In the illustrated embodiment, the inner end of the groove 386 has an oppositely curved cross-sectional orientation from the concavely curved cross-sectional orientation of the inboard end of the tang 382 (e.g., the void space of the groove has a convexly curved middle end and the hub 378 has a concavely curved surface at the inner end of the groove). A gap between the inner end of the groove 386 and the inner end of the tang 382 is configured to receive a portion of the connector tube 380 therein as described in further detail below. The gap has opposed, flat cross-sectional sides defined by the flat sides of the groove 386 and opposed curved cross-sectional ends defined by the curved inner end of the groove and the free end of the tang 382.

The illustrated hub 376 also has diametrically opposite cross-sectional exterior flats that are configured to engage the opposed internal cross-sectional flats of the driven gear 374. The engagement between the internal flats of the driven gear 374 and the external flats of the hub 376 prevent relative rotation of the hub with respect to the driven gear about the axis A1. The hub 376 is configured to be press fit into the hub opening 376 of the driven gear 374. The perimeter of the hub 376 (e.g., the external flats) is configured to engage and crush the crush ribs 384 as the hub is pressed into the hub opening 376, thereby creating an interference fit (or press fit) between the hub and the driven gear 374 that attaches the hub to the driven gear.

Figure 36:
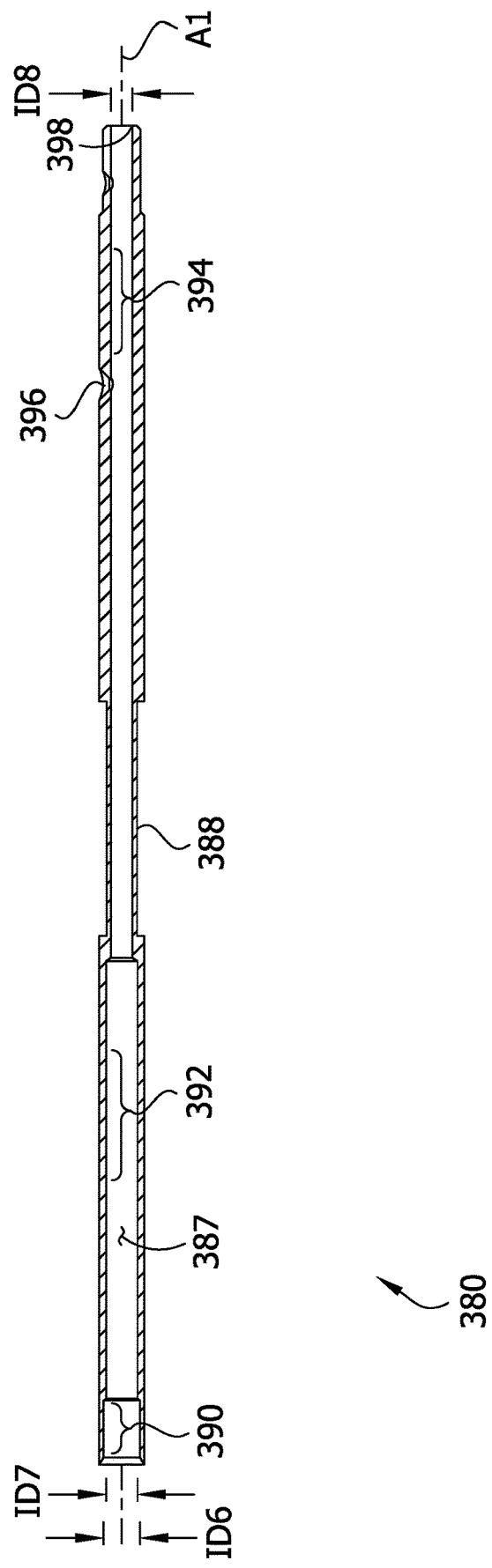
FIG. 36 a longitudinal cross section of a connector tube of the catheter.

The connector tube 380 is configured to be received in the gap between the tang 382 and the hub 378 for conjoint rotation with hub and the driven gear 374 about the axis A1. Referring to FIGS. 35 and 36, the connector tube 380 generally comprises a cylindrical tube (e.g., a metal tube, such as a hypotube) having a length extending along the rotational axis A1, and proximal and distal end portions spaced apart along the length. The illustrated connector tube 380 also has lumen 387 extending along the axis A1. The guidewire G is passable along the axis A1 through the lumen 387. In addition, as explained below, the proximal end portion of the catheter body 14 is received in the lumen 387 and joined to the connector tube 380 for conjoint rotation with the connector tube about the axis A1. As is further explained below, the connector tube 380 is also configured to act as a manifold that establishes both flushing and inflation fluid connections. The lumen 387 functions as a main passage of the fluid manifold provided by the connector tube 380 as explained below. Thus the connector tube 380 functions as both a rotational connector shaft and a fluid manifold in the illustrated embodiment.

The connector tube 380 has a rotational key portion 388 that defines two external cross-sectional flats at diametrically opposite positions with respect to the axis A1. The key portion 388 is spaced apart between the proximal and distal end portions of the connector tube 380 such that each flat is formed by a respective depression in the exterior of the connector tube and each depression has opposite proximal and distal ends. The rotational key portion 382 of the connector tube 380 is configured to be inserted laterally or radially into the groove or keyway 386 of the hub 378 before the hub is pressed into the driven gear 374. The flats of the key portion 388 engage the flat sides of the groove 386 to connect the connector tube 380 to the hub 378 for conjoint rotation with the hub about the axis A1. The ends of the depressions defining the flats of the key portion 388 are configured to engage the ends of the hub 378 to prevent movement of the connector tube 380 along the axis A1 with respect to the hub. After the key portion 388 is inserted into the groove 386, the connector tube 380 and the hub 378 can be inserted conjointly into the hub opening 376 by pressing the hub into hub opening of the driven gear 374 along the axis A1. The key portion 388 of the connector tube 380 is radially captured between the hub 378 and the driven gear 374. The flat sides of the groove 386 prevent movement of the connector tube 380 along one radial axis and the free end of the tang 384 and inner end of the groove prevent movement along another, orthogonal radial axis. The connector tube 380 is thus connected to the drive gear 374 for conjoint rotation with the driven gear about the axis A1.

Figure 37:
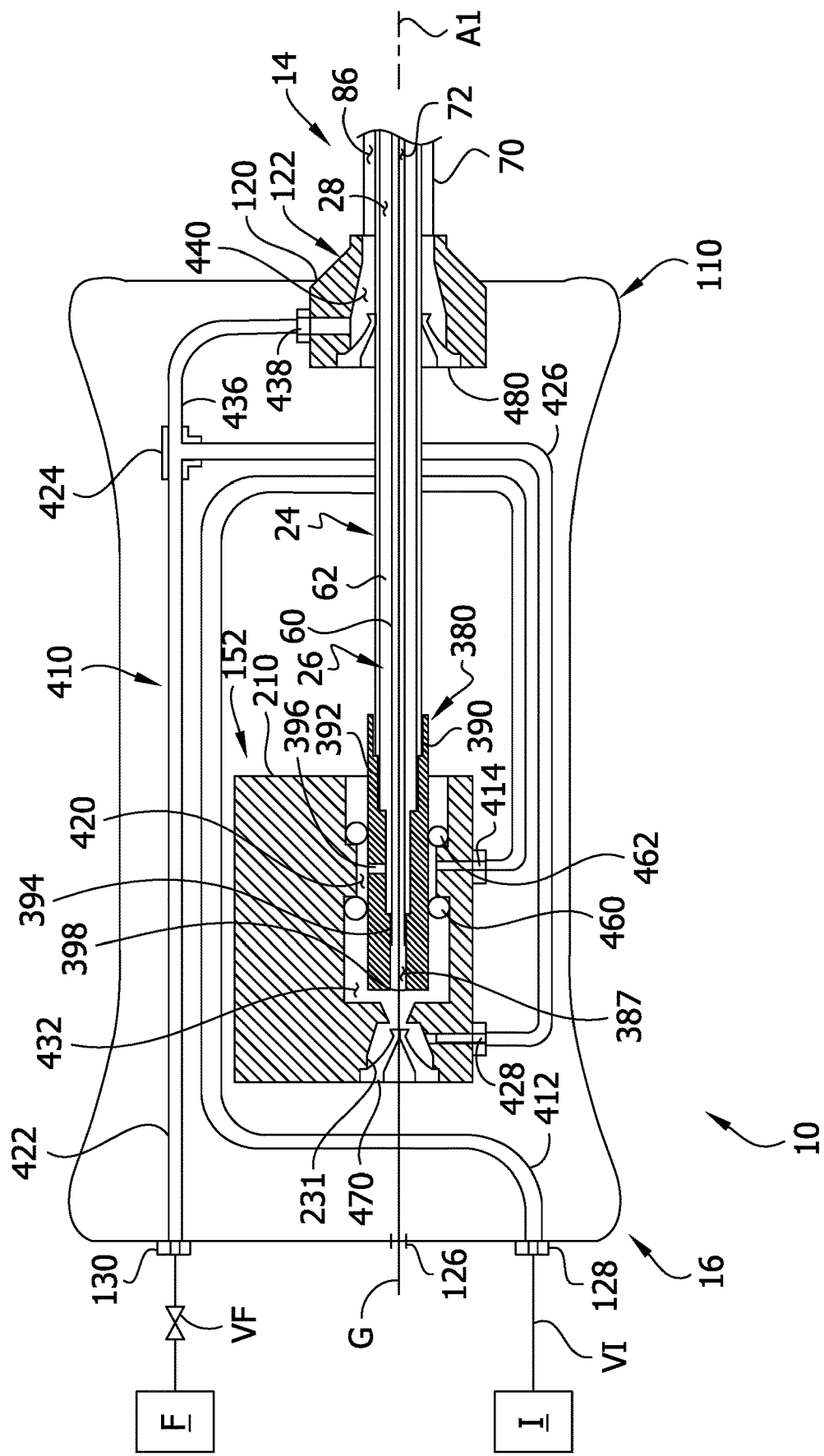
FIG. 37 is a schematic illustration of fluid passaging of the handle.

Referring to FIGS. 36 and 37, in the illustrated embodiment, the catheter body 14 is configured to be rotationally and fluidly coupled to the handle 316 inside the connector tube 380. For example, the proximal end portion drive shaft 24 is configured extend into the lumen 387 and be rotationally connected to connector tube at a drive shaft joint 390 (in FIG. 36, the reference number 390 indicates the location of the drive shaft joint). A suitable method of connecting the drive shaft 24 to the connector tube 380 at the joint 390 such that the drive shaft rotates conjointly with the connector tube about the axis A1 can be used. In one or more embodiments, the drive shaft 24 is connected to the connector tube 380 at the joint 390 by one of an adhesive bond, a weld, a heat bond, and/or a chemical bond. The connector tube 380 can suitably have an inner diameter ID6 that is about the same as the outer diameter OD9 (FIG. 8) of the drive shaft 24 such that, at the location of the joint 390, the drive shaft is received in the lumen 387 in a close tolerance fit with the connector tube 380.

The inflation conduit 26 is configured to be both rotationally and fluidly coupled to the connector tube 380 inside the lumen 387. For example, the outer inflation tube inflation tube 62 protrudes into the lumen 387 proximally of the proximal end of the drive shaft 24 and is rotationally and fluidly connected to the connector tube 380 at an outer inflation tube joint 392 (in FIG. 36, the reference number 392 indicates the location of the outer inflation tube joint). The outer inflation tube joint 392 is spaced apart proximally along the axis A1 from the drive shaft joint 390. In the illustrated embodiment, each of the drive shaft joint 390 and the outer inflation tube joint 392 is spaced apart distally of the key portion 388 of the connector tube 380. The joint locations can be other than as illustrated in one or more embodiments. The connector tube 380 has an inner diameter ID7 at the outer inflation tube joint location 392 that is less than the inner diameter ID6 at the drive shaft joint location 390. Suitably, the inner diameter ID7 is about the same as the outer diameter OD8 (FIG. 8) of the outer inflation tube 62 such that, at the joint 392, the outer inflation tube is received in the lumen 387 in a close tolerance fit with the connector tube 380. Any suitable method can be used to connect the outer inflation tube 62 to the connector tube 380 at the joint 392 such that the outer inflation tube (1) rotates conjointly with the connector tube about the axis A1 and (2) is fluidly sealed to the connector tube. In one or more embodiments, the outer inflation tube 62 is connected to the connector tube 380 at the joint 392 by one of an adhesive bond, a weld, a heat bond, and/or a chemical bond. The fluid seal between the outer inflation tube 62 and the connector tube 380 extends about the entire cross-sectional perimeter of the outer inflation tube and is configured to prevent fluid (e.g., inflation fluid) from passing through the fluid seal through the interface radially between the outer inflation tube and the connector tube.

The inner inflation tube inflation tube 60 protrudes proximally of the proximal end of the outer inflation tube 62 and is connected to the connector tube 380 at an inner inflation tube joint 394 (in FIG. 36, the reference number 394 indicates the location of the inner inflation tube joint). The inner inflation tube joint 394 is spaced apart proximally along the axis A1 from the outer inflation tube joint 392. In the illustrated embodiment, the inner inflation tube joint 394 is spaced apart proximally from the key portion 388 of the connector tube 380. The inner inflation tube joint 394 is located along the axis A1 between an inflation fluid port 396 and a flushing fluid port 398. As will be explained in further detail below, the inflation fluid port 396 and the flushing fluid port 398 are configured to provide fluid communication between the lumen 387 and each of a source of inflation fluid I and a source of flushing fluid F, respectively. In the illustrated embodiment, the inflation fluid port 396 is located between the inflation tube joints 392, 394 along the axis A1, and the flushing fluid port 398 is spaced apart proximally from the inner inflation tube joint. The joint locations can be other than as illustrated in one or more embodiments.

The connector tube 380 has an inner diameter ID8 at the inner inflation tube joint 394. The inner diameter ID8 is less than the inner diameter ID7 at the outer inflation tube joint 392. Suitably, the inner diameter ID8 can be greater than the outer diameter OD7 (FIG. 8) of the inner inflation tube 60 to define an annular inflation fluid channel in the lumen 387 that extends radially between the inner inflation tube 60 and the connector tube 380 and axially from the inner inflation tube joint 394 to the outer inflation tube joint 392. As can be appreciated, this annular fluid channel formed in the lumen 387 provides fluid communication between the inflation port 396 and the inflation lumen 28 of the inflation conduit 26 (see FIG. 37). Any suitable method can be used to connect the inner inflation tube 60 to the connector tube 380 at the joint 394 such that the inner inflation tube (1) rotates conjointly with the connector tube about the axis A1 and (2) is fluidly sealed to the connector tube. In one or more embodiments, the inner inflation tube 60 is connected to the connector tube 380 at the joint 394 by one of an adhesive bond, a weld, a heat bond, and/or a chemical bond. The fluid seal between the inner inflation tube 60 and the connector tube 380 extends around the entire cross-sectional perimeter of the inner inflation tube 60 and is configured to prevent fluid (e.g., flushing fluid or inflation fluid) from passing through the fluid seal radially between the inner inflation tube and the connector tube.

The flushing port 398 is spaced apart proximally from the fluid seal between the inner inflation tube 60 and the connector tube 380 at the joint 394. Suitably, the fluid seal between the inner inflation tube 60 and the connector tube 380 is liquid tight. Thus, the joint 394 fluidly couples the guidewire lumen 72 inside the inner inflation tube 60 to a proximal portion of the connector tube lumen 387, which is in fluid communication with the flushing port 398 (see FIG. 37). Accordingly, the fluid seal provided by the joint 394 fluidly couples the guidewire lumen 72 to the inflation port 398.

Figure 38:
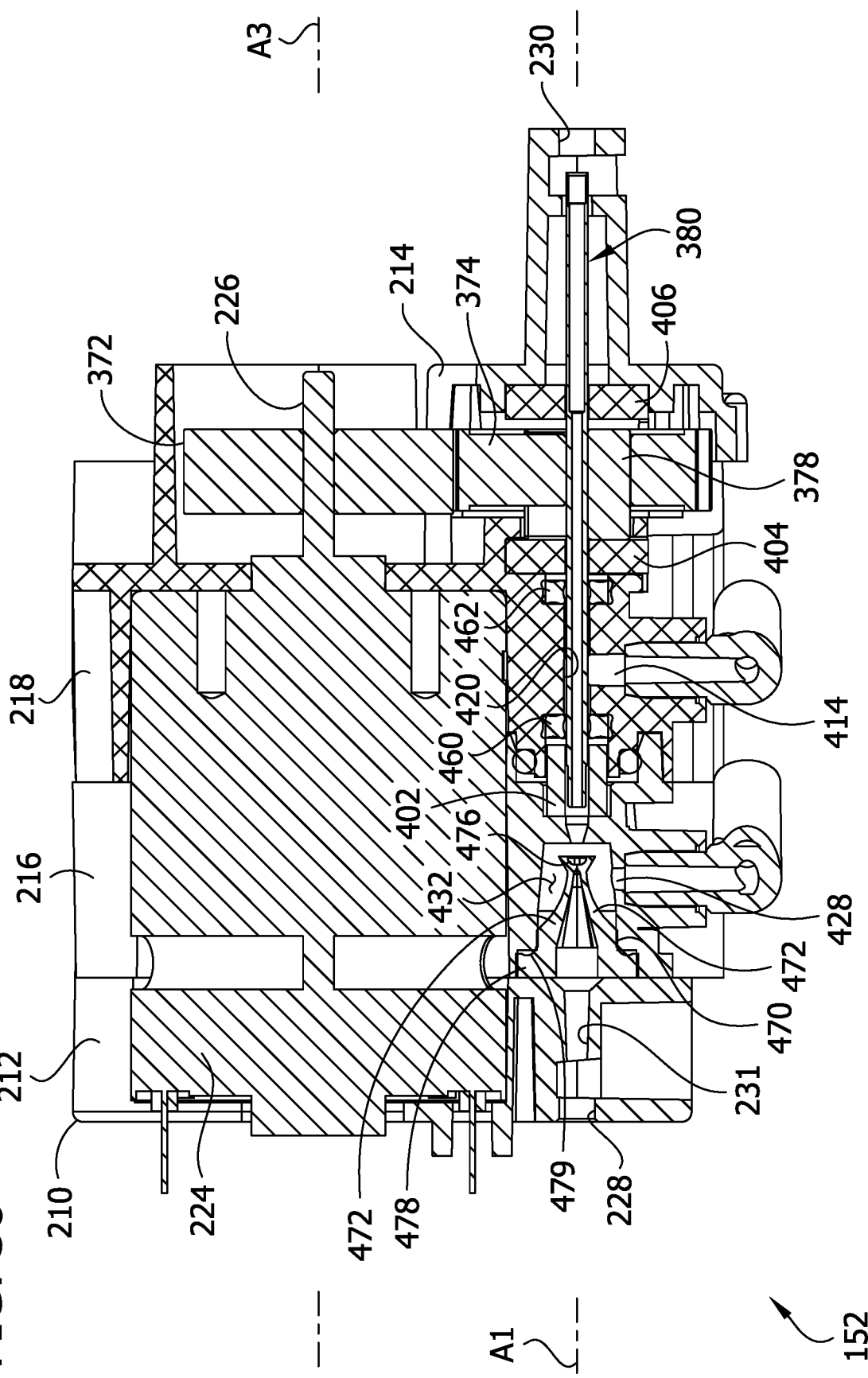
FIG. 38 is a cross section taken in the plane of line 38-38 of FIG. 17.
Figure 39:
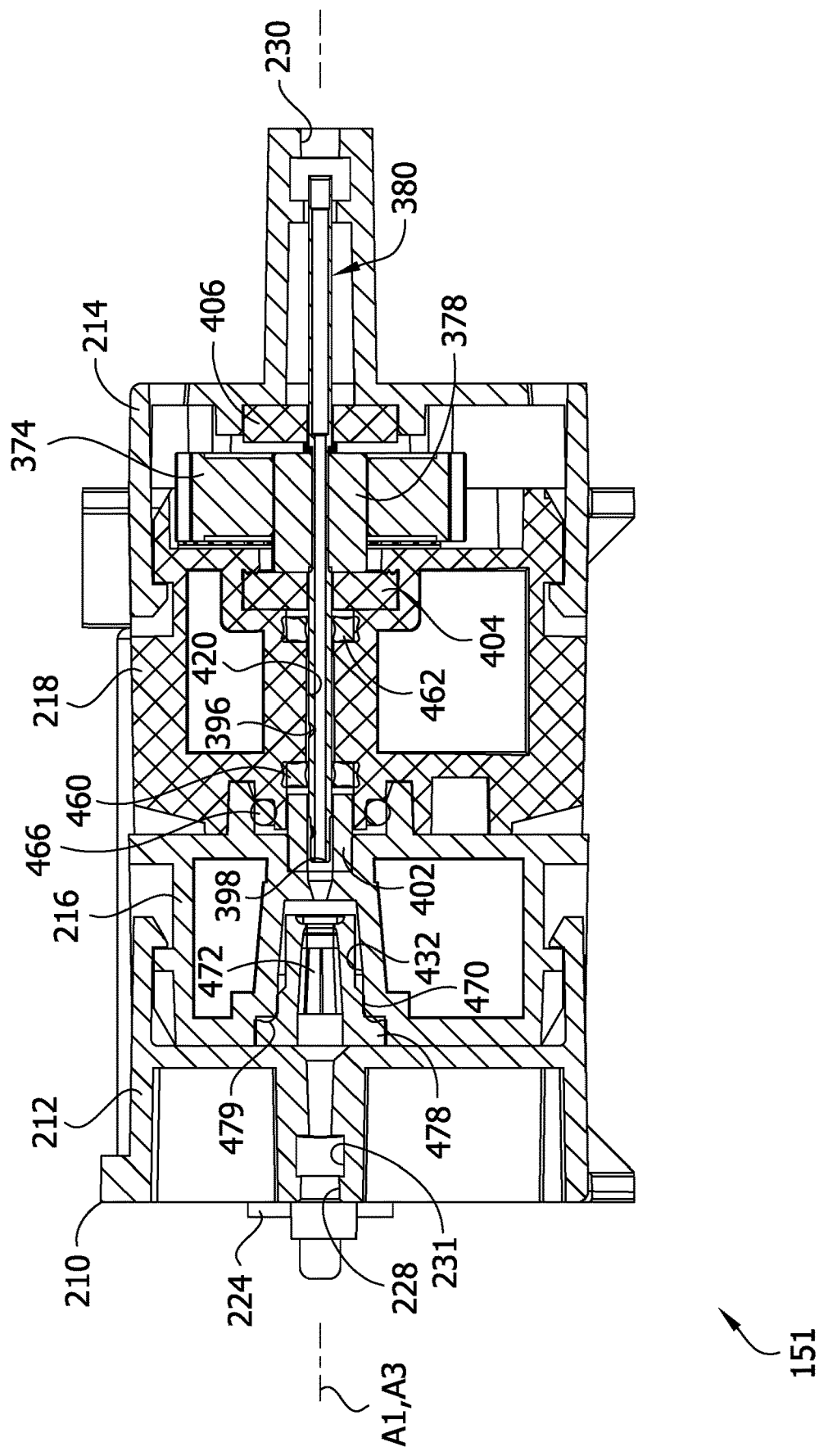
FIG. 39 is a cross section taken in the plane of line 39-39 of FIG. 18.
Figure 39A:
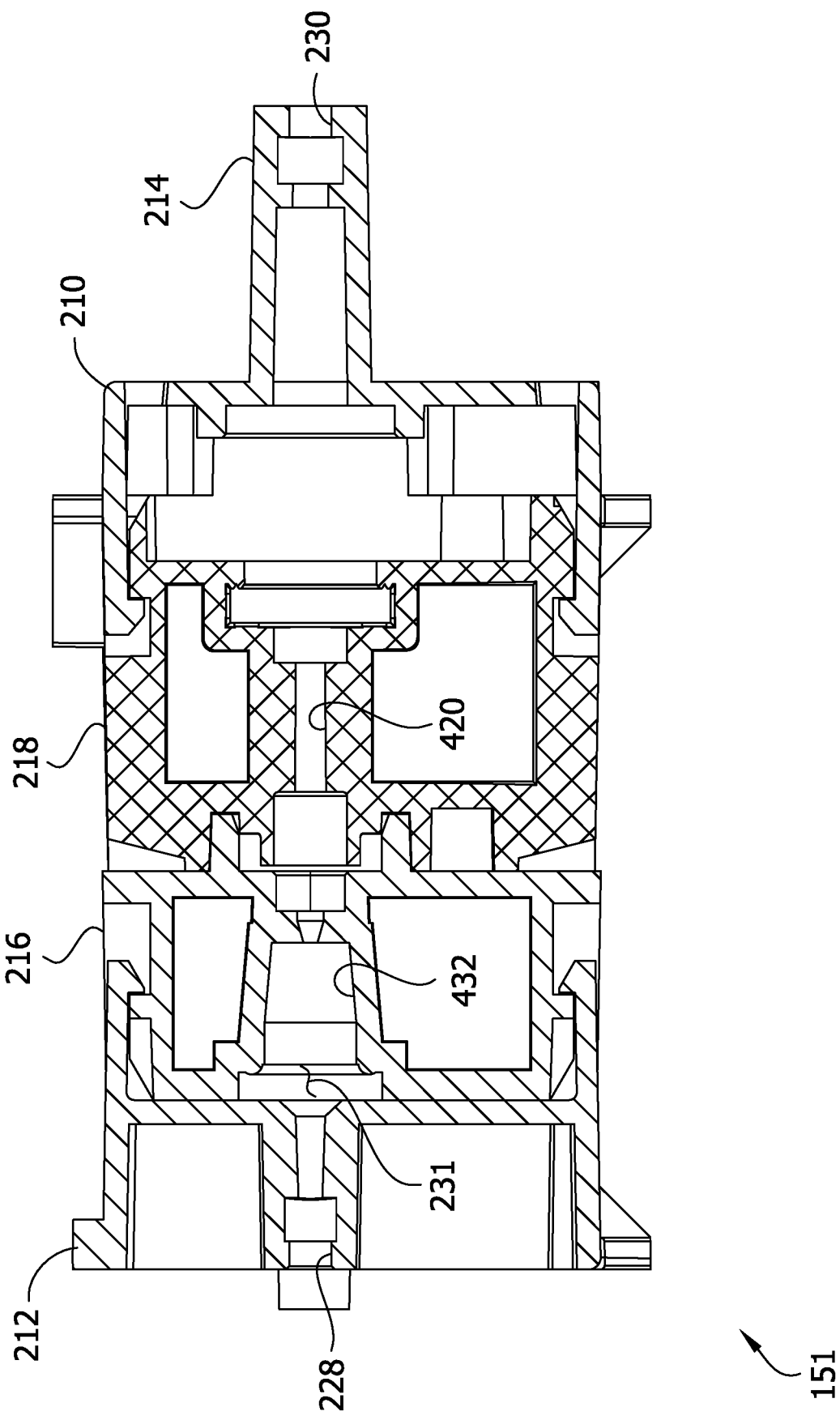
FIG. 39A is similar to FIG. 39 except that internal components of a block assembly are removed.

Referring to FIGS. 19, 38, and 39, in the illustrated embodiment, the carriage block assembly 210 is configured to support the connector tube 380 for balanced rotation about the axis A1. For example, in the illustrated embodiment, the block assembly 210 comprises a cylindrical bearing 402 that defines a longitudinal passage configured to receive a proximal end portion of the connector tube 380 therein. The bearing 402 is captured between opposed recesses of the flushing block member 216 and the inflation block member 218, and the connector tube 380 is rotatably received in the longitudinal passage extending through the bearing. The bearing 402 is configured to support the proximal end portion of the connector tube 380 for rotation about the axis A1 with respect to the bearing. In one or more embodiments, the bearing can align the proximal end portion of the connector tube 380 along the axis A1 without imparting substantial frictional forces on the connector tube. In the illustrated embodiment, the block assembly 210 includes first and second square bushing 404, 406 through which the connector tube 380 passes as it extends along the axis A1. In one or more embodiments, the bushings 404, 406 are configured to limit movement of the gear 374 along the axis A. The connector tube can be supported for rotation in other ways in one or more embodiments.

In use, the drive linkage 370 rotatably couples the motor 224 to the drive shaft 24 and the inflation conduit 26 of the catheter body 14. When the motor 224 rotates the shaft 226 about the drive axis A3, the drive gear 372 rotates conjointly with the shaft. The driven gear 374 is thereby rotated about the rotational axis A1 and conjointly rotates the hub 378 and connector tube 380. Since the joints 390, 392, 394 connect the drive shaft 24 and the inflation conduit 26 to the connector tube 380 for conjoint rotation with the connector tube, the drive shaft and the inflation conduit are driven in conjoint rotation with the driven gear 374 about the axis A1. Since the drive shaft 24 and inflation conduit 26 are configured to rotate relative to the catheter body alignment guide 272 and the isolation sheath 70 as explained above, actuation of the motor 224 drives rotation of the drive shaft and the inflation conduit inside the catheter body alignment guide and the isolation sheath 70. Moreover, since the distal end portions of the drive shaft 24 and the inflation conduit 26 are conjointly connected to the burr 22 and the balloon 20 as explained above, actuation of the motor 24 also drives rotation of the burr assembly 12 about the rotational axis A1.

F. Fluid Passaging

Referring to FIG. 37, fluid passaging inside the handle 16 is illustrated schematically and generally indicated at reference number 410. In general, the handle passaging 410 is configured to (1) fluidly connect a source of inflation fluid I to the inflation lumen 28 and (2) fluidly connect a source of flushing fluid F to the guidewire lumen 72 and the flushing lumen 86. Portions of the passaging 410 are omitted from the non-schematic drawings in order to show other components more clearly. In one or more embodiments, the omitted portions of the passaging can comprise one or more flexible hoses or tubing that provide fluid communication as described in further detail below. Suitably, the hoses or tubing can be configured to move as required to accommodate movement of the carriage 152 along the handle 16 while maintaining the fluid connections described below.

In FIG. 37, the single external inflation port 128 (broadly, an inflation fluid inlet) is configured to fluidly connect to a source of inflation fluid I and the single external flushing port 130 (broadly, a flushing fluid inlet) is configured to be fluidly connected to a source of flushing fluid F. Valves VI, VF are respectively connected between the fluid sources I, F and the ports 128, 130. The valves VI, VF are configured to control the flow of the fluids from the sources I, F to the respective ports 128, 130. In the illustrated embodiment, the external valves VI, VF are also used to respectively control the flow of the inflation fluid and the flow flushing fluid through the catheter 10. For example, a user can selectively open the inflation fluid valve VI to inflate the balloon 22 or selectively open the flushing fluid valve VF to direct flushing fluid through the catheter body 14. The illustrated catheter 10 does not include an internal mechanism for selectively controlling the flow of inflation fluid or flushing fluid through the device. In one or more embodiments, however, the catheter can comprise integral or internal fluid controls (e.g., valves) for controlling the flow of inflation fluid and/or flushing fluid through the device.

The passaging 410 is supported inside the handle 16 and is configured to provide fluid communication between the inflation port 128 and the inflation lumen 28 of the catheter body inflation conduit 26. The handle passaging 410 includes an inflation conduit 412 (e.g., a handle inflation conduit) that extends from the external inflation port 128 to an inflation port 414 on the carriage 152 (e.g., a carriage inflation port). As explained below, the carriage inflation port 414 is configured to provide fluid communication between the handle inflation conduit 412 and an inflation chamber 420 formed in the block assembly 210. As is further explained below, the inflation chamber 420 is configured to provide fluid communication between the carriage inflation port 414 and the inflation port 396 of the connector tube 380 (e.g., a connector tube inflation port). As explained above, the fluid seals at the joints 392, 394 fluidly connect the connector tube inflation port 396 to the inflation lumen 28 of the inflation conduit 26. Accordingly, the passaging 410 is configured to establish an inflation fluid flow path that extends from the handle inflation port 128—through the handle inflation tube 412, the carriage inflation port 414, the inflation chamber 420, and the connector tube inflation port 396—into the inflation lumen 28 of the catheter body 14.

The handle passaging 410 is also configured to provide fluid communication between the flushing port 130 and the guidewire lumen 72. The handle passaging 410 comprises a main flushing conduit 422 that extends from the flushing port 130 to a flow splitter 424 (e.g., a tee fitting, a wye fitting, or other fittings). A first branch conduit 426 extends from the flow splitter 424 to a flushing port 428 on the carriage 152 (e.g., a carriage flushing port). As explained below, the carriage flushing port 428 is configured to provide fluid communication between the first branch conduit 426 and a carriage flushing chamber 432 that is formed in the block assembly 210. As is further explained below, the carriage flushing chamber 432 is in fluid communication with the flushing port 398 of the connector tube 380 (e.g., a connector tube flushing port). (In the illustrated embodiment, the flushing port 398 is formed solely at the axial end of the lumen 387; but in one or more embodiments, the flushing port could also comprise one or more radial openings through the connector tube 380 located proximally of the seal 394. What appears to be such a radial port in the illustrated connector tube 380 functions as a glue port during manufacturing in one or more embodiments.) As explained above, the fluid seal provided by the joint 394 between the inner inflation tube 60 and the connector tube 380 fluidly couples the flushing port 398 (and also the open proximal end) of the connector tube to the guidewire lumen 72. Accordingly, the handle passaging 410 is configured to establish a first flushing fluid flow path that extends from the handle flushing port 130—through the main flushing tube 422, the flow splitter 424, the first branch conduit 426, the carriage inflation port 428, the carriage flushing chamber 432, and the connector tube flushing port 398—into the guidewire lumen 72 of the catheter body 14.

The handle passaging 410 is also configured to provide fluid communication between the flushing port 130 and the flushing lumen 86 of the isolation sheath 70. The illustrated passaging 410 comprises a second branch conduit 436 that extends from the flow splitter 424 to a flushing port 438 on the distal hub 122 (e.g., a hub flushing port). As explained below, the hub flushing port 438 is configured to provide fluid communication between the branch conduit 436 and a hub flushing chamber 440 defined by the hub 122. As is further explained below, the hub 122 is fluidly coupled to the isolation sheath 70 such that the flushing chamber 440 is in fluid communication with the flushing lumen 86. Accordingly, the passaging 410 is configured to establish a second flushing fluid flow path that extends from the handle flushing port 130—through the main flushing tube 422, the flow splitter 424, the second branch conduit 436, the hub flushing port 438, and the hub flushing chamber 440—into the flushing lumen 86 of the isolation sheath 70.

As can be seen, the illustrated passaging 410 is configured to provide fluid communication from a single handle flushing port 130 to each of a guidewire lumen 72 and a fluidly separate flushing lumen 86 of the catheter body 14. More specifically, the catheter 10 uses one flushing chamber 432 that is movable with the carriage 152 with respect to the handle 16 to provide fluid communication between the passaging 410 and the guidewire lumen 72 and another flushing chamber 440 that has a fixed position with respect to the handle to provide fluid communication between the passaging and the flushing lumen 86. One or more embodiments can have other passaging configurations, e.g., separate dedicated external flushing fluid ports for each of the guidewire lumen and the flushing lumen, etc.

1. Carriage-Mounted Fluid Block

Referring to FIGS. 38 and 39, the block assembly 210 of the carriage 152 is configured to provide fluid communication between the inflation lumen 28 and a source of inflation fluid I (FIG. 37) and to provide fluid communication between the guidewire lumen 72 and a source of flushing fluid F (FIG. 37). As set forth above, the illustrated block assembly 210 defines the main passage 231 (FIG. 39A), which generally extends along the axis A1 through the block assembly 210 from the proximal opening 228 through the distal opening 230. Each of the blocks 212, 214, 216, 218 defines a respective portion of the main passage 231. The guidewire G is passable along the axis A1 through the main passage 231 of the block assembly 210. The main passage 231 includes spaced apart portions defining the inflation chamber 420 and the flushing chamber 432. Thus each of the inflation chamber 420 and the flushing chamber 432 is defined in the block assembly 210 of the carriage 152 and is therefore movable with the carriage with respect to the handle housing 110. Each of the chambers 420, 432 extends along the length of the main passage 231 from a respective proximal end to a respective distal end. In the illustrated embodiments, the ends of the chambers 420, 432 are spaced apart along the axis A1 from one another and from the openings 228, 230 at the ends of the main passage 231. The portion of the main passage 231 that is defined by the inflation block member 218 generally corresponds to the inflation chamber 420. The portion of the main passage 231 that is defined by the flushing block member 216 generally corresponds to the flushing chamber 432. As explained below, the block assembly 210 is configured to support seals in the main passage 231 to hold inflation fluid in the inflation chamber 420 and flushing fluid in the flushing chamber 432, as well as maintain fluid separation between the inflation chamber and the flushing chamber.

Referring to FIG. 38, the carriage inflation port 414 is defined by a lateral passage formed in the inflation block member 218. The lateral inflation passage 414 is fluidly connected to the main passage 231 at the inflation chamber 420 and extends laterally from the main passage. In the illustrated embodiment, an elbow fitting is connected to the lateral inflation passage 414 for connecting the lateral passage to the handle inflation conduit 412 (FIG. 37). Similarly, the carriage flushing port 428 is defined by a lateral passage formed in the flushing block member 216. The lateral flushing passage 428 is fluidly connected to the main passage 231 at the flushing chamber 432 and extends laterally from the main passage. In the illustrated embodiment, an elbow fitting is connected to the lateral flushing passage 428 for connecting the lateral flushing passage to the branch conduit 426 (FIG. 37). Other fluid block passaging configurations can be used in one or more embodiments.

The connector tube 380 is rotatably received in the main passage 231 of the block assembly 210 such that the inflation port 396 is in fluid communication with the inflation chamber 420 and the flushing port 398 is in fluid communication with the flushing chamber 432. As explained above, the proximal end portion of the catheter body 14 is sealed to the connector tube at the joints 392, 394 (FIG. 37) such that a portion of the connector tube lumen 387 provides fluid communication between the inflation port 396 and the inflation lumen 28 and another, fluidly separate portion of the connector tube lumen provides fluid communication between flushing port 398 and the guidewire lumen 72. The connector tube 380 is thus configured to provide fluid communication between the inflation chamber 420 and the inflation lumen 28 and is further configured to provide fluid communication between the flushing chamber 432 and the guidewire lumen 72. Moreover, each of the inflation chamber 420 and flushing chamber 432 extends circumferentially around the entire cross-sectional perimeter of connector tube 380 such that the inflation port 396 and the flushing port 398 are each in continuous fluid communication with the respective chamber as the connector tube rotates 360° about the axis A1 during use.

Referring to FIGS. 37-39, the block assembly 210 is configured to mount a proximal radial seal 460 in the main passage 231 radially between the inflation block member 218 and the connector tube 380. The proximal radial seal 460 provides a radial fluid seal between the connector tube 380 and the block assembly 210 that seals a proximal end of the inflation chamber 420 about the connector tube. The proximal radial seal 460 provides a fluid seal that prevents inflation fluid from egressing from the proximal end of the inflation chamber 420 through the interface between the connector tube 380 and the fluid block assembly 210. The proximal radial seal 460 also provides a fluid seal between the inflation chamber 420 and the flushing chamber 432 that maintains fluid separation between the inflation chamber and the flushing chamber. Flushing fluid is thereby prevented from egressing from the distal end of the flushing chamber 432 through the interface between the connector tube 380 and the block assembly 210. As explained above, the connector tube 380 is configured to rotate about the axis A1 to drive rotation of the drive shaft 24 and the inflation conduit 26. The proximal radial seal 460 is configured to maintain the fluid seal about the connector tube 380 as the connector tube rotates about the rotational axis A1. In the illustrated embodiment, the proximal radial seal 460 comprises a stationary X-ring gasket that is received in a pocket formed in the proximal end portion of the inflation block member 218. The pocket is radially enlarged with respect to the axis A1 in comparison to the flushing chamber 420. The X-ring seal 460 is captured between the cylindrical bearing 402 and a proximal end wall of the inflation block member 218. Other seal configurations can also be used to provide a fluid seal of an end of an inflation chamber and/or to maintain fluid separation between an inflation chamber and a flushing chamber in one or more embodiments.

The block assembly 210 is further configured to mount a distal radial seal 462 in the main passage radially between the inflation block member 218 and the connector tube 380. The distal radial seal 462 provides a radial fluid seal between the connector tube 380 and the block assembly 210 that seals a distal end of the inflation chamber 420. The distal radial seal 462 provides a fluid seal that prevents inflation fluid from egressing from the distal end of the inflation chamber 420 through the interface between the connector tube 380 and the fluid block assembly 210. Like the proximal radial seal 460, the distal radial seal 462 is configured to maintain the fluid seal as the connector tube 380 rotates about the rotational axis A1 with respect to the block assembly 210. In the illustrated embodiment, the distal radial seal 462 comprises a stationary X-ring gasket that is received in a pocket formed at the distal end portion of the inflation block member 218. The distal pocket is radially enlarged with respect to the axis A1 in comparison to the flushing chamber 420. The X-ring seal 462 is captured between the distal end wall of the inflation block member 218 and the square bushing 404. Other seal configurations can also be used to provide a fluid seal of an end of an inflation chamber in one or more embodiments.

The distal radial seal 462 is located distal of the inflation port 396 in the connector tube 380 and the proximal radial seal 460 is located proximal of the connector tube inflation port. Thus, the connector tube inflation port 396 is located along the axis A1 between the proximal and distal radial seals 460, 462. The connector tube 380 and proximal and distal end seals 460, 462 are thus arranged so that the connector tube inflation port 396 is located along the axis A1 between the fluid seals at the proximal and distal ends of the inflation chamber 420. Thus, the connector tube inflation port 396 can thus maintain continuous fluid communication with the inflation chamber 396 as the connector tube 380 rotates 360° about the axis A1.

Referring to FIG. 37, when the expandable burr assembly 12 of the catheter 10 is positioned at the site of an occlusion and expansion of the burr 20 is desired, the user can use the valve VI to couple inflation fluid from the inflation fluid source I to the external inflation port 128. The inflation fluid flows from the port 128 through the handle inflation conduit 412. From the conduit 412, the inflation fluid flows into the carriage port 414 into the inflation chamber 420. The radial seals 460, 462 prevent the inflation fluid from escaping the chamber 420, even when the motor 224 is actuated and drives rotation of the connector tube 380 about the axis A1 (e.g., even at rotation speeds on the order of 10,000 rpm to 12,000 rpm). The inflation fluid flows from the inflation chamber 420 through the port 396 in the connector tube 380 into the lumen 387 of the connector tube 380. The sealed joints 392, 394 force the inflation fluid entering the lumen 387 to flow distally along the annular gap between the inner inflation tube 60 and the connector tube 380 until it enters the inflation lumen 28. The inflation fluid flows along the inflation lumen 28 into the interior of the balloon 22, thereby inflating the balloon and expanding the burr 20.

Referring to FIGS. 62 and 63, in one or more embodiments, each of the proximal and distal radial seals 460, 462 comprises a spring-energized rotary seal. Each spring-energized rotary seal 460, 462 comprises a gland body 610 having an inboard end 612 and an outboard end 614 spaced apart along the axis A1 when the seal is installed in the inflation block member 218. Here the terms "inboard" and "outboard" relate to position with respect to the inflation block member 218. When installed, the inboard ends 612 of the proximal and distal radial seals 460, 462 oppose one another such that each inboard end is in fluid communication with the inflation chamber 420. In one or more embodiments, the inboard end 612 of each spring-energized rotary seal 460, 462 is in contact with a separate sleeve bearing (not shown) located along the axis A1 between the respective inboard end and the opposing wall of the inflation block member 218. The sleeve bearings can limit extrusion of the gland bodies 610 in certain embodiments. In addition, each sleeve bearing can provide a bearing surface for the connector tube 380 as it rotates. When installed in the inflation block member 218, the outboard ends 614 of the spring-energized rotary seals 460, 462 face outward along the axis A1 away from one another.

The gland body 610 has a generally annular shape and comprises a central longitudinal channel 616 that extends along the axis A1 from the inboard end 612 through the outboard end 614. The connector tube 380 extends through the channel 616 in use. An annular recess 618 is formed in a radially outer surface of the gland body, and an annular gasket 620 is received in the annular recess. Each gasket 618 is configured to provide a fluid seal between the gland body 610 and the inflation block member 218 when the proximal and distal radial seals 460, 462 are installed. The illustrated gland body 610 further comprises an annular spring recess 622 radially inward of the recess 618. The spring recess 622 opens through the inboard axial end 612 of the gland body, and a flexible annular sealing web 624 of the gland body 610 defines a radially inner end of the spring recess 622. The spring recess 622 is sized and arranged for receiving an annular energizer spring 626 therein.

In general, the energizer spring 626, when energized, is configured to impart a radially inward force on the sealing web 624 to urge the sealing web 624 into sealing engagement with a respective segment of the connector tube 380 as the connector tube rotates about the axis A1. When inflation fluid is imparted in the inflation chamber 420, fluid pressure is conveyed to the inboard end 612 of each seal 460, 462, which compresses each spring 626 axially and thereby causes an inner cross-sectional dimension of the spring (e.g., an inner diameter) to decrease or contract generally uniformly about the axis A1. This causes the spring 626 to press the flexible sealing web 624 firmly against the connector tube 380 to maintain the fluid seal between the gland body 610 and the connector tube. The sealing web 624 thus provides the fluid seal between the gland body 610 and the connector tube 380 that prevents inflation fluid imparted in the inflation chamber 218 from escaping, even as the shaft rotates about the axis A1. The active rotary inflation seals 460, 462 thereby direct inflation fluid imparted into the inflation chamber 218 to flow through the port 396 in the connector tube 380 into the lumen 387. In the illustrated embodiment, the energizer spring 626 comprises an annular canted coil spring, however other types of springs can also be used in one or more embodiments. Examples of suitable active rotary inflation seals of the type described herein are sold by Bal Seal Engineering, Inc. of Lake Forest, California.

Referring again to FIGS. 38 and 39, the flushing chamber 432 in the carriage 152 has a proximal end and a distal end spaced apart from the proximal end along the axis A1. As explained above, the distal end of the flushing chamber 432 is sealed by the radial seal 460. Moreover, a liquid-tight connection between the block assembly 210 and the catheter body 14 is provided by the combination of the radial seal 460 between the block assembly and the connector tube 380 and the fluid-tight joint 396 between the connector body and the inner inflation tube 60. Substantially all of the liquid imparted into the flushing chamber 432 can therefore be directed into the guidewire lumen 72. Furthermore, the liquid-tight seal provided by the radial seal 460 ensures that substantially all of the liquid imparted into the flushing chamber 432 is directed into the guidewire lumen 72 even as the catheter body 14 rotates about the axis A1 with respect to the fluid block assembly 210. A secondary O-ring 466 (broadly, a flushing block interface seal) is also included to provide a liquid-tight seal about the flushing chamber 432 at the interface between the flushing block member 216 and the inflation block member 218. The O-ring 466 is configured to prevent fluid in the flushing chamber 432 from egressing through the interface between the flushing block member 216 and the inflation block member 218.

In the illustrated embodiment, the guidewire G is configured to extend through the main passage 231 of the block assembly 210. More specifically, the guidewire G is configured to extend from guidewire lumen 72, through the lumen 387 of the connector tube 380, through the flushing chamber 432, and through the proximal opening 228. A duckbill seal 470 is positioned across the otherwise open proximal end of the flushing chamber 432 to provide a seal of the proximal end of the flushing chamber. The duckbill seal 470 is configured to sealingly engage the guidewire G when it is received in the flushing chamber 432 to provide a liquid-tight seal of the proximal end of the flushing chamber as the guidewire G extends through the flushing chamber. Suitably, the duckbill seal 470 is configured to maintain the liquid tight seal with the guidewire G as the handle 16 moves along the guidewire, or in other words, as the guidewire slides with respect to the handle. Although a duckbill seal 470 is used to provide the guidewire seal and proximal end seal of the flushing chamber 432 in the illustrated embodiment, one or more embodiments can use other types of seals.

As shown in FIG. 38, the duckbill seal 470 can comprise a one-piece body of elastomeric material that is configured to sealingly engage the guidewire G about the entire cross-sectional perimeter of the guidewire. The illustrated duckbill seal 470 comprises opposing duckbill members 472 that extend from adjacent a proximal end portion toward a distal end portion of the duckbill seal. The duckbill members 472 are configured to slidingly accept the guidewire G therebetween. The opposing duckbill members 472 can taper as they extend toward the distal end portion of the duckbill seal 470. The duckbill members 472 also extend toward one another as they extend toward the distal end portion of the duckbill seal 470. The flushing chamber 432 extends circumferentially around the opposing duckbill members 472. In addition, the lateral flushing port 428 is radially aligned with the duckbill members 472 with respect to the axis A1.

As flushing fluid fills and pressurizes the flushing chamber 432, the duckbill members 472 are urged toward each other, enhancing the strength with which the duckbill seal 470 sealingly engages the guidewire G.

The duckbill seal 470 has an open proximal end and defines a recess between the duckbill members 472 that extends from the open proximal end toward the distal end portion of the seal. The recess tapers as it extends toward the distal end portion of the guidewire seal 470. In the illustrated embodiment, the distal end portions of the duckbill members 472 are initially connected by an imperforate web 476 that defines the distal end of the recess. The web 476 extends transverse (e.g., perpendicular) to the axis A1. The web 476 is configured to be pierced as the guidewire G is inserted through the catheter 10 and passes proximally out of the flushing chamber 432. In one embodiment, the tip of the guidewire G pierces the imperforate web 476. In another embodiment, an introducer tool (not shown) is inserted through the guidewire opening 126 in the handle housing 110 and the proximal opening 128 of the carriage and pierces the imperforate web 476 and then the guidewire G is loaded into the handle distally through the introducer tool. After the web 476 is pierced, the web 476 engages the guidewire G to provide a liquid seal about the guidewire that prevents flushing fluid from egressing through the proximal end of the flushing chamber 432.

In the illustrated embodiment, the proximal block member 212 (broadly, a cap) is secured to the flushing block member 416 (broadly, a fluid block) such that the duckbill seal 470 is captured between the proximal block member and the flushing block member. The proximal end of the duckbill seal 470 defines an annular, radially outwardly extending flange 478. The proximal end portion of the flushing block member 216 defines an annular recess for receiving the flange 478 therein. The flushing block member 216 comprises an annular end surface 479 defining the annular recess. The annular flange 478 is sized and arranged for being compressed between the distal end of the proximal block member 212 and the end surface. In the illustrated embodiment, the end surface 479 has a convex cross-sectional shape that is rotated or swept 360° about the axis A1 to form the annular end surface. The annular flange 478 is configured to be compressed against the convex surface 479 when the proximal block member 212 is secured to the flushing block member 216 to form an annular liquid-tight seal (e.g., fluid tight seal) between convex annular surface and the annular flange. Accordingly, the annular flange 478 is configured to form a fluid seal with the convex annular end surface 479 that inhibits fluid from egressing from the flushing chamber 432 through the interface between the duckbill seal 470 and the hub member 122.

In use, the guidewire G can be loaded into the catheter 10 by inserting the guidewire proximally into the guidewire lumen 72. After passing through the guidewire lumen 72, the guidewire G then passes through the connector tube 380 until the proximal tip engages the imperforate web 476. Pushing the guidewire G further proximally causes the tip to piece the web 476. After piercing the web 476, the guidewire G moves proximally through the recess between the duckbill members 472 and the portion of the main passage 231 defined by the proximal block member 212. Finally, the guidewire passes proximally through the guidewire opening 126.

Referring to FIG. 37, if flushing fluid in the guidewire lumen 72 is desired, the user can use the valve VF to couple flushing fluid from the flushing fluid source F to the external flushing port 130. The flushing fluid flows from the port 130 through the main flushing conduit 422 and the splitter 424 into the first branch conduit 426. (Flow through the second branch conduit 428 is discussed below). From the branch conduit 426, the flushing fluid flows through the carriage flushing port 428 into the flushing chamber 432. The duckbill seal 470 prevents the flushing fluid from egressing through proximal end of the flushing chamber 432, even as the guidewire G slides relative to the duckbill seal. Furthermore, the radial seal 460 prevents the flushing chamber 432 from communicating with the inflation chamber 420, and the secondary seal 466 prevents flushing fluid in the flushing chamber from egressing through the interface between the flushing block member 216 and the inflation block member 218. The flushing fluid is thus directed to flow from the flushing chamber 432, through the port 398 of the connector tube 380, into the proximal end portion of the connector tube lumen 387. Because of the sealed joint 394 between the inner inflation tube 60 and the connector tube 380, flushing fluid flows into the open proximal end of the guidewire lumen 72. The flushing fluid flows distally along the guidewire lumen 72 around the guidewire G received therein. Flushing fluid is discharged past the distal end of the burr assembly 12 through the open distal end of the inner inflation tube 60.

2. Distal Hub Assembly and Fluid Connection to Isolation Sheath

Figure 40:
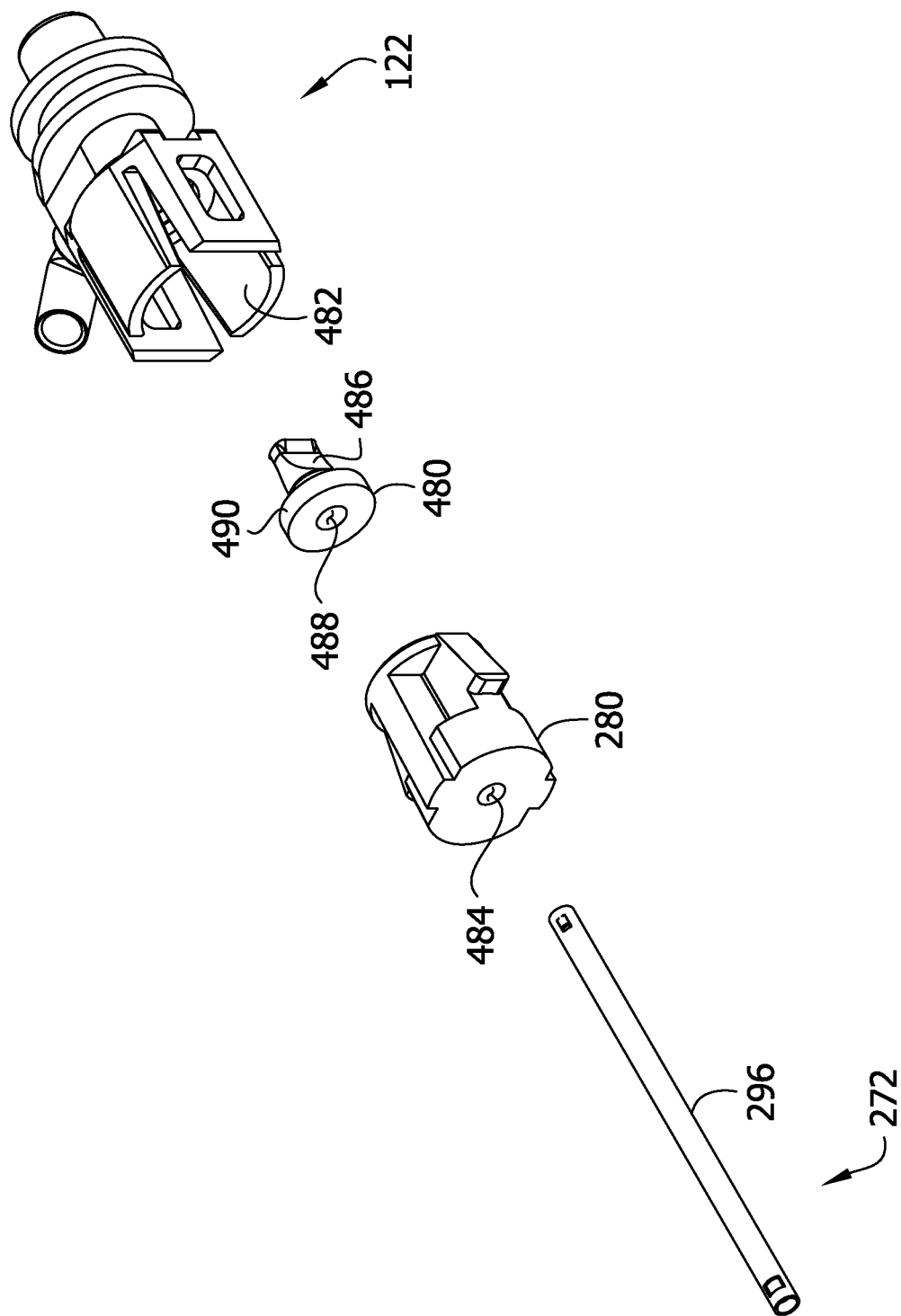
FIG. 40 is an exploded perspective of a distal hub assembly of the catheter and a distal tube of a distal one of the telescoping alignment guides.
Figure 41:
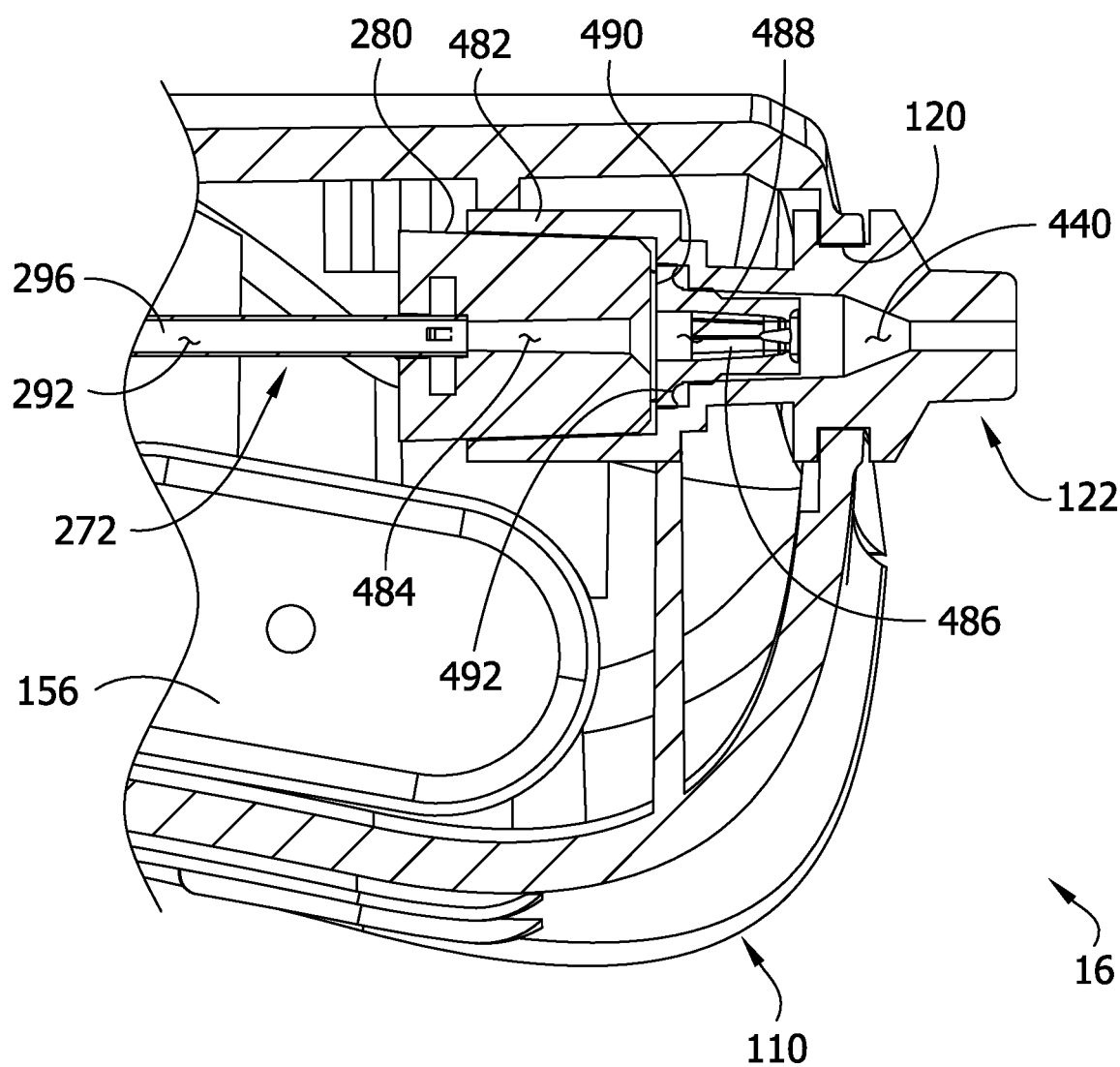
FIG. 41 is an enlarged view of a portion of FIG. 15.
Figure 42:
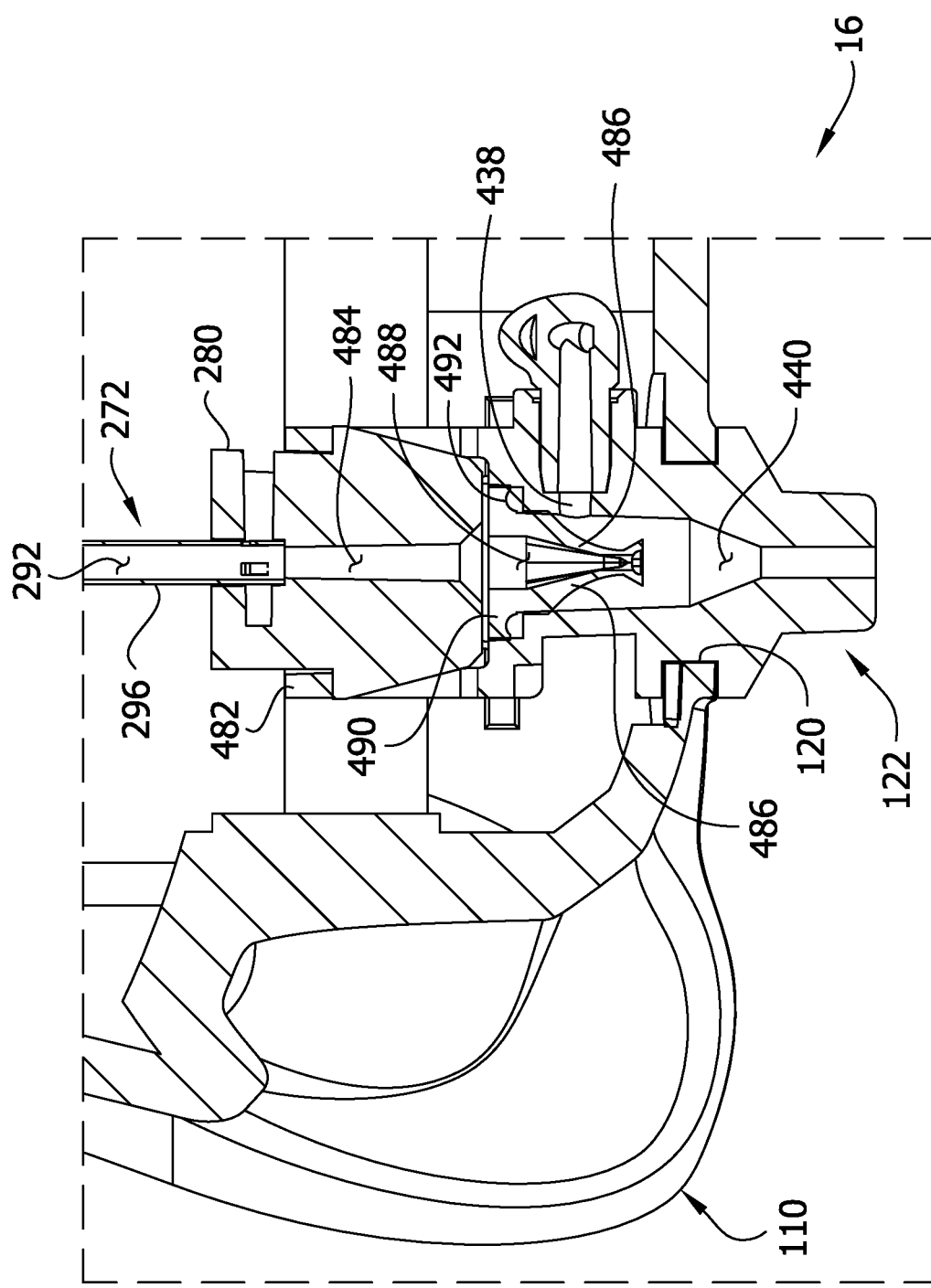
FIG. 42 is an enlarged partial cross section of a portion of the handle taken in the plane of line 42-42 of FIG. 17.

Referring to FIGS. 40-42, the distal hub 122 is configured to be fluidly coupled to the isolation sheath 70 and defines the flushing chamber 440. The illustrated hub 122 has an open proximal end portion and an open distal end portion. The flushing chamber 440 extends along the axis A1 from adjacent the open proximal end portion to the open distal end portion. The flushing chamber 440 tapers distally between the proximal end portion and the distal end portion. The hub flushing port 438 is defined by a lateral passage that extends through a wall of the hub 122 and fluidly communicates with the flushing chamber 440. In the illustrated embodiment, an elbow fitting is configured to fluidly connect the lateral hub port 438 to the branch conduit 436 of the passaging 410 (FIG. 37). The drive shaft 24 and the inflation conduit 26 are configured to extend along the axis A1 through the flushing chamber 440 into the isolation sheath 70. As will be explained in further detail below, a catheter body seal 480 is located in the hub 122 to provide a fluid seal about the catheter body 14 at the proximal end of the flushing chamber 440. The distal end of the flushing chamber 440 is in open fluid communication with the flushing lumen 86 of the isolation sheath 70 as described below.

The distal end portion of the hub 122 is configured to be secured in the catheter body opening 120 of the handle housing 110. Thus, the distal hub 122 and the flushing chamber 440 defined therein are configured to be fixed in place with respect to the housing 110. The distal end portion of the hub 122 is configured to receive the proximal end portion of the isolation sheath 70 therein. In the illustrated embodiment, the isolation sheath 70 is sealingly received in the hub 122. For example, the isolation sheath 70 is sealed to the internal surface of the hub 122 about an entire external cross-sectional perimeter of the isolation sheath. A fluid seal is provided radially between the isolation sheath 70 and the hub 122 that is configured to prevent of fluid in the flushing chamber 440 from egressing through the interface between the isolation sheath and the hub. Thus, the distal hub 122 is fluidly coupled to the isolation sheath 70 such that the flushing chamber 440 is in fluid communication with the flushing lumen 86.

The proximal end portion of the hub 122 forms a receiver 482 for receiving the anchor member 280 therein. As explained above, the anchor member 280 is configured to secure the distal end portion (e.g., the small end tube 296) of the catheter body alignment guide 272 to the housing 110. The anchor member 280 has a proximal end portion, a distal end portion, and a passage 484 extending longitudinally from the proximal end portion through the distal end portion. The longitudinal passage 484 is configured so that the catheter body 14 is passable along the axis A1 through the longitudinal passage. For example, the drive shaft 24 and the inflation conduit 26 extend from the passage 292 of the catheter body alignment guide 272 through the longitudinal passage 284 into the flushing chamber 440. Suitably, the drive shaft 24 and the inflation conduit 26 are configured to rotate in the passage 484 with respect to the anchor member 280 about the axis A1. In the illustrated embodiment, the receiver 482 has a distal end wall. The anchor member 280 is configured to be secured in the receiver 482 such that the distal end of the anchor member engages the distal end wall of the receiver. Furthermore, the illustrated anchor member 280 is configured be secured in the receiver 482 by interlocking engagement of the anchor member and the receiver. For example, the illustrated anchor member 280 includes tabs (broadly, locking formations) that are configured to be lockingly received in slots defined by the receiver 482 as the anchor member is pressed distally into the receiver member (see FIG. 40). In one or more embodiments, anchor members can be mounted in other ways.

In the illustrated embodiment, a duckbill seal 480 is configured to form a fluid seal about the catheter body 14 at the proximal end portion of the flushing chamber 440. Thus in the illustrated embodiment, the handle comprises a first, proximal duckbill seal 470 that is mounted on the carriage 152 for movement along the handle and a second, distal duckbill seal 480 that is fixed in place with respect to the handle. That is, the illustrated handle 16 comprises a first duckbill seal 470 that is configured to seal a first flushing chamber 432 and a second duckbill seal that is configured to seal a second flushing chamber 440. In one or more embodiments, other types of seals can be used in place of one or both duckbill seals 470, 480.

In one or more embodiments, the duckbill seal 480 can comprise a one-piece body of elastomeric material that is configured to sealingly engage the drive shaft 24 of the catheter body 14 about the entire cross-sectional perimeter of the catheter body. The duckbill seal 480 has a proximal end portion and a distal end portion spaced apart from the proximal end portion along the axis A1. The duckbill seal 480 comprises first and second duckbill members 486 that taper as they extend distally from adjacent the proximal end of the duckbill seal. The duckbill members 486 also extend toward one another as they extend distally. The duckbill members 486 are configured to engage the drive shaft 24 to form a liquid-tight seal (e.g., a fluid-tight seal) about the external cross-sectional perimeter of the drive shaft that prevents flushing fluid from egressing from the proximal end portion of the flushing chamber 440 through the interface between the duckbill seal and the drive shaft. For example, the duckbill seal 480 is configured to form the liquid seal about the drive shaft 24 at a sealing band that compressively conforms to the perimeter of the drive shaft 24. The flushing chamber 440 extends circumferentially around the opposing duckbill members 486. In addition, the lateral flushing port 438 is radially aligned with the duckbill members 486 with respect to the axis A1. As the flushing chamber 440 is pressurized, the duckbill members 486 are urged toward each other, enhancing the strength with which the duckbill seal 480 sealingly engages the drive shaft 24.

The duckbill members 486 are configured to extend circumferentially about a longitudinal passage 488 through the duckbill seal. The longitudinal passage 488 is configured so that the drive shaft 24 can extend through the passage along the axis A1. Thus, in contrast to the duckbill seal 470, the duckbill seal 480 lacks an imperforate web between the duckbill members 486. The duckbill members 486 are configured to slidably accept the drive shaft 24 of the catheter body 14 therebetween. Suitably, the drive shaft 24 can slide along the passage 488 between the duckbill members 486 (e.g., as it moves conjointly with the carriage 152 and the slider knob 150 as described above) without breaking the fluid seal between the duckbill seal 480 and the drive shaft. In addition, the duckbill seal 480 is configured to maintain the fluid seal about the drive shaft 24 as the drive shaft rotates about the rotational axis A1 with respect to the duckbill seal, even at rotational speeds on the order of 10,000 rpm to 12,000 rpm.

The duckbill seal 480 is configured to be secured in the hub 122 by being captured between the hub and the anchor member 280. The proximal end portion of the duckbill seal 480 comprises an annular flange 490. The hub 122 includes an annular recess extending distally from the distal wall of the receiver 482 that is sized and arranged for receiving the annular flange 490. The hub 122 comprises an annular end surface 492 defining the annular recess. The annular flange 490 is sized and arranged for being compressed between the distal end of the anchor member 280 and the end surface 492. In the illustrated embodiment, the end surface 492 has a convex cross-sectional shape that is rotated or swept 360° about the axis A1 to form the annular end surface. The annular flange 490 is configured to be compressed against the convex surface 492 when the anchor member 480 is installed in the hub 122 to form an annular liquid-tight seal (e.g., fluid tight seal) between convex annular surface and the annular flange. Accordingly, the annular flange 490 is configured to form a fluid seal with the convex annular end surface 492 that inhibits fluid from egressing from the flushing chamber 440 through the interface between the duckbill seal 480 and the hub member 122.

Referring to FIG. 37, when it is desired to deliver flushing fluid through the flushing lumen 86, the user can use the valve VF to couple flushing fluid from the flushing fluid source F to the external flushing port 130. The flushing fluid flows from the port 130 through the main conduit 422 and the splitter 424 into the branch conduit 436. From the branch conduit 436, the flushing fluid flows through the hub port 438 into the hub flushing chamber 440. The duckbill seal 480 prevents the flushing fluid from egressing through the proximal end of the flushing chamber 440, even as the slide knob 150 is used to extend and withdraw the catheter body 14 through the hub 12. The duckbill seal 480 likewise prevents flushing fluid from egressing through the proximal end of the flushing chamber 440 as the drive shaft 24 is driven in rotation about the axis A1 with respect to the duckbill seal and hub 122. The flushing fluid flows through the distal end of the flushing chamber 440 into the flushing lumen 86 and then flows distally through the flushing lumen along the exterior of the drive shaft 24 until it is discharged at the distal end of the isolation sheath 70.

As explained above, in the illustrated embodiment, both flushing chambers 432, 440 are fluidly coupled to the flushing fluid by the same main passage 422 and external flushing port 430. Furthermore, there are no valves for separately selecting one of the flushing chambers 432, 440 or lumens 72, 86. Thus, in the illustrated embodiment, whenever the valve VF is opened, flushing fluid is always simultaneously delivered into both flushing chambers 432, 440 and through both the guidewire lumen 72 and the flushing lumen 86. It is contemplated that the catheter can be configured so that the flushing fluid can be separately delivered to the flushing chambers or otherwise can be separately delivered to the guidewire lumen and the flushing lumen in one or more embodiments.

G. Controls

Figure 43:
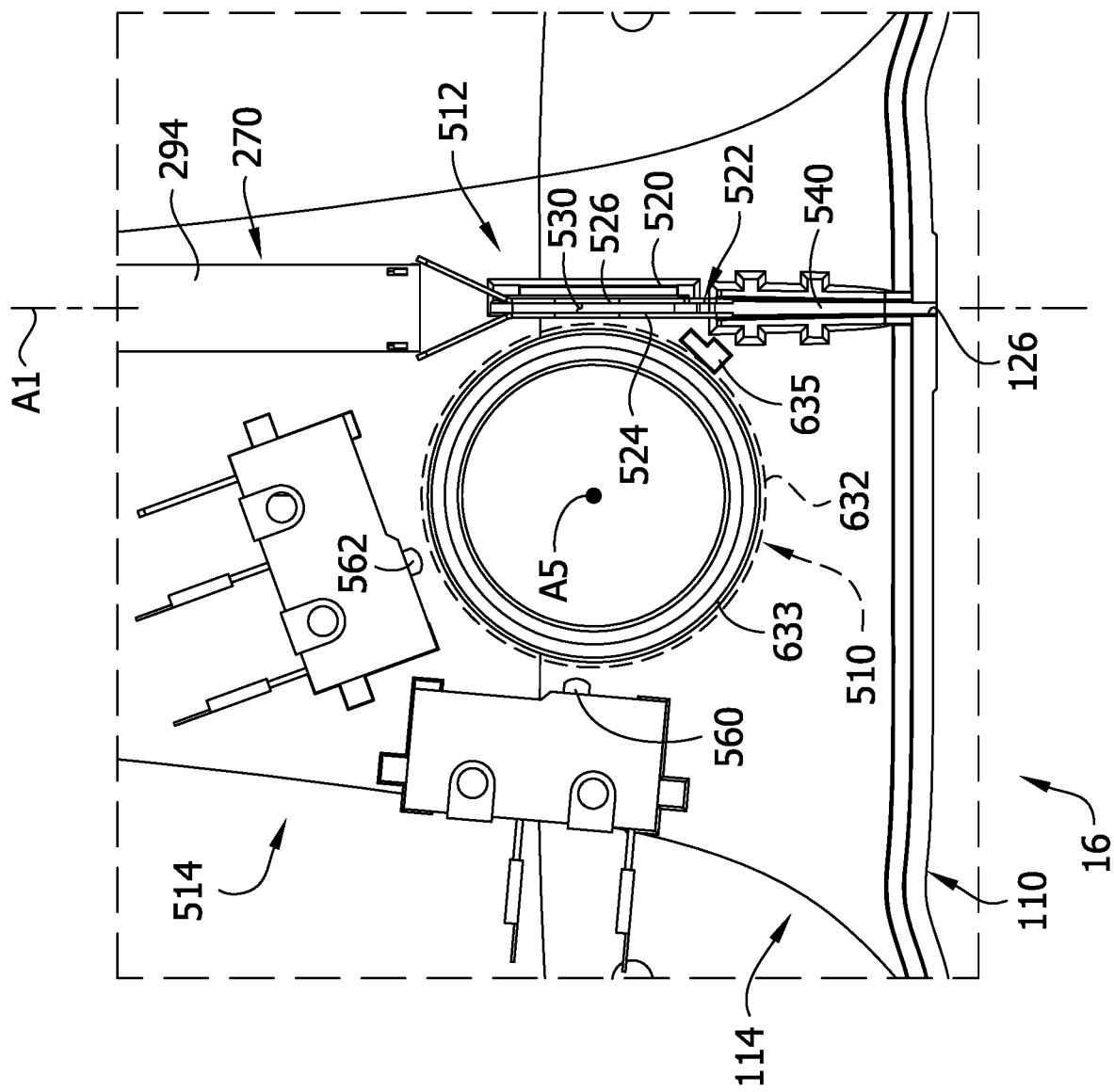
FIG. 43 is a an enlarged partial top plan view of a portion of a subassembly of the handle including the bottom housing member, switches of a motor regulator, and a guidewire brake.

Referring to FIGS. 1 and 15, in the illustrated embodiment, the handle 16 comprises a multipurpose control knob (broadly, a lever), generally indicated at 510. The control knob 510 is mounted on the handle 16 adjacent the proximal end portion such that the control knob is pivotable about a pivot axis A5 through a range of motion with respect to the housing 16. As will be explained in further detail below, the illustrated control knob 510 is configured to function as both a guidewire brake control and a mode selector for adjusting a rotational drive mode of the catheter 10. In one or more embodiments, these functions can be controlled by separate user controls. As shown in FIG. 43, the illustrated handle 16 includes a guidewire brake, generally indicated at 512, which is configured to selectively impart a braking force on the guidewire G. The catheter 10 further comprises a motor regulator (broadly, driver regulator), generally indicated at 514, which is configured to adjust the motor 224 between a plurality of different operating modes in which the motor responds differently to the push button 136 being depressed (the push button being depressed is broadly understood to be performing an operation on a user control). As will be explained in further detail below, the illustrated control knob 510 is in communication with both the guidewire brake 512 and the motor regulator 514 such that the control knob is configured to actuate the guidewire brake and the motor regulator as the control knob pivots about the pivot axis A5. One or more embodiments can lack one or both of a guidewire brake or a motor regulator. One or more embodiments of a guidewire brake 512 and a motor regulator 514 will now be described before describing an embodiment of a control knob 510 in greater detail.

Figure 44:
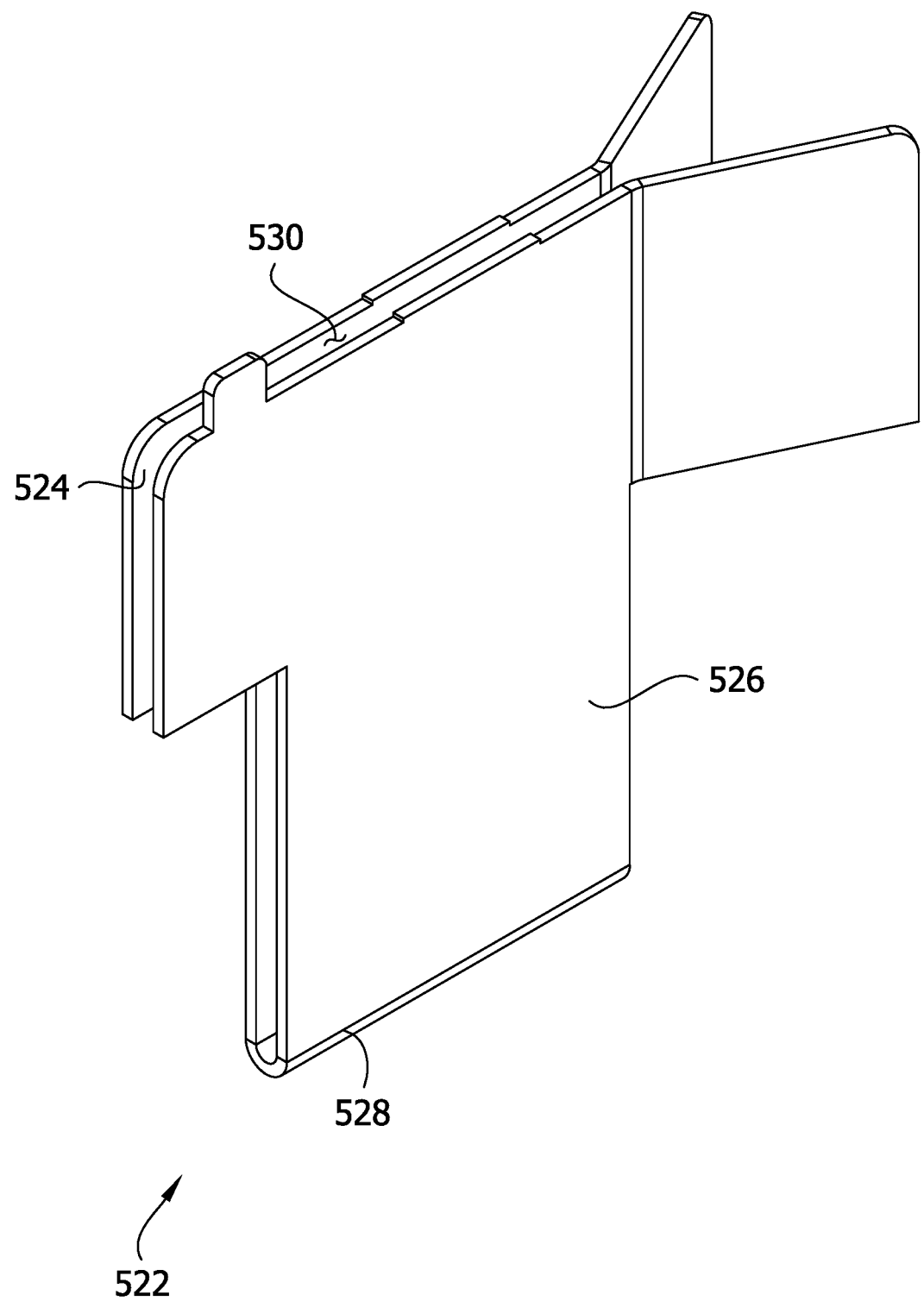
FIG. 44 is a perspective of a braking clip or clamp of the guidewire brake.

Referring to FIGS. 43 and 44, the guidewire brake 512 is generally configured to selectively impart a braking force on the guidewire G that inhibits the guidewire from moving relative to the handle 16. The handle 16 includes a fixed braking support 520. When the guidewire G extends through the handle 16 along the axis A1, the braking support 520 and the control knob 510 are positioned on opposite sides of the guidewire G. As will be explained in further detail below, the control knob 510 is configured to urge the guidewire G toward the braking support 520 to impart the braking force on the guidewire. In one embodiment, the braking support 520 comprises a projection that extends upward from the bottom wall of the bottom housing member 114 to support a braking clip, such as a braking spring, generally indicated at 522. In the illustrated embodiment, the braking spring 522, and not the braking support 520, is configured to directly engage or contact the guidewire G when the guidewire brake 512 is applied. In one or more embodiments, it is contemplated that the control knob can be configured to urge the guidewire into direct contact with the braking support to apply guidewire brake. Still other guidewire brake configurations are possible in one or more embodiments.

The braking spring 522 comprises a first leg 524 and a second leg 526. The first leg 524 and the second leg 526 are connected at their bottom ends by a resilient connecting portion 528. The spring 522 is configured to be mounted in the handle 16 such that the first leg 524 and the second leg 526 each extend generally along the axis A1 from a respective proximal end to a respective distal end. In the illustrated embodiment, the spring support 520 is configured to mount the spring 522 on the housing 110 and rigidly support the second leg 526. The spring 522 is supported such that, when the legs 524, 526 are subject to a laterally compressive force transverse to the axis A1, the connecting portion 528 can bend resiliently to allow the first leg to move toward the second leg. When the force is released, the connecting portion 528 is configured to rebound such that the first leg 524 moves away from the rigidly supported second leg 526.

The braking spring 522 is received in the housing 110 such that the guidewire G can extend between the first leg 524 and the second leg 526 as the guidewire G extends along the axis A1 through the handle 16. The braking spring 522 is resiliently biased to a position in which the first leg 524 and the second leg 526 are spaced apart from one another to define a guidewire channel 530 that is configured to slidably receive a portion of the guidewire G therein. The guidewire channel 530 extends generally along the axis A1 from a proximal end adjacent the guidewire opening 126 to a distal end adjacent the proximal end portion of the guidewire alignment guide 270. The distal end portions of the first and second legs 524, 526 of the braking spring 522 flare outwardly away from each other as they extend distally toward the distal end of the guidewire alignment guide 270. Accordingly, the width of the guidewire channel 530 tapers proximally along the distal end portion thereof such that the proximal end of the guidewire is guided from the alignment guide 270 into the guidewire channel when the guidewire is inserted proximally through the catheter 10. Suitably, the width of the guidewire channel at the distal tip of the braking spring 522 can be about the same as the diameter of the large tube 294 of the guidewire alignment guide 270. In the illustrated embodiment, the handle 16 further includes a structure defining a guide channel 540 that extends along the axis A1 from the proximal end of the braking spring 522 to the guidewire opening 126. The guide channel 540 is configured such that the guidewire G is passable through the guide channel from the channel 530 formed between the spring legs 524, 526 to the proximal guidewire opening 126.

The brake 512 is configured to impart a braking force on the guidewire G by compressing the segment of the guidewire received in the channel 530 between the first and second legs 524, 526 of the spring 522. As explained in further detail below, the control knob 510 is configured to be pivoted to an angular braking position about the axis A5 in which the knob urges the first leg 524 toward the second leg 526 (and thereby urges the guidewire G toward the second leg and the brake support 520) to grip the guidewire G between the first and second legs and impart a braking force on the guidewire. The resilient connecting portion 528 is configured to resiliently bend or deflect to allow the first leg 524 to move toward the second leg 526 to apply the braking force to the guidewire G. When the control knob 510 is pivoted away from the braking position about the axis A5, the connecting portion 528 is configured to resiliently rebound such that the first leg 524 moves away from the second leg 526. After the spring 522 rebounds, the guidewire G is slidable through the channel 530 between the legs 524, 526.

Referring to FIG. 43, the motor regulator 514 is generally configured to selectively operate the motor 224 in a plurality of different operating modes. In each of the plurality of operating modes, the motor regulator 514 operates the motor 224 differently in response to the push button 136 being depressed. Pressing the push button 136 is broadly understood to be performing a type of operation (e.g., pressing) on a user control (e.g., the push button). As explained below, the motor regulator 514 is configured to operate the motor 224 differently in response to the same type of operation (e.g., pressing) of the user control (e.g., the push button 136) depending on the position of the control knob 510 about the axis A5.

In one embodiment, the motor regulator 514 includes the control circuit 171 (FIG. 15). The control circuit 171 can be generally configured to regulate the response of the motor 224 to the push button 136 being depressed. In one embodiment, the control circuit 171 comprises hard-programmed control circuitry that is configured to execute a motor regulator control scheme. In another embodiment, the control circuit 171 comprises memory storing control software and a processor in communication with the memory that is configured to execute the motor regulator control scheme based on the control software. It is understood that the control software can also be stored in other memory and/or the control software can be executed using other processors in one or more embodiments. For example, in one embodiment, the catheter 10 can be configured communicate with a remote computing device (e.g., a desktop computer, a laptop computer, or a mobile device) that stores and/or executes the motor regulator control software. Other motor regulator configurations are also possible.

In the illustrated embodiment, the motor regulator 514 is configured to execute a motor regulator control scheme that selectively operates the motor 224 in the following operating modes: (i) a tissue-removing mode (broadly, a first mode) in which the motor regulator actuates the motor to continuously drive rotation of the drive shaft 24 and the burr assembly 12 in response to the push button 136 being depressed; (ii) a navigation mode (broadly, a second mode) in which the motor regulator actuates the motor to drive a discrete burst of rotation in response to the push button being depressed; and (iii) a deactivated mode (broadly, a third mode) in which the motor regulator prevents the motor from being actuated in response to the push button being depressed. In one or more embodiments, the motor regulator 514 is configured to operate the motor 224 to rotate the drive shaft 24 at predefined rotational speeds in each of the tissue-removing mode and the navigation mode and the predefined rotational speed of the navigation mode is less than the predefined rotational speed of the tissue-removing mode. In one or more embodiments, motor regulators can be configured to execute other motor regulator control schemes, such as motor regulator control schemes that are configured to selectively operate a motor in other distinct operating modes.

In one embodiment of the tissue-removing mode, the motor regulator 514 is configured to operate the motor 224 as if the push button 136 were an alternate action switch; e.g., by operating the motor to continuously drive rotation of the drive shaft 24 and the burr assembly 12 after the push button is depressed until the push button is depressed again, whereby the motor regulator deactivates the motor. In another embodiment of the tissue-removing mode, the motor regulator 514 can operate the motor 224 as if the push button 136 were a momentary action switch; e.g., by operating the motor to continuously drive rotation of the drive shaft 24 and the burr assembly 12 as long as the push button is depressed and deactivating the motor when the push button is released. In one embodiment, in the navigation mode the motor regulator 514 is configured in response to the push button 136 being depressed to operate the motor 224 to drive rotation of the drive shaft 24 and the burr assembly 12 in a discrete burst of rotation that is sustained for only a predefined duration, regardless of the manner in which the push button is depressed (e.g., even if the push button is held down). For example the predefined duration of the discrete burst of rotation can be less than 5 seconds (e.g., less than 4 seconds, less than 3 seconds, less than 2 seconds, less than 1 second, less than 0.5 seconds, or less than 0.25 seconds). Other ways of regulating continuous rotation and/or discrete bursts of rotation can also be used in one or more embodiments. For example, in one embodiment, the motor regulator is configured to operate the motor as a momentary action switch in the navigation mode such that a user can control the duration of the discrete burst of rotation based on a duration over which the user continuously performs an operation on a user control.

In the illustrated embodiment, the motor regulator 514 comprises first and second switches 560, 562 that are operatively connected to the circuit board 171. The first and second switches 560, 562 are angularly spaced apart about the axis A5 and vertically spaced apart along the axis. As explained below, the control knob 510 is configured to sequentially engage the switches 560, 562 at different points along its range of motion about the pivot axis A5 to adjust the operating mode of the motor regulator 514. As shown in FIG. 43, the first switch 560 is spaced apart in the counter-clockwise direction about the axis A5 with respect to the second switch 562. In addition, the first switch 560 is spaced apart above the second switch 562 along the axis A5 (see FIGS. 53 and 54). The switches can have other arrangements in one or more embodiments. As explained in further detail below, each switch 560, 562 is adjustable between an engaged position (broadly, a first position) and a disengaged position (broadly, a second position) as the control knob 510 pivots about the axis A5. In the illustrated embodiment, the switches 560, 562 have a normally-disengaged position in which the switches extend radially inward with respect to the axis A5 and are configured to be pressed radially outward with respect to the axis A5 in the respective engaged positions. The switches can have other configurations in one or more embodiments.

In one embodiment, the switches 560, 562 are operatively connected to the control circuit 171 such that the control circuit is configured to receive a signal from each switch representing whether the switch is in the engaged position or the disengaged position. As explained below, the knob 510 is configured to adjust each of the switches 560, 562 between the engaged and disengaged positions as the knob pivots about the axis A5 through its range of motion. In the illustrated embodiment, when the knob 510 positons both switches 560, 562 in the engaged position, the motor regulator 514 is configured to operate the motor 524 in the tissue-removing mode. When the knob 510 positions the first switch 560 in the engaged position and positions the second switch 562 in the disengaged position, the motor regulator 514 is configured to operate the motor 224 in the navigation mode. When the knob 510 positions both switches 560, 562 in the disengaged position, the motor regulator is configured to operate the motor 224 in the in the deactivated mode. In one or more embodiments, the operating modes can be based on other configurations of the switches.

Figure 45:
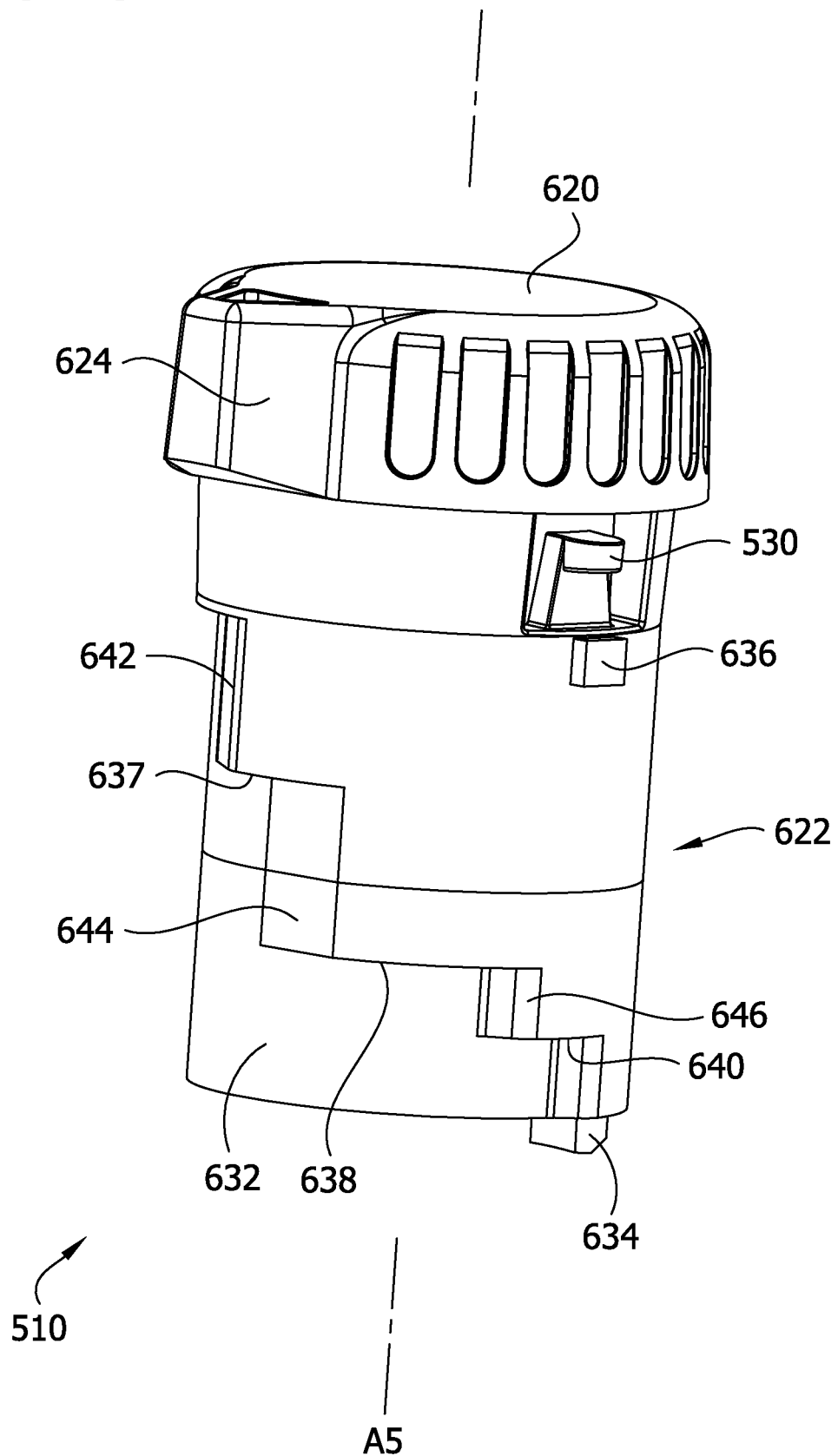
FIG. 45 is a perspective of a control knob of the handle.
Figure 46:
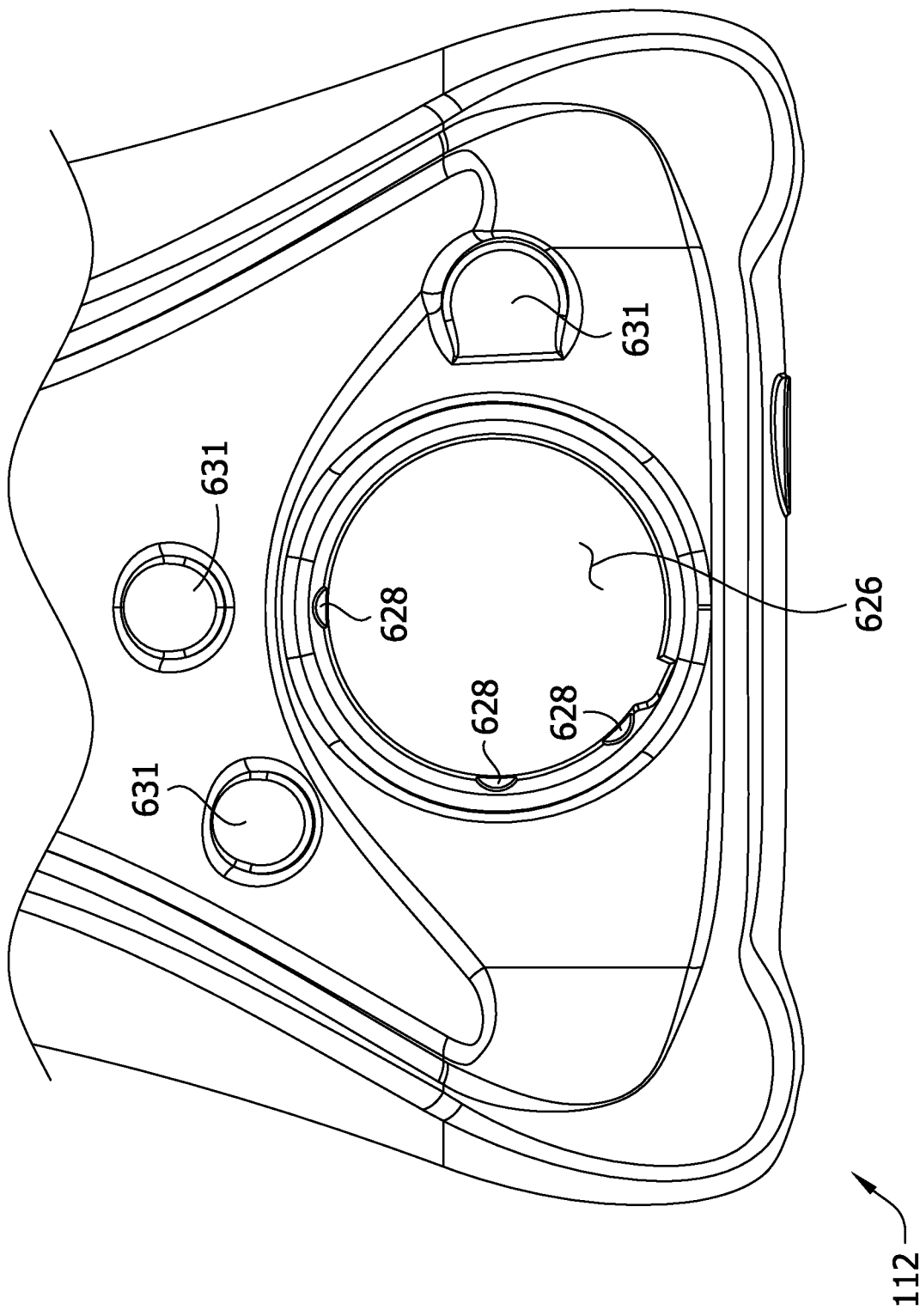
FIG. 46 is an enlarged partial top plan view of a proximal end portion of the top handle member.

Referring to FIG. 45, the control knob 510 is configured to be pivoted about the axis A5 with respect to the handle housing 110. The control knob 510 comprises a head 620 and a camshaft, generally indicated at 622. The camshaft 622 extends downward from the head 620 along the pivot axis A5. The head 620 includes an indicator portion 624 that protrudes radially and points in a circumferential direction. The indicator portion 624 can provide an indication of the angular position of the knob 510 about the pivot axis A5. Other ways of indicating the angular position of the knob about the pivot axis can also be used in one or more embodiments. Referring to FIG. 15, the knob 510 is configured to be mounted on the handle housing 110 such that the head 620 is exposed through the top wall of the housing. Referring to FIG. 46, in the illustrated embodiment, the camshaft 622 is configured to extend along the axis A5 through a hole 626 in the top housing member 112. Suitably, the hole 626 provides sufficient clearance for the camshaft 622 to pivot about the pivot axis A5.

Figure 51:
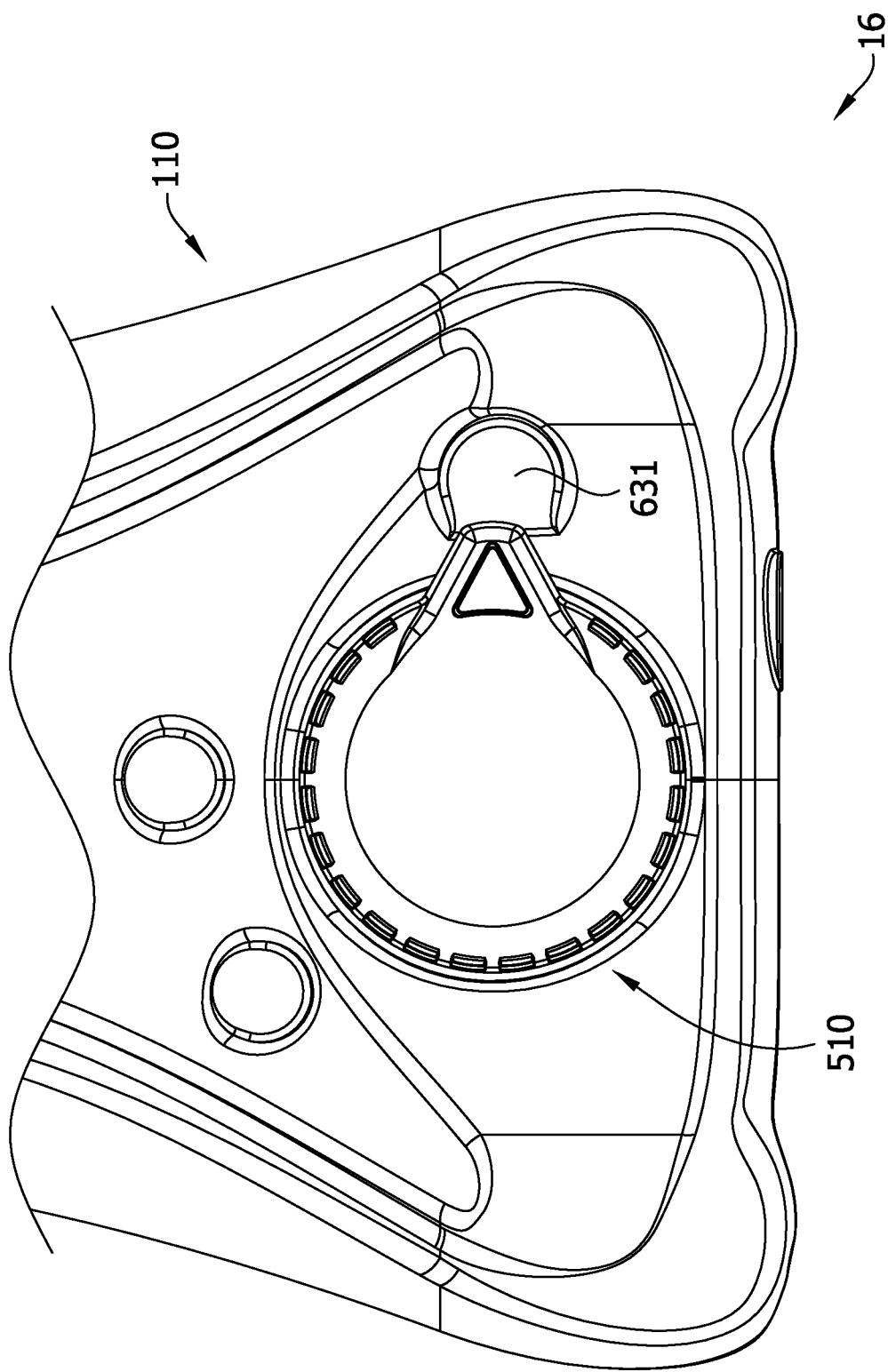
FIG. 51 is a partial top plan view of a proximal end portion of the handle illustrating the control knob in a tissue-removing mode position.

The handle 16 can include a detent mechanism that defines detent positions of the knob 510 about the axis A5 that correspond with operative positions of the knob with respect to the guidewire brake 512 and/or the motor regulator 514. For example, referring still to FIG. 46, the rim defining the hole 626 can include a plurality of detent recesses 628 at detent positions about the axis A5. As shown in FIG. 45, the illustrated camshaft 622 includes a detent tab 630 that is configured to nest in the recesses 628 as it pivots about the axis A5. For example, the detent recesses 628 can be configured so that the detent tab 630 can nest in one of the recesses at each angular position that corresponds with a different operating mode of the motor regulator 514. In the illustrated embodiment, the indicator portion 624 of the head 622 is angularly aligned about the axis A5 with a respective mode indicator 631 of handle housing 110 at each of the detent positions of the knob (see FIGS. 51, 55, and 58). A user can grip the head 620 to pivot the knob 510 and the camshaft 622 about the axis A5. If the knob 510 is at a detent position, the tab 630 is configured to bend radially inward to clear the recess 628 when a moderate pivot force is applied to the knob.

Referring to FIGS. 43 and 45, the camshaft 622 comprises an annular wall 632 configured to extend around a cylindrical bearing 633 formed in the bottom housing member 114. The general location of the annular wall 632 relative to the bearing 633 is shown in broken line in FIG. 43. The bearing 632 has a circular cross-sectional shape and extends generally along the axis A1. The annular wall 632 is received about the bearing 633 such that the bearing constrains the camshaft 622 and the knob 510 to pivot about the axis A5 with respect to the housing 110. The knob and the camshaft can also be pivotably mounted on the handle in other ways in one or more embodiments.

Figure 47:
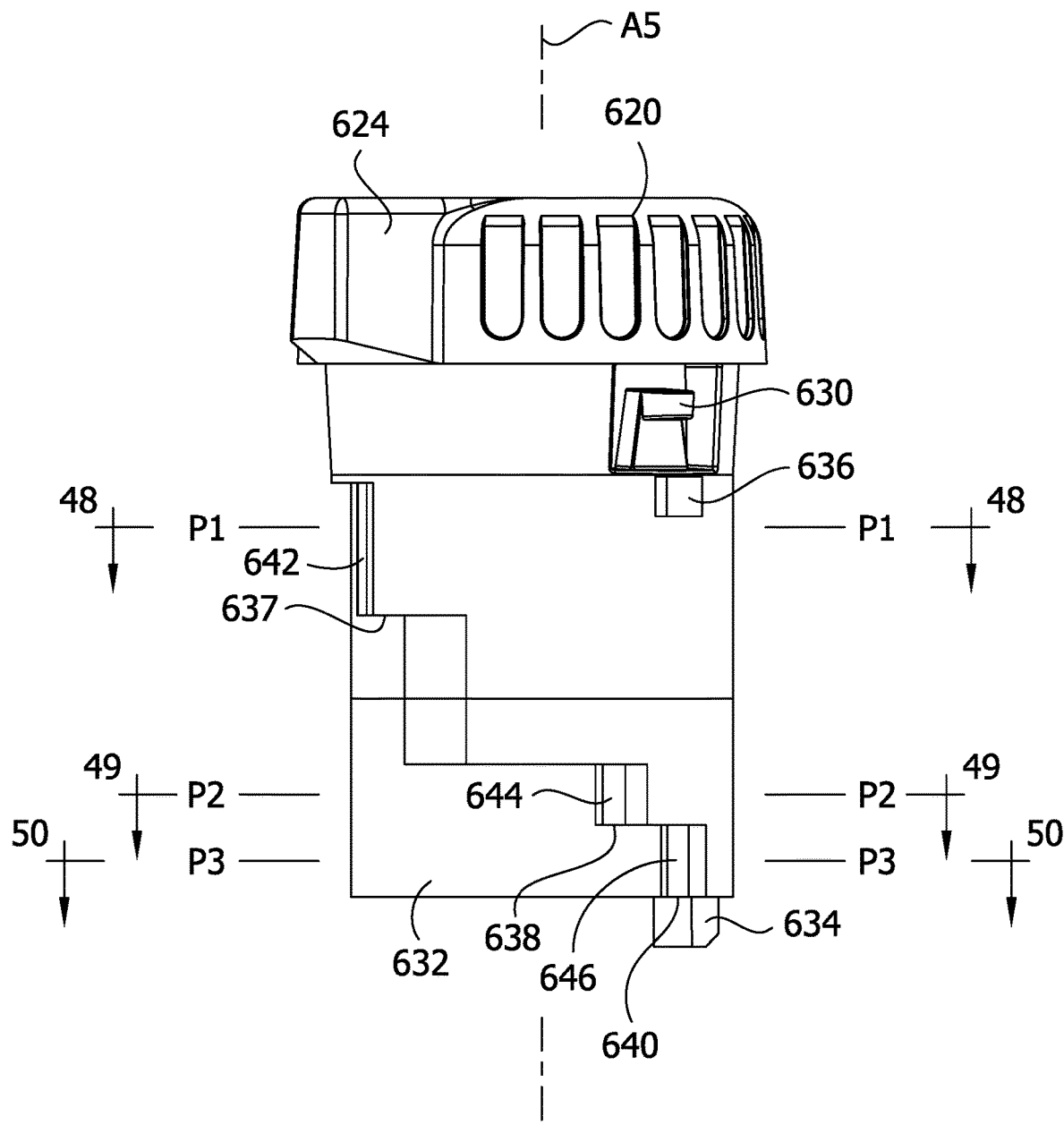
FIG. 47 is an elevation of the control knob.

In one or more embodiments, the handle 16 can be configured to limit the range of motion of the knob 510 about the axis A5. For example, as shown in FIGS. 45 and 47, the illustrated camshaft 622 includes a stop 634 that protrudes from the bottom end of the camshaft and is configured to engage a corresponding stop 635 (FIG. 43) of the bottom housing member 114 as the knob 510 and the camshaft 622 are pivoted in the counter-clockwise direction about the axis A5. In addition, the camshaft 622 includes a radially protruding stop 636 adjacent the top end portion thereof that is configured to engage another stop of the top housing member 112 (not shown) as the knob 510 and the camshaft are pivoted in the clockwise direction. One or more embodiments can have other configurations for limiting the range of motion of the knob and the camshaft about the pivot axis.

Figure 48:
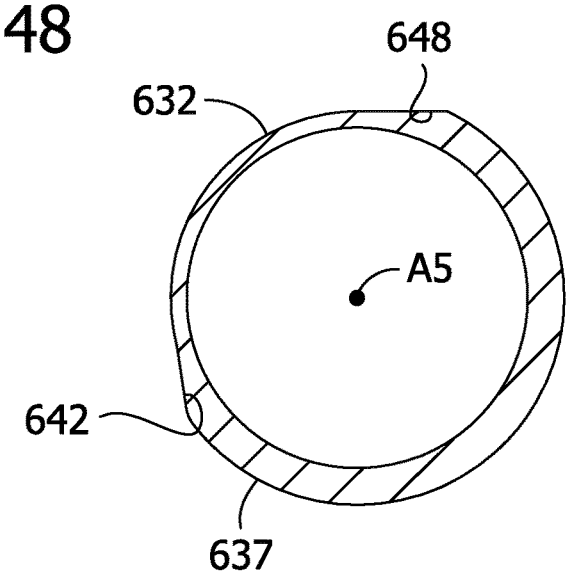
FIG. 48 is a cross section taken in the plane of line 48-48 of FIG. 47.
Figure 49:
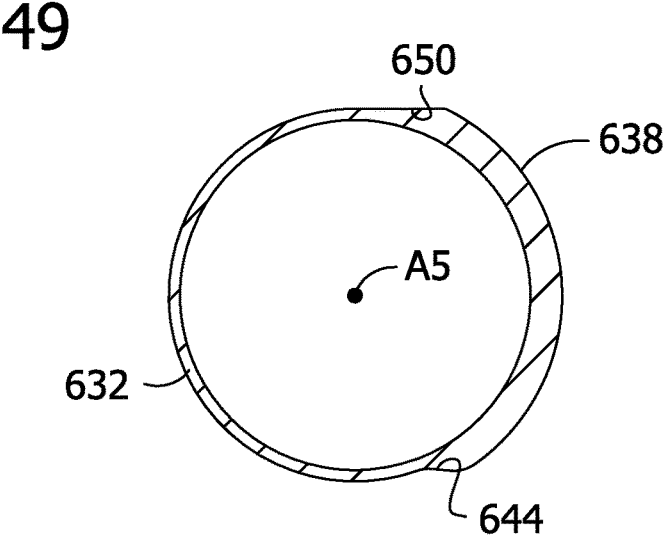
FIG. 49 is a cross section taken in the plane of line 49-49 of FIG. 47.
Figure 50:
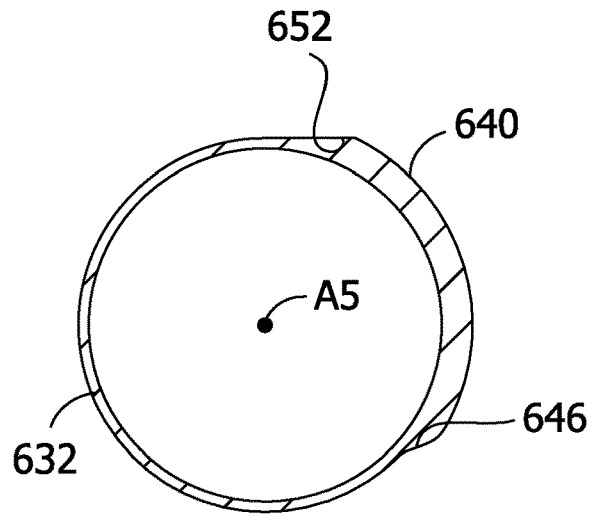
FIG. 50 is a cross section taken in the plane of line 50-50 of FIG. 47.

Referring to FIGS. 47-50, the illustrated camshaft 622 includes three cams 637, 638, 340 that, as explained below, are configured to engage and actuate the guidewire brake 512 and motor regulator 514 as the camshaft pivots about the axis A1. More specifically, the camshaft 622 includes a braking cam 637 that is configured to selectively engage the guidewire brake 512 and first and second mode selector cams 638, 640 that are configured to engage the switches 560, 562 of the motor regulator 514. Each cam 637, 638, 640 extends circumferentially from a respective cross-sectional ramp surface 642, 644, 646 to a respective cross-sectional end surface 648, 650, 652. As shown in FIGS. 48-50, the cross-sectional end surfaces 648, 650, 652 are spaced apart from the respective cross-sectional ramp surfaces 642, 644, 646 in a counter clockwise direction. Each cross-sectional ramp surface 642, 644, 646 is angled generally at a tangent with respect to an adjacent portion of the annular wall 632 such that the ramp surface extends radially outwardly as it extends circumferentially toward the end surface 648, 650, 652 of the respective cam 637, 638, 640. The outer cross-sectional surfaces of the cams 637, 638, 640 are spaced apart radially from the axis A5 by a greater distance than the outer cross-sectional surface of other portions of the annular wall 632. As shown in FIG. 47, the cams 637, 638, 640 are spaced apart from one another along the pivot axis A5. In addition, the ramp surfaces 642, 644, 646 are angularly spaced apart from one another about the pivot axis A5. In the illustrated embodiment, each of the end surfaces 648, 650, 652 of the cams 637, 638, 640 is angularly aligned about the pivot axis A5. In one or more embodiments, the camshaft can have other configurations. For example, the camshaft can have other numbers (e.g., one or more) and shapes of cams in one or more embodiments. In still one or more embodiments, the control knob can actuate the guidewire brake and/or the motor regulator by a mechanism or structure other than a camshaft.

Referring to FIGS. 47 and 52-54, the knob 510 is mounted on the housing 110 so that the camshaft 622 is positioned along the pivot axis A5 (e.g., along the height of the handle 16) in operative alignment with the guidewire brake 512 and the motor regulator 514. For example, in the illustrated embodiment, the camshaft 622 is positioned along the pivot axis A5 such that each of the braking cam 637, the braking spring 522, and the guidewire G intersect a first camming plane P1 that extends radially with respect to the pivot axis (see FIG. 52) (e.g., the braking cam, the braking spring, and/or the guidewire are radially aligned with respect to the pivot axis A5). The first mode selector cam 638 and the first motor regulator switch 560 intersect a second camming plane P2 that extends radially with respect to the pivot axis A5 (FIG. 53) (e.g., the first mode selector cam and the first motor regulator switch are radially aligned with respect to the pivot axis). And furthermore, the second mode selector cam 640 and the second motor regulator switch 562 intersect a third camming plane P3 that extends radially with respect to the pivot axis A5 (FIG. 54) (e.g., the second mode selector cam and the second motor regulator switch are radially aligned with respect to the pivot axis). As shown in FIG. 47, the first, second, and third camming planes P1, P2, P3 are spaced apart from one another along the axis A5 in the illustrated embodiment. The control knob 510 can have other arrangements with respect to the guidewire brake and/or motor regulator in one or more embodiments.

Figure 52:
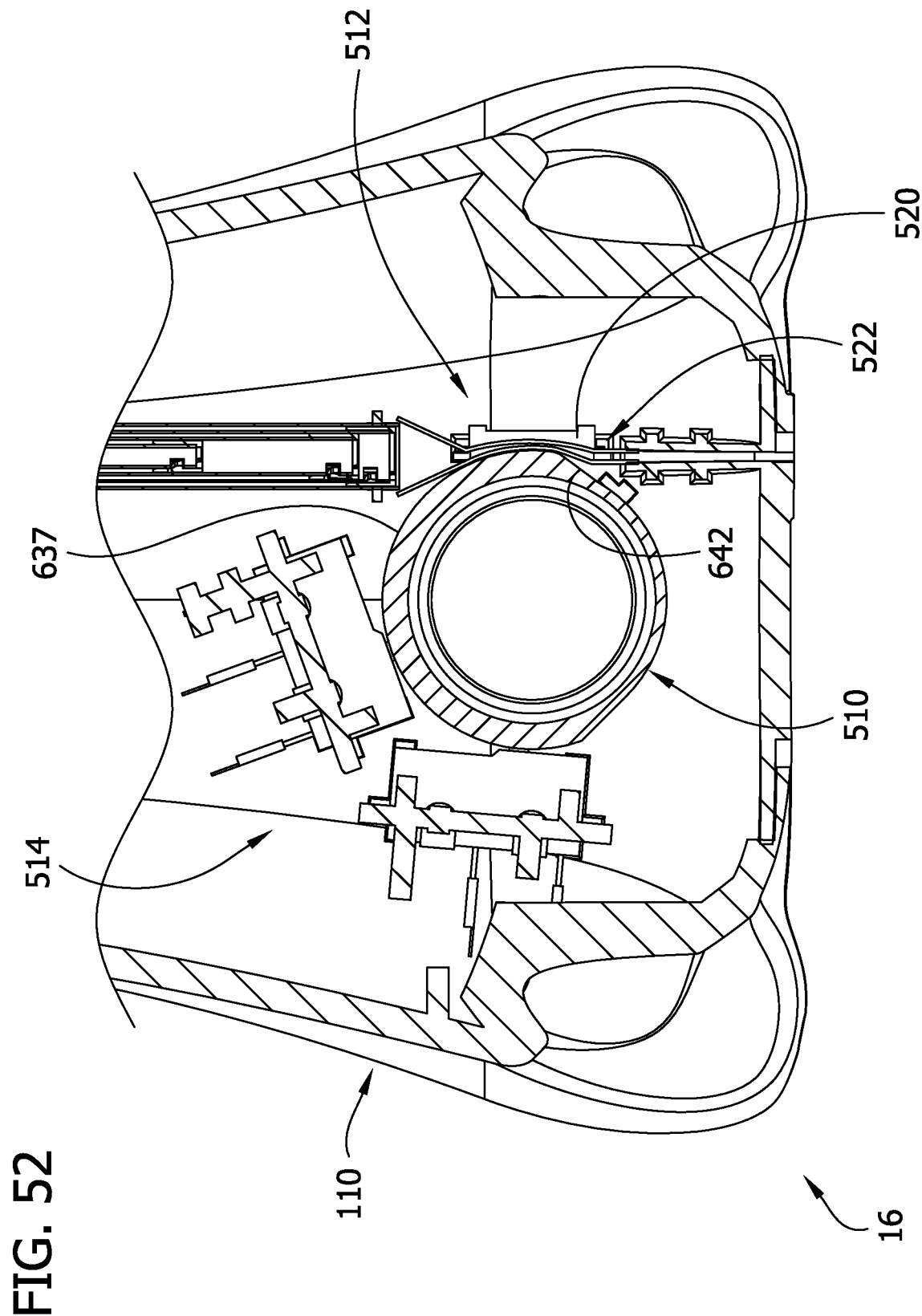
FIG. 52 is a partial cross section of the proximal end portion of the handle taken in the plane of line 52-52 of FIG. 12 and illustrating the control knob in the tissue-removing mode position.
Figure 53:
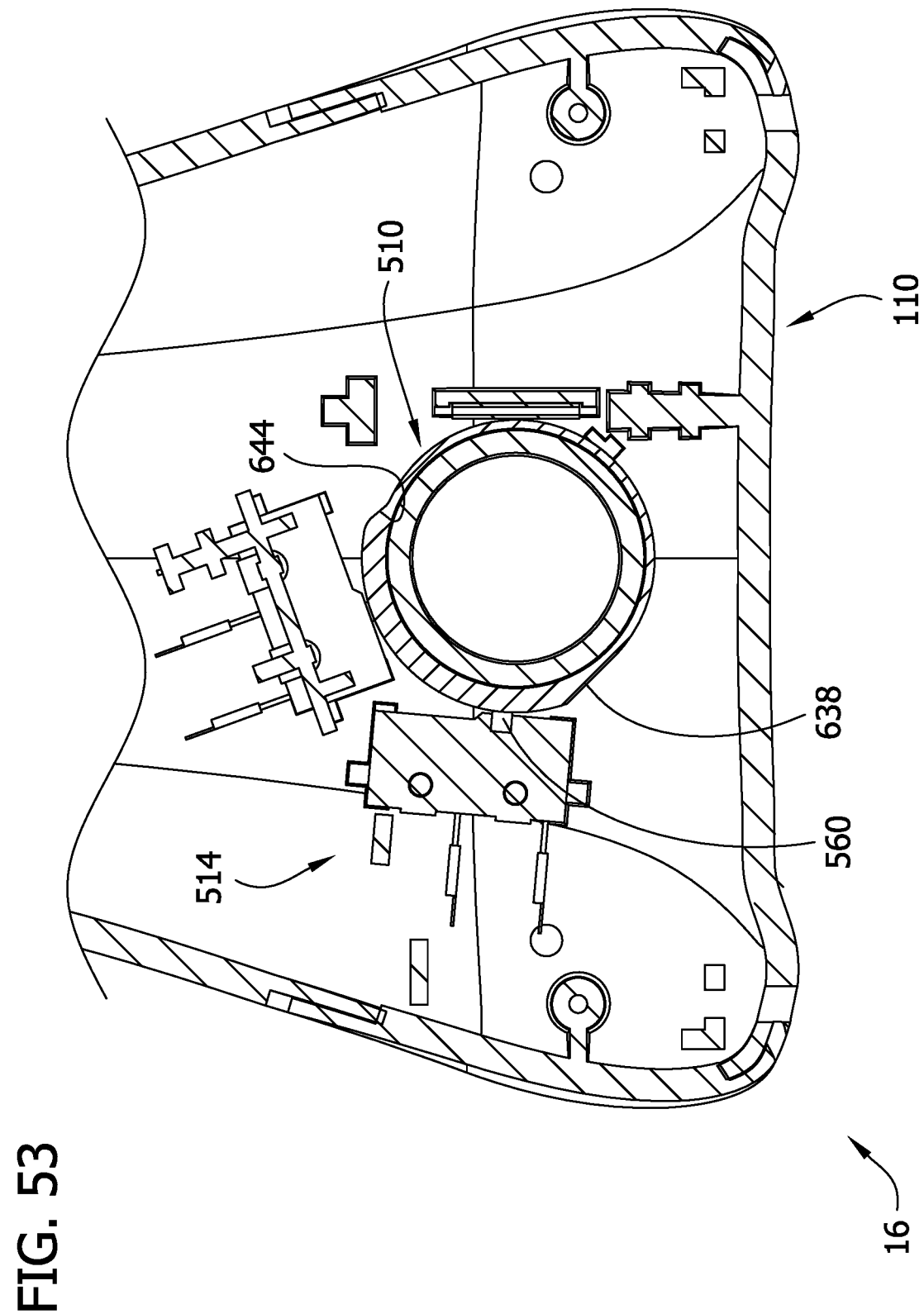
FIG. 53 is a partial cross section of the proximal end portion of the handle taken in the plane of line 53-53 of FIG. 12 and illustrating the control knob in the tissue-removing mode position.
Figure 54:
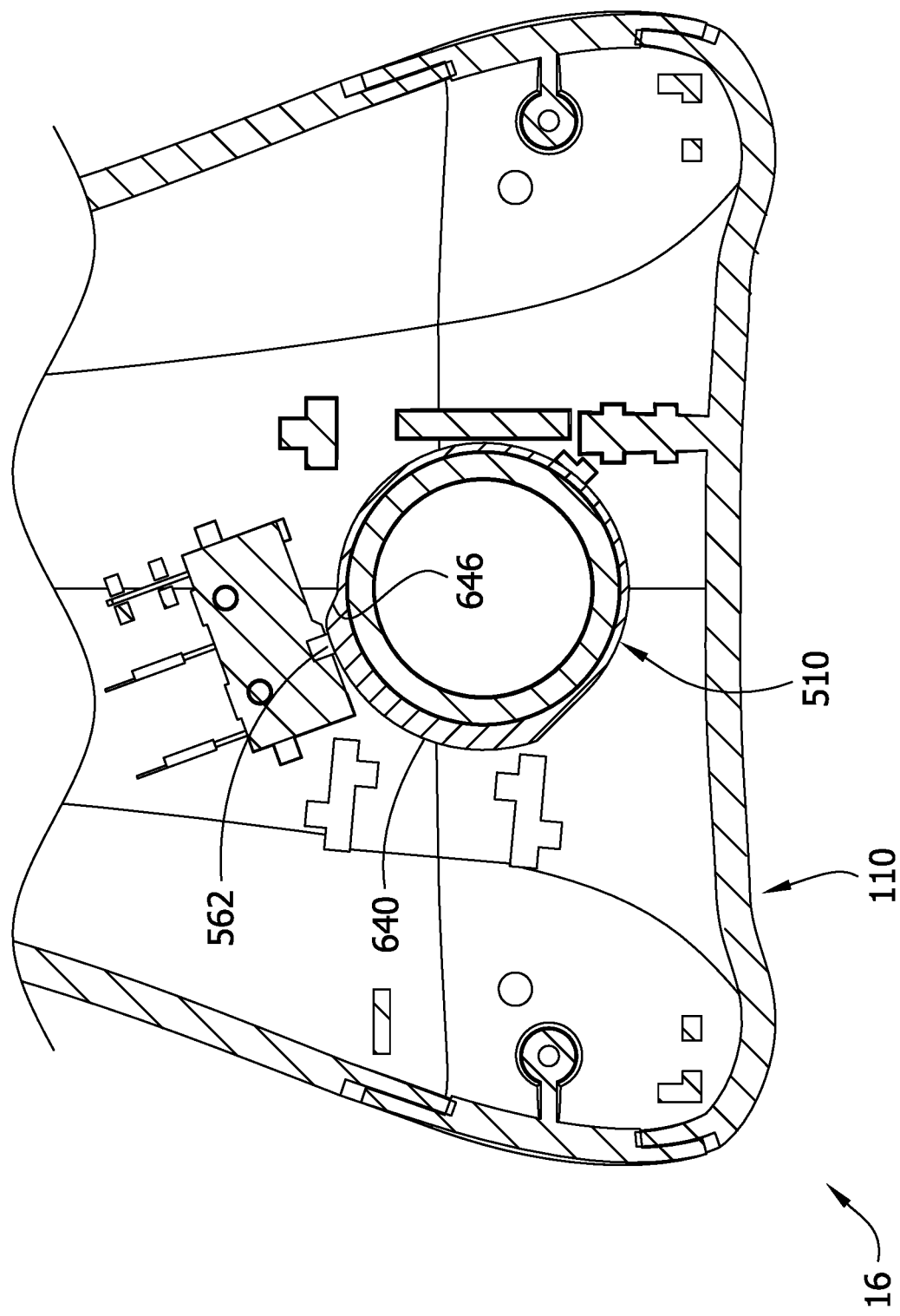
FIG. 54 is a partial cross section of the proximal end portion of the handle taken in the plane of line 54-54 of FIG. 12 and illustrating the control knob in the tissue-removing mode position.

FIGS. 51-54 show the control knob 510 in a tissue-removing mode position of the illustrated catheter handle 16. In one embodiment, in the tissue-removing mode position, the control knob 510 is pivoted about the axis A5 to about the end of its range of motion in the clockwise direction. In the tissue-removing mode position the braking cam 637 is circumferentially aligned with the guidewire brake 512 (FIG. 52). The braking cam 637 urges the first leg 524 of the braking spring 522 toward the second leg 526, which is rigidly supported by the brake support 520. The first and second legs 524, 526 thus impart a compressive braking force on the guidewire G that limits movement of the guidewire with respect to the handle 16. Thus, in the tissue-removing mode position, the control knob 510 is configured to actuate and apply the guidewire brake 512. As shown in FIGS. 53 and 54, in the tissue-removing mode position, the first mode selector cam 638 engages the first motor regulator switch 560 (FIG. 53) and the second mode selector cam 640 engages the second motor regulator switch 562 (FIG. 54). Accordingly, in the illustrated tissue-removing mode position, the control knob 510 is configured to actuate both motor regulator switches 560, 562 and thereby configure the motor regulator 514 to operate the motor 524 in the tissue-removing mode.

As can be seen, when the illustrated control knob 510 is pivoted to the tissue-removing mode position, the control knob is configured to simultaneously (a) engage the guidewire brake 512 to limit movement of the guidewire G with respect to the handle 16 and (b) select the tissue-removing mode of the motor regulator 514 so that the motor 224 is continuously actuated when the push button 136 is depressed. In one embodiment, a user pivots the control knob 510 to the tissue-removing mode position after the catheter 10 has been loaded onto the guidewire G and moved along the guidewire through a body lumen to a position in which the burr assembly 12 is located adjacent an occlusion in the body lumen. With the guidewire brake 512 applied and the motor regulator 514 operating the motor 224 in the tissue-removing mode, the user can depress the push button to continuously drive rotation of the drive shaft 24 and the burr assembly 12 and use the slider knob 150 to advance the burr assembly (e.g., by hammer action) into or through the occlusion.

Figure 55:
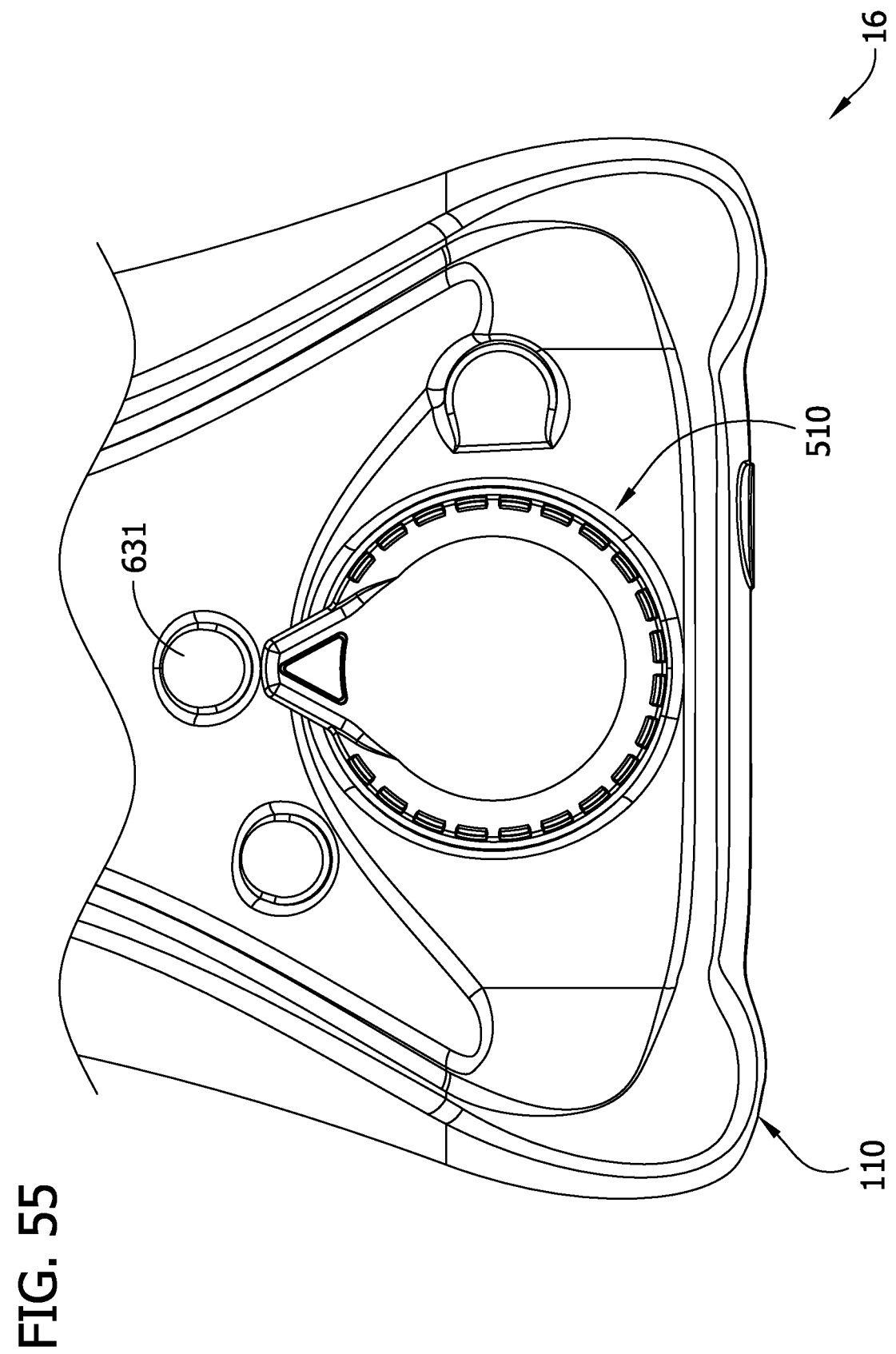
FIG. 55 is a partial top elevation of the proximal end portion of the handle similar to FIG. 51 but illustrating the control knob in a navigation mode position.
Figure 56:
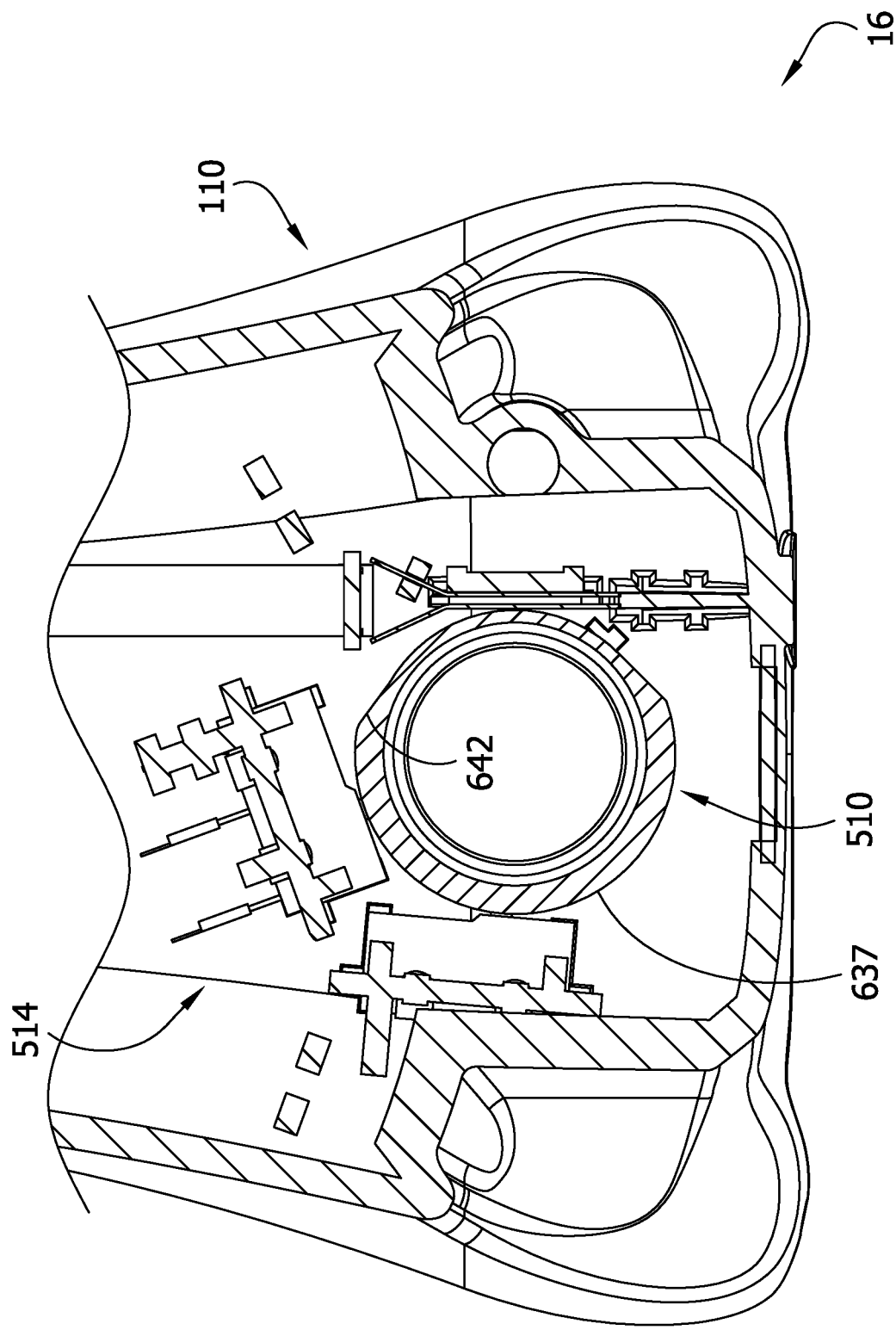
FIG. 56 is a partial cross section similar to FIG. 52 but illustrating the control knob is in the navigation mode position.
Figure 57:
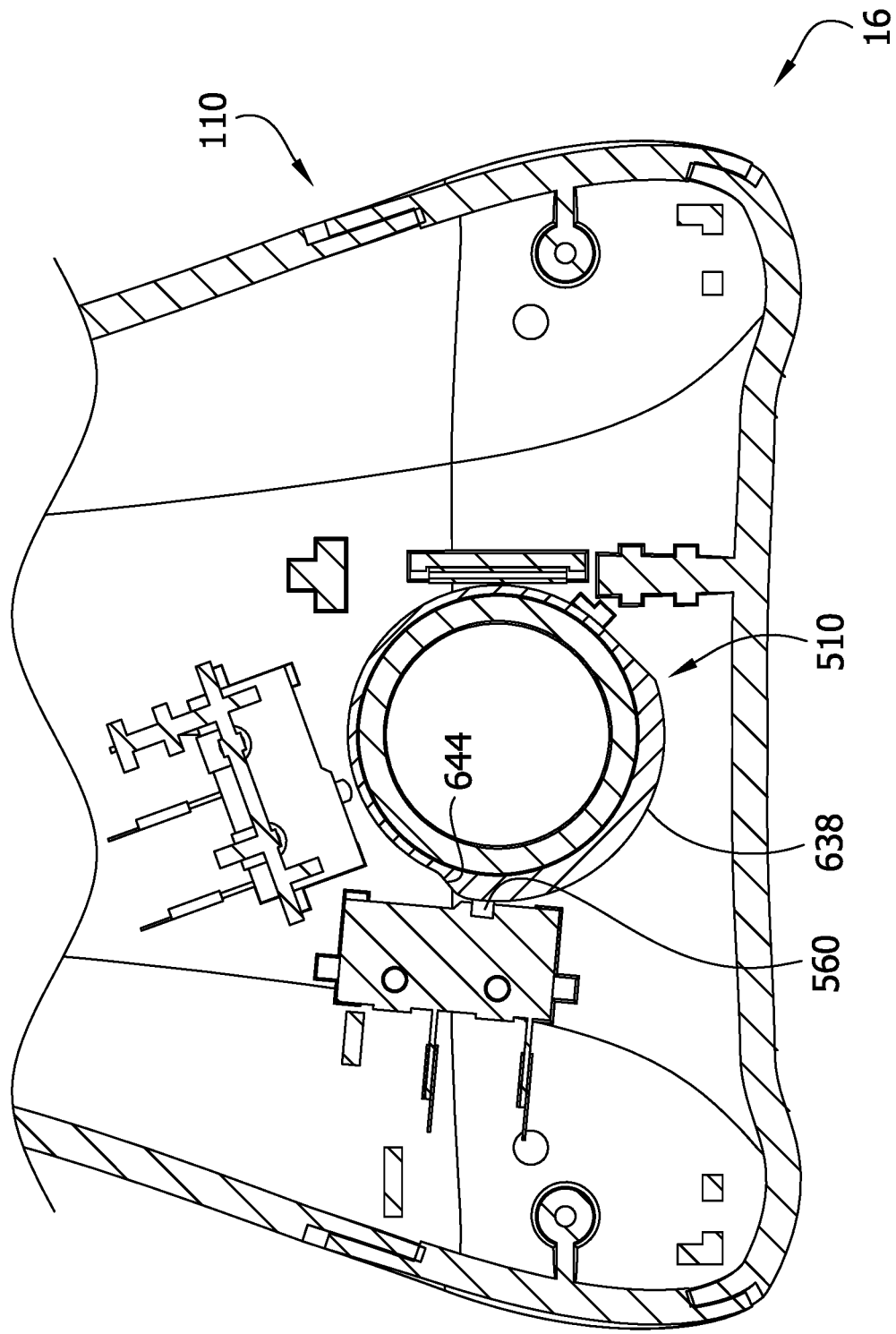
FIG. 57 is a partial cross section similar to FIG. 53 but illustrating the control knob is in the navigation position.

The illustrated control knob 510 is configured to be pivoted counter-clockwise about the axis A5 from the tissue-removing mode position to a navigation mode positon shown in FIGS. 55-57. As the control knob 510 is pivoted to the navigation mode position, the braking cam 637 disengages the braking spring 522 and thereby disengages the guidewire brake 512. For example, the ramp surface 642 pivots counter-clockwise past the angular position of the guidewire brake 612 with respect to the axis A5. As the ramp surface 642 pivots away from the guidewire brake 612, the compressive forces on the braking spring 522 and the braking forces on the guidewire G decrease. The connecting portion of the spring 522 then rebounds such that the first spring leg 524 moves away from the second spring leg 526. When the ramp surface 642 is angularly spaced apart from the guidewire brake 512 about the axis A5, the guidewire G is slidable through the guidewire channel 530. Releasing the guidewire brake 512 therefore configures the guidewire brake to permit relative movement between the guidewire G and the handle 16. As shown in FIG. 57, in the navigation mode position, the first mode selector cam 638 engages the first motor regulator switch 560 and the camshaft 622 does not engage the second motor regulator switch 562. More specifically, the second mode selector cam 640 is spaced apart from the second motor regulator switch 562 in the counter-clockwise direction about the axis A5. Accordingly, in the illustrated navigation mode position, the control knob 510 positions the first motor regulator switch in the engaged position and positions the second motor regulator switch in the disengaged position and thereby selects the navigation mode of the motor regulator 514.

As can be seen, when the illustrated control knob 510 is pivoted to the navigation mode position, the control knob is configured to (a) release the guidewire brake 512 to allow relative movement between guidewire G and the handle 16 and (b) select the navigation mode of the motor regulator 514 so that the motor 224 is actuated to drive only discrete bursts of rotation when the push button 136 is depressed. In one embodiment, a user pivots the control knob 510 to the navigation mode position while the catheter 10 is being moved along the guidewire G through a body lumen to the site of an occlusion in the body lumen. With the guidewire brake 512 released, the catheter 10 can freely slide along the guidewire through the body lumen. And moreover, with the motor regulator 514 operating the motor 224 in the navigation mode, the user can depress the push button 136 to rotate the burr assembly 12 in discrete bursts of rotation to while the catheter 10 is sliding along the guidewire G. The discrete bursts of rotation are believed to assist the burr assembly 12 in overcoming static friction and enhance the burr assembly's ability to pass obstacles in the body lumen. In addition, the short duration, and in one or more embodiments, low rotational speed of the discrete bursts of rotation are believed to limit the likelihood that the patient can be injured by rotation of the burr assembly 12 while the catheter 10 is being moved through a body lumen to a treatment site.

Figure 58:
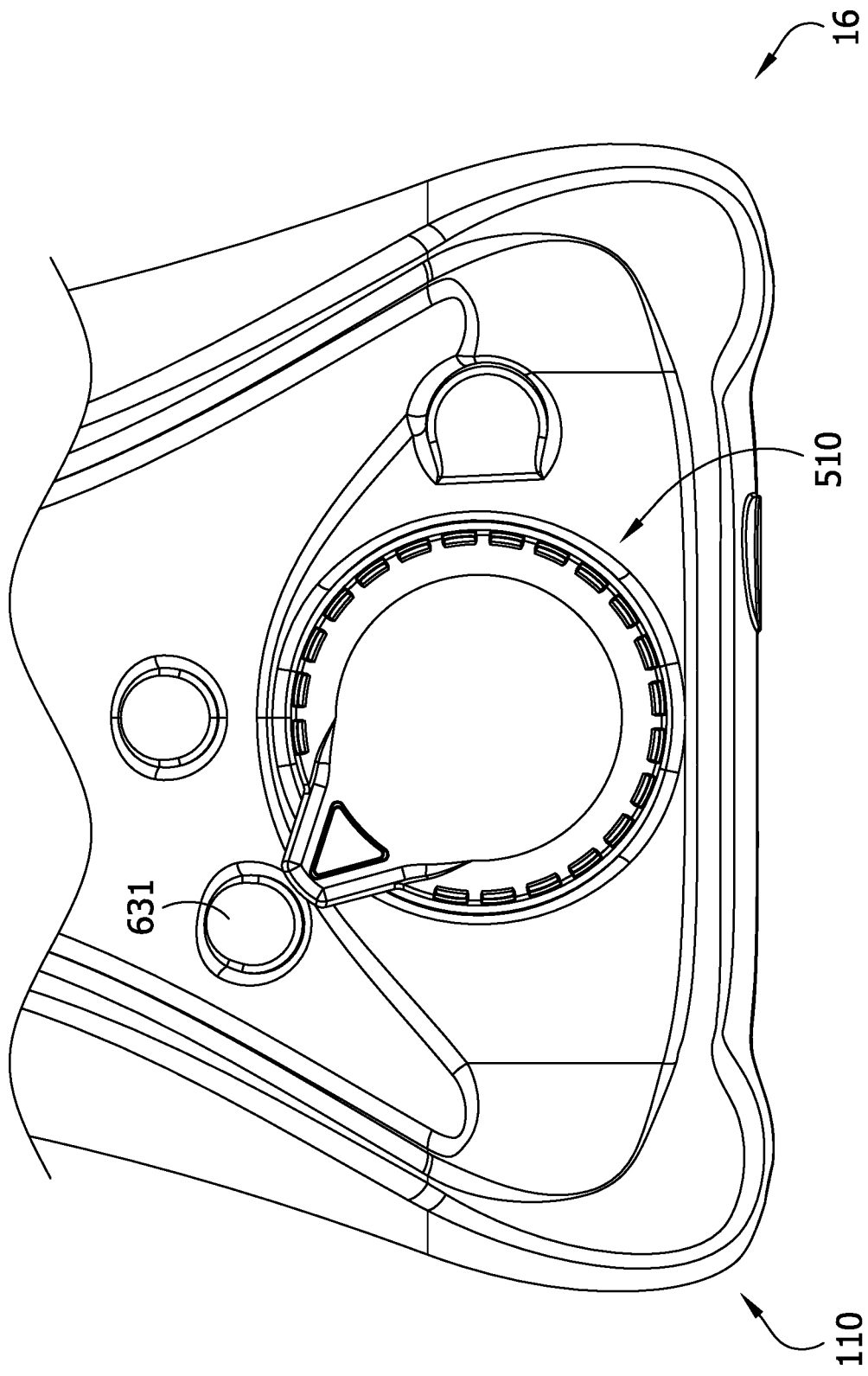
FIG. 58 is a partial top elevation of the proximal end portion of the handle similar to FIG. 51 but illustrating the control knob is in a deactivated mode position.
Figure 59:
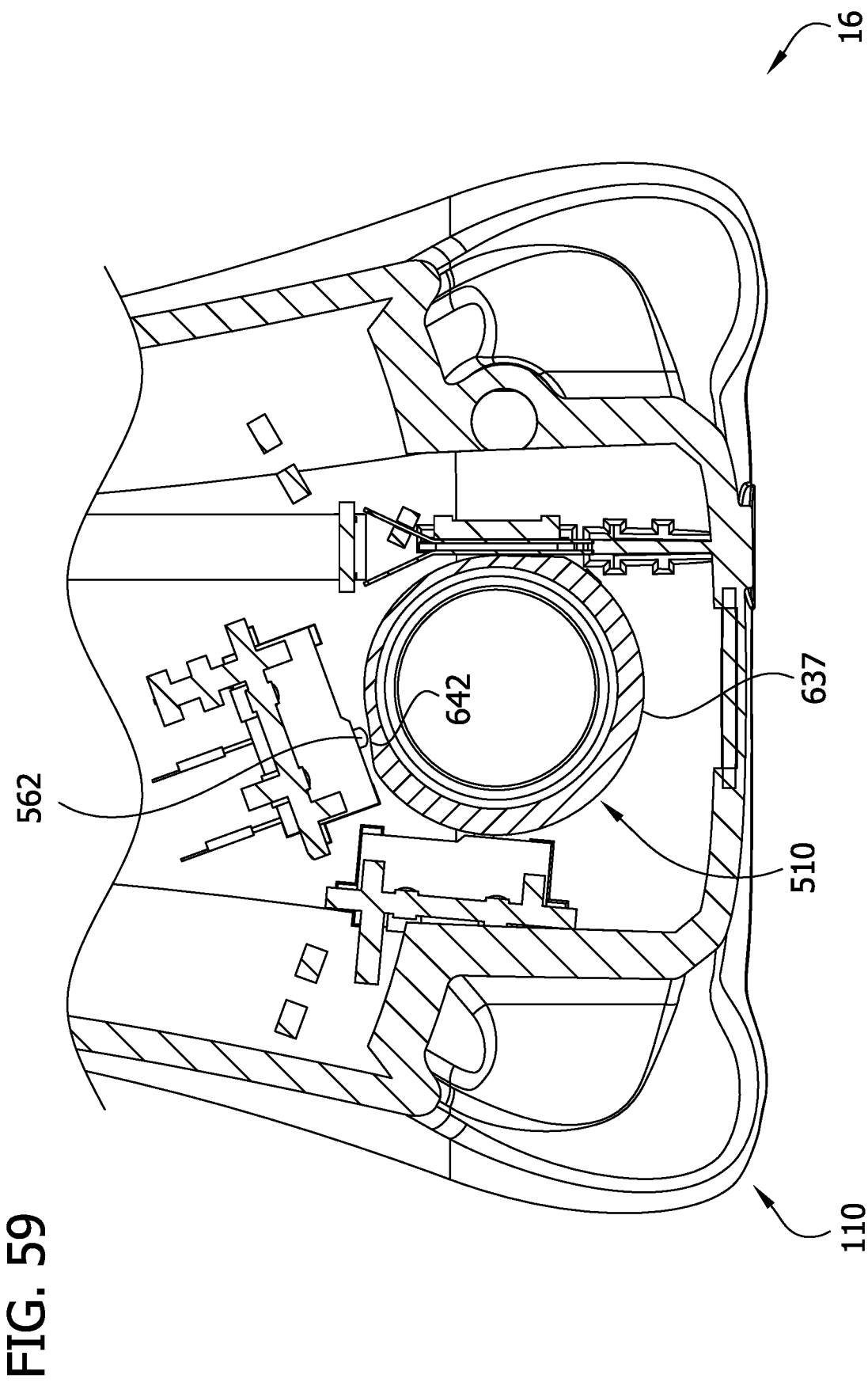
FIG. 59 is a partial cross section similar to FIG. 52 but illustrating the control knob is in the deactivated mode position.
Figure 60:
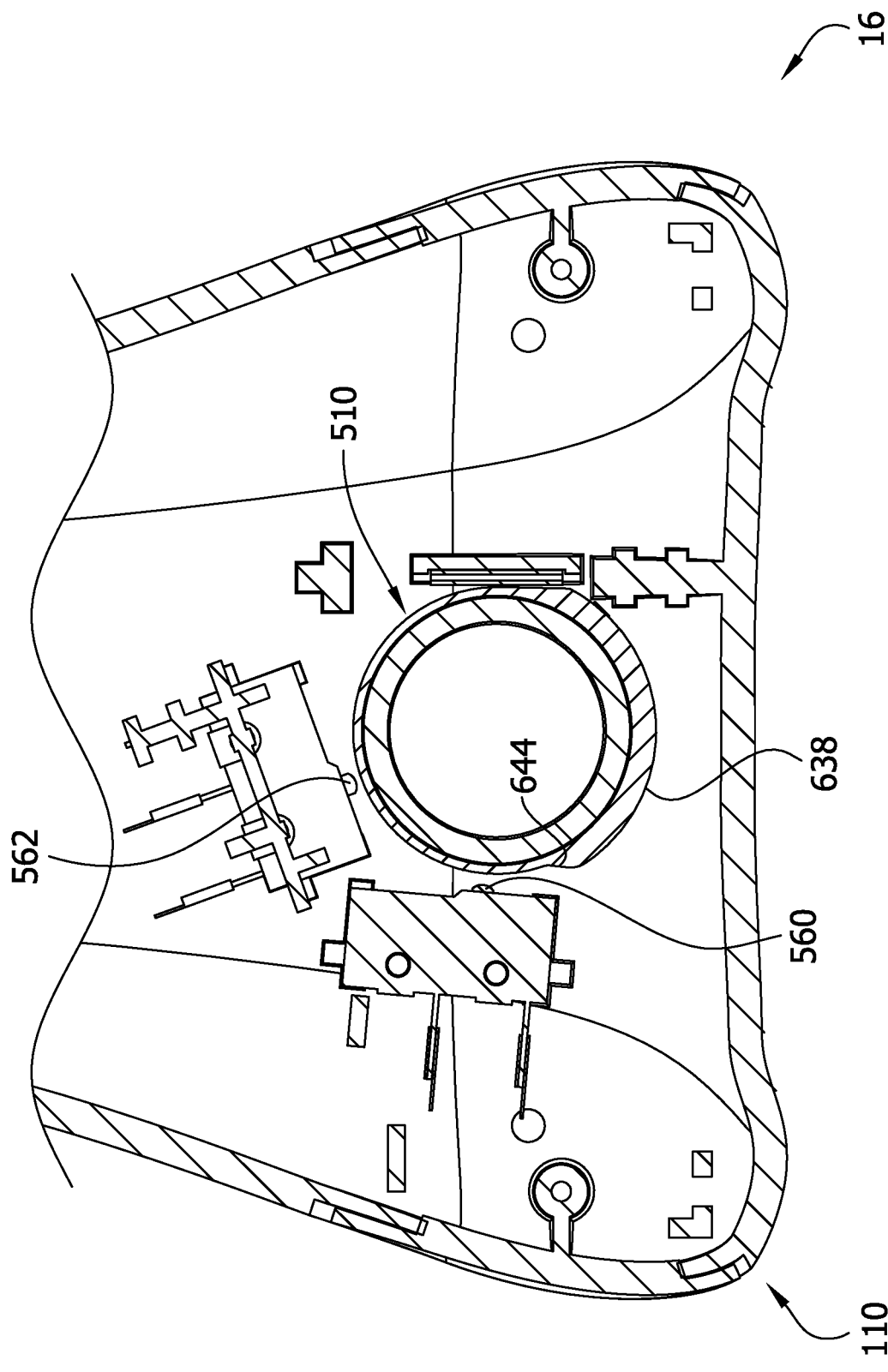
FIG. 60 is a partial cross section similar to FIG. 53 but illustrating the control knob is in the deactivated mode position.

The control knob 510 is configured to be pivoted counter-clockwise about the axis A5 from the navigation mode position to a deactivated mode positon shown in FIGS. 58-60. In the illustrated embodiment, the deactivated mode position is at about the counter-clockwise end of the range of motion of the knob 510. The braking cam 637 does not engage the braking spring 522 when the control knob 510 is in the deactivated mode position (or at any point in the range of motion between the navigation mode position and the deactivated mode position). Thus, the guidewire brake 512 remains in the released configuration so that relative movement between the guidewire G and the handle 16 is permitted. As shown in FIG. 60, in the navigation mode position, both the first motor regulator switch 560 and the second mode regulator switch 562 are disengaged. More specifically, each of the first and second mode selector cams 638, 640 is angularly spaced apart from the respective motor regulator switch 560, 562 in a counter-clockwise direction about the axis A5. Accordingly, in the illustrated deactivated mode position, the control knob 510 positions each of the motor regulator switches 560, 562 in the disengaged position. The control knob 510 thus configures the motor regulator 514 to operate the motor 524 in the deactivated mode. In this position, depressing the push button 136 does not actuate the motor.

When pivoting the control knob 510 clockwise from the deactivated mode position, the ramp surface 644 of the first mode selector cam 638 engages the first motor regulator switch 560 as the knob approaches the navigation mode position. The first mode selector cam 638 positions the first motor regulator switch 560 in the engaged position when the control knob 510 is pivoted to the navigation mode position. The camshaft 22 does not engage the second motor regulator switch 562 and thus the knob 510 positions the second motor regulator switch in the disengaged position. The guidewire brake 512 is not engaged as the control knob 510 is pivoted from the deactivated mode position to the navigation mode position. Thus, when the knob 510 reaches the navigation mode position, the knob 510 does not apply the guidewire brake 512 and configures the motor regulator 514 to operate the motor 524 in the navigation mode of operation. If the knob 510 is pivoted further in the clockwise direction, the ramp surface 644 of the second mode selector cam 640 initially engages the second motor regulator switch 562 as the knob 510 approaches the tissue-removing mode position. The second mode selector cam 640 positions the second motor regulator switch 562 in the engaged position when the control knob 510 is pivoted to the tissue-removing mode position. The first mode selector cam 638 remains engaged with the first motor regulator switch 560 as the control knob 510 pivots from the navigation mode position to the tissue-removing mode position. Thus, the knob 510 maintains the first motor regulator switch 560 in the engaged position. As the control knob 510 pivots toward the tissue-removing mode position, the ramp surface 542 of the braking cam 637 engages the first leg 524 of the guidewire brake 512 and presses it toward the second leg 526 and the brake support 520. Thus, when the knob 510 reaches the tissue-removing mode position, the knob 510 applies the guidewire brake 512 and configures the motor regulator 514 to operate the motor 524 in the tissue-removing mode of operation.

IV. Method of Removing Tissue Using Catheter

An exemplary method of using the catheter 10 in a tissue-removing procedure will now be briefly described. In the embodiment described in this section, the catheter 10 is used to perform an atherectomy tissue-removing procedure in an artery. For example, in one or more embodiments, the catheter 10 is used for a procedure in a patient artery having a vessel diameter in an inclusive range of from about 1.9 mm (e.g., about 0.075 inches) to about 5.0 mm (e.g., about 0.200 inches). It will be appreciated that the catheter can also be used to perform a tissue-removing procedure in other body lumens in one or more embodiments. In addition, certain aspects of the catheter can be used in procedures other than tissue-removing procedures in one or more embodiments.

Initially, the guidewire G (e.g., a guidewire having a length of about 330 cm) is loaded proximally through the catheter body 14 and the handle 16 as explained above. The step of loading the guidewire G through the catheter 10 can be performed while the control knob 510 is in the deactivated mode position. In one or more embodiment, the slider knob 150 is in the homed position or a locked orientation while the guidewire G is inserted proximally through the catheter 10. The user can also couple a source of inflation fluid I to the external inflation port 128 and a source of flushing fluid F to the external flushing port 130. After loading the catheter 10 onto the guidewire G, the user routes the distal end portion of the guidewire G through the artery until the guidewire extends past the occlusion. In one or more embodiments, the catheter 10 has an exchange length that is at least about 150 cm less than the length of the guidewire G that is used (e.g., at least about 160 cm less, at least about 170 cm less, at least about 175 cm less, or about 180 cm less). Thus, the distal end of the guidewire G can be positioned deep within the patient's anatomy while the proximal end portion of the guidewire still protrudes proximally from the guidewire opening 126 in the handle 16. The protruding proximal end portion of the guidewire G can allow a user to maintain guidewire control (e.g., a grip on the guidewire) throughout an entire procedure.

After positioning the guidewire G in the artery, the user pivots the control knob 510 to the navigation mode position. The user advances the catheter 10 distally along the guidewire G and advances the catheter body 14 distally through the artery. In one or more embodiment, the slider knob 150 is in the homed position or a locked orientation while advancing the catheter 10 along the guidewire G. Suitably, the user does not open the inflation valve VI while navigating the catheter body 14 through the artery. Accordingly, as the catheter body 14 passes through the artery to the treatment site, the balloon 22 is not inflated and the burr assembly 12 remains in the non-expanded configuration in which it has the minimum cross-sectional dimension D1. It is believed that the non-expanded burr assembly 12 can navigate through lumens of smaller cross-section than the expanded burr assembly. If resistance to advancement is encountered during navigation, the user can depress the push button 136 and the motor regulator 514 will operate the motor 524 to drive the burr assembly 12 in a discrete burst of rotation. The user can also open the flushing fluid valve VF to deliver flushing fluid along the guidewire lumen 72 and the flushing lumen 86 (as explained above) while advancing the catheter 10 along the guidewire G.

When the catheter 10 is advanced so that the burr assembly 12 is located adjacent the occlusion, the user can pivot the control knob 510 to the tissue-removing mode position. As explained above, the guidewire brake 512 is thus engaged to limit movement of the handle 16 with respect to the guidewire G and the motor regulator 514 becomes configured to operate the motor 524 in the tissue-removing mode of operation. The user can open the inflation valve VI to deliver inflation fluid from the source of inflation fluid I through the inflation conduit 26 to the balloon 22 (as explained above). The balloon 22 is thus inflated and expands the abrasive burr 20 from the minimum cross-sectional dimension D1 to the expanded cross-sectional dimension D2. The user can then depress the push button 134. In response, the motor regulator 514 drives continuous rotation of the expanded burr assembly 12. The user can pivot the slider knob 150 to the slide position and move the slider knob along the race 140 to move the rotating drive shaft 24, inflation conduit 26, and expanded burr assembly 12 along the guide wire G. For example, the user can advance the rotating expanded burr assembly 12 distally to engage the occlusion and abrade tissue. In one or more embodiments, the user can move the slider knob 150 distally and proximally in a repetitive sequence to engage the tissue in a hammer action. It is believed that the expanded burr assembly 12 can engage and abrade a greater radial cross-section of tissue in the body lumen than is possible with the non-expanded burr. While abrading tissue, the user can open and close the flushing valve VF as desired to deliver flushing fluid through the guidewire lumen 72 and the flushing lumen 86. The user can manipulate the rotating expanded burr assembly 12 using the slider knob 150 until the occlusion is removed. If necessary, the user can reposition the catheter 10 along the guidewire G for removing other occlusions or other portions of the same occlusion by pivoting the control knob 510 between the navigation mode position and the tissue-removing mode position to move the catheter along the guidewire to the desired position(s) and abrasively remove tissue at the desired position(s).

When the tissue-removing procedure is complete, the inflation valve VI can be adjusted to a position that releases the inflation fluid from the balloon 22 and the inflation lumen 28, thereby deflating the balloon. The control knob 510 can be pivoted to the navigation mode position, the slider knob 150 can be pivoted to a locked orientation or moved to the homed position, and the catheter 10 can be withdrawn proximally from the body lumen along the guidewire G. In another embodiment, the guidewire G is withdrawn from the body lumen with the elongate catheter body 14.

V. Drive Shaft Laminates

Figure 61:
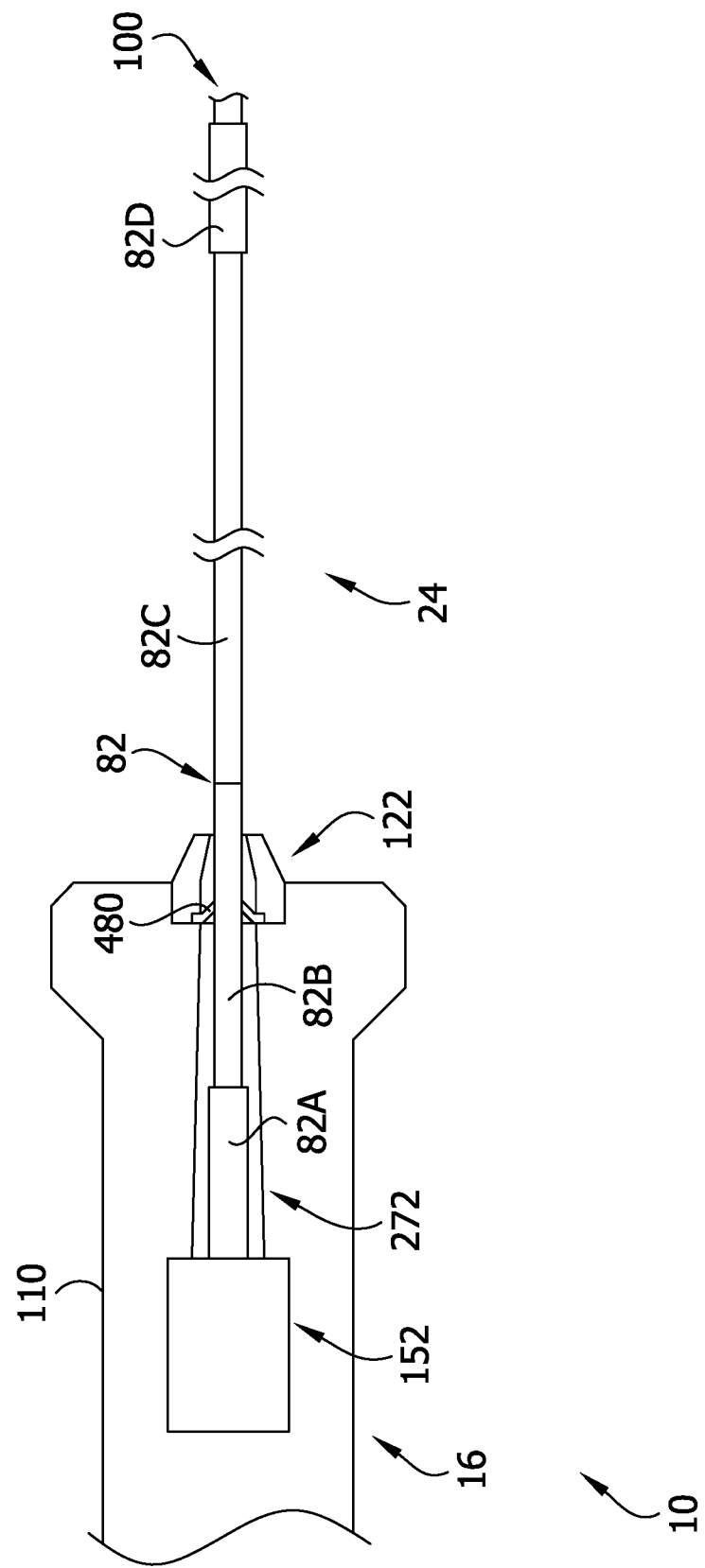
FIG. 61 is a schematic illustration of the laminated drive coil and a portion of the handle, illustrating discrete longitudinal sections of a laminate on the drive coil.

Referring to FIG. 61, in an embodiment such as the illustrated embodiment, the drive shaft laminate 82 comprises a plurality of discrete longitudinal sections having different properties. In the illustrated embodiment, the drive shaft laminate 82 has four discrete longitudinal sections 82A, 82B, 82C, 82D, although other numbers of discrete longitudinal sections can be used in one or more embodiments. Discrete longitudinal sections of a drive shaft laminate can differ from one another in terms of the type of material used for each section, the hardness of material used for each section, and/or the outer diameter of each section (broadly, the outer cross-sectional dimension of each section), among other parameters. In certain embodiments, each longitudinal section 82A, 82B, 82C, 82D can be formed of the same type of polymer. For example, in an embodiment, each longitudinal section is formed from a polyurethane, e.g., each longitudinal section is formed from a thermoplastic polyurethane (TPU) such as Pellethane® TPU. In an embodiment, the discrete longitudinal sections 82A, 82B, 82C, 82D are arranged end-to-end with no overlap between the sections. In other embodiments, adjacent longitudinal sections can overlap slightly where they join together.

The properties of each longitudinal section 82A, 82B, 82C, 82D can vary depending on the requirements of the corresponding longitudinal section of the drive shaft 24 during operation. For example, in an embodiment, a proximal end section 82A of the laminate 82 extends along a proximal end section of the drive shaft 24 that remains inside the handle 16 during use of the catheter 10. The section of the drive shaft 24 along which the proximal end section 82A extends is configured to remain within the handle 16 along the entire throw (range of motion) of the carriage 152. Moreover, at least a portion of the respective section of the drive shaft 24 is received in the catheter body alignment guide 272. Thus, during operation, the proximal end section 82A of the drive shaft laminate interfaces with the catheter body alignment guide 272, and the catheter body alignment guide maintains the corresponding section of the drive shaft 24 in a substantially straight configuration, substantially free of any bending. Suitably, therefore, the proximal end section 82A of the drive shaft laminate 82 is sufficiently robust to withstand any engagement with the catheter body alignment guide 272 as the drive shaft 24 rotates and/or the carriage 152 moves axially relative to the housing 110 of the handle 16. The proximal end section 82A does not need to be substantially flexible, however, because the catheter body alignment guide 272 limits bending during use. Further, the primary consideration affecting the maximum outer diameter (broadly, maximum cross-sectional dimension) of the proximal end section 82A is whether the proximal end section will fit within the catheter body alignment guide 272 with sufficient clearance.

A middle-proximal section 82B of the drive shaft laminate 82 extends along the longitudinal section of the drive shaft 24 that crosses the hub 122 along the entire throw of the carriage 152. In other words, the middle-proximal section 82B corresponds to the longitudinal section of the drive shaft 24 that extends from a location inside the handle 16 to a location outside the handle, regardless of the longitudinal position of the carriage 152 during use of the catheter 10. Thus, in the illustrated embodiment, the middle-proximal section 82B is sized and arranged for sealing engagement with the duckbill seal 480. The middle-proximal section 82B is suitably configured to withstand the wear associated with rotating and sliding longitudinally while sealingly engaging the stationary duckbill seal 480 during use. Thus, in certain embodiments, the middle-proximal section 82B is formed from a material that has a hardness that is greater than the hardness of the material of the proximal end section 82A. In an exemplary embodiment, the middle-proximal section 82B is formed from 75D Pellethane® TPU, while the proximal end section 82A is formed from 55D Pellethane® TPU. In an embodiment, the middle-proximal section 82B has an outer diameter that is less than the outer diameter of the proximal end section 82A. The reduction in outer diameter allows the middle-proximal section 82B to properly seal against the duckbill seal 480 within the isolation sheath hub 122. In addition, the reduction in outer diameter allows the middle-proximal section 82B to be more flexible than the proximal end section 82A. This is advantageous because some bending of the middle-proximal section 82B may be required during use of the catheter 10, whereas the proximal section 82A is held substantially straight by the catheter body alignment guide 272.

A middle-distal section 82C of the drive shaft laminate 82 extends along a longitudinal section of the drive shaft 24 that is located outside of the handle 16 along the entire throw of the carriage 152. In an embodiment, the middle-distal section 82C is configured to be relatively flexible to facilitate use the respective section of the drive shaft 24 in tortuous human anatomy. In contrast, the proximal-middle section 82B is rarely, if ever, received directly in tortuous anatomy. Thus, in an embodiment, the middle-distal section 82C is more flexible than the middle-proximal section 82B and/or the proximal end section 82A. In the illustrated embodiment, the middle-distal section 82C has the same outer diameter as the middle-proximal section 82B, but the middle distal section is formed from a material having a hardness that is less than the hardness of the middle-proximal section. For example, in an exemplary embodiment, the proximal-middle section 82B is formed for 75D Pellethane® TPU, while the middle-distal section 82C is formed from 65D Pellethane® TPU. In an embodiment, the middle-distal section 82C has an outer diameter that is less than the outer diameter of the proximal end section 82A and a hardness that is greater than the hardness of the proximal end section.

A distal end section 82D of the drive shaft laminate 82 extends along a longitudinal section of the drive shaft 24 that attaches to the burr adaptor 100. The connection between the drive shaft 24 and the burr adaptor 100 transitions from a relatively flexible section of the catheter body 12 proximal of the burr adaptor to a substantially rigid section at the burr adaptor. This transition region can experience forces during use that tend to cause delamination of the laminate 82. To limit the possibility of delamination, in the illustrated embodiment, the distal end section 82D has a greater outer diameter than the middle-distal section 82C and the distal end section is formed from a material having a hardness that is less than the hardness of the middle-distal section. For example, in an exemplary embodiment, the distal end section 82D is formed from 55D Pellethane® TPU, and the middle-distal section 82C is formed from 65D Pellethane® TPU. In the illustrated embodiment, the distal end section 82D also has a greater outer diameter than the middle-proximal section 82B and is formed from a material having a hardness that is less than the hardness of the middle-proximal section. The illustrated distal end section 82D has an outer diameter that is less than the outer diameter of the proximal end section 82A and a hardness that is about the same as the hardness of the proximal end section.

The single wall thickness and material of each of the longitudinal sections 82A, 82B, 82C, 82D of an exemplary embodiment of a drive shaft laminate 82 are described in the table below. In an embodiment, each section of the laminate is applied to the same drive coil 80, which has a substantially constant outer diameter. Thus, the single wall thickness of the laminate material along each of the longitudinal sections 82A, 82B, 82C, 82D corresponds directly with the outer diameter of the drive shaft 24 along the respective longitudinal section, in one or more embodiments. As can be seen from the table below, in one or more embodiments, the single wall thickness of the proximal end section 82A is greater than the single wall thicknesses of the middle-proximal section 82B, middle-distal section 82C, and the distal end section 82D. The single wall thicknesses of each of the middle-proximal section 82B and the middle-distal section 82C (together broadly, a middle section) are about the same and less than the single wall thicknesses of the proximal end section 82A and the distal end section 82D. The single wall thickness of the distal end section 82D is less than the single wall thickness of the proximal end section 82A and greater than the thicknesses of the middle-proximal section 82B and the middle-distal section 82C.

| Section | Single Wall Thickness | Material |
| --- | --- | --- |
| Proximal End Section 82A | about 0.0035 inches (about 89 micrometers) | 55D Pellethane ® TPU |
| Middle-Proximal Section 82B | about 0.0020 inches (about 51 micrometers) | 75D Pellethane ® TPU |
| Middle-Distal Section 82C | about 0.0020 inches (about 51 micrometers) | 65D Pellethane ® TPU |
| Distal End Section 82D | about 0.0030 inches (about 76 micrometers) | 55D Pellethane ® TPU |

Modifications and variations of the disclosed embodiments are possible without departing from the scope of the invention defined in the appended claims.

When introducing elements of the present invention or the embodiment(s) thereof, the articles "a", "an", "the" and "said" are intended to mean that there are one or more of the elements. The terms "comprising", "including" and "having" are intended to be inclusive and mean that there can be additional elements other than the listed elements. As various changes can be made in the above constructions, products, and methods without departing from the scope of the disclosure, it is intended that all matter contained in the above description and shown in the accompanying drawings shall be interpreted as illustrative and not in a limiting sense.

What is claimed is:
1. A tissue-removing catheter comprising:
a drive shaft extending longitudinally from a proximal end portion to a distal end portion, the drive shaft being configured for rotation about a rotational axis;
an ablation burr coupled to the drive shaft for conjoint rotation with the drive shaft about the rotational axis, the ablation burr being configured to radially expand and having an outer abrasive surface;
an inflation conduit extending longitudinally through the drive shaft, the inflation conduit being coupled to the drive shaft for conjoint rotation with the drive shaft about the rotational axis, the inflation conduit comprising an outer inflation tube and an inner inflation tube inside the outer inflation tube, the inflation conduit defining a longitudinal inflation lumen radially between the inner inflation tube and the outer inflation tube, the inner inflation tube defining a longitudinal guide wire lumen for slidably receiving a guidewire therein, wherein the inner inflation tube comprises a reinforcing coil;
a balloon coupled to the inflation conduit, in fluid communication with the inflation lumen, and configured to rotate conjointly with the inflation conduit about the rotational axis, the balloon being disposed in the ablation burr and configured to be inflated by a pressurized inflation fluid in the inflation lumen to radially expand the ablation burr, wherein the reinforcing coil of the inner inflation tube is configured to limit radial compression of the inner inflation tube in response to the pressurized inflation fluid in the inflation lumen inflating the balloon to enable rotation of the inflation conduit about the guide wire when the balloon is inflated, wherein the drive shaft is joined to the outer inflation tube at a joint location adjacent the distal end portion of the drive shaft for transferring torque between the drive shaft and the outer inflation tube.

2. A tissue-removing catheter as set forth in claim 1, wherein the reinforcing coil comprises one of nitinol and stainless steel.

3. A tissue-removing catheter as set forth in claim 1, wherein the reinforcing coil comprises a single-helix coil.

4. A tissue-removing catheter as set forth in claim 1, wherein the reinforcing coil has from about 50 wraps-per-inch to about 250 picks-per-inch.

5. A tissue-removing catheter as set forth in claim 1, wherein the inner inflation tube comprises a polyimide tube, the reinforcing coil being embedded in the polyimide tube.

6. A tissue-removing catheter as set forth in claim 1, wherein the outer inflation tube comprises a nylon tube.

7. A tissue-removing catheter as set forth in claim 1, wherein the drive shaft comprises a laminated drive coil.

8. A tissue-removing catheter as set forth in claim 7, wherein the drive coil comprises one of nitinol and stainless steel.

9. A tissue-removing catheter as set forth in claim 1, further comprising an isolation sheath, the drive shaft being received in the isolation sheath.

10. A tissue-removing catheter as set forth in claim 9, wherein the drive shaft is slidable longitudinally with respect to the isolation sheath.

11. A tissue-removing catheter as set forth in claim 9, wherein the isolation sheath comprises an inner polymer layer, an outer polymer layer, and a braid layer radially between the inner polymer layer and the outer polymer layer.

12. A tissue-removing catheter as set forth in claim 11, wherein the inner polymer layer and the outer polymer layer comprise the same material.

13. A tissue-removing catheter as set forth in claim 11, wherein the inner polymer layer and the outer polymer layer comprise different materials.

14. A tissue-removing catheter as set forth in claim 9, wherein the isolation sheath comprises a braid formed from one of nitinol and stainless steel.

15. A tissue-removing catheter as set forth in claim 9, further comprising a longitudinal flushing lumen radially between the isolation sheath and the drive shaft.

16. A tissue-removing catheter as set forth in claim 9, wherein the isolation sheath comprises a distal end that is spaced apart proximally from the ablation burr.

17. A tissue-removing catheter set forth in claim 1, wherein a distal end portion of the inner inflation tube is coupled to a distal neck of the balloon.

18. A tissue-removing catheter set forth in claim 17, wherein the distal end portion of the inner inflation tube protrudes distally from a distal end portion of the outer inflation tube.

19. A tissue-removing catheter as set forth in claim 1, wherein the drive shaft is heat bonded to the outer inflation tube.

* * * * *